(12) United States Patent
Cao et al.

(10) Patent No.: US 11,970,548 B2
(45) Date of Patent: Apr. 30, 2024

(54) NANOBODY TARGET GCC AND USES IN CHIMERIC ANTIGEN RECEPTOR CELL THERAPY

(71) Applicants: Innovative Cellular Therapeutics Holdings, Ltd., George Town (KY); Innovative Cellular Therapeutics, Inc., Rockville, MD (US)

(72) Inventors: Zhiyuan Cao, Shanghai (CN); Yuzhe Peng, Shanghai (CN); Lei Xiao, Rockville, MD (US); Zhao Wu, Shanghai (CN); Le Tian, Rockville, MD (US)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 0 days.

(21) Appl. No.: 17/821,706

(22) Filed: Aug. 23, 2022

(65) Prior Publication Data
US 2023/0074145 A1    Mar. 9, 2023

Related U.S. Application Data

(60) Provisional application No. 63/237,729, filed on Aug. 27, 2021.

(51) Int. Cl.
| | |
|---|---|
| C12P 21/08 | (2006.01) |
| A61K 35/17 | (2015.01) |
| A61K 39/395 | (2006.01) |
| A61K 47/68 | (2017.01) |
| A61P 35/00 | (2006.01) |
| C07K 14/725 | (2006.01) |
| C07K 16/28 | (2006.01) |
| C07K 16/30 | (2006.01) |
| C07K 16/40 | (2006.01) |
| A61K 38/00 | (2006.01) |

(52) U.S. Cl.
CPC ............. *C07K 16/40* (2013.01); *A61K 35/17* (2013.01); *A61P 35/00* (2018.01); *C07K 14/7051* (2013.01); *A61K 38/00* (2013.01); *C07K 2317/56* (2013.01); *C12Y 406/01002* (2013.01)

(58) Field of Classification Search
None
See application file for complete search history.

(56) References Cited

U.S. PATENT DOCUMENTS

| | | | | |
|---|---|---|---|---|
| 9,029,636 | B2 * | 5/2015 | Wu | C07K 14/415 800/320.2 |
| 9,193,780 | B2 * | 11/2015 | Hultberg | C07K 16/1018 |
| 2011/0053865 | A1 * | 3/2011 | Saunders | A61P 35/00 536/23.1 |
| 2013/0330335 | A1 * | 12/2013 | Bremel | G16B 20/00 435/69.6 |
| 2017/0355776 | A1 | 12/2017 | Xiao et al. | |
| 2019/0322746 | A1 * | 10/2019 | Bobilev | A61P 35/00 |
| 2020/0055912 | A1 | 2/2020 | Kley et al. | |
| 2020/0078399 | A1 | 3/2020 | Fan et al. | |
| 2020/0317802 | A1 * | 10/2020 | Buyse | C07K 16/2896 |
| 2021/0038648 | A1 | 2/2021 | Waldman | |
| 2022/0119505 | A1 | 4/2022 | Laustsen et al. | |

FOREIGN PATENT DOCUMENTS

| | | | | |
|---|---|---|---|---|
| WO | WO-2018102795 A2 * | 6/2018 | | A61K 35/17 |
| WO | WO-2019224716 A2 * | 11/2019 | | A61P 35/00 |
| WO | WO-2020073345 A1 * | 4/2020 | | A61K 31/337 |
| WO | WO2021057866 A1 | 4/2021 | | |

OTHER PUBLICATIONS

PCT Invitation to Pay Additional Fees dated Oct. 31, 2023 for PCT Application No. PCT/US2023/030846, 3 pages.
Gallery et al., "A Monomethyl Auristatln E-Conjugated Antibody to Guanylyl Cyclase C is Cytotoxic to Target-Expressing Cells In Vitro and In Vivo," PLoS One, Jan. 2018, 13(1):e0191046. 20 pages.
International Search Report and Written Opinion mailed on Jan. 29, 2024, for PCT Application No. PCT/US23/30846, 16 pages.
Lisby et al., "GUCY2C as a Biomarker to Target Precision Therapies for Patients with Colorectal Cancer," Expert Rev Precis Med Drug Dev, 2021, 6(2):117-129.
Magee et al., "Human GUCY2C-Targeted Chimeric Antigen Receptor (CAR}-Expressing T Cells Eliminate Colorectal Cancer Metastases," Cancer Immunol Res. May 2018, 6(5):509-516.

\* cited by examiner

*Primary Examiner* — Daniel E Kolker
*Assistant Examiner* — Brianna K Swartwout
(74) *Attorney, Agent, or Firm* — Lee & Hayes, P.C.

(57) ABSTRACT

The compositions and methods described herein are directed to treating solid tumors using CAR T therapy and/or antibodies targeting GCC. The compositions include CAR comprising an extracellular domain that binds GCC.

9 Claims, 6 Drawing Sheets

Specification includes a Sequence Listing.

NANOBODY TARGET GCC AND USES IN CHIMERIC ANTIGEN RECEPTOR CELL THERAPY

CROSS REFERENCE TO RELATED APPLICATIONS

This application claims the benefit of U.S. Provisional Application 63/237,729, filed Aug. 27, 2021, which is hereby incorporated by reference in its entirety.

SEQUENCE LISTING INFORMATION

A computer-readable XML file, entitled "1071-0098US.xml" was created on or about Aug. 29, 2022 with a file size of about 482,761 bytes, contains the sequence listing for this application and is hereby incorporated by reference in its entirety.

TECHNICAL FIELD

The present disclosure relates to modified cells and uses, in particular to compositions and methods for treating cancer using Chimeric Antigen Receptor (CAR) cells.

BACKGROUND

A heavy chain (VHH) antibody (or nanobody) is the antigen binding fragment of heavy chain only antibodies. It has been reported that single VHH directed BCMA CAR T cells caused remission of relapsed/refractory multiple myeloma. Therefore, VHH antibodies can be used to direct CAR T cells to target solid tumors.

SUMMARY

Embodiments relate to an antibody that binds GCC, wherein the antibody comprises a VHH domain comprising one of the amino acid sequences of SEQ ID NO: 200-269 or one or more CDRs comprising the amino acid sequence of SEQ ID NO: 200-269.

Embodiments relate to the discovery that some antigens are expressed at a relatively low level on tumor cells compared to their expression on normal tissues. Further, while expressed in normal tissues, these antigens are expressed explicitly on a specific group of cells, tissue, or organ, so that the killing of normal cells of a tissue or organ does not cause a life-threatening event (e.g., complications) to the subject. Therefore, treatment targeting these antigens on nonessential tissues would not cause a serious adverse-affect to the subject. Examples of the nonessential tissues include organs such as the prostate, breast, or melanocyte. Accordingly, the embodiments of the present disclosure relate to a chimeric antigen receptor (CAR), including an extracellular domain that binds at least one of these antigens and treats cancer using cells including the CAR.

Embodiments relate to compositions and methods for treating cancer using CAR cells. Embodiments relate to an isolated nucleic acid encoding a CAR, wherein the CAR comprises an extracellular domain, a transmembrane domain, and an intracellular domain, wherein the extracellular domain of the CAR binds an antigen of a solid tumor. In embodiments, the antigen comprises GCC (i.e., GUCY2C), SIGLEC15, SLC6A3, KISS1R, QRFPR, GPR119, CLDN6, UPK2, ADAM12, SLC45A3, ACPP, MUC21, MUC16, MS4A12, ALPP, SLC2A14, GS1-259H13.2, ERVFRD-1, ADGRG2, ECEL1, CHRNA2, GP2, or PSG9.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
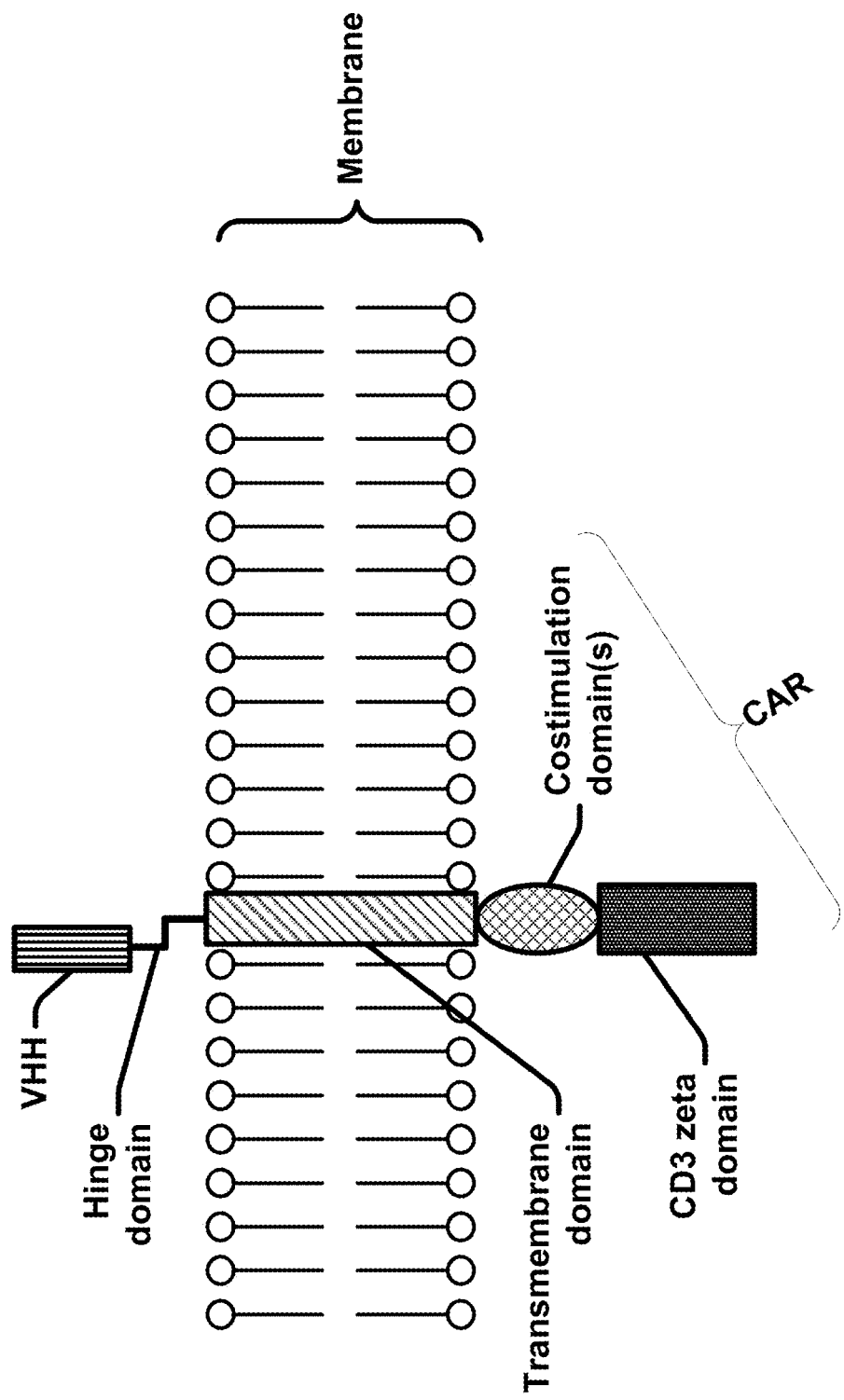
FIG. 1 shows a schematic diagram illustrating an example of a CAR structure.
Figure 2:
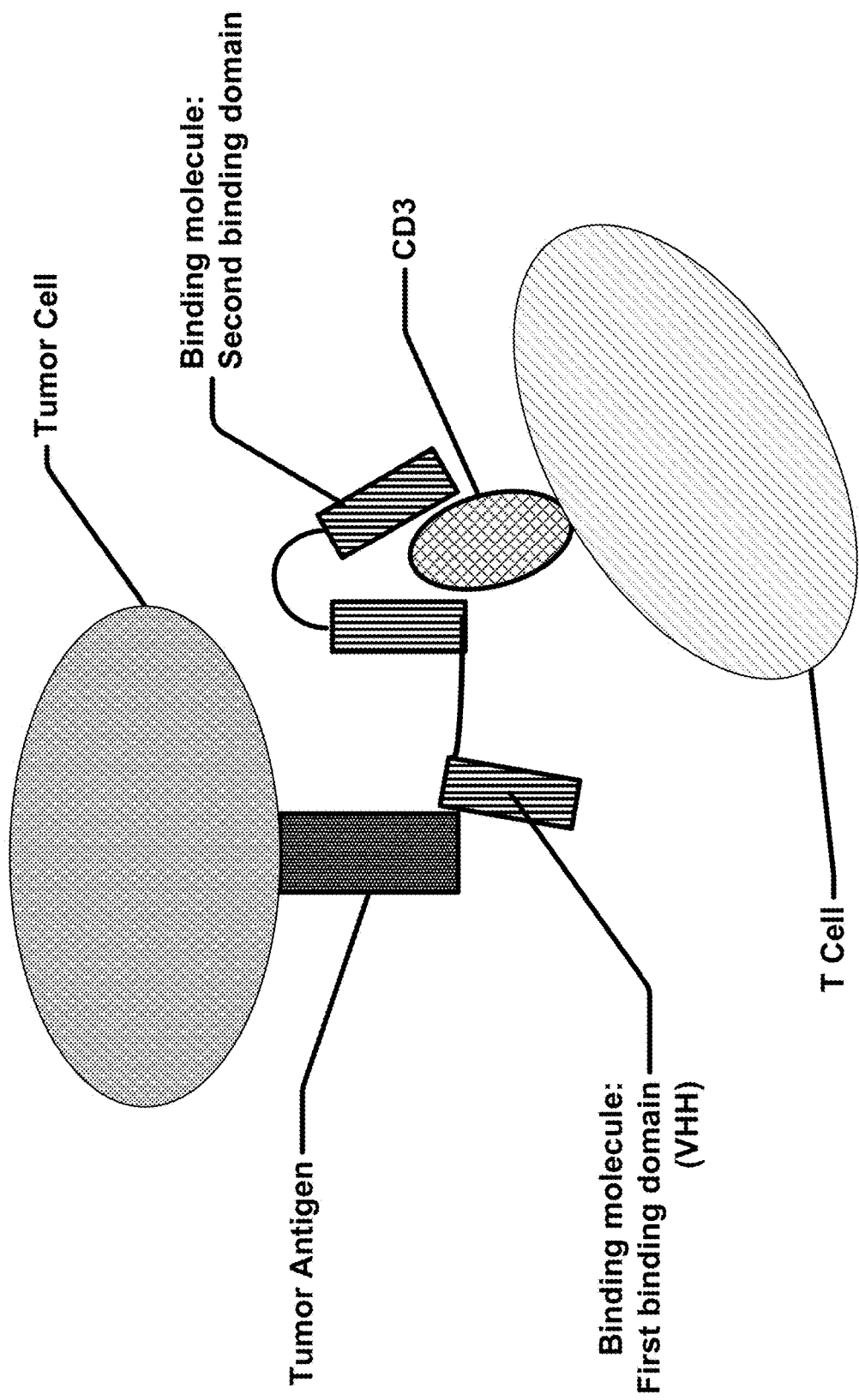
FIG. 2 shows an exemplary structure of a binding molecule.
Figure 3:
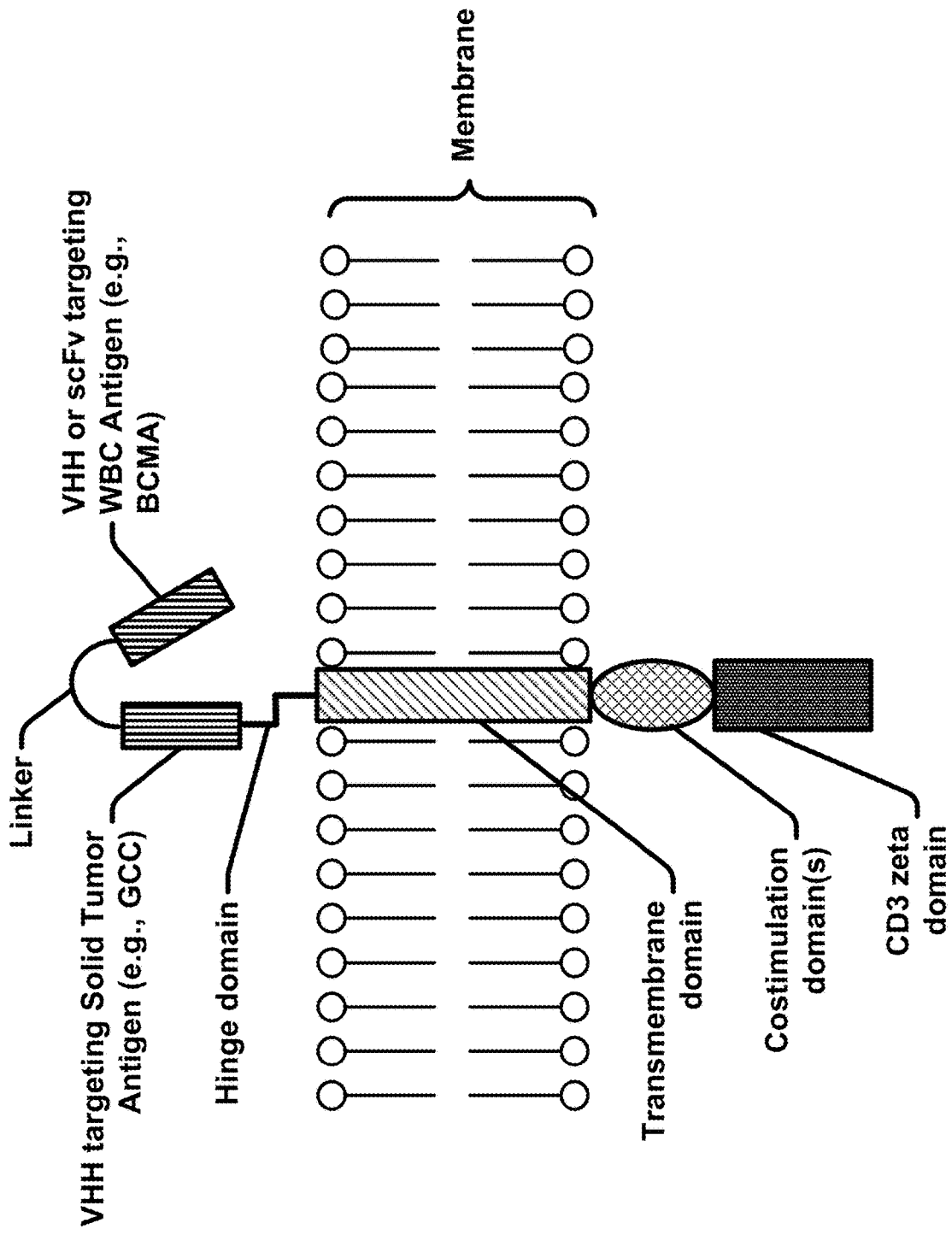
FIG. 3 shows an exemplary structure of a CAR.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms, including, for example, polyclonal antibodies, monoclonal antibodies, Fv, Fab, and F(ab)2, as well as single chain antibodies and humanized antibodies (Harlow et al., 1999, In Using Antibodies: A Laboratory Manual, Cold Spring Harbor Laboratory Press, NY; Harlow et al., 1989, In Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment containing a complete antigen-recognition and -binding site. This fragment consists of a dimer of one heavy- and one light-chain variable region domain in a tight, non-covalent association. From the folding of these two domains emanates six hypervariable loops (3 loops each from the H and L chain) that contribute to the amino acid residues for antigen binding and confer antigen binding specificity to the antibody. However, even a single variable domain (or half of an Fv including only three complementarity determining regions (CDRs) specific for an antigen) can recognize and bind antigen, although at a lower affinity than the entire binding site (the dimer).

An "antibody heavy chain," as used herein, refers to the larger two types of polypeptide chains present in all antibody molecules in their naturally occurring conformations. An "antibody light chain," as used herein, refers to the smaller two types of polypeptide chains present in all antibody molecules in their naturally occurring conformations. K and A light chains refer to the two major antibody light chain isotypes.

The term "synthetic antibody" refers to an antibody generated using recombinant DNA technology, such as, for example, an antibody expressed by a bacteriophage. The term also includes an antibody generated by synthesizing a DNA molecule encoding the antibody and the expression of the DNA molecule to obtain the antibody or to obtain an amino acid encoding the antibody. Synthetic DNA is obtained using technology that is available and well known in the art.

In embodiments, an antibody is a single variable domain on a heavy chain (VHH) antibodies, also referred to as Nanobodies®, were discovered nearly 25 years ago. Heavy chain only antibodies (HcAb) are naturally produced by camelids and sharks. The antigen binding portion of the HcAb is comprised of the VHH fragment (See FIGS. 4 and 5).

The term "antigen" refers to a molecule that provokes an immune response, which may involve either antibody production, the activation of specific immunologically-competent cells, or both. Antigens include any macromolecule, including all proteins or peptides or molecules derived from recombinant or genomic DNA. For example, DNA includes a nucleotide sequence or a partial nucleotide sequence encoding a protein or peptide that elicits an immune response and, therefore, encodes an "antigen," as the term is used herein. An antigen need not be encoded solely by a full-length nucleotide sequence of a gene. An antigen can be generated, synthesized, or derived from a biological sample, including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, a decrease in tumor cell proliferation, a decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies the prevention the occurrence of tumors in the first place.

The term "auto-antigen" refers to an antigen mistakenly recognized by the immune system as being foreign. Autoantigens include cellular proteins, phosphoproteins, cellular surface proteins, cellular lipids, nucleic acids, and glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be a related or unrelated recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" refers to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Cancers that may be treated include tumors that are not vascularized or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia, and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high-grade forms), multiple myeloma, Waldenstrom's macroglobulinemia, heavy chain disease, myelodysplastic syndrome, hairy cell leukemia, and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
| --- | --- |
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |
| EGFR | Glioma-NSCL cancer |
| tMUC 1 | Cholangiocarcinoma, Pancreatic cancer, Breast Cancer |
| PSCA | pancreas, stomach, or prostate cancer |

Throughout this specification, unless the context requires otherwise, the words "comprise," "includes," and "including" will be understood to imply the inclusion of a stated step or element (ingredients or components) or group of steps or elements (ingredients or components) but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T" is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "costimulatory ligand" refers to a molecule on an antigen-presenting cell (e.g., an APC, dendritic cell, B cell, and the like) that specifically binds a cognate costimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A costimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, in combination with a primary signal, such as TCR/CD3 ligation, that leads to T cell proliferation and/or upregulation or downregulation of key molecules.

The terms "co-stimulatory signaling region", "co-stimulatory domain", and "co-stimulation domain" are used interchangeably to refer to one or more additional stimulatory domain in addition to a stimulatory or signaling domain such as CD3 zeta. The terms "stimulatory" or "signaling" domain (or region) are also used interchangeably, when referring to, for example, CD3 zeta. In embodiments, the co-stimulatory signaling domain and the stimulatory signaling domain can be on the same molecule or different molecules in the same cell.

The terms "disease" and "condition" may be used interchangeably or may be different in that the particular malady or condition may not have a known causative agent (so that etiology has not yet been worked out), and it is therefore not yet recognized as adisease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated, then the subject's health continues to deteriorate. In contrast, a "disorder" in a subject is a state of health in which the animal is able to maintain homeostasis but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for the synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide, including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared to ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig" refers to a class of proteins that function as antibodies. The five members included in this class of proteins are IgA, IgG, IgM, IgD, and IgE. IgA is the primary antibody that is present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule, such as a protein or nucleic acid. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may, in some versions, contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables the integration of genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when it is placed into a functional relationship with another nucleic acid sequence. For example, DNA for a sequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," "individual," and the like are used interchangeably herein and refer to any human, animal, or living organism amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for the prevention of a disease, condition, or disorder. In embodiments, the disease is cancer.

The term "polynucleotide" or "nucleic acid" refers to mRNA, RNA, cRNA, rRNA, cDNA, or DNA. The term typically refers to a polymeric form of nucleotides of at least ten bases in length, either ribonucleotides or deoxynucleotides or a modified form of either type of nucleotide. The term includes all forms of nucleic acids, including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations, inclusive of mutations, additions, deletions, and substitutions, can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions, and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "promoter" refers to a DNA sequence recognized by the synthetic machinery of the cell or introduced synthetic machinery required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody that recognizes a specific antigen but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding" can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A," and the antibody will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein), and/or a protein molecule (a protein-binding protein). In the case of a protein-binding protein, it can bind to itself (to form homodimers, homotrimers, etc.), and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example, via engineering (altering one or more amino acids) of the recognition helix region of a naturally occurring zinc finger protein. Further, a Zinc finger binding domain may be fused with a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes).

"Cleavage" refers to the breakage of the covalent backbone of a DNA molecule. Cleavage can be initiated by a variety of methods, including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, sequence five 'GAATTC 3' is a target site for the Eco RI restriction endonuclease.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide and a fusion between a minor groove binder and a nucleic acid.

Expression of a fusion protein in a cell can result from the delivery of the fusion protein to the cell or by delivery of a polynucleotide encoding the fusion protein to a cell, wherein the polynucleotide is transcribed and the transcript is translated to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences, or introns, or within nontranscribed regions, either upstream or downstream of the coding region. A region of interest can be as small as a single nucleotide pair or up to 2,000 nucleotide pairs in length or any integral value of nucleotide pairs.

By "statistically significant," it is meant that the result was unlikely to have occurred by chance. Statistical significance can be determined by any method known in art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount and may include a decrease that is about 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-β and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T cell receptors" PNAS, 1993 Jan. 15; 90(2):720-4, showed that two CAR constructs in which an scFv was fused to "either the FcR gamma chain or the CD3 complex chain" triggered T cell activation and target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al. ("A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl. 1, May 2014, page S57) tested a CAR molecule in which an scFv was fused to "the transmembrane and the cytoplasmic domain of" a killer immunoglobulin-like receptor (KIR). Wang et al. reported that "a KIR-based CAR targeting mesothelin (SS 1-KIR) triggers antigen-specific cytotoxic activity and cytokine production that is comparable to CD3~-based CARs." A second publication from the same group, Wang et al. ("Generation of Potent T-cell Immunotherapy for Cancer Using DAP12-Based, Multichain, Chimeric Immunoreceptors" Cancer Immunol Res. 2015 July; 3(7):815-26), showed that a CAR molecule in which "a single-chain variable fragment for antigen recognition was fused to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that, when present on an antigen presenting cell (e.g., an APC, a dendritic cell, a B-cell, and the like), can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to the treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor, or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, its severity, and the age, weight, etc., of the subject to be treated.

The term "treat a disease" refers to the reduction of the frequency or severity of at least one sign or symptom of a disease or disorder experienced by a subject.

The term "transfected," "transformed," or "transduced" refers to a process by which an exogenous nucleic acid is transferred or introduced into the host cell. A "transfected" or "transformed" or "transduced" cell is one that has been transfected, transformed, or transduced with an exogenous nucleic acid. The cell includes the primary subject cell and its progeny.

The term "vector" refers to a polynucleotide that comprises an isolated nucleic acid and which can be used to deliver the isolated nucleic acid to the interior of a cell in vitro and in vivo (in a subject). Numerous vectors are known in the art, including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural functions. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes; for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, a description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

T cells, or T lymphocytes, are a type of white blood cell of the immune system. There are various types of T cells including T helper (TH) cells, cytotoxic T (TC) cells (T killer cells, killer T cells), natural killer T (NKT) cells, memory T (Tm) cells, regulatory T (Treg) cells, and gamma delta T (γδ T) cells.

T helper (TH) cells assist other lymphocytes, for example, activating cytotoxic T cells and macrophages and maturation of B cells into plasma cells and memory B cells. These T helper cells express CD4 glycoprotein on their surface and are also known as CD4+ T cells. Once activated, these T cells divide rapidly and secrete cytokines.

Cytotoxic T (TC) cells destroy virus-infected cells and tumor cells and are also involved in transplant rejection. They express CD8 protein on their surface. Cytotoxic T cell release cytokines.

Natural Killer T (NKT) cells are different from natural killer cells. NKT cells recognize glycolipid antigens presented by CD1d. Once activated, NKT cells produce cytokine and release cell killing molecules.

Memory T (Tm) cells are long-lived and can expand to large number of effector T cells upon re-exposure to their cognate antigen. Tm cells provide the immune system with memory against previously encountered pathogens. There are various subtypes of Tm cells including central memory T (TCM) cells, effector memory T (TEM) cells, tissue resident memory T (TRM) cells, and virtual memory T cells. Tm cells are either CD4+ or CD8+ and usually CD45RO.

Regulatory T (Treg) cells shut down T cell mediated immunity at the end of an immune reaction and suppress autoreactive T cells that escaped the process of negative selection in the thymus. Subsets of Treg cells include thymic Treg and peripherally derived Treg. Both subsets of Treg require the expression of the transcription factor FOXP3.

Gamma delta T (γδ T) cells are a subset of T cells that possess a γδ T cell receptor (TCR) on the cell surface, as most T cells express the αβ TCR chains. γδ T cells are less common in human and mice and are mainly found in the gut mucosa, skin, lung, and uterus. They are involved in the initiation and propagation of immune responses.

Embodiments of the present disclosure relate to treating cancer using chimeric antigen receptor (CAR) cells. Embodiments relate to an isolated nucleic acid encoding a CAR, wherein the CAR comprises an extracellular domain, a transmembrane domain, and an intracellular domain, wherein the extracellular domain of the CAR binds an antigen of a solid tumor. For example, transcriptional data shows that the expression of antigens such as SLC6A3, KISS1R, and QRFPR in normal tissues is very low, but the expression of such antigens in cells related to renal cancer is high. Information on some of the antigens is provided below in Table 2.

TABLE 2

| Gene name | Subcellular localization | Organ mainly expressing | Target Tumor | Target SEQ ID NO. |
|---|---|---|---|---|
| SIGLEC15 | Plasma membrane | Expression in all normal tissues is very low | Urothelial cancer | 17 |
| SLC6A3 | Plasma membrane | Expression in all normal tissues is very low | Renal cancer | 18 |
| KISS1R | Plasma membrane | Expression in all normal tissues is very low | Renal cancer | 19 |
| QRFPR | Plasma membrane | Expression in all normal tissues is very low | Renal cancer: | 20 |
| GPR119 | Plasma membrane | Expression in all normal tissues is very low | Pancreatic cancer | 21 |
| CLDN6 | Plasma membrane | Expression in all normal tissues is very low | Endometrial cancer/ Urothelial cancer | 22 |
| UPK2 | Plasma membrane | Urethra/bladder | Urothelial cancer (including bladder cancer) | 1 |
| ADAM12 | Plasma membrane | placenta | Breast cancer, pancreatic cancer, and the like | 2 |
| SLC45A3 | Plasma membrane | prostate | Prostate cancer | 3 |
| ACPP | Plasma membrane | prostate | Prostate cancer | 4 |
| MUC21 | Plasma membrane | esophagus | Esophageal cancer | 5 |
| MUC16 | Plasma membrane | Cervical/ Fallopian tube | Ovarian cancer | 6 |
| MS4A12 | Plasma membrane | the large intestine | Colorectal cancer | 7 |

TABLE 2-continued

| Gene name | Subcellular localization | Organ mainly expressing | Target Tumor | Target SEQ ID NO. |
|---|---|---|---|---|
| ALPP | Plasma membrane | Placenta/cervix | Endometrial cancer | 8 |
| SLC2A14 | Plasma membrane | testis | Testicular cancer | 9 |
| GS1-259H13.2 | Plasma membrane | testis | Thyroid cancer or glioma or testicular cancer, and other | 10 |
| ERVFRD-1 | Plasma membrane | Placenta or parathyroid | Kidney cancer, Urethral cancer, and many others | 11 |
| ADGRG2 | Plasma membrane | Epididymis | Ovarian cancer | 12 |
| ECEL1 | Plasma membrane | Ovary | Endometrial cancer | 13 |
| CHRNA2 | Plasma membrane | Prostate or cortex | Prostate cancer | 14 |
| GP2 | Plasma membrane | pancreas | Pancreatic cancer | 15 |
| PSG9 | Plasma membrane | placenta | Kidney cancer or liver cancer | 16 |

In embodiments, the extracellular domain of the CAR binds SIGLEC15. SIGLEC15 is a receptor protein expressed on the cell membrane, which recognizes sialylated glycans. Transcriptional data predict that it is overexpressed in urothelial cancer cells and is expressed at a low level in normal tissues. It is mainly found in the spleen and lymph nodes, and other immune organs have a certain amount of low expression. For example, the extracellular domain of the CAR binds SIGLEC15 having the amino acid sequence of SEQ ID NO: 17. In embodiments, the extracellular domain comprises one of the amino acid sequences of SEQ ID NOs: 45-56. Embodiments relate to a method of eliciting and/or enhancing T cell response in a subject having a solid tumor or treating the solid tumor of the subject, the method comprising administering an effective amount of T cells comprising the CAR to the subject. In embodiments, the tumor is associated with urothelial cancer.

The T cell response in a subject refers to cell-mediated immunity associated with a helper, killer, regulatory, and other types of T cells. For example, T cell response may include activities such as providing assistance to other white blood cells in immunologic processes and identifying and destroying virus-infected cells and tumor cells. T cell response in the subject may be measured via various indicators such as the number of virus-infected cells and/or tumor cells that T cells kill, the number of cytokines that T cells release in co-culturing with virus-infected cells and/or tumor cells, a level of proliferation of T cells in the subject, a phenotype change of T cells (e.g., changes to memory T cells), and level longevity or lifetime of T cells in the subject.

In embodiments, in vitro killing assay may be performed by measuring the killing efficacy of CAR T cells by co-culturing CAR T cells with antigen-positive cells. CAR T cells may be considered to have a killing effect on the corresponding antigen-positive cells by showing a decrease in the number of corresponding antigen-positive cells co-cultured with CAR T cells and an increase in the release of IFNγ, TNFα, etc. as compared to control cells that do not express the corresponding antigen. Further, in vivo antitumor activity of the CAR T cells may be tested. For example, xenograft models may be established using the antigens described herein in immunodeficient mice. Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, -247-250 (2007)). To evaluate the anti-tumor activity of CAR T cells in vivo, immunodeficient mice bearing tumor xenografts were evaluated for CAR T cell anti-tumor activity (e.g., a decrease in mouse tumors and mouse blood IFNγ, TNFα, et al.).

The term "chimeric antigen receptor" or alternatively "CAR" refers to a recombinant polypeptide construct comprising at least an extracellular antigen binding domain, a transmembrane domain, and an intracellular signaling domain (e.g., cytoplasmic domain). In embodiments, the domains in the CAR polypeptide construct are on the same polypeptide chain (e.g., comprising a chimeric fusion protein). In embodiments, the domains of the CAR polypeptide are not on the same molecule, e.g., not contiguous with each other or are on different polypeptide chains.

In embodiments, the intracellular signaling domain includes a functional signaling domain derived from a stimulatory molecule and/or a co-stimulatory molecule as described herein. In embodiments, the intracellular signaling domain includes a functional signaling domain derived from a primary signaling domain (e.g., a primary signaling domain of CD3-zeta). In embodiments, the intracellular signaling domain further includes one or more functional signaling domains derived from at least one co-stimulatory molecule. The co-stimulatory signaling region refers to a portion of the CAR, including the intracellular domain of a co-stimulatory molecule. Co-stimulatory molecules can include cell surface molecules for inducing an efficient response from the lymphocytes (in response to an antigen).

Between the extracellular domain and the transmembrane domain of the CAR, there can be incorporated a spacer domain. As used herein, the term "spacer domain" generally means any oligo- or polypeptide that functions to link the transmembrane domain to the extracellular domain and/or the cytoplasmic domain in the polypeptide chain. A spacer domain may include up to 300 amino acids, 10 to 100 amino acids, or 25 to 50 amino acids.

In embodiments, the extracellular domain of a CAR includes an antigen binding domain (e.g., an scFv, a single domain antibody, or TCR, such as a TCR alpha binding domain or a TCR beta binding domain) that targets a specific tumor marker (e.g., a tumor antigen). Tumor antigens are proteins that are produced by tumor cells that elicit an immune response, particularly T cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, and mesothelin. For example, when the antigen that the CAR binds is CD19, the CAR thereof is referred to as CD19CAR.

In embodiments, the extracellular ligand-binding domain comprises an scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID: 24), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides comprising about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor a 2, IL-11 receptor a, MUC1, MUC16, CA9, GD2, GD3, HMW-MAA, CD171, Lewis Y, G250/CAIX, HLA-A1 MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by a tumor. In embodiments, the binding element of the CAR may include any antigen binding moiety that, when bound to its cognate antigen, affects a tumor cell such that the tumor cell fails to grow or is promoted to die or diminish.

In embodiments, the extracellular domain of the CAR binds KISS1R (KISS1 Receptor). KISS1R is a galanin-like G protein-coupled receptor that binds Kisspeptin (metastin), a peptide encoded by the metastasis suppressor gene KISS1. KISS1R is involved in the regulation of endocrine function. For example, the extracellular domain of the CAR binds KISS1R having the amino acid sequence of SEQ ID NO: 19. In embodiments, the extracellular domain of the CAR comprises one of the amino acid sequences of SEQ ID NOs: 71 and 72. Embodiments relate to a method of eliciting and/or enhancing T cell response in a subject having a solid tumor or treating a solid tumor in the subject, wherein the method comprises administering an effective amount of T cells comprising the CAR. In embodiments, the solid tumor is associated with renal cancer.

In embodiments, the extracellular domain of the CAR binds CLDN6 (Claudin-6). CLDN6 is a component of tight junction strands, which is a member of the claudin family, an integral membrane protein. Transcriptional data predict high expression in endometrial cancer, and urothelial cancer, whereas expression in normal tissues is a component of tight junction strands, which are members of the claudin family Low volume. For example, the extracellular domain of the CAR binds CLDN6 having the amino acid sequence of SEQ ID NO: 22. In embodiments, the extracellular domain of the CAR comprises one of the amino acid sequences of SEQ ID NOs: 29-44. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with endometrial cancer and/or urothelial cancer.

In embodiments, the extracellular domain of the CAR binds MUC16 (Mucin 16). MUC21 (Mucin 21) and MUC16 are large membrane-bound glycoproteins that belong to the mucin family. Mucins are O-glycosylated proteins that play an essential role in forming protective mucous barriers on epithelial surfaces. MUC21 has restricted expression toward the esophagus for esophageal cancer. MUC16 has low expression in normal tissues and low expression in the endometrium. In ovarian cancer, MUC16 is highly expressed. For example, the extracellular domain of the CAR binds MUC16 having the amino acid sequence of SEQ ID NO: 6. In embodiments, the extracellular domain of the CAR comprises one of the amino acid sequences of SEQ ID NOs: 63-70. Embodiments relate to a method of eliciting and/or enhancing T cell response in a subject having a solid tumor or treating a solid tumor in the subject, wherein the method comprises administering an effective amount of T cells comprising the CAR. In embodiments, the solid tumor is associated with ovarian cancer.

In embodiments, the extracellular domain of the CAR binds SLC6A3 (Solute Carrier Family 6 Member 3). SLC6A3 is a dopamine transporter, a member of the sodium- and chloride-dependent neurotransmitter transporter family. For example, the extracellular domain of the CAR binds SLC6A3 having the amino acid sequence of SEQ ID NO: 18. Embodiments include a method of eliciting and/or enhancing T-cell response in a subject having a solid tumor or treating a solid tumor in the subject, wherein the method comprises administering an effective amount of T cells comprising the CAR. In embodiments, the tumor comprises renal cancer.

In embodiments, the extracellular domain of the CAR binds QRFPR. QRFPR is a pyroglutamylated RFamide peptide receptor and may be involved in adipogenesis with its ligand, QRFP. For example, the extracellular domain of the CAR binds QRFPR having the amino acid sequence of SEQ ID NO: 20. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with renal cancer.

In embodiments, the extracellular domain of the CAR binds GPR119 (G Protein-Coupled Receptor 119). GPR119 is a member of the rhodopsin subfamily of G-protein-coupled receptors, has low expression in the pancreas and gastrointestinal tract, and may be involved in glucose homeostasis. Transcriptional data predict high expression in pancreatic cancer. For example, the extracellular domain of the CAR binds GPR119 having the amino acid sequence of SEQ ID NO: 21. Embodiments relate to a method of eliciting and/or enhancing T-cell response in a subject having a solid tumor or treating a solid tumor of the subject, wherein the method comprises administering an effective amount of T cells comprising the CAR. In embodiments, the tumor is associated with pancreatic cancer.

In embodiments, the extracellular domain of the CAR binds UPK2 (Uroplakin 2). UPK2 is one of the proteins of the highly conserved urothelium-specific integral membrane proteins of the asymmetric unit membrane, expressed primarily in the urinary bladder in normal tissues and urothelial carcinoma, including bladder cancer. For example, the extracellular domain of the CAR binds UPK2 having the amino acid sequence of SEQ ID NO: 1. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with urothelial cancer and/or bladder cancer.

In embodiments, the extracellular domain of the CAR binds ADAM12 (Metalloproteinase 12). ADAM12 is a member of a family of proteins that are structurally related to snake venom disintegrins, involved in cell-cell and cell-matrix interactions, and is highly expressed in tumors such as placenta and breast/pancreatic cancer. For example, the extracellular domain of the CAR binds ADAM12 having the amino acid sequence of SEQ ID NO: 2. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with breast cancer and/or pancreatic cancer.

In embodiments, the extracellular domain of the CAR binds SLC45A3 (Solute Carrier Family 45 Member 3). SLC45A3 is a plasma membrane protein; normal tissue is mainly expressed in the prostate for prostate cancer. For example, the extracellular domain of the CAR binds SLC45A3 having the amino acid sequence of SEQ ID NO: 3. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with prostate cancer.

In embodiments, the extracellular domain of the CAR binds ACPP (Acid Phosphatase, Prostate). ACPP is an enzyme that catalyzes the conversion of orthophosphoric monoester to alcohol and orthophosphate, contains a transmembrane domain, and is localized in the plasma membrane-endosomal-lysosomal pathway. Normal tissue is specifically expressed in the prostate for prostate cancer. For example, the extracellular domain of the CAR binds ACPP having the amino acid sequence of SEQ ID NO: 4. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with prostate cancer.

In embodiments, the extracellular domain of the CAR binds MUC21 (Mucin 21). MUC21 and MUC16 are large membrane-bound glycoproteins that belong to the mucin family. Mucins are O-glycosylated proteins that play an essential role in forming protective mucous barriers on epithelial surfaces. MUC21 has restricted expression toward the esophagus when the subject has esophageal cancer. For example, the extracellular domain of the CAR binds MUC21 having the amino acid sequence of SEQ ID NO: 5. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with esophageal cancer.

In embodiments, the extracellular domain of the CAR binds MS4A12 (Membrane-Spanning 4-Domains Subfamily A12). MS4A12 is a cell surface protein found in the apical membrane of colonocytes, the restricted expression on the colon, and may be used against colorectal cancer. For example, the extracellular domain of the CAR binds MS4A12 having the amino acid sequence of SEQ ID NO: 7. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with colorectal cancer.

In embodiments, the extracellular domain of the CAR binds ALPP. ALPP is alkaline phosphatase (placental type), a metalloenzyme that catalyzes the hydrolysis of phosphoric acid monoesters. The expression of ALPP is restricted to the placenta; strong ectopic expression of ALPP has been detected in ovarian adenocarcinoma, serous cystadenocarcinoma, and other ovarian cancer cells. For example, the extracellular domain of the CAR binds ALPP having the amino acid sequence of SEQ ID NO: 8. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with endometrial cancer.

In embodiments, the extracellular domain of the CAR binds SLC2A14 (Solute Carrier Family 2 Member 14). For example, the extracellular domain of the CAR binds SLC2A14 having the amino acid sequence of SEQ ID NO: 9. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with testicular cancer.

In embodiments, the extracellular domain of the CAR binds GS1-259H13.2 (TMEM225B, Transmembrane Protein 225B). For example, the extracellular domain of the CAR binds GS1-259H13.2 having the amino acid sequence of SEQ ID NO: 10. Embodiments relate to a method of eliciting and/or enhancing T-cell response in a subject having a solid tumor or treating a solid tumor of the subject, wherein the method comprises administering an effective amount of T cells comprising the CAR. In embodiments, the tumor is associated with thyroid cancer or glioma, or testicular cancer.

In embodiments, the extracellular domain of the CAR binds ERVFRD-1 (Endogenous Retrovirus Group FRD Member). For example, the extracellular domain of the CAR binds ERVFRD-1 having the amino acid sequence of SEQ ID NO: 11. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with kidney cancer or Urethral cancer.

In embodiments, the extracellular domain of the CAR binds ADGRG2 (Adhesion G Protein-Coupled Receptor G2). For example, the extracellular domain of the CAR binds ADGRG2 having the amino acid sequence of SEQ ID NO: 12. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with ovarian cancer.

In embodiments, the extracellular domain of the CAR binds ECEL1 (Endothelin Convertin Enzyme Like 1). For example, the extracellular domain of the CAR binds ECEL1 having the amino acid sequence of SEQ ID NO: 13. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with endometrial cancer.

In embodiments, the extracellular domain of the CAR binds CHRNA2 (Cholinergic Receptor Nicotinic Alpha 2 Subunit). For example, the extracellular domain of the CAR binds CHRNA2 having the amino acid sequence of SEQ ID NO: 14. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with prostate cancer.

In embodiments, the extracellular domain of the CAR binds GP2 (Glycoprotein 2). For example, the extracellular domain of the CAR binds GP2 having the amino acid sequence of SEQ ID NO: 15. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with pancreatic cancer.

In embodiments, the extracellular domain of the CAR binds PSG9 (Pregnancy Specific Beta-1-Glycoprotein 9). For example, the extracellular domain of the CAR binds PSG9 having the amino acid sequence of SEQ ID NO: 16. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with Kidney cancer or liver cancer.

The present disclosure also relates to a bispecific chimeric antigen receptor (See FIG. 26), a polynucleotide encoding the bispecific chimeric antigen receptor, and/or a modified cell comprising the polynucleotide, wherein the bispecific chimeric antigen receptor comprises a first antigen binding domain, a second antigen binding domain, a cytoplasmic domain, and a transmembrane domain, and wherein the first antigen binding domain recognizes a first antigen, and the second antigen binding domain recognizes a second antigen. In embodiments, the first antigen is an antigen associated with a white blood cell, and the second antigen is a solid tumor antigen. In embodiments, the first and second antigens are identical or different. In embodiments, the first and second antigens are both solid tumor antigens. For example, the first antigen is a tumor-associated MUC1, and the second antigen is selected from one of the antigens of SEQ ID NO: 1-22. In embodiments, the first binding domain and the second binding domain are connected via a linker (e.g., SEQ ID NO: 188).

In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In embodiments, the intracellular domain comprises a CD3 zeta signaling domain. Embodiments relate to a vector comprising the isolated nucleic acid sequence described herein. Embodiments relate to an isolated cell comprising the isolated nucleic acid sequence described herein.

Embodiments relate to a composition comprising a population of cells, including T cells comprising the CAR described herein. Embodiments relate to a CAR encoded by the isolated nucleic acid sequence described herein.

The cells, including CAR cells and modified cells, described herein can be derived from a stem cell. The stem cells may be adult stem cells, embryonic stem cells, non-human stem cells, cord blood stem cells, progenitor cells, bone marrow stem cells, induced pluripotent stem cells, totipotent stem cells, or hematopoietic stem cells. The cells can also be a dendritic cell, an NK-cell, a B-cell, or a T cell selected from the group consisting of inflammatory T lymphocytes, cytotoxic T lymphocytes, regulatory T lymphocytes, and helper T lymphocytes. In embodiments, the cells can be derived from the group consisting of CD4+T-lymphocytes and CD8+T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art can be used. In embodiments, the cells may be derived from a healthy donor, from a patient diagnosed with cancer, or from a patient diagnosed with an infection. In embodiments, the cells are part of a mixed population of cells that present different phenotypic characteristics.

The term "stem cell" refers to any type of cell which has the capacity for self-renewal and the ability to differentiate into other kinds of cells. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished on the basis of their origin and/or on the extent of their capacity for differentiation into other types of cells. Stem cells can include embryonic stem (ES) cells (i.e., pluripotent stem cells), somatic stem cells, induced pluripotent stem cells, and any other types of stem cells.

Pluripotent embryonic stem cells can be found in the inner cell mass of a blastocyst and have a high innate capacity for differentiation. For example, pluripotent embryonic stem cells have the potential to form any type of cell in the body. When grown in vitro for long periods of time, ES cells maintain pluripotency, and progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited number of different types of cells and have been described as multipotent. "Tissue-specific" stem cells normally give rise to only one type of cell. For example, embryonic stem cells can differentiate into blood stem cells (e.g., Hematopoietic stem cells (HSCs)), which can further differentiate into various blood cells (e.g., red blood cells, platelets, white blood cells, etc.).

Induced pluripotent stem cells (iPS cells or iPSCs) can include a type of pluripotent stem cell artificially derived from a non-pluripotent cell (e.g., an adult somatic cell) by inducing the expression of specific genes. Induced pluripotent stem cells are similar to naturally occurring pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be isolated from an adult stomach, liver, skin cells, and blood cells.

In embodiments, the CAR cells, the modified cell, or the cell is a T cell, an NK cell, a macrophage, or a dendritic cell. For example, the CAR cells, the modified cell, or the cell is T cell.

In embodiments, the antigen binding molecule is a T Cell Receptor (TCR). In embodiments, the TCR is modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1. In embodiments, the TCR comprises TCRγ and TCRδ chains or TCRα and TCR chains. In embodiments, a T cell clone that expresses a TCR with a high affinity for the target antigen may be isolated. In embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC—peptide tetramer staining and/or the ability to recognize and lyse target cells pulsed with low titrated concentrations of cognate peptide antigen. After the clone has been selected, the TCRα and TCR chains or TCRγ and TCRδ chains are identified and isolated by molecular cloning. For example, for TCRα and TCR chains, the TCRα and TCRβ gene sequences are then used to generate an expression construct that ideally promotes stable, high-level expression of both TCR chains in human T cells. The transduction vehicle (e.g., a gammaretrovirus or lentivirus) may then be generated and tested for functionality (antigen specificity and functional avidity) and used to produce a clinical lot of the vector. An aliquot of the final product is then used to transduce the target T cell population (generally purified from patient PBMCs), which is expanded before infusion into the subject.

In embodiments, the binding element of the CAR may include any antigen binding moiety that, when bound to its cognate antigen, affects a tumor cell; for example, it kills the tumor cell, inhibits the growth of the tumor cell, or promotes the death of the tumor cell.

The nucleic acid sequences coding for the desired molecules can be obtained using recombinant methods known in the art, such as, for example by screening libraries from cells expressing the gene, deriving the gene from a vector known to include the same, or isolating directly from cells and tissues containing the same, using standard techniques. Alternatively, the gene of interest can be produced synthetically rather than cloned.

The embodiments of the present disclosure further relate to vectors in which the DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Viruses can be used to deliver nucleic acids into a cell in vitro and in vivo (in a subject). Examples of viruses useful for the delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetoreception, and the use of oligonucleotides, lipoplexes, dendrimers, and inorganic nanoparticles.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration into eukaryotes. Typical cloning vectors contain transcription and translation terminators, initiation sequences, and promoters useful for the regulation of the expression of the desired nucleic acid sequence.

Additional information related to the expression of synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "a tumor-inhibiting effective amount," or "therapeutic amount" is indicated, the precise amount of the compositions of the present disclosure to be administered can be determined by a physician with consideration of individual differences in age, weight, tumor size, the extent of infection or metastasis, and condition of the patient (subject). It can be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, certain populations of T cells may be selected.

The administration of the pharmaceutical compositions described herein may be carried out in any convenient manner, including by aerosol inhalation, injection, ingestion, transfusion, implantation, or transplantation. The compositions described herein may be administered to a patient subcutaneously, intradermally, intratumorally, intranodal, intramedullary, intramuscularly, by intravenous (i. v.) injection, or intraperitoneally. In embodiments, the T cell compositions of the present disclosure are administered to a patient by intradermal or subcutaneous injection. In embodiments, the T cell compositions of the present disclosure are preferably administered by i.v. Injection. The compositions of T cells may be injected directly into a tumor, lymph node, or site of infection. In embodiments of the present disclosure, cells activated and expanded using the methods described herein, or other methods known in the art where T cells are expanded to therapeutic levels, are administered to a patient in conjunction with (e.g., before, simultaneously, or following) any number of relevant treatment modalities, including but not limited to treatment with agents such as antiviral therapy, cidofovir, and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions of the present disclosure are administered to a patient in conjunction with (e.g., before, simultaneously, or following) bone marrow transplantation, T cell ablative therapy using either chemotherapy agents such as fludarabine, external-beam radiation therapy (XRT), cyclophosphamide, or antibodies such as OKT3 or CAMPATH. In embodiments, the cell compositions of the present disclosure are administered following B-cell ablative therapy such as agents that react with CD20, e.g., Rituxan. For example, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

In embodiments, the population of cells described herein is used in autologous CAR T cell therapy. In embodiments, the CAR T cell therapy is allogeneic CAR T cell therapy, TCR T cell therapy, and NK cell therapy.

Embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances the proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

Embodiments of the present disclosure relate to treating cancer using Chimeric Antigen Receptor (CAR) cells using a molecule associated with a gene fusion. Embodiments relate to an isolated nucleic acid sequence encoding a chimeric antigen receptor (CAR), wherein the CAR comprises an extracellular domain, a transmembrane domain, and an intracellular domain, wherein the extracellular domain binds a gene fusion antigen of a gene fusion.

As used herein, the term "gene fusion" refers to the fusion of at least a portion of a gene to at least a portion of an additional gene. The gene fusion need not include entire genes or exons of genes. In some instances, gene fusion is associated with alternations in cancer. A gene fusion product refers to a chimeric genomic DNA, a chimeric messenger RNA, a truncated protein, or a chimeric protein resulting from a gene fusion. The gene fusion product may be detected by various methods described in U.S. Pat. No. 9,938,582, which is incorporated as a reference herein. A "gene fusion antigen" refers to a truncated protein or a chimeric protein that results from a gene fusion. In embodiments, an epitope of a gene fusion antigen may include a part of the gene fusion antigen or an immunogenic part of another antigen caused by the gene fusion. In embodiments, the gene fusion antigen interacts with or is part of cell membranes.

In embodiments, the gene fusion comprises a fusion of at least a portion of a first gene to at least a portion of a second gene. In embodiments, the first gene and the second gene comprise a first gene and a second gene of a fusion listed in Table 3. In embodiments, the gene fusion antigen is associated with a condition listed in Table 3.

In embodiments, detection of mRNA and protein expression levels of the target molecules (listed in Table 2) in human cells may be performed using experimental methods such as qPCR and FACS. Further, target molecules specifically expressed in the corresponding tumor cells with very low expression or undetectable expression in normal tissue cells may be identified.

In embodiments, In Vitro Killer Assay as well as killing experiment of CAR T Cells Co-Cultured with Antigen-Positive Cells may be performed. CAR T cells may exhibit a killing effect on the corresponding antigen-positive cells, a decrease in the number of corresponding antigen-positive cells co-cultured with CAR T cells, and an increase in the release of IFNγ, TNFα, etc. as compared to control cells that did not express the corresponding antigen.

In embodiments, in vivo Killing Assay may be performed. For example, mice may be transplanted with corresponding antigen tumor cells, and tumorigenic transfusion of CAR T cells, and a decrease in mouse tumors and mouse blood IFNγ, TNFα, and other signals may be detected.

Embodiments relate to a method of eliciting and/or enhancing T cell response in a subject having a solid tumor or treating a solid tumor in the subject, the method comprising administering an effective amount of T cells comprising the CAR described herein. In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the intracellular domain comprises a CD3 zeta signaling domain.

Embodiments relate to a vector comprising the isolated nucleic acid described herein.

Embodiments relate to an isolated cell comprising the isolated nucleic acid sequence described herein. Embodiments relate to a composition comprising a population of T cells comprising the CAR described herein. Embodiments relate to a CAR encoded by the isolated nucleic acid sequence described herein. Embodiments relate to a method of eliciting and/or enhancing T-cell response in a subject or treating a tumor of the subject, the method comprising: administering an effective amount of T cell comprising the CAR described herein.

TABLE 3

| Conditions | Type | Fusion | First gene | Gene description | sub-location | Second Gene | Gene description | sub-location |
| --- | --- | --- | --- | --- | --- | --- | --- | --- |
| breast invasive carcinoma | BRCA | GNAS--NECTIN2 | GNAS | GNAS complex locus | Plasma membrane | NECTIN2 | Nectin cell adhesion molecule 2 | Plasma membrane |
| breast invasive carcinoma | BRCA | FGFR1--ADAM18 | FGFR1 | Fibroblast growth factor receptor 1 | Plasma membrane | ADAM18 | ADAM metallo-peptidase domain 18 | Plasma membrane |
| cervical squamous cell carcinoma and endocervical adenocarcinoma | CESC | WHRN--TNC | WHRN | Whirlin | Cytoplasm; Plasma membrane | TNC | Tenascin C | Extra-cellular; Plasma membrane |
| head and neck squamous cell carcinoma | HNSC | PQLC1--HSBP1L1 | PQLC1 | PQ loop repeat containing 1 | Plasma membrane | HSBP1L1 | Heat shock factor binding protein 1 like 1 | Plasma membrane |
| kidney renal papillary cell carcinoma | KIRP | FNDC3B--BCHE | FNDC3B | Fibronectin type III domain containing 3B | Plasma membrane | BCHE | Butyryl-cholinesterase | Plasma membrane |
| brain lower grade glioma | LGG | GRIA4--NAALAD2 | GRIA4 | Glutamate ionotropic receptor AMPA type subunit 4 | Plasma membrane | NAALAD2 | N-acetylated alpha-linked acidic dipeptidase 2 | Plasma membrane |
| brain lower grade glioma | LGG | EPHB2--PDZD4 | EPHB2 | EPH receptor B2 | Plasma membrane | PDZD4 | PDZ domain containing 4 | Cytoplasm; Plasma membrane |
| brain lower grade glioma | LGG | SEC24A--KCNK7 | SEC24A | SEC24 homolog A, COPII coat complex component | Plasma membrane | KCNK7 | Potassium two pore domain channel subfamily K member 7 | Plasma membrane |
| liver hepatocellular carcinoma | LIHC | ACVR1B--ACVRL1 | ACVR1B | Activin A receptor type 1B | Plasma membrane | ACVRL1 | Activin A receptor like type 1 | Plasma membrane |
| liver hepatocellular carcinoma | LIHC | ABCC2--CTNNA3 | ABCC2 | ATP binding cassette subfamily C member 2 | Plasma membrane | CTNNA3 | Catenin alpha 3 | Cytoplasm; Cytoskeleton; Plasma membrane |
| liver hepatocellular carcinoma | LIHC | EFNA1--ADAM15 | EFNA1 | Ephrin A1 | Extra-cellular; Plasma membrane | ADAM15 | ADAM metallo-peptidase domain 15 | Plasma membrane |
| lung adenocarcinoma | LUAD | CPNE8--CADM2 | CPNE8 | Copine 8 | Plasma membrane | CADM2 | Cell adhesion molecule 2 | Plasma membrane |
| lung adenocarcinoma | LUAD | NOTCH2--ADAM30 | NOTCH2 | Notch 2 | Plasma membrane | ADAM30 | ADAM metallo-peptidase domain 30 | Plasma membrane |

TABLE 3-continued

| Conditions | Type | Fusion | First gene | Gene description | sub-location | Second Gene | Gene description | sub-location |
|---|---|---|---|---|---|---|---|---|
| lung adenocarcinoma | LUAD | CELSR1--CD52 | CELSR1 | Cadherin EGF LAG seven-pass G-type receptor 1 | Plasma membrane | CD52 | CD52 molecule | Plasma membrane |
| lung adenocarcinoma | LUAD | ILVBL--SLC1A6 | ILVBL | IlvB acetolactate synthase like | Plasma membrane | SLC1A6 | Solute carrier family 1 member 6 | Plasma membrane |
| lung adenocarcinoma | LUAD | F11R--NOS1AP | F11R | F11 receptor | Plasma membrane | NOS1AP | Nitric oxide synthase 1 adaptor protein | Cytoplasm; Plasma membrane |
| lung squamous cell carcinoma | LUSC | CELSR1--SEZ6L | CELSR1 | Cadherin EGF LAG seven-passG-type receptor 1 | Plasma membrane | SEZ6L | Seizure related 6 homolog like | Plasma membrane |
| lung squamous cell carcinoma | LUSC | KIRREL--CD1A | KIRREL | Kin of IRRE like (Drosophila) | Plasma membrane | CD1A | CD1a molecule | Endosome; Golgi apparatus; Plasma membrane |
| lung squamous cell carcinoma | LUSC | ATP10D--GABRA2 | ATP10D | ATPase phospholipid transporting 10D (putative) | Plasma membrane | GABRA2 | Gamma-aminobutyric acid type A receptor alpha2 subunit | Plasma membrane |
| pancreatic adenocarcinoma | PAAD | ORAI2--SLC47A2 | ORAI2 | ORAI calcium release-activated calcium modulator 2 | Plasma membrane | SLC47A2 | Solute carrier family 47 member 2 | Plasma membrane |
| pheochromocytoma and paraganglioma | PCPG | ADCYAP1R1--GHRHR | ADCYAP1R1 | ADCYAP receptor type I | Plasma membrane | GHRHR | Growth hormone releasing hormone receptor | Plasma membrane |
| pheochromocytoma and paraganglioma | PCPG | TMEM178B--DPP6 | TMEM178B | Transmembrane protein 178B | Plasma membrane | DPP6 | Dipeptidyl peptidase like 6 | Plasma membrane |
| prostate adenocarcinoma | PRAD | ADAM9--RGS20 | ADAM9 | ADAM metallo-peptidase domain 9 | Plasma membrane | RGS20 | Regulator of G-protein signaling 20 | Plasma membrane |
| prostate adenocarcinoma | PRAD | FAM160B1--VTI1A | FAM160B1 | Family with sequence similarity 160 member B1 | Plasma membrane | VTI1A | Vesicle transport through interaction with t-SNAREs 1A | Plasma membrane |
| prostate adenocarcinoma | PRAD | TMPRSS2-PDE9A | TMPRSS2 | Transmembrane protease, serine 2 | Plasma membrane | PDE9A | Phospho-diesterase 9A | Plasma membrane |
| prostate adenocarcinoma | PRAD | PDE9A--TMPRSS2 | PDE9A | Phospho-diesterase 9A | Plasma membrane | TMPRSS2 | Transmembrane protease, serine 2 | Plasma membrane |
| rectum adenocarcinoma | READ | LHFPL2--PTPRK | LHFPL2 | Lipoma HMGIC fusion partner-like 2 | Plasma membrane | PTPRK | Protein tyrosine phosphatase, receptor type K | Plasma membrane |
| sarcoma | SARC | TM7SF3--KCNC2 | TM7SF3 | Transmembrane 7 superfamily member 3 | Plasma membrane | KCNC2 | Potassium voltage-gated channel subfamily C member 2 | Plasma membrane |
| sarcoma | SARC | MPZL1--TNFSF4 | MPZL1 | Myelin protein zero-like 1 | Plasma membrane | TNFSF4 | Tumor necrosis factor superfamily member 4 | Plasma membrane |
| sarcoma | SARC | GNG7--PAQR5 | GNG7 | G protein subunit gamma 7 | Plasma membrane | PAQR5 | Progestin and adipoQ receptor family member 5 | Plasma membrane |
| sarcoma | SARC | KIRREL--CD1A | KIRREL | Kin of IRRE like (Drosophila) | Plasma membrane | CD1A | CD1a molecule | Endosome; Golgi apparatus; Plasma membrane |
| sarcoma | SARC | P2RX5--TRPV1 | P2RX5 | Purinergic receptor P2X 5 | Plasma membrane | TRPV1 | Transient receptor potential cation channel | Plasma membrane |

TABLE 3-continued

| Conditions | Type | Fusion | First gene | Gene description | sub-location | Second Gene | Gene description | sub-location |
|---|---|---|---|---|---|---|---|---|
| skin cutaneous melanoma | SKCM | PTPRG--SYNPR | PTPRG | Protein tyrosine phosphatase, receptor type G | Plasma membrane | SYNPR | subfamily V member 1 Synaptoporin | Plasma membrane |

Embodiments relate to methods or uses of the polynucleotides described herein. The methods or uses include providing a viral particle (e.g., AAV, lentivirus, or their variants) comprising a vector genome, the vector genome comprising the polynucleotide, wherein the polynucleotide is operably linked to an expression control element conferring transcription of the polynucleotide, and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information on the administration and preparation of the viral particle may be found in the U.S. Pat. No. 9,840,719 and Milani et al., Sci. Transl. Med. 11, eaav7325 (2019) 22 May 2019, which are incorporated herein by reference.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further, since an antibody has two heavy chains and two light chains, an antibody has twelve CDRs altogether for binding antigens. In embodiments, the CAR molecules comprise one or more CDRs of SIGLEC15, SLC6A3, KISS1R, QRFPR, GPR119, CLDN6, UPK2, ADAM12, SLC45A3, ACPP, MUC21, MUC16, MS4A12, or ALPP.

The present disclosure describes modified cells that include one or more different antigen binding domains. The modified cells can include at least two different antigen binding domains: a first antigen binding domain for expanding and/or maintaining the genetically modified cells and a second antigen binding domain for killing a target cell, such as a tumor cell. For example, the first antigen binding domain binds a surface marker, such as a cell surface molecule of a white blood cell (WBC) (e.g., CD19), and the second antigen binding domain binds a target antigen on tumor cells. In embodiments, the cell surface molecule is a surface antigen of a WBC. In embodiments, the target antigen on tumor cells comprises one or more of SIGLEC15, SLC6A3, KISS1R, QRFPR, GPR119, CLDN6, UPK2, ADAM12, SLC45A3, ACPP, MUC21, MUC16, MS4A12, or ALPP. The at least two antigen binding domains may be located on the same or different modified cells. For example, the modified cells may include a modified cell including a CAR binding CD19, a modified cell including a CAR binding to ACPP, a modified cell including a CAR binding CD19 and ACPP, and/or a modified cell including two CARs that respectively bind CD19 and ACPP. In embodiments, the modified cells may be used to treat a subject having cancer.

In embodiments, the modified cells described herein include a CAR molecule comprising at least two different antigen binding domains. The CAR molecule can be a bispecific CAR molecule. For example, the two antigen binding domains can be on the same CAR molecule, on different CAR molecules, or on a CAR molecule and T cell receptor (TCR). A single CAR can include at least two different antigen binding domains, or the two different antigen binding domains are each on a separate CAR molecule. The at least two different antigen binding domains can be on the same CAR molecule or different CAR molecules but in the same modified cell. Moreover, the at least two different antigen binding domains can be on a CAR molecule and a T cell receptor in the same modified cell. In embodiments, the bispecific CAR molecule may include a binding domain binding an antigen of WBC (e.g., CD19) and a binding domain binding a solid tumor antigen. In embodiments, the bispecific CAR molecule may include two binding domains binding two different solid tumor antigens.

In embodiments, the at least two different antigen binding domains are on different CAR molecules, which are expressed by different modified cells. Further, the one or more different antigen binding domains are on a CAR molecule and a T cell receptor, which are expressed by different modified cells.

Related sequences are provided in this Application and Innovative Cellular Therapeutics' PCT Patent Applications Nos: PCT/CN2016/075061, PCT/CN2018/08891, PCT/US21/28429, and PCT/US19/13068, which are incorporated by reference in their entirety.

In embodiments, the compositions and/or methods described herein can be combined with techniques associated with CoupledCAR® described in PCT Publication Nos: WO2020106843 and WO2020146743, which are incorporated in their entirety.

The present disclosure describes an antibody that binds GCC (GUCY2C, Guanylate Cyclase 2C), wherein the antibody comprises a VHH domain comprising one of the amino acid sequences of SEQ ID NO: 200-269 or comprising multiple CDRs of each of the amino acid sequences of SEQ ID NO: 200-269.

In embodiments, the antibody is a nanobody (single-domain antibody, sdAb) comprising or consisting essentially of a VHH (single variable domain on a heavy chain) domain. In embodiments, the antibody is conjugated to a cytotoxic agent, and the cytotoxic agent is a radioactive isotope or a toxin. In embodiments, the antibody is a bispecific antibody comprising a VHH domain, an antibody or antibody fragment (e.g., scFv) targeting CD3 and a linker.

In embodiments, the antibody comprises or consists essentially of a VHH domain and one or more constant domains, such as CH2 and CH3. In embodiments, the antibody is structurally similar to an alpaca antibody comprising or consisting essentially of a VHH domain, a CH2 domain, and a CH3 domains. In embodiments, the antibodies described herein comprising the VHH domain do not include the VL (variable light) and CL (constant light) domains.

The present disclosure describes a CAR comprising an antigen binding domain comprising the antibody that binds GCC, as described above. Embodiments describe a polynucleotide that encodes the antibody or the CAR. Embodiments describe a modified cell comprising the polynucleotide. In embodiments, the modified cell is a T cell or NK cell.

The present disclosure describes a population of modified immune cells comprising the CAR. In embodiments, the composition comprises a first population of cells comprising a first CAR binding a first antigen and a second population of cells comprising a second CAR binding a second antigen, wherein the second antigen is a tumor antigen and is different from the first antigen, and the first population and/or the second population of cells comprise one or more polynucleotides described herein.

The present disclosure describes the use of the composition comprising a first population and a second of population of cells or a method of using the composition to enhance the expansion of cells in a subject in need thereof or treating a subject having cancer, the method comprising: administering an effective amount of the composition to the subject, the subject having a form of cancer expressing a tumor antigen. In embodiments, expansion of the second population of cells in the subject is greater than the expansion of the second population of cells in a subject that is administered with the second population of cells but not the first population of cells. In embodiments, the expansion is measured based on numbers of the second population of cells or copy numbers of DNA encoding the second CAR. In embodiments, the cells are T cells, NK cells, macrophages, or dendritic cells. In embodiments, the first antigen comprises a cell surface molecule of a white blood cell (WBC), a tumor antigen, or a solid tumor antigen. In embodiments, the WBC is a granulocyte, a monocyte, or a lymphocyte. In embodiments, the WBC is a B cell. In embodiments, the cell surface molecule of the WBC is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the WBC is CD19, CD20, CD22, or BCMA. In embodiments, the cell surface molecule of the WBC is CD19 or BCMA. In embodiments, the tumor antigen is a solid tumor antigen.

In embodiments, the modified cells comprise a nucleic acid sequence encoding a binding molecule and a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), and CD160. In embodiments, the inhibitory immune checkpoint molecule is modified PD-1. In embodiments, the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

In embodiments, the modified cell has a reduced expression of the endogenous TRAC gene. In embodiments, the modified cells include a nucleic acid sequence encoding hTERT or a nucleic acid encoding SV40LT, or a combination thereof. In embodiments, the modified cells include a nucleic acid sequence encoding hTERT and a nucleic acid encoding SV40LT. In embodiments, the expression of hTERT is regulated by an inducible expression system. In embodiments, the expression of SV40LT gene is regulated by an inducible expression system. In embodiments, the inducible expression system is rTTA-TRE, which increases or activates the expression of SV40LT gene or hTERT gene, or a combination thereof. In embodiments, the modified cells include a nucleic acid sequence encoding a suicide gene. In embodiments, the suicide gene includes an HSV-TK suicide gene system, and/or the modified cell can be induced to undergo apoptosis.

In embodiments, the modified cells include a nucleic acid sequence encoding a cytokine. In embodiments, the modified cells include a nucleic acid sequence encoding IL-6, IFNγ, IL-12, and/or IL-2.

The present disclosure describes an antibody that binds GCC, wherein the antibody comprises a VHH domain comprising complementarity determining region 1 (CDR1), CDR2, and CDR3, and wherein: CDR1, CDR2, and CDR3 comprise SEQ ID NO: 294-296, respectively, CDR1, CDR2, and CDR3 comprise SEQ ID NO: 345-347, respectively, or CDR1, CDR2, and CDR3 comprise SEQ ID NO: 381-383, respectively. Embodiments describe a polynucleotide that encodes the antibody. Embodiments describe a modified cell comprising the polynucleotide. Embodiments describe a CAR comprising an extracellular domain comprising the antibody described above. In embodiments, the modified cell is a T cell or NK cell. In embodiments, the antibody comprises SEQ ID NO: 208, 225, or 237. In embodiments, the antibody is a nanobody. In embodiments, the antibody is conjugated to a cytotoxic agent, and the cytotoxic agent is a radioactive isotope or a toxin. In embodiments, the antibody is a bispecific antibody comprising the VHH domain, a linker, and an antibody targeting CD3. The antibody targeting CD3 can be a scFv antibody.

The present disclosure describes a composition comprising a population of the modified cells comprising a CAR comprising the antibody described above. In embodiments, the modified cells comprise a polynucleotide encoding a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), and CD160. In embodiments, the modified cells have reduced expression of endogenous TRAC gene. In embodiments, the modified cells comprise a polynucleotide encoding hTERT or a nucleic acid encoding SV40LT, or a combination thereof. In embodiments, the modified cells comprise a polynucleotide encoding a cytokine. In embodiments, the modified cells include a polynucleotide encoding at least one of IL-6, IFNγ, IL-12, and IL-2.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples but rather should be construed to encompass any and all variations which become evident as a result of the teaching provided herein.

Exemplary Embodiments

The following are exemplary embodiments:
1. An isolated nucleic acid sequence encoding a chimeric antigen receptor (CAR), wherein the CAR comprises an extracellular domain, a transmembrane domain, and an intracellular domain, wherein the extracellular domain binds an antigen of a solid tumor.
2. The isolated nucleic acid sequence of embodiment 1, wherein the extracellular domain binds SIGLEC15.
3. The isolated nucleic acid sequence of embodiment 1, wherein the extracellular domain binds SIGLEC15 having the amino acid sequence of SEQ ID NO: 17.
4. The isolated nucleic acid sequence of embodiment 1, wherein the extracellular domain comprises one of the amino acid sequences of SEQ ID NOs: 45-56.
5. A method of eliciting and/or enhancing T-cell response in a subject having a solid tumor or treating a solid tumor in the subject, the method comprising administering an effective amount of T cells comprising the CAR of any one of embodiments 2-4.
6. The isolated nucleic acid sequence or the method of any one of embodiments 1-5, wherein the tumor is associated with urothelial cancer.
7. The isolated nucleic acid sequence of embodiment 1, wherein the extracellular domain binds KISS1R.
8. The isolated nucleic acid sequence of embodiment 1, wherein the extracellular domain binds KISS1R having the amino acid sequence of SEQ ID NO: 19.
9. The isolated nucleic acid sequence of embodiment 1, wherein the extracellular domain comprises one of the amino acid sequences of SEQ ID NOs: 71 and 72.
10. A method of eliciting and/or enhancing T-cell response in a subject having a solid tumor or treating the solid tumor of the subject, the method comprising administering an effective amount of T cell comprising the CAR of any one of embodiments 7-9.
11. The isolated nucleic acid sequence or the method of any one of embodiments 1 and 7-10, wherein the tumor is associated with renal cancer.
12. The isolated nucleic acid sequence of embodiment 1, wherein the extracellular domain binds CLDN6.
13. The isolated nucleic acid sequence of embodiment 1, wherein the extracellular domain binds CLDN6 having the amino acid sequence of SEQ ID NO: 22.
14. The isolated nucleic acid sequence of embodiment 1, wherein the extracellular domain comprises one of the amino acid sequences of SEQ ID NOs: 29-44.
15. A method of eliciting and/or enhancing T cell response in a subject having a solid tumor or treating a solid tumor in the subject, the method comprising administering an effective amount of T cells comprising the CAR of any one of embodiments 12-15.
16. The isolated nucleic acid sequence or the method of any one of embodiments 1 and 12-16, wherein the tumor is associated with endometrial cancer and/or urothelial cancer.
17. The isolated nucleic acid sequence of embodiment 1, wherein the extracellular domain binds MUC16.
18. The isolated nucleic acid sequence of embodiment 1, wherein the extracellular domain binds MUC16 having the amino acid sequence of SEQ ID NO: 6.
19. The isolated nucleic acid sequence of embodiment 1, wherein the extracellular domain comprises one of the amino acid sequences of SEQ ID NOs: 63-70.
20. A method of eliciting and/or enhancing T-cell response in a subject having a solid tumor or treating the solid tumor of the subject, the method comprising administering an effective amount of T cell comprising the CAR of any one of embodiments 17-19.
21. The isolated nucleic acid sequence or the method of any one of embodiments 1 and 17-20, wherein the tumor is associated with ovarian cancer.
22. The isolated nucleic acid sequence of embodiment 1, wherein the extracellular domain binds SLC6A3.
23. The isolated nucleic acid sequence of embodiment 1, wherein the extracellular domain binds SLC6A3 having the amino acid sequence of SEQ ID NO: 18.
24. A method of eliciting and/or enhancing T-cell response in a subject having a solid tumor or treating the solid tumor of the subject, the method comprising administering an effective amount of T cell comprising the CAR of any one of embodiments 22 and 23.
25. The isolated nucleic acid sequence or the method of any one of embodiments 1 and 22-24, wherein the tumor is associated with renal cancer.
26. The isolated nucleic acid sequence of embodiment 1, wherein the extracellular domain binds QRFPR. 27 The isolated nucleic acid sequence of embodiment 1, wherein the extracellular domain binds QRFPR having the amino acid sequence of SEQ ID NO: 20.
28. A method of eliciting and/or enhancing T-cell response in a subject having a solid tumor or treating the solid tumor of the subject, the method comprising administering an effective amount of T cell comprising the CAR of any one of embodiments 26 and 27.
29. The isolated nucleic acid sequence or the method of any one of embodiments 1 and 26-28, wherein the tumor is associated with renal cancer.
30. The isolated nucleic acid sequence of embodiment 1, wherein the extracellular domain binds GPR119.
31 The isolated nucleic acid sequence of embodiment 1, wherein the extracellular domain binds GPR119 having the amino acid sequence of SEQ ID NO: 21.
32. A method of eliciting and/or enhancing T-cell response in a subject having a solid tumor or treating the solid tumor of the subject, the method comprising administering an effective amount of T cell comprising the CAR of any one of embodiments 30 and 31.
33. The isolated nucleic acid sequence or the method of any one of embodiments 1 and 30-32, wherein the tumor is associated with pancreatic cancer.
34. The isolated nucleic acid sequence of embodiment 1, wherein the extracellular domain binds UPK2.
35 The isolated nucleic acid sequence of embodiment 1, wherein the extracellular domain binds UPK2 having the amino acid sequence of SEQ ID NO: 1.
36. A method of eliciting and/or enhancing T-cell response in a subject having a solid tumor or treating the solid tumor of the subject, the method comprising administering an effective amount of T cell comprising the CAR of any one of embodiments 34 and 35.

37. The isolated nucleic acid sequence or the method of any one of embodiments 1 and 34-36, wherein the tumor is associated with urothelial cancer and/or bladder cancer.
38. The isolated nucleic acid sequence of embodiment 1, wherein the extracellular domain binds ADAM12.
39 The isolated nucleic acid sequence of embodiment 1, wherein the extracellular domain binds ADAM12 having the amino acid sequence of SEQ ID NO: 2.
40. A method of eliciting and/or enhancing T-cell response in a subject having a solid tumor or treating the solid tumor of the subject, the method comprising administering an effective amount of T cell comprising the CAR of any one of embodiments 38 and 39.
41. The isolated nucleic acid sequence or the method of any one of embodiments 1 and 38-40, wherein the tumor is associated with breast cancer and/or pancreatic cancer.
42. The isolated nucleic acid sequence of embodiment 1, wherein the extracellular domain binds SLC45A3.
43 The isolated nucleic acid sequence of embodiment 1, wherein the extracellular domain binds SLC45A3 having the amino acid sequence of SEQ ID NO: 3.
44. A method of eliciting and/or enhancing T-cell response in a subject having a solid tumor or treating the solid tumor of the subject, the method comprising administering an effective amount of T cell comprising the CAR of any one of embodiments 42 and 43.
45. The isolated nucleic acid sequence or the method of any one of embodiments 1 and 42-44, wherein the tumor is associated with prostate cancer.
46. The isolated nucleic acid sequence of embodiment 1, wherein the extracellular domain binds ACPP. 47 The isolated nucleic acid sequence of embodiment 1, wherein the extracellular domain binds ACPP having the amino acid sequence of SEQ ID NO: 4.
48. A method of eliciting and/or enhancing T-cell response in a subject having a solid tumor or treating the solid tumor of the subject, the method comprising administering an effective amount of T cell comprising the CAR of any one of embodiments 46 and 47.
49. The isolated nucleic acid sequence or the method of any one of embodiments 1 and 46-48, wherein the tumor is associated with prostate cancer.
50. The isolated nucleic acid sequence of embodiment 1, wherein the extracellular domain binds MUC21.
51 The isolated nucleic acid sequence of embodiment 1, wherein the extracellular domain binds MUC21 having the amino acid sequence of SEQ ID NO: 5.
52. A method of eliciting and/or enhancing T-cell response in a subject having a solid tumor or treating the solid tumor of the subject, the method comprising administering an effective amount of T cell comprising the CAR of any one of embodiments 50 and 51.
53. The isolated nucleic acid sequence or the method of any one of embodiments 1 and 50-52, wherein the tumor is associated with esophageal cancer.
54. The isolated nucleic acid sequence of embodiment 1, wherein the extracellular domain binds MS4A12.
55 The isolated nucleic acid sequence of embodiment 1, wherein the extracellular domain binds MS4A12 having the amino acid sequence of SEQ ID NO: 7.
56. A method of eliciting and/or enhancing T-cell response in a subject having a solid tumor or treating the solid tumor of the subject, the method comprising administering an effective amount of T cell comprising the CAR of any one of embodiments 54 and 55.
57. The isolated nucleic acid sequence or the method of any one of embodiments 1 and 54-56, wherein the tumor is associated with colorectal cancer.
58. The isolated nucleic acid sequence of embodiment 1, wherein the extracellular domain binds ALPP.
59 The isolated nucleic acid sequence of embodiment 1, wherein the extracellular domain binds ALPP having the amino acid sequence of SEQ ID NO: 8.
60. A method of eliciting and/or enhancing T-cell response in a subject having a solid tumor or treating the solid tumor of the subject, the method comprising administering an effective amount of T cell comprising the CAR of any one of embodiments 58 and 59.
61. The isolated nucleic acid sequence or the method of any one of embodiments 1 and 58-60, wherein the tumor is associated with endometrial cancer.
62. The isolated nucleic acid sequence of embodiment 1, wherein the extracellular domain binds SLC2A14.
63 The isolated nucleic acid sequence of embodiment 1, wherein the extracellular domain binds SLC2A14 having the amino acid sequence of SEQ ID NO: 9.
64. A method of eliciting and/or enhancing T-cell response in a subject having a solid tumor or treating the solid tumor of the subject, the method comprising administering an effective amount of T cell comprising the CAR of any one of embodiments 62 and 63.
65. The isolated nucleic acid sequence or the method of any one of embodiments 1 and 62-64, wherein the tumor is associated with testicular cancer.
66. The isolated nucleic acid sequence of embodiment 1, wherein the extracellular domain binds GS1-259H13.2.
67 The isolated nucleic acid sequence of embodiment 1, wherein the extracellular domain binds GS1-259H13.2 has the amino acid sequence of SEQ ID NO: 10.
68. A method of eliciting and/or enhancing T-cell response in a subject having a solid tumor or treating the solid tumor of the subject, the method comprising administering an effective amount of T cell comprising the CAR of any one of embodiments 66 and 67.
69. The isolated nucleic acid sequence or the method of any one of embodiments 1 and 66-69, wherein the tumor is associated with thyroid cancer or glioma, or testicular cancer.
70. The isolated nucleic acid sequence of embodiment 1, wherein the extracellular domain binds ERVFRD-1.
71 The isolated nucleic acid sequence of embodiment 1, wherein the extracellular domain binds ERVFRD-1 has the amino acid sequence of SEQ ID NO: 11.
72. A method of eliciting and/or enhancing T-cell response in a subject having a solid tumor or treating the solid tumor of the subject, the method comprising administering an effective amount of T cell comprising the CAR of any one of embodiments 70 and 71.
73. The isolated nucleic acid sequence or the method of any one of embodiments 1 and 70-72, wherein the tumor is associated with kidney cancer or Urethral cancer.
74. The isolated nucleic acid sequence of embodiment 1, wherein the extracellular domain binds ADGRG2.
75 The isolated nucleic acid sequence of embodiment 1, wherein the extracellular domain binds ADGRG2 having the amino acid sequence of SEQ ID NO: 12.
76. A method of eliciting and/or enhancing T-cell response in a subject having a solid tumor or treating the solid tumor of the subject, the method comprising administering an effective amount of T cell comprising the CAR of any one of embodiments 74 and 75.

77. The isolated nucleic acid sequence or the method of any one of embodiments 1 and 74-76, wherein the tumor is associated with ovarian cancer.
78. The isolated nucleic acid sequence of embodiment 1, wherein the extracellular domain binds ECEL1.
79 The isolated nucleic acid sequence of embodiment 1, wherein the extracellular domain binds ECEL1 having the amino acid sequence of SEQ ID NO: 13.
80. A method of eliciting and/or enhancing T-cell response in a subject having a solid tumor or treating the solid tumor of the subject, the method comprising administering an effective amount of T cell comprising the CAR of any one of embodiments 78 and 29.
81. The isolated nucleic acid sequence or the method of any one of embodiments 1 and 78-80, wherein the tumor is associated with endometrial cancer.
82. The isolated nucleic acid sequence of embodiment 1, wherein the extracellular domain binds CHRNA2.
83 The isolated nucleic acid sequence of embodiment 1, wherein the extracellular domain binds CHRNA2 having the amino acid sequence of SEQ ID NO: 14.
84. A method of eliciting and/or enhancing T-cell response in a subject having a solid tumor or treating the solid tumor of the subject, the method comprising administering an effective amount of T cell comprising the CAR of any one of embodiments 82 and 83.
85. The isolated nucleic acid sequence or the method of any one of embodiments 1 and 82-84, wherein the tumor is associated with prostate cancer.
86. The isolated nucleic acid sequence of embodiment 1, wherein the extracellular domain binds GP2.
87 The isolated nucleic acid sequence of embodiment 1, wherein the extracellular domain binds GP2 having the amino acid sequence of SEQ ID NO: 15.
88. A method of eliciting and/or enhancing T-cell response in a subject having a solid tumor or treating the solid tumor of the subject, the method comprising administering an effective amount of T cell comprising the CAR of any one of embodiments 86 and 87.
89. The isolated nucleic acid sequence or the method of any one of embodiments 1 and 86-88, wherein the tumor is associated with pancreatic cancer.
90. The isolated nucleic acid sequence of embodiment 1, wherein the extracellular domain binds PSG9.
91 The isolated nucleic acid sequence of embodiment 1, wherein the extracellular domain binds PSG9 having the amino acid sequence of SEQ ID NO: 16.
92. A method of eliciting and/or enhancing T-cell response in a subject having a solid tumor or treating the solid tumor of the subject, the method comprising administering an effective amount of T cell comprising the CAR of any one of embodiments 90 and 91.
93. The isolated nucleic acid sequence or the method of any one of embodiments 1 and 90-92, wherein the tumor is associated with Kidney cancer or liver cancer.
94. The isolated nucleic acid sequence or the method of any one of embodiments 1-93, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
95. The isolated nucleic acid sequence or the method of any one of embodiments 1-93, wherein the intracellular domain comprises a CD3 zeta signaling domain.
96. A vector comprising the isolated nucleic acid sequence of any one of embodiments 1-93.
97. An isolated cell comprising the isolated nucleic acid sequence of any one of embodiments 1-93.
98. A composition comprising a population of T cells comprising the CAR of any one of embodiments 96 or 97.
99. A CAR encoded by the isolated nucleic acid sequence of any one of embodiments 1-93.
100. An isolated nucleic acid sequence encoding a chimeric antigen receptor (CAR), wherein the CAR comprises an extracellular domain, a transmembrane domain, and an intracellular domain, wherein the extracellular domain binds a gene fusion antigen of a gene fusion.
101. The isolated nucleic acid sequence of embodiment 100, wherein the gene fusion comprises a fusion of at least a portion of a first gene to at least a portion of a second gene.
102. The isolated nucleic acid sequence of embodiment 101, wherein the first gene and the second gene comprise a first gene and a second gene of a fusion listed in Table 5.
103. The isolated nucleic acid sequence of embodiment 102, wherein the gene fusion antigen is associated with a condition listed in Table 3.
104. A method of eliciting and/or enhancing T-cell response in a subject having a solid tumor or treating the solid tumor of the subject, the method comprising administering an effective amount of T cell comprising the CAR of any of embodiments 100-103.
105. The isolated nucleic acid sequence or the method of any one of embodiments 100-103, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
106. The isolated nucleic acid sequence or the method of any one of embodiments 100-103, wherein the intracellular domain comprises a CD3 zeta signaling domain.
107. A vector comprising the isolated nucleic acid sequence of any one of embodiments 100-106.
108. An isolated cell comprising the isolated nucleic acid sequence of any one of embodiments 100-106.
109. A composition comprising a population of T cells comprising the CAR of any one of embodiments 8 or 9.
110. A CAR encoded by the isolated nucleic acid sequence of any one of embodiments 100-106.
111. The isolated nucleic acid sequence, modified T cell, or the method of one of the embodiments 1-110, wherein the cell or modified cell is a T cell derived from a healthy donor or a subject having cancer, and the modified T cell comprises a dominant negative form of a receptor associated with an immune checkpoint inhibitor.
112. The isolated nucleic acid sequence, modified T cell, or the method of one of the embodiments 1-110, wherein the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD160.

113. The isolated nucleic acid sequence, modified T cell, or the method of embodiment 112, wherein immune checkpoint inhibitor is modified PD-1.

114. The isolated nucleic acid sequence, modified T cell, or the method of embodiment 112, wherein the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds PD-L1 of a certain cell.

115. The isolated nucleic acid sequence, modified T cell or the method of embodiment 112, wherein an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.

116. The isolated nucleic acid sequence modified T cell or the method of one of embodiments 1-104, wherein the modified T cell is engineered to express and secrete a therapeutic agent such as a cytokine.

117. The isolated nucleic acid sequence, modified T cell or the method of embodiment 116, wherein the therapeutic agent that is or comprises IFN-γ.

118. The isolated nucleic acid sequence, modified T cell or the method of embodiment 116, wherein the therapeutic agent is or comprises at least one of IL-6 or IFN-γ, IL-17, and CCL19.

119. The isolated nucleic acid sequence, modified T cell, or the method of embodiment 116, wherein the therapeutic agent that is or comprises IL-15 or IL-12, or a combination thereof.

120. The isolated nucleic acid sequence, modified T cell, or the method of embodiment 116, wherein the small protein or the therapeutic agent is or comprises a recombinant or native cytokine.

121. The isolated nucleic acid sequence, modified T cell, or the method of embodiment 116, wherein the therapeutic agent comprises an FC fusion protein associated with a small protein.

122. The isolated nucleic acid sequence, modified T cell, or the method of embodiment 116, wherein the small protein is or comprises IL-12, IL-15, IL-6, or IFN-γ.

123. The isolated nucleic acid sequence, modified T cell, or the method of embodiment 116, wherein the therapeutic agent is regulated by Hif1a, NFAT, FOXP3, and/or NFκB.

124. The isolated nucleic acid sequence, modified T cell, or the method of embodiment 116, wherein the small protein or the therapeutic agent is or comprises two or more recombinant or native cytokines, are collected via 2A or/IRES component.

125. The isolated nucleic acid sequence, modified T cell, or the method of one of the embodiments 1-124, wherein the modified T cell comprises a first targeting vector and a second targeting vector, the first targeting vector comprising a nucleic acid sequence encoding a CAR binding a blood antigen and the therapeutic agent, and the second targeting vector comprises a nucleic acid sequence encoding a CAR biding solid tumor antigen and a dominant negative form of the immune checkpoint molecule.

126. The isolated nucleic acid sequence, modified T cell, or the method of one of embodiments 1-124, wherein the modified T cell comprises a first targeting vector and a second targeting vector, the first targeting vector comprising a nucleic acid sequence encoding a CAR binding CD19 and the therapeutic agent, and the second targeting vector comprises a nucleic acid sequence encoding a CAR biding UPK2, ACPP, SIGLEC15 or KISS1R and a dominant negative form of PD-1.

127. The isolated nucleic acid sequence, modified T cell, or the method of one of embodiments 1-124, wherein the modified T cell comprises a first targeting vector and a second targeting vector, the first targeting vector comprising a nucleic acid sequence encoding a CAR binding a blood antigen, and the second targeting vector comprises a nucleic acid sequence encoding a CAR biding solid tumor antigen.

128. The isolated nucleic acid sequence, modified T cell, or the method of one of embodiments 1-124, wherein the modified T cell comprises a first targeting vector and a second targeting vector, the first targeting vector comprising a nucleic acid sequence encoding a CAR binding a B cell antigen, and the second targeting vector comprises a nucleic acid sequence encoding a CAR biding solid tumor antigen.

129. The isolated nucleic acid sequence, modified T cell, or the method of embodiment 128, wherein the solid tumor antigen is at least one of the antigens listed in Table 2, and/or the B cell antigen is CD19, CD20, CD22, or BCMA.

130. The isolated nucleic acid sequence, modified T cell, or the method of embodiment 128, wherein the solid tumor antigen comprises at least one of the antigens listed in Table 2.

131. A method of eliciting and/or enhancing T cell expansion in a subject in need thereof, 0 the method comprising administering an effective amount of the composition of T cells of embodiment 130 to the subject, the subject having a higher level of T cell expansion as compared with a subject that is administered an effective amount of the CAR T cells that do not have the CAR binding the B cell antigen.

132. The isolated nucleic acid sequence, modified T cell, or the method of one of embodiments 1-131, wherein the modified T cell comprises a nucleic acid sequence encoding hTERT, SV40LT, or a combination thereof.

133. The isolated nucleic acid sequence, modified T cell, or the method of embodiment 132, wherein the modified T cell is more proliferable than T cells without nucleic acid sequence.

134. The isolated nucleic acid sequence, modified T cell, or the method of embodiment 133, wherein the proliferable cell remains functions of normal T cells/CAR T cells such as cell therapy functions.

135. The isolated nucleic acid sequence, modified T cell or the method of embodiment 133, wherein the T cell comprises a CAR and is cultured in the presence of an agent that is recognized by the extracellular domain of the CAR, thereby producing a modified CAR cell.

136. The isolated nucleic acid sequence, modified T cell or the method of one of embodiments 1-135, wherein the integration of the nucleic acid sequence encoding hTERT, the nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof.

137. The isolated nucleic acid sequence, modified T cell or the method of one of embodiments 1-136, wherein expression of hTERT, SV40LT, or a combination thereof, is regulated by an inducible expression system such as a rtTA-TRE system.

138. The isolated nucleic acid sequence, modified T cell, or the method of one of embodiments 1-136, wherein modified T cell comprises a nucleic acid sequence encoding a suicide gene such as an HSV-TK system.

139. The isolated nucleic acid sequence, modified T cell, or the method of one of embodiments 1-138, wherein the cell has a reduced graft-versus-host disease (GVHD) response in a bioincompatible human recipient as compared to the GVHD response of the primary human T cell.

140. The isolated nucleic acid sequence, modified T cell, or the method of one of embodiments 1-138, wherein the cell has a reduced expression of endogenous TRAC gene.

141. An antibody that binds ACPP, wherein the antibody comprises a heavy chain variable region (HVR) sequence comprising the amino acid sequence of SEQ ID NO: 83, 87, 89, or 85 and a light chain variable region (LVR) sequence comprising the amino acid sequences of SEQ ID NO: 82, 86, 88, or 84.

142. The antibody of embodiment 141, wherein the HVR comprises the amino acid sequences of SEQ ID NO: 82, and the comprises the amino acid sequence of SEQ ID NO: 83.

143. The antibody of embodiment 141, wherein the HVR comprises the amino acid sequences of SEQ ID NO: 86, and the HVR comprises the amino acid sequence of SEQ ID NO: 87.

144. The antibody of embodiment 141, wherein the HVR comprises the amino acid sequences of SEQ ID NO: 88, and the HVR comprises the amino acid sequence of SEQ ID NO: 89.

145. The antibody of embodiment 141, wherein the HVR comprises the amino acid sequences of SEQ ID NO: 84, and the HVR comprises the amino acid sequence of SEQ ID NO: 85.

146. The antibody of one of embodiments 141-145, wherein the antibody is an scFv comprising the LVR, a linker, and the HVR.

147. The antibody of one of embodiments 141-146, wherein the HVR is joined to a human IgG chain constant region.

148. The antibody of embodiment 147, wherein the human IgG is IgG1 or IgG3.

149. The antibody of one of embodiments 141-146, wherein the antibody is conjugated to a cytotoxic agent.

150. The antibody of one of embodiments 141-146, wherein the cytotoxic agent is a radioactive isotope or a toxin.

151. The antibody of one of embodiments 141-146, wherein the antibody is conjugated to a sequence derived from 4-1 BB or CD28, or a combination thereof.

152. The antibody of one of embodiments 141-146, wherein the antibody or fragment is produced in HEK293 cells.

153. A composition comprising the antibody or fragment of one of embodiments 141-152 and a pharmaceutically acceptable carrier.

154. An article of manufacture comprising a container and a composition contained therein, wherein the composition comprises the antibody or fragment of one of embodiments 141-152.

155. A polynucleotide that encodes the antibody or fragment of one of embodiments 141-152.

156. An expression vector encoding the antibody or fragment of one of embodiments 141-152.

157. A host cell comprising a nucleic acid of one of embodiments 155 and 156.

158. A method of treating a subject with cancer, comprising administering to the subject a therapeutically effective amount of the antibody or fragment of one of embodiments 141-152.

159. A method of treating a subject having prostate cancer comprises administering to the subject a therapeutically effective amount of the antibody or fragment of one of embodiments 141-152.

160. A modified cell comprising a chimeric antigen receptor (CAR) comprising an antigen recognition domain comprising the antibody or fragment of one of embodiments 141-152 and an intracellular domain.

161. A method for treating a subject having cancer the method comprising: administering a modified cell to the subject, wherein the modified cell comprises an antigen recognition domain comprising the antibody or fragment of one of embodiments 141-152 and an intracellular domain.

162. The modified cell or the method of one of embodiments 160 and 161, wherein the modified cell comprises at least one of a B cell, a T cell, an NK cell, an embryonic cell, a dendritic cell, or a macrophage.

163. The method of embodiment 162, wherein the genetically modified cell replicates in vivo.

164. The method of embodiment 161, wherein the modified cell forms memory cells in the subject.

165. The method of embodiment 161, wherein the modified cells are administered intravenously to the subject.

166. The method of embodiment 161, wherein the modified cells persist in the subject.

167. The method of embodiment 161, wherein the modified cell is an autologous T cell.

168. A modified cell comprising a nucleic acid sequence encoding a chimeric antigen receptor (CAR), wherein the CAR comprises an ACPP antigen binding domain comprising the amino acid sequence of SEQ ID NO:83 and 82, 87 and 86, 89 and 88, or 85 and 84.

169. The modified cell of embodiment 168, wherein the CAR further comprises a transmembrane domain, an intracellular domain, and a signaling domain of a co-stimulatory molecule.

170. The modified cell of embodiment 169, wherein the intracellular domain comprising a CD3-zeta signaling domain 171. The modified cell of embodiment 169, wherein the antigen binding fragment is an scFv.

172. The modified cell of embodiment 169, wherein the scFv comprises the amino acid sequence of SEQ ID NO:83 and 82.

173. The modified cell of embodiment 169, wherein the scFv comprises the amino acid sequence of SEQ ID NO:87 and 86.

174. The modified cell of embodiment 169, wherein the scFv comprises the amino acid sequence of SEQ ID NO:89 and 88.

175. The human T cell of embodiment 169, wherein the scFv comprises the amino acid sequence of SEQ ID NO:85 and 84.

176. The modified cell of embodiment 167, wherein the T cell comprises a vector that comprises the nucleic acid sequence.

177. The modified cell of embodiment 176, wherein the vector is a lentiviral vector.

178. The modified cell of one of embodiments 168-177, wherein the modified cell comprises an additional CAR, and the additional CAR binds an antigen of a white blood cell.

179. The modified cell of embodiment 178, wherein the antigen of the white blood cell is a B cell antigen.

180. The modified cell of embodiment 179, wherein the antigen of the B cell antigen is CD19, CD20, CD22, or BCMA.

181. The modified cell of one of embodiments 168-180, wherein the modified cell comprises a dominant negative PD-1.

182. The modified cell of embodiments 168-180, wherein the modified cell comprises a modified PD-1 lacking a functional PD-1 intracellular domain.

183. The modified cell of one of embodiments 168-180, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

184. The modified cell of embodiment 183, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Rα2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

185. The modified cell of one of embodiment 168-184, wherein the modified cell is a T cell, NK cell, or dendritic cell.

186. The modified cell of one of embodiment 168-185, wherein the modified cell further comprises a nucleic acid sequence encoding a therapeutic agent 187. The modified cell of embodiment 186, wherein the therapeutic agent is present in the modified cell in a recombinant DNA construct, in an mRNA, or in a viral vector.

188. The modified cell of embodiment 186, wherein the modified cell comprises a therapeutic agent mRNA encoding the therapeutic agent, and the mRNA is not integrated into the genome of the modified cell.

189. The modified cell of embodiment 186, wherein the modified cell comprises a nucleic acid sequence comprising or the isolated nucleic acid sequence comprises a promoter comprising a binding site for a transcription modulator that modulates the expression and/or secretion of the therapeutic agent in the cell.

190. The modified cell of embodiment 189, wherein the transcription modulator is or includes Hif1a, NFAT, FOXP3, and/or NFκB.

191. The modified cell of embodiment 189, wherein the promoter is responsive to the transcription modulator.

192. The modified cell of embodiment 189, wherein the promoter is operably linked to the nucleic acid sequence encoding the therapeutic agent such that the promoter drives expression and/or secretion of the therapeutic agent in the cell.

193. A pharmaceutical composition comprising the modified cell of one of embodiments 168-53.

194. A method of eliciting and/or enhancing a T cell response in a subject in need thereof and/or treating a tumor of the subject, the method comprising administering an effective amount of the composition of embodiment 193 to the subject.

195. An antibody or antibody fragment that binds UPK2, wherein the antibody or antibody fragment comprises a heavy chain variable region (HVR) sequence comprising the amino acid sequence of SEQ ID NO: 94, 98, 102, 106, 110, 114, 118, or 122 and a light chain variable region (LVR) sequence comprising the amino acid sequences of SEQ ID NO: 93, 97, 101, 105, 109, 113, 117, or 121.

196. The antibody or antibody fragment of embodiment 195, wherein the HVR comprises the amino acid sequences of SEQ ID NO: 93, and HVR comprises the amino acid sequences of SEQ ID NO: 94.

197. The antibody or antibody fragment of embodiment 195, wherein the HVR comprises the amino acid sequences of SEQ ID NO: 97, and HVR comprises the amino acid sequences of SEQ ID NO: 98.

198. The antibody or antibody fragment of embodiment 195, wherein the HVR comprises the amino acid sequences of SEQ ID NO: 101, and HVR comprises the amino acid sequences of SEQ ID NO: 102.

199. The antibody or antibody fragment of embodiment 195, wherein the HVR comprises the amino acid sequences of SEQ ID NO: 105, and HVR comprises the amino acid sequences of SEQ ID NO: 106.

200. The antibody or antibody fragment of embodiment 195, wherein the HVR comprises the amino acid sequences of SEQ ID NO: 109, and HVR comprises the amino acid sequences of SEQ ID NO: 110.

201. The antibody or antibody fragment of embodiment 195, wherein the HVR comprises the amino acid sequences of SEQ ID NO: 113, and HVR comprises the amino acid sequences of SEQ ID NO: 114.

202. The antibody or antibody fragment of embodiment 195, wherein the HVR comprises the amino acid sequences of SEQ ID NO: 117, and HVR comprises the amino acid sequences of SEQ ID NO: 118.

203. The antibody or antibody fragment of embodiment 195, wherein the HVR comprises the amino acid sequences of SEQ ID NO: 121, and HVR comprises the amino acid sequences of SEQ ID NO: 122.

204. The antibody or antibody fragment of one of embodiments 195-203, wherein the HVR is joined to a human IgG chain constant region.

205. The antibody or antibody fragment of embodiment 204, wherein the human IgG is IgG1 or IgG3.

206. The antibody or antibody fragment of one of embodiments 195-205, wherein the antibody or antibody fragment is conjugated to a cytotoxic agent.

207. The antibody or antibody fragment of 12, wherein the cytotoxic agent is a radioactive isotope or a toxin.

208. The antibody or antibody fragment of one of embodiments 195-207, wherein the antibody or antibody fragment is conjugated to a sequence derived from 4-1 BB or CD28, or a combination thereof.

209. The antibody or antibody fragment of one of embodiments 195-208, wherein the antibody or fragment is produced in HEK293 cells.

210. The antibody or antibody fragment of one of embodiments 195-209, wherein the antibody is an scFv.

211. The antibody or antibody fragment of embodiment 210, wherein the scFv comprises or is the SEQ ID NO: 92, 96, 100, 104, 108, 112, 116, or 120.

212. The antibody or antibody fragment of embodiment 210, wherein the antibody or antibody fragment comprises the SEQ ID NO: 92, 96, 100, 104, 108, 112, 116, or 120.

213. A composition comprising the antibody or fragment of one of embodiments 195-212 and a pharmaceutically acceptable carrier.

214. An article of manufacture comprising a container and a composition contained therein, wherein the composition comprises the antibody or fragment of one of embodiments 195-212.

215. A polynucleotide that encodes the antibody or fragment of one of embodiments 195-212.

216. An expression vector encoding the antibody or fragment of one of embodiments 195-212.

217. A host cell comprising a nucleic acid of any one of embodiments 21 or 216.

218. A method of treating a subject having a UPK2 positive tumor (e.g., urothelial cancer and bladder cancer) comprises administering to the subject a therapeutically effective amount of the antibody or fragment of one of embodiments 195-212.

219. A method of treating a subject having urothelial cancer or bladder cancer comprises administering to the subject a therapeutically effective amount of the antibody or fragment of one of embodiments 195-212.

220. A chimeric antigen receptor (CAR) comprises an antigen binding domain comprising the antibody or fragment of one of embodiments 195-212

221. A polynucleotide that encodes the CAR of embodiment 220.

222. A modified cell comprising a nucleic acid sequence encoding a chimeric antigen receptor (CAR), wherein the CAR comprises a UPK2 antigen binding domain comprising the antibody or fragment of one of embodiments 195-212.

223. The modified cell of embodiment 222, wherein the CAR further comprises a transmembrane domain, an intracellular domain, and a signaling domain of a co-stimulatory molecule.

224. The modified cell of embodiment 223, wherein the intracellular domain comprising a CD3-zeta signaling domain 225. The modified cell of one of embodiments 222-224, wherein the antigen binding fragment is an scFv.

226. The modified cell of one of embodiments 222-224, wherein the scFv comprises the amino acid sequence of SEQ ID NO: 92. 96, 100, 104, 108, 112, 116, or 120.

227. The modified cell of one of embodiments 222-224, wherein the modified cell comprises a vector that comprises a nucleic acid sequence comprising the SEQ ID NO: 91, 95, 99, 103, 107, 111, 115, or 119.

228. The modified cell of embodiment 227, wherein the vector is a lentiviral vector.

229. The modified cell of one of embodiments 222-228, wherein the modified cell is a T cell derived from a primary human T cell isolated from a patient.

230. The modified cell of one of embodiments 222-228, wherein the modified cell is a T cell derived from a primary human T cell isolated from a human donor.

231. The modified cell of embodiment 229, wherein the cell has a reduced expression of endogenous TRAC gene.

232. The modified cell of one of embodiments 222-231, wherein the modified cell comprises an additional CAR, and the additional CAR binds an antigen of a white blood cell.

233. The modified cell of embodiment 232, wherein the antigen of the white blood cell is a B cell antigen.

234. The modified cell of embodiment 233, wherein the antigen of the B cell antigen is CD19, CD20, CD22, or BCMA.

235. The modified cell of one of embodiments 222-234, wherein the modified cell comprises a dominant negative PD-1.

236. The modified cell of embodiments 222-234, wherein the modified cell comprises a modified PD-1 lacking a functional PD-1 intracellular domain.

237. The modified cell of one of embodiments 222-234, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

238. The modified cell of embodiment 237, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

239. The modified cell of one of embodiment 222-238, wherein the modified cell is a T cell, NK cell, or dendritic cell.

240. The modified cell of one of embodiment 222-239, wherein the modified cell further comprises a nucleic acid sequence encoding a therapeutic agent 241. The modified cell of embodiment 240, wherein the therapeutic agent is present in the modified cell in a recombinant DNA construct, in an mRNA, or in a viral vector.

242. The modified cell of embodiment 240, wherein the modified cell comprises a therapeutic agent mRNA encoding the therapeutic agent, and the mRNA is not integrated into the genome of the modified cell.

243. The modified cell of embodiment 240, wherein the modified cell comprises a nucleic acid sequence comprising or the isolated nucleic acid sequence comprises a promoter comprising a binding site for a transcription modulator that modulates the expression and/or secretion of the therapeutic agent in the cell.
244. The modified cell of embodiment 243, wherein the transcription modulator is or includes Hif1a, NFAT, FOXP3, and/or NFκB.
245. The modified cell of embodiment 243, wherein the promoter is responsive to the transcription modulator.
246. The modified cell of embodiment 243, wherein the promoter is operably linked to the nucleic acid sequence encoding the therapeutic agent such that the promoter drives expression and/or secretion of the therapeutic agent in the cell.
247. A pharmaceutical composition comprising the modified cell of one of embodiments 168-53.
248. A method of eliciting and/or enhancing T cell response in a subject in need thereof and/or treating a tumor of the subject, the method comprising administering an effective amount of the composition of embodiment 247 to the subject.
249. An isolated nucleic acid sequence encoding a binding molecule comprising a first and a second binding domain, wherein the first binding domain binds an antigen, and the second binding domain binds the T cell CD3 receptor complex.
250. The isolated nucleic acid of embodiment 249, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.
251. The isolated nucleic acid sequence of embodiment 249, wherein the second binding domain binds CD3 epsilon and/or the first binding domain comprises one of an acid sequence of SEQ ID NO: 30, 34, 38, 42, 46, 64, 68, 92, 96, 100, 104, 108, 112, 116, 120, and 136-172.
252. The isolated nucleic acid sequence of embodiment 249, wherein the first binding domain binds ta-Muc1, TSHR, FZD10, PRLR, Muc 16, Muc 17, GUCY2C, CD207, CLDN18.2, CLDN6, or SIGL1C.
253. The isolated nucleic acid sequence of embodiment 249, wherein the isolated nucleic acid sequence encodes a polypeptide comprising one of the amino acid sequences of SEQ ID NO: 123-135.
254. A vector comprising a nucleic acid sequence as defined in any one of embodiments 249-253.
255. A host cell transformed or transfected with the nucleic acid sequence as defined in any one of embodiments 1-5 or with the vector as defined in embodiment 254.
256. A method for the production of a binding molecule according to any one of embodiments 1 to 4, the method comprising culturing a host cell as defined in embodiment 254 under conditions allowing the expression of the binding molecule as defined in any one of embodiments 1 to 4 and recovering the produced binding molecule from the culture.
257. A pharmaceutical composition comprising a binding molecule according to any one of embodiments 1 to 4 or produced according to the method of embodiment 256.
258. A kit comprising a binding molecule as defined in any one of embodiments 1 to 4, a nucleic acid molecule as defined in any one of embodiments 1-4, a vector as defined in embodiment 253, and/or a host cell as defined in embodiment 7.
259. A method for the treatment or amelioration of a disease, comprising administering to a subject in need thereof the binding molecule according to any one of embodiments 1 to 4, or method according to the method of embodiment 256.
260. The method of embodiment 259, further comprising: administering to the subject in need thereof an effective amount of T cell comprising an antigen binding molecule that binds a cell surface molecule of a white cell, wherein the cell surface molecule of the white cell is CD19, CD22, CD20, BCMA, CD5, CD7, CD2, CD16, CD56, CD30, CD14, CD68, CD11 b, CD18, CD169, CD1c, CD33, CD38, CD138, or CD13.
261. The method of embodiment 260, wherein the antigen binding molecule comprises the antigen binding domain, a transmembrane domain, a co-stimulatory signaling region, and a CD3 zeta signaling domain.
262. The method of embodiment 261, wherein the T cell has an additional CAR binding the antigen.
263. An isolated nucleic acid sequence encoding a chimeric antigen receptor (CAR), wherein the CAR comprises an extracellular domain, a transmembrane domain, and an intracellular domain, the extracellular domain comprising at least two binding domains binding a tumor antigen.
264. The isolated nucleic acid sequence of embodiment 263, wherein the at least two binding domains are scFv binding ta-Muc1 and not ta-Muc1 antigen, respectively.
265. The isolated nucleic acid sequence of embodiment 263, wherein the least two binding domains comprise an antigen binding domain binding ta-Muc1, and an additional antigen binding domain binding an antigen different from ta-Muc1.
266. The isolated nucleic acid sequence of embodiment 265, wherein the antigen different from ta-Muc1 is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Folate receptor-α (FR-α), CD19, FZD10, TSHR, PRLR, Muc 17, GUCY2C, CD207, CD3, CD5, B-Cell Maturation Antigen (BCMA), or CD4.
267. The isolated nucleic acid sequence of embodiment 263, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

268. The isolated nucleic acid sequence of embodiment 263, wherein the at least two binding domains comprise SEQ ID NO: 135 and one of SEQ ID NO: 30, 34, 38, 42, 46, 64, 68, 92, 96, 100, 104, 108, 112, 116, 120, and 136-172.
269. The isolated nucleic acid sequence of embodiment 15, wherein the at least two binding domains comprise SEQ ID NO: 70 and one of SEQ ID NO: 59-84.
270. A population of CAR cells comprising the isolated nucleic acid sequence of any one of embodiments 249-253 and 263-268.
271. A pharmaceutical composition comprising the population of the CAR cells of embodiment 270.
272. A method of eliciting and/or enhancing T cell response, eliciting or causing T cell response in a subject in need thereof, and/or treating a tumor of the subject, the method comprising administering an effective amount of the composition of embodiment 271 to the subject.
273. One or more modified cells including two or more different antigen binding domains, wherein at least a first antigen binding domain binds a cell surface marker and the second antigen binding domain binds tumor antigen.
274. The one or more modified cells of embodiment 273, wherein the cell surface marker includes the cell surface marker of a white blood cell.
275. The one or more modified cells of embodiment 273 or 274, wherein the tumor antigen includes one or more of SIGLEC15, SLC6A3, KISS1R, QRFPR, GPR119, CLDN6, UPK2, ADAM12, SLC45A3, ACPP, MUC21, MUC16, MS4A12, or ALPP.
276. The one or more modified cells of any one of embodiments 273-275, wherein the antigen binding domains are on the same CAR molecule, different CAR molecules, or on a CAR molecule and a T cell receptor.
277. The one or more modified cells of any one of embodiments 273-276, wherein the two or more different antigen binding domains are on different CAR molecules on different modified cells.
278. The one or more modified cells of any one of embodiments 273-277, wherein the two or more different antigen binding domains are on a CAR molecule and a T cell receptor which are on different modified cells.
279. A population of cells comprising the one or more modified cells of any one of embodiments 273-278.
280. Use of the nucleic acid sequences, the CAR molecules, the antibodies, the vectors, the cells, the population of cells, the compositions, the pharmaceutical compositions, the kit, or the methods of any one of embodiments 1-279 for use in a method of treating a subject's body by therapy.
281. The use of embodiment 280, wherein the subject is a human or animal.
282. The use of embodiment 280 or 281, wherein the subject is suffering from cancer.
283. The use of any one of embodiments 280-282, wherein the use elicits and/or enhances a T cell response in the subject.
284. Use of the nucleic acid sequences, the CAR molecules, the antibodies, the vectors, the cells, the population of cells, the compositions, the pharmaceutical compositions, the kit, or the methods of any one of embodiments 1-279 for use in a method of eliciting and/or enhancing a T cell response in a subject.
285. The use of embodiment 284, wherein the subject is a human or animal.
286. The use of embodiment 284 or 285, wherein the subject is suffering from cancer.

EXAMPLES

The present disclosure is further described by reference to the following examples. These examples are provided for purposes of illustration only and are not intended to be limiting unless otherwise specified. Thus, the present disclosure should in no way be construed as being limited to the following examples but rather should be construed to encompass any and all variations which become evident as a result of the teaching provided herein.

Various nanoantibodies targeting GCC have been generated. Methods of preparing the nanoantibodies may be found in Bever C S, Dong J X, Vasylieva N, et al. VHH antibodies: emerging reagents for the analysis of environmental chemicals, Anal Bioanal Chem. 2016; 408(22):5985-6002, doi: 10.1007/500216-016-9585-x; Bao, C., Gao, Q., Li, L.-L., Han, L., Zhang, B., Ding, Y., Song, Z., Zhang, R., Zhang, J., Wu, X.-H., The Application of Nanobody in CAR-T Therapy. Biomolecules 2021, 11, 238; and Han, L., Zhang, J S., Zhou, J. et al., Single VHH-directed BCMA CAR-T cells cause remission of relapsed/refractory multiple myeloma. Leukemia (2021), all of which are incorporated herein by their entirety. VHH domains and their CDRs are identified and provided in Table 4.

Figure 4:
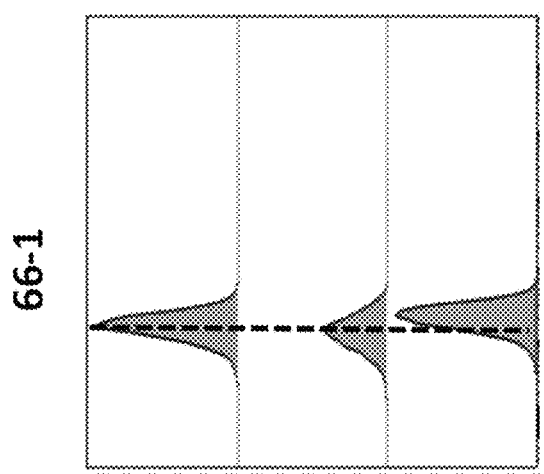
FIG. 4 shows flow cytometry results of antibody binding assay.
Figure 4:
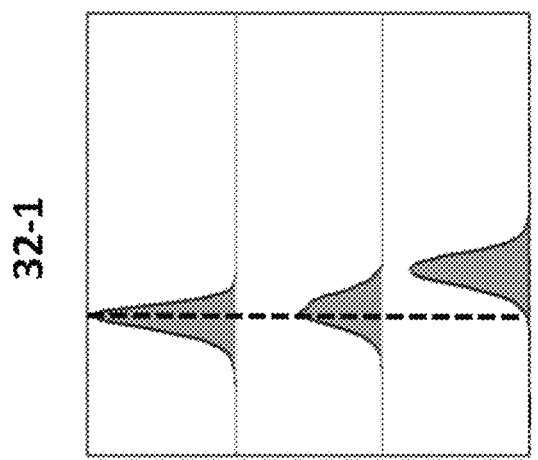
Figure 4:
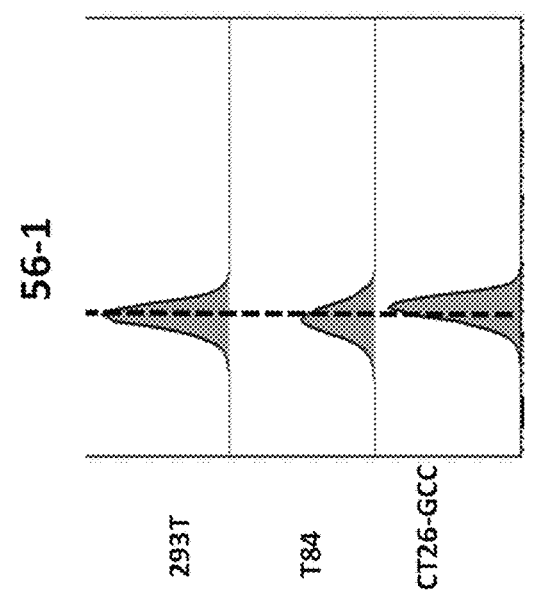
Figure 5:
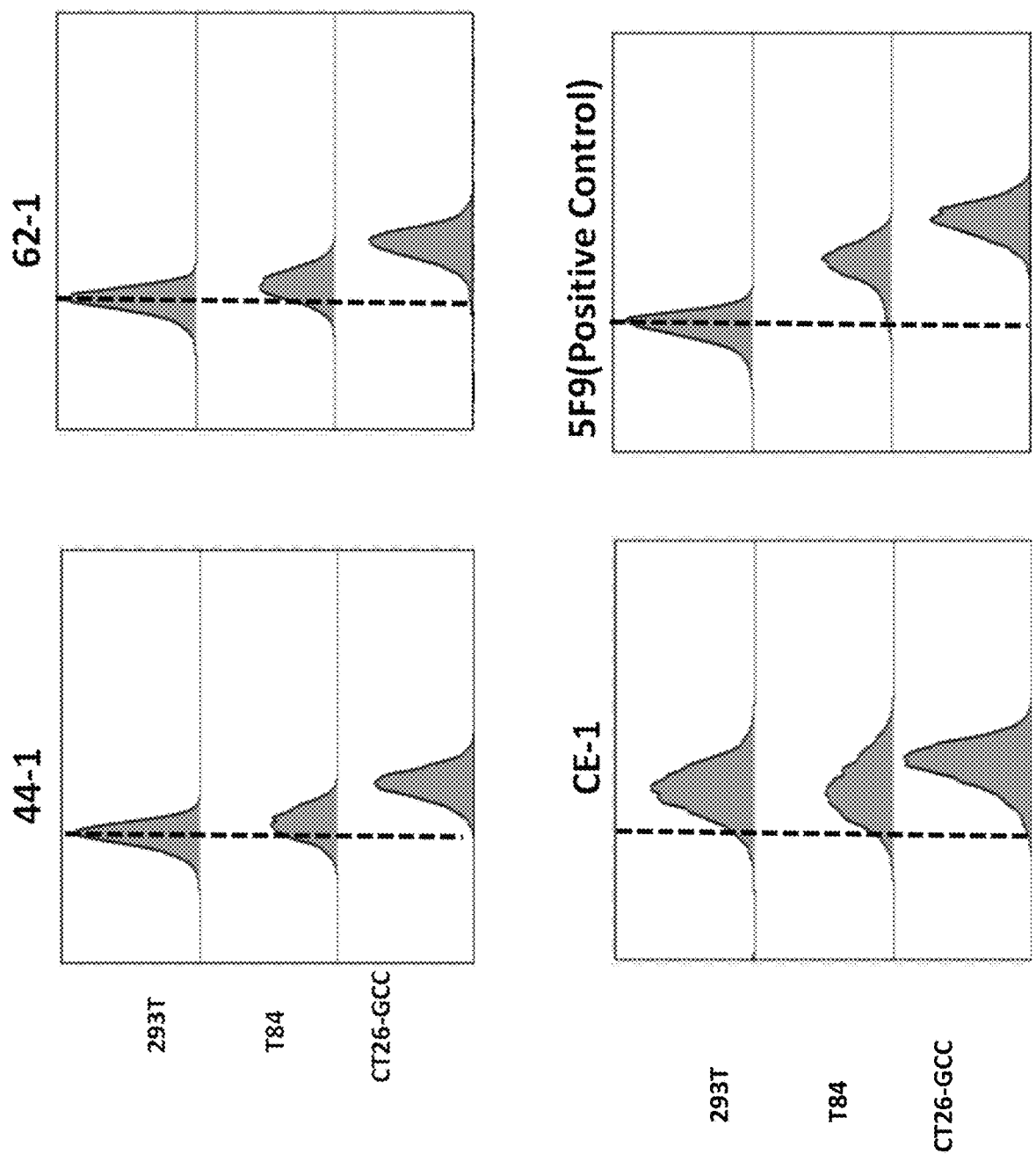
FIG. 5 shows flow cytometry results of antibody binding assay.
Figure 6:
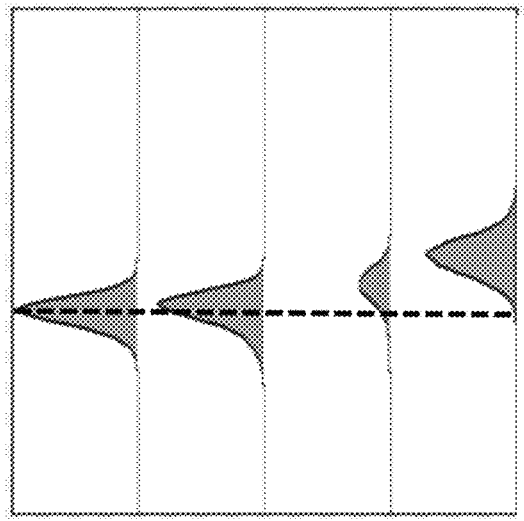
FIG. 6 shows flow cytometry results of antibody binding assay.
Figure 6:
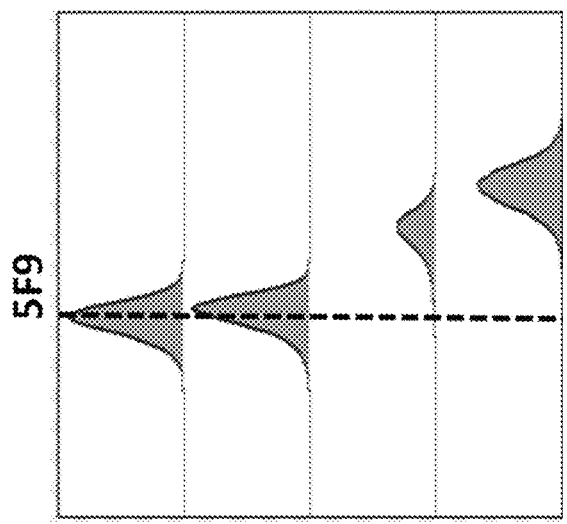
Figure 6:
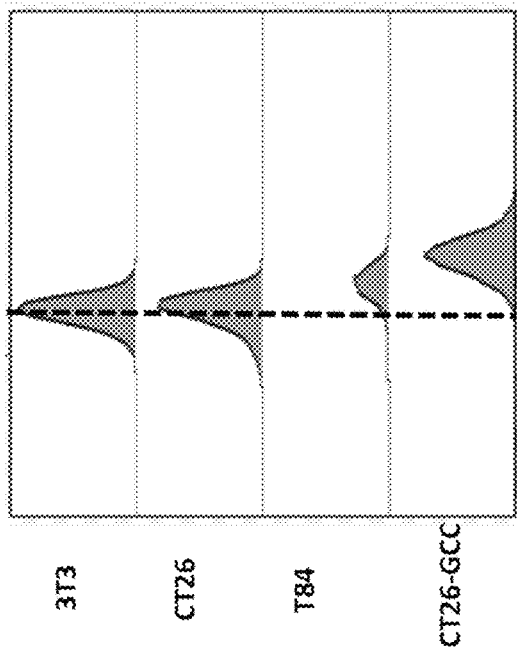
Figure 6:
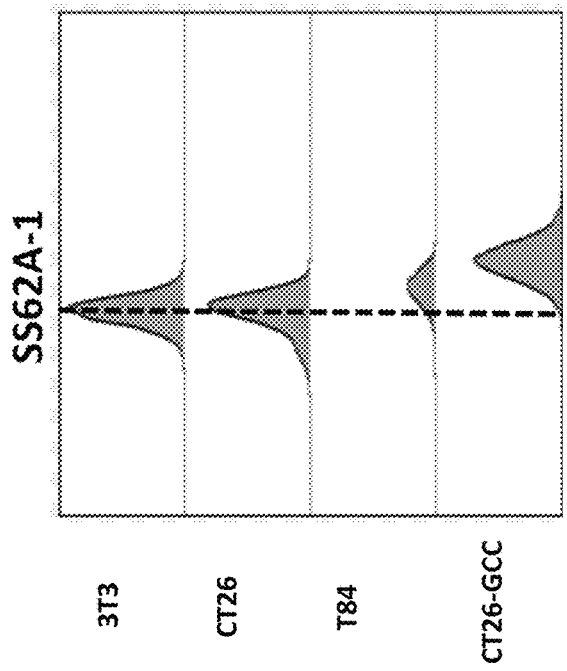

FIGS. 4 and 5 show flow cytometry results of antibody binding assay. VHH antibodies were screened using ELISA of which GCC was used as the antigen. Several VHH antibodies were identified based on the measurement of antibody affinity by the ELISA. These VHH antibodies were analyzed using GCC positive cells and GCC negative cells, and the 59E GCC antibody was used as a positive control. As shown in FIGS. 4 and 5, VHH antibodies #32 (SEQ ID NO: 237), #44 (SEQ ID NO: 225), and #62 (SEQ NO: ID: 208) specifically bind GCC positive cells but not GCC negative cells. FIG. 6 shows flow cytometry results of antibody binding assay. Bivalent antibodies of VHH antibodies #32, #64, #44, and #62 were generated, and these bivalent antibodies specifically bind GCC positive cells but not GCC negative cells.

VHH antibody #32, #64, #44, and #62 were selected for construction of CAR T cells. Lentiviral vectors that encode individual CAR molecules were generated and transduced into T cells, and the expression of the CARs were confirmed by flow cytometry assay. Further, these CAR T cells and GCC expressing cells were co-cultured, and CAR T cells' responses (e.g., cytokine release) induced by the GCC expressing cells were observed. Techniques related to cell cultures and construction of cytotoxic T lymphocyte assay may be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in their entirety.

TABLE 4

VHH Domains and Their CDRs

| SEQ ID NO | VHH or CDR | SEQ ID NO | VHH or CDR |
|---|---|---|---|
| SEQ ID NO: 200 | VHH | SEQ ID NO: 235 | VHH |
| SEQ ID NO: 270 | CDR1 | SEQ ID NO: 375 | CDR1 |
| SEQ ID NO: 271 | CDR2 | SEQ ID NO: 376 | CDR2 |
| SEQ ID NO: 272 | CDR3 | SEQ ID NO: 377 | CDR3 |
| SEQ ID NO: 201 | VHH | SEQ ID NO: 236 | VHH |
| SEQ ID NO: 273 | CDR1 | SEQ ID NO: 378 | CDR1 |
| SEQ ID NO: 274 | CDR2 | SEQ ID NO: 379 | CDR2 |
| SEQ ID NO: 275 | CDR3 | SEQ ID NO: 380 | CDR3 |
| SEQ ID NO: 202 | VHH | SEQ ID NO: 237 | VHH |
| SEQ ID NO: 276 | CDR1 | SEQ ID NO: 381 | CDR1 |
| SEQ ID NO: 277 | CDR2 | SEQ ID NO: 382 | CDR2 |
| SEQ ID NO: 278 | CDR3 | SEQ ID NO: 383 | CDR3 |
| SEQ ID NO: 203 | VHH | SEQ ID NO: 238 | VHH |
| SEQ ID NO: 279 | CDR1 | SEQ ID NO: 384 | CDR1 |
| SEQ ID NO: 280 | CDR2 | SEQ ID NO: 385 | CDR2 |
| SEQ ID NO: 281 | CDR3 | SEQ ID NO: 386 | CDR3 |
| SEQ ID NO: 204 | VHH | SEQ ID NO: 239 | VHH |
| SEQ ID NO: 282 | CDR1 | SEQ ID NO: 387 | CDR1 |
| SEQ ID NO: 283 | CDR2 | SEQ ID NO: 388 | CDR2 |
| SEQ ID NO: 284 | CDR3 | SEQ ID NO: 389 | CDR3 |
| SEQ ID NO: 205 | VHH | SEQ ID NO: 240 | VHH |
| SEQ ID NO: 285 | CDR1 | SEQ ID NO: 390 | CDR1 |
| SEQ ID NO: 286 | CDR2 | SEQ ID NO: 391 | CDR2 |
| SEQ ID NO: 287 | CDR3 | SEQ ID NO: 392 | CDR3 |
| SEQ ID NO: 206 | VHH | SEQ ID NO: 241 | VHH |
| SEQ ID NO: 288 | CDR1 | SEQ ID NO: 393 | CDR1 |
| SEQ ID NO: 289 | CDR2 | SEQ ID NO: 394 | CDR2 |
| SEQ ID NO: 290 | CDR3 | SEQ ID NO: 395 | CDR3 |
| SEQ ID NO: 207 | VHH | SEQ ID NO: 242 | VHH |
| SEQ ID NO: 291 | CDR1 | SEQ ID NO: 396 | CDR1 |
| SEQ ID NO: 292 | CDR2 | SEQ ID NO: 397 | CDR2 |
| SEQ ID NO: 293 | CDR3 | SEQ ID NO: 398 | CDR3 |
| SEQ ID NO: 208 | VHH | SEQ ID NO: 243 | VHH |
| SEQ ID NO: 294 | CDR1 | SEQ ID NO: 399 | CDR1 |
| SEQ ID NO: 295 | CDR2 | SEQ ID NO: 400 | CDR2 |
| SEQ ID NO: 296 | CDR3 | SEQ ID NO: 401 | CDR3 |
| SEQ ID NO: 209 | VHH | SEQ ID NO: 244 | VHH |
| SEQ ID NO: 297 | CDR1 | SEQ ID NO: 402 | CDR1 |
| SEQ ID NO: 298 | CDR2 | SEQ ID NO: 403 | CDR2 |
| SEQ ID NO: 299 | CDR3 | SEQ ID NO: 404 | CDR3 |
| SEQ ID NO: 210 | VHH | SEQ ID NO: 245 | VHH |
| SEQ ID NO: 300 | CDR1 | SEQ ID NO: 405 | CDR1 |
| SEQ ID NO: 301 | CDR2 | SEQ ID NO: 406 | CDR2 |
| SEQ ID NO: 302 | CDR3 | SEQ ID NO: 407 | CDR3 |
| SEQ ID NO: 211 | VHH | SEQ ID NO: 246 | VHH |
| SEQ ID NO: 303 | CDR1 | SEQ ID NO: 408 | CDR1 |
| SEQ ID NO: 304 | CDR2 | SEQ ID NO: 409 | CDR2 |
| SEQ ID NO: 305 | CDR3 | SEQ ID NO: 410 | CDR3 |
| SEQ ID NO: 212 | VHH | SEQ ID NO: 247 | VHH |
| SEQ ID NO: 306 | CDR1 | SEQ ID NO: 411 | CDR1 |
| SEQ ID NO: 307 | CDR2 | SEQ ID NO: 412 | CDR2 |
| SEQ ID NO: 308 | CDR3 | SEQ ID NO: 413 | CDR3 |
| SEQ ID NO: 213 | VHH | SEQ ID NO: 248 | VHH |
| SEQ ID NO: 309 | CDR1 | SEQ ID NO: 414 | CDR1 |
| SEQ ID NO: 310 | CDR2 | SEQ ID NO: 415 | CDR2 |
| SEQ ID NO: 311 | CDR3 | SEQ ID NO: 416 | CDR3 |
| SEQ ID NO: 214 | VHH | SEQ ID NO: 249 | VHH |
| SEQ ID NO: 312 | CDR1 | SEQ ID NO: 417 | CDR1 |
| SEQ ID NO: 313 | CDR2 | SEQ ID NO: 418 | CDR2 |
| SEQ ID NO: 314 | CDR3 | SEQ ID NO: 419 | CDR3 |
| SEQ ID NO: 215 | VHH | SEQ ID NO: 250 | VHH |
| SEQ ID NO: 315 | CDR1 | SEQ ID NO: 420 | CDR1 |
| SEQ ID NO: 316 | CDR2 | SEQ ID NO: 421 | CDR2 |
| SEQ ID NO: 317 | CDR3 | SEQ ID NO: 422 | CDR3 |
| SEQ ID NO: 216 | VHH | SEQ ID NO: 251 | VHH |
| SEQ ID NO: 318 | CDR1 | SEQ ID NO: 423 | CDR1 |
| SEQ ID NO: 319 | CDR2 | SEQ ID NO: 424 | CDR2 |
| SEQ ID NO: 320 | CDR3 | SEQ ID NO: 425 | CDR3 |
| SEQ ID NO: 217 | VHH | SEQ ID NO: 252 | VHH |
| SEQ ID NO: 321 | CDR1 | SEQ ID NO: 426 | CDR1 |
| SEQ ID NO: 322 | CDR2 | SEQ ID NO: 427 | CDR2 |
| SEQ ID NO: 323 | CDR3 | SEQ ID NO: 428 | CDR3 |
| SEQ ID NO: 218 | VHH | SEQ ID NO: 253 | VHH |
| SEQ ID NO: 324 | CDR1 | SEQ ID NO: 429 | CDR1 |
| SEQ ID NO: 325 | CDR2 | SEQ ID NO: 430 | CDR2 |
| SEQ ID NO: 326 | CDR3 | SEQ ID NO: 431 | CDR3 |
| SEQ ID NO: 219 | VHH | SEQ ID NO: 254 | VHH |
| SEQ ID NO: 327 | CDR1 | SEQ ID NO: 432 | CDR1 |
| SEQ ID NO: 328 | CDR2 | SEQ ID NO: 433 | CDR2 |
| SEQ ID NO: 329 | CDR3 | SEQ ID NO: 434 | CDR3 |
| SEQ ID NO: 220 | VHH | SEQ ID NO: 255 | VHH |
| SEQ ID NO: 330 | CDR1 | SEQ ID NO: 435 | CDR1 |
| SEQ ID NO: 331 | CDR2 | SEQ ID NO: 436 | CDR2 |
| SEQ ID NO: 332 | CDR3 | SEQ ID NO: 437 | CDR3 |
| SEQ ID NO: 221 | VHH | SEQ ID NO: 256 | VHH |
| SEQ ID NO: 333 | CDR1 | SEQ ID NO: 438 | CDR1 |
| SEQ ID NO: 334 | CDR2 | SEQ ID NO: 439 | CDR2 |
| SEQ ID NO: 335 | CDR3 | SEQ ID NO: 440 | CDR3 |
| SEQ ID NO: 222 | VHH | SEQ ID NO: 257 | VHH |
| SEQ ID NO: 336 | CDR1 | SEQ ID NO: 441 | CDR1 |
| SEQ ID NO: 337 | CDR2 | SEQ ID NO: 442 | CDR2 |
| SEQ ID NO: 338 | CDR3 | SEQ ID NO: 443 | CDR3 |
| SEQ ID NO: 223 | VHH | SEQ ID NO: 258 | VHH |
| SEQ ID NO: 339 | CDR1 | SEQ ID NO: 444 | CDR1 |
| SEQ ID NO: 340 | CDR2 | SEQ ID NO: 445 | CDR2 |
| SEQ ID NO: 341 | CDR3 | SEQ ID NO: 446 | CDR3 |
| SEQ ID NO: 224 | VHH | SEQ ID NO: 259 | VHH |
| SEQ ID NO: 342 | CDR1 | SEQ ID NO: 447 | CDR1 |
| SEQ ID NO: 343 | CDR2 | SEQ ID NO: 448 | CDR2 |
| SEQ ID NO: 344 | CDR3 | SEQ ID NO: 449 | CDR3 |
| SEQ ID NO: 225 | VHH | SEQ ID NO: 260 | VHH |
| SEQ ID NO: 345 | CDR1 | SEQ ID NO: 450 | CDR1 |
| SEQ ID NO: 346 | CDR2 | SEQ ID NO: 451 | CDR2 |
| SEQ ID NO: 347 | CDR3 | SEQ ID NO: 452 | CDR3 |
| SEQ ID NO: 226 | VHH | SEQ ID NO: 261 | VHH |
| SEQ ID NO: 348 | CDR1 | SEQ ID NO: 453 | CDR1 |
| SEQ ID NO: 349 | CDR2 | SEQ ID NO: 454 | CDR2 |
| SEQ ID NO: 350 | CDR3 | SEQ ID NO: 455 | CDR3 |
| SEQ ID NO: 227 | VHH | SEQ ID NO: 262 | VHH |
| SEQ ID NO: 351 | CDR1 | SEQ ID NO: 456 | CDR1 |
| SEQ ID NO: 352 | CDR2 | SEQ ID NO: 457 | CDR2 |
| SEQ ID NO: 353 | CDR3 | SEQ ID NO: 458 | CDR3 |
| SEQ ID NO: 228 | VHH | SEQ ID NO: 263 | VHH |
| SEQ ID NO: 354 | CDR1 | SEQ ID NO: 459 | CDR1 |
| SEQ ID NO: 355 | CDR2 | SEQ ID NO: 460 | CDR2 |
| SEQ ID NO: 356 | CDR3 | SEQ ID NO: 461 | CDR3 |
| SEQ ID NO: 229 | VHH | SEQ ID NO: 264 | VHH |
| SEQ ID NO: 357 | CDR1 | SEQ ID NO: 462 | CDR1 |
| SEQ ID NO: 358 | CDR2 | SEQ ID NO: 463 | CDR2 |
| SEQ ID NO: 359 | CDR3 | SEQ ID NO: 464 | CDR3 |
| SEQ ID NO: 230 | VHH | SEQ ID NO: 265 | VHH |
| SEQ ID NO: 360 | CDR1 | SEQ ID NO: 465 | CDR1 |
| SEQ ID NO: 361 | CDR2 | SEQ ID NO: 466 | CDR2 |
| SEQ ID NO: 362 | CDR3 | SEQ ID NO: 467 | CDR3 |
| SEQ ID NO: 231 | VHH | SEQ ID NO: 266 | VHH |
| SEQ ID NO: 363 | CDR1 | SEQ ID NO: 468 | CDR1 |
| SEQ ID NO: 364 | CDR2 | SEQ ID NO: 469 | CDR2 |
| SEQ ID NO: 365 | CDR3 | SEQ ID NO: 470 | CDR3 |
| SEQ ID NO: 232 | VHH | SEQ ID NO: 267 | VHH |
| SEQ ID NO: 366 | CDR1 | SEQ ID NO: 471 | CDR1 |
| SEQ ID NO: 367 | CDR2 | SEQ ID NO: 199 | CDR2 |
| SEQ ID NO: 368 | CDR3 | SEQ ID NO: 198 | CDR3 |
| SEQ ID NO: 233 | VHH | SEQ ID NO: 268 | VHH |
| SEQ ID NO: 369 | CDR1 | SEQ ID NO: 197 | CDR1 |
| SEQ ID NO: 370 | CDR2 | SEQ ID NO: 196 | CDR2 |
| SEQ ID NO: 371 | CDR3 | SEQ ID NO: 195 | CDR3 |
| SEQ ID NO: 234 | VHH | SEQ ID NO: 194 | VHH |
| SEQ ID NO: 372 | CDR1 | SEQ ID NO: 193 | CDR1 |
| SEQ ID NO: 373 | CDR2 | SEQ ID NO: 192 | CDR2 |
| SEQ ID NO: 374 | CDR3 | SEQ ID NO: 191 | CDR3 |

All publications, patents, and patent applications cited in this specification are incorporated herein by reference in their entireties as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. An antibody that binds GCC, wherein the antibody comprises a VHH domain comprising complementarity determining region (CDR) 1, CDR2, and CDR3, and wherein:
- CDR1, CDR2, and CDR3 comprise SEQ ID NO: 294-296, respectively,
- CDR1, CDR2, and CDR3 comprise SEQ ID NO: 345-347, respectively, or
- CDR1, CDR2, and CDR3 comprise SEQ ID NO: 381-383, respectively.

2. The antibody of claim 1, wherein the antibody comprises SEQ ID NO: 208, 225, or 237.

3. The antibody of claim 1, wherein the antibody is a VHH antibody.

4. The antibody of claim 1, wherein the antibody is conjugated to a cytotoxic agent.

5. The antibody of claim 4, wherein the cytotoxic agent is a radioactive isotope or a toxin.

6. The antibody of claim 1, wherein the antibody is a bispecific antibody comprising the VHH domain, a linker, and an antibody binding CD3.

7. A chimeric antigen receptor (CAR) comprising an extracellular domain comprising the antibody of claim 3.

8. The CAR of claim 7, wherein the CAR comprises a transmembrane domain and an intracellular domain.

9. The CAR of claim 8, wherein the intracellular domain comprises a co-stimulatory signaling region that comprises an intracellular domain of a co-stimulatory molecule comprising at least one of CD27, CD28, 4-1BB, OX40, CD30, CD40, PD-1, ICOS, lymphocyte function-associated antigen-1 (LFA-1), CD2, CD7, LIGHT, NKG2C, and B7-H3.

* * * * *

```
                              SEQUENCE LISTING

Sequence total quantity: 470
SEQ ID NO: 1            moltype = AA  length = 184
FEATURE                 Location/Qualifiers
source                  1..184
                        mol_type = protein
                        organism = Homo sapiens
SEQUENCE: 1
MAPLLPIRTL PLILILLALL SPGAADFNIS SLSGLLSPAL TESLLVALPP CHLTGGNATL  60
MVRRANDSKV VTSSFVVPPC RGRRELVSVV DSGAGFTVTR LSAYQVTNLV PGTKFYISYL 120
VKKGTATESS REIPMSTLPR RNMESIGLGM ARTGGMVVIT VLLSVAMFLL VLGFIIALAL 180
GSRK                                                              184

SEQ ID NO: 2            moltype = AA  length = 909
FEATURE                 Location/Qualifiers
source                  1..909
                        mol_type = protein
                        organism = Homo sapiens
SEQUENCE: 2
MAARPLPVSP ARALLLALAG ALLAPCEARG VSLWNQGRAD EVVSASVGSG DLWIPVKSFD  60
SKNHPEVLNI RLQRESKELI INLERNEGLI ASSFTETHYL QDGTDVSLAR NYTVILGHCY 120
YHGHVRGYSD SAVSLSTCSG LRGLIVFENE SYVLEPMKSA TNRYKLFPAK KLKSVRGSCG 180
SHHNTPNLAA KNVFPPPSQT WARRHKRETL KATKYVELVI VADNREFQRQ GKDLEKVKQR 240
LIEIANHVDK FYRPLNIRIV LVGVEVWNDM DKCSVSQDPF TSLHEFLDWR KMKLLPRKSH 300
DNAQLVSGVY FQGTTIGMAP IMSMCTADQS GGIVMDHSDN PLGAAVTLAH ELGHNFGMNH 360
DTLDRGCSCQ MAVEKGGCIM NASTGYPFPM VFSSCSRKDL ETSLEKGMGV CLFNLPEVRE 420
SFGGQKCGNR FVEEGEECDC GEPEECMNRC CNATTCTLKP DAVCAHGLCC EDCQLKPAGT 480
ACRDSSNSCD LPEFCTGASP HCPANVYLHD GHSCQDVDGY CYNGICQTHE QQCVTLWGPG 540
AKPAPGICFE RVNSAGDPYG NCGKVSKSSF AKCEMRDAKC GKIQCQGGAS RPVIGTNAVS 600
IETNIPLQQG GRILCRGTHV YLGDDMPDPG LVLAGTKCAD GKICLNRQCQ NISVFGVHEC 660
AMQCHGRGVC NNRKNCHCEA HWAPPFCDKF GFGGSTDSGP IRQADNQGLT IGILVTILCL 720
LAAGFVVYLK RKTLIRLLFT NKKTTIEKLR CVRPSRPPRG FQPCQAHLGH LGKGLMRKPP 780
DSYPPKDNPR RLLQCQNVDI SRPLNGLNVP QPQSTQRVLP PLHRAPRAPS VPARPLPAKP 840
ALRQAQGTCK PNPPQKPLPA DPLARTTRLT HALARTPGQW ETGLRLAPLR PAPQYPHQVP 900
RSTHTAYIK                                                        909

SEQ ID NO: 3            moltype = AA  length = 553
FEATURE                 Location/Qualifiers
source                  1..553
                        mol_type = protein
                        organism = Homo sapiens
SEQUENCE: 3
MVQRLWVSRL LRHRKAQLLL VNLLTFGLEV CLAAGITYVP PLLLEVGVEE KFMTMVLGIG  60
PVLGLVCVPL LGSASDHWRG RYGRRRPFIW ALSLGILLSL FLIPRAGWLA GLLCPDPRPL 120
ELALLILGVG LLDFCGQVCF TPLEALLSDL FRDPDHCRQA YSVYAFMISL GGCLGYLLPA 180
IDWDTSALAP YLGTQEECLF GLLTLIFLTC VAATLLVAEE AALGPTEPAE GLSAPSLSPH 240
CCPCRARLAF RNLGALLPRL HQLCCRMPRT LRRLFVAELC SWMALMTFTL FYTDFVGEGL 300
YQGVPRAEPG TEARRHYDEG VRMGSLGLFL QCAISLVFSL VMDRLVQRFG TRAVYLASVA 360
AFPVAAGATC LSHSVAVVTA SAALTGFTFS ALQILPYTLA SLYHREKQVF LPKYRGDTGG 420
ASSEDSLMTS FLPGPKPGAP FPNGHVGAGG SGLLPPPPAL CGASACDVSV RVVVGEPTEA 480
RVVPGRGICL DLAILDSAFL LSQVAPSLFM GSIVQLSQSV TAYMVSAAGL GLVAIYFATQ 540
VVFDKSDLAK YSA                                                   553

SEQ ID NO: 4            moltype = AA  length = 418
FEATURE                 Location/Qualifiers
source                  1..418
                        mol_type = protein
                        organism = Homo sapiens
SEQUENCE: 4
MRAAPLLLAR AASLSLGFLF LLFFWLDRSV LAKELKFVTL VFRHGDRSPI DTFPTDPIKE  60
SSWPQGFGQL TQLGMEQHYE LGEYIRKRYR KFLNESYKHE QVYIRSTDVD RTLMSAMTNL 120
AALFPPEGVS IWNPILLWQP IPVHTVPLSE DQLLYLPFRN CPRFQELESE TLKSEEFQKR 180
LHPYKDFIAT LGKLSGLHGQ DLFGIWSKVY DPLYCESLSN FTLPSWATED TMTKLRELSE 240
LSLLSLYGIH KQKEKSRLQG GVLVNEILNH MKRATQIPSY KKLIMYSAHD TTVSGLQMAL 300
DVYNGLLPPY ASCHLTELYF EKGEYFVEMY YRNETQHEPY PLMLPGCSPS CPLERFAELV 360
GPVIPQDWST ECMTTNSHQV LKVIFAVAFC LISAVLMVLL FIHIRRGLCW QRESYGNI   418

SEQ ID NO: 5            moltype = AA  length = 560
FEATURE                 Location/Qualifiers
source                  1..560
                        mol_type = protein
                        organism = Homo sapiens
SEQUENCE: 5
MKMQKGNVLL MFGLLLHLEA ATNSNETSTS ANTGSSVISS GASTATNSGS SVTSSGVSTA  60
```

| | | | | | |
|---|---|---|---|---|---|
| TISGSSVTSN | GVSIVTNSEF | HTTSSGISTA | TNSEFSTVSS | GISIATNSES | STTSSGASTA 120 |
| TNSESSTPSS | GASTATNSDS | STTSSGASTA | TNSDSSTTSS | EASTATNSES | STTSSGASTA 180 |
| TNSESSTVSS | RASTATNSES | STTSSGASTA | TNSESRTTSN | GAGTATNSES | STTSSGASTA 240 |
| TNSESSTPSS | GAGTATNSES | STTSSGAGTA | TNSESSTVSS | GISTVTNSES | STPSSGANTA 300 |
| TNSESSTTSS | GANTATNSES | STTSSGASTA | TNSESSTVSS | GASTATNSES | STTSSGASTA 360 |
| TNSGSSTTSS | GTSTATNSDS | STVSSGASTA | TTSESSTTSS | GASTATNSES | STVSSGASTA 420 |
| TNSESSTTSS | GANTATNSGS | SVTSAGSGTA | ALTGMHTTSH | SASTAVSEAK | PGGSLVPWEI 480 |
| FLITLVSVVA | AVGLFAGLFF | CVRNSLSLRN | TFNTAVYHPH | GLNHGLGPGP | GGNHGAPHRP 540 |
| RWSPNWFWRR | PVSSIAMEMS | | | | 560 |

```
SEQ ID NO: 6            moltype = AA  length = 14507
FEATURE                 Location/Qualifiers
source                  1..14507
                        mol_type = protein
                        organism = Homo sapiens
SEQUENCE: 6
```

| | | | | | |
|---|---|---|---|---|---|
| MLKPSGLPGS | SSPTRSLMTG | SRSTKATPEM | DSGLTGATLS | PKTSTGAIVV | TEHTLPFTSP 60 |
| DKTLASPTSS | VVGRTTQSLG | VMSSALPEST | SRGMTHSEQR | TSPSLSPQVN | GTPSRNYPAT 120 |
| SMVSGLSSPR | TRTSSTEGNF | TKEASTYTLT | VETTSGPVTE | KYTVPTETST | TEGDSTETPW 180 |
| DTRYIPVKIT | SPMKTFADST | ASKENAPVSM | TPAETTVTDS | HTPGRTNPSF | GTLYSSFLDL 240 |
| SPKGTPNSRG | ETSLELILST | TGYPFSSPEP | GSAGHSRIST | SAPLSSSASV | LDNKISETSI 300 |
| FSGQSLTSPL | SPGVPEARAS | TMPNSAIPFS | MTLSNAETSA | ERVRSTISSL | GTPSISTKQT 360 |
| AETILTFHAF | AETMDIPSTH | IAKTLASEWL | GSPGTLGGTS | TSALTTTSPS | TTLVSEETNT 420 |
| HHSTSGKETE | GTLNTSMTPL | ETSAPGEESE | MTATLVPTLG | FTTLDSKIRS | PSQVSSSHPT 480 |
| RELRTTGSTS | GRQSSSTAAH | GSSDILRATT | SSTSKASSWT | SESTAQQFSE | PQHTQWVETS 540 |
| PSMKTERPPA | STSVAAPITT | SVPSVVSGFT | TLKTSSTKGI | WLEETSADTL | IGESTAGPTT 600 |
| HQFAVPTGIS | MTGGSSTRGS | QGTTHLLLTRA | TASSESADL | TLATNGVPVS | VSPAVSKTAA 660 |
| GSSPPGGTKP | SYTMVSSVIP | ETSSLQSSAF | REGTSLGLTP | LNTRHPFSSP | EPDSAGHTKI 720 |
| STSIPLLSSA | SVLEDKVSAT | STFSHHKATS | SITTGTPEIS | TKTKPSSAVL | SSMTLSNAAT 780 |
| SPERVRNATS | PLTHPSPSGE | ETAGSVLTLS | TSAETTDSPN | IHPTGTLTSE | SSESPSTLSL 840 |
| PSVSGVKTTF | SSSTPSTHLF | TSGEETEETS | NPSVSQPETS | VSRVRTTLAS | TSVPTPVFPT 900 |
| MDTWPTRSAQ | FSSSHLVSEL | RATSSTSVTN | STGSALPKIS | HLTGTATMSQ | TNRDTFNDSA 960 |
| APQSTTWPET | SPRFKTGLPS | ATTTVSTSAT | SLSATVMVSK | FTSPATSSME | ATSIREPSTT 1020 |
| ILTTETTNGP | GSMAVASTNI | PIGKGYITEG | RLDTSHLPIG | TTASSETSMD | FTMAKESVSM 1080 |
| SVSPSQSMDA | AGSSTPGRTS | QFVDTFSDDV | YHLTSREITI | PRDGTSSALT | PQMTATHPPS 1140 |
| PDPGSARSTW | LGILSSSPSS | PTPKVTMSST | FSTQRVTTSM | IMDTVETSRW | NMPNLPSTTS 1200 |
| LTPSNIPTSG | AIGKSTLVPL | DTPSPATSLE | ASEGGLPTLS | TYPESTNTPS | IHLGAHASSE 1260 |
| SPSTIKLTMA | SVVKPGSYTP | LTFPSIETHI | HVSTARMAYS | SGSSPEMTAP | GETNTGSTWD 1320 |
| PTTYITTTDP | KDTSSAQVST | PHSVRTLRTT | ENHPKTESAT | PAAYSGSPKI | SSSPNLTSPA 1380 |
| TKAWTIIDTT | EHSTQLHYTK | LAEKSSGFET | QSAPGPVSVV | IPTSPTIGSS | TLELTSDVPG 1440 |
| EPLVLAPSEQ | TTITLPMATW | LSTSLTEEMA | STDLDISSPS | SPMSTFAIFP | PMSTPSHELS 1500 |
| KSEADTSAIR | NTDSTTLDQH | LGIRSLGRTG | DLTTVPITPL | TTTWTSVIEH | STQAQDTLSA 1560 |
| TMSPTHVTQS | LKDQTSIPAS | ASPSHLTEVY | PELGTQGRSS | SEATTFWKPS | TDTLSREIET 1620 |
| GPTNIQSTPP | MDNTTTGSSS | SGVTLGIAHL | PIGTSSPAET | STNMALERRS | STATVSMAGT 1680 |
| MGLLVTSAPG | RSISQSLGRV | SSVLSESTTE | GVTDSSKGSS | PRLNTQGNTA | LSSSLEPSYA 1740 |
| EGSQMSTSIP | LTSSPTTPDV | EFIGGSTFWT | KEVTTVMTSD | ISKSSARTES | SSATLMSTAL 1800 |
| GSTENTGKEK | LRTASMDLPS | PTPSMEVTPW | ISLTLSNAPN | TTDSLDLSHG | VHTSSAGTLA 1860 |
| TDRSLNTGVT | RASRLENGSD | TSSKSLSMGN | STHTSMTYTE | KSEVSSSIHP | RPETSAPGAE 1920 |
| TTLTSTPGNR | AISLTLPFSS | IPVEEVISTG | ITSGPDINSA | PMTHSPITPP | TIVWTSTGTI 1980 |
| EQSTQPLHAV | SSEKVSVQTQ | STPYVNSVAV | SASPTHENSV | SSGSSTSSPY | SSASLESLDS 2040 |
| TISRRNAITS | WLWDLTTSLP | TTTWPSTSLS | EALSSGHSGV | PSSTTTEF | PLFSAASTSA 2100 |
| AKQRNPETET | HGPQNTAAST | LNTDASSVTG | LSETPVGASI | SSEVPLPMAI | TSRSDVSGLT 2160 |
| SESTANPSLG | TASSAGTKLT | RTISLPTSES | LVSFRMNKDP | WTVSIPLGSH | PTTNTETSIP 2220 |
| VNSAGPPGLS | TVASDVIDTP | SDGAESIPTV | SFSPSPDTEV | TTISHFPEKT | THSFRTISSL 2280 |
| THELTSRVTP | IPGDWMSSAM | STKPTGASPS | ITLGERRTIT | SAAPTTSPIV | LTASFTETST 2340 |
| VSLDNETTVK | TSDILDARKT | NELPSDSSSS | SDLINTSIAS | STMDVTKTAS | ISPTSISGMT 2400 |
| ASSSPSLFSS | DRPQVPTSTT | ETNATSPSV | SSNTYSLDGG | SNVGGTPSTL | PPFTITHPVE 2460 |
| TSSALLAWSR | PVRTFSTMVS | TDTASGENPT | SSNSVVTSVP | APGTWTSVGS | TTDLPAMGFL 2520 |
| KTSPAGEAHS | LLASTIEPAT | AFTPHLSAAV | VTGSSATSEA | SLLTTSESKA | IHSSPQTPTT 2580 |
| PTSGANWETS | ATPESLLVVT | ETSDTTLTSK | ILVTDTILFS | TVSTPPSKFP | STGTLSGASF 2640 |
| PTLLPDTPAI | PLTATEPTSS | LATSFDSTPL | VTIASDSLGT | VPETTLTMSE | TSNGDALVLK 2700 |
| TVSNPDRSIP | GITIQGVTES | PLHPSSTSPS | KIVAPRNTTY | EGSITVALST | LPAGTTGSLV 2760 |
| FSQSSENSET | TALVDSSAGL | ERASVMPLTT | GSQGMASSGG | IRSGSTHSTG | TKTFSSLPLT 2820 |
| MNPGEVTAMS | EITTNRLTAT | QSTAPKGIPV | KPTSAESGLL | TPVSASSSPS | KAFASLTTAP 2880 |
| PTWGIPQSTL | TFEFSEVPSL | DTKSASLPTT | GQSLNTIPDS | DASTASSSLS | KSPEKNPRAR 2940 |
| MMTSTKAISA | SSFQSTGFTE | TPEGSASPSM | AGHEPRVPTS | GTGDPRYASE | SMSYPDPSKA 3000 |
| SSAMTSTSLA | SKLTTLFSTG | QAARSGSSSS | PISLSTEKET | SFLSPTASTS | RKTSLFLGPS 3060 |
| MARQPNILVH | LQTSALTLSP | TSTLNMSQEE | PPELTSSQTI | AEEEGTTAET | QTLTFTPSET 3120 |
| PTSLLPVSSP | TEPTARRKSS | PETWASSISV | PAKTSLVETT | DGTLVTTIKM | SSQAAQGNST 3180 |
| WPAPAEETGS | SPAGTSPGSP | EMSTTLKIMS | SKEPSISPEI | RSTVRNSPWK | TPETTVPMET 3240 |
| TVEPVTLQST | ALGSGTSTIS | HLPTGTTSPT | KSPTENMLAT | ERVSLSPSPP | EAWTNLYSGT 3300 |
| PGGTRQSLAT | MSSVSLESPT | ARSITGTGQQ | SSPELVSKTT | GMEFSMWHGS | TGGTTGDTHV 3360 |
| SLSTSSNILE | DPVTSPNSVS | SLTDKSKHKT | ETWVSTTAIP | STVLNNKIMA | AEQQTSRSVD 3420 |
| EAYSSTSSWS | DQTSGSDITL | GASPDVTNTL | YITSTAQTTS | LVSLPSGDQG | ITSLTNPSGG 3480 |
| KTSSASSVTS | PSIGLETLRA | NVSAVKSDIA | PTAGHLSQTS | SPAEVSILDV | TTAPTPGIST 3540 |
| TITTMGTNSI | STTTPNPEVG | MSTMDSTPAT | ERRTTSTEHP | STWSSTAASD | SWTVTDMTSN 3600 |
| LKVARSPGTI | STMHTTSFLA | SSTELDSMST | PHGRITVIGT | SLVTPSSDAS | AVKTETSTSE 3660 |
| RTLSPSDTTA | STPISTFSRV | QRMSISVPDI | LSTSWTPSST | EAEDVPVSMV | STDHASTKTD 3720 |
| PNTPLSTFLF | DSLSTLDWDT | GRSLSSATAT | TSAPQGATTP | QELTLETMIS | PATSQLPFSI 3780 |

| | | | | | |
|---|---|---|---|---|---|
|GHITSAVTPA|AMARSSGGVTF|SRPDPTSKKA|EQTSTQLPTT|TSAHPGQVPR|SAATTLDVIP 3840|
|HTAKTPDATF|QRQGQTALTT|EARATSDSWN|EKEKSTPSAP|WITEMMNSVS|EDTIKEVTSS 3900|
|SSVLRTLNTL|DINLESGTTS|SPSWKSSPYE|RIAPSESTTD|KEAIHPSTNT|VETTGWVTSS 3960|
|EHASHSTIPA|HSASSKLTSP|VVTTSTREQA|IVSMSTTTWP|ESTRARTEPN|SFLTIELRDV 4020|
|SPYMDTSSTT|QTSIISSPGS|TAITKGPRTE|ITSSKRISSS|FLAQSMRSSD|SPSEAITRLS 4080|
|NFPPAMTESGG|MILAMQTSPP|GATSLSAPTL|DTSATASWTG|TPLATTQRFT|YSEKTTLFSK 4140|
|GPEDTSQPSP|PSVEETSSSS|SLVPIHATTS|PSNILLTSQG|HSPSSTPPVT|SVFLSETSGL 4200|
|GKTTDMSRIS|LEPGTSLPPN|LSSTAGEALS|TYEASRDTKA|IHHSADTAVT|NMEATSSEYS 4260|
|PIPGHTKPSK|ATSPLVTSHI|MGDITSSTSV|FGSSETTEIE|TVSSVNQGLQ|ERSTSQVASS 4320|
|ATETSTVITH|VSSGDATTHV|TKTQATFSSG|TSISSPHQFI|TSTNTFTDVS|TNPSTSLIMT 4380|
|ESSGVTITTQ|TGPTGAATQG|PYLLDTSTMP|YLTETPLAVT|PDFMQSEKTT|LISKGPKDVS 4440|
|WTSPPSVAET|SYPSSLTPFL|VTTIPPATST|LQGQHTSSPV|SATSVLTSGL|VKTTDMLNTS 4500|
|MEPVTNSPQN|LNNPSNEILA|TLAATTDIET|IHPSINKAVT|NMGTASSAHV|LHSTLPVSSE 4560|
|PSTATSPMVP|ASSMGDALAS|ISIPGSETTD|IEGEPTSSLT|AGRKENSTLQ|EMNSTTESNI 4620|
|ILSNVSVGAI|TEATKMEVPS|FDATFIPTPA|QSTKFPDIFS|VASSRLSNSP|PMTISTHMTT 4680|
|TQTGSSGATS|KIPLALDTST|LETSAGTPSV|VTEGFAHSKI|TTAMNNDVKD|VSQTNPPFQD 4740|
|EASSPSSQAP|VLVTTLPSSV|AFTPQWHSTS|SPVSMSSVLT|SSLVKTAGKV|DTSLETVTSS 4800|
|PQSMSNTLDD|ISVTSAATTD|IETTHPSINT|VVTNVGTTGS|AFESHSTVSA|YPEPSKVTSP 4860|
|NVTTSTMEDT|TISRSIPKSS|KTTRTETETT|SSLTPKLRET|SISQEITSST|ETSVPYKEL 4920|
|TGATTEVSRT|DVTSSSSTSF|PGPDQSTVSL|DISTETNTRL|STSPIMTESA|EITITTQTGP 4980|
|HGATSQDTFT|MDPSNTTPQA|GIHSAMTHGF|SQLDVTTLMS|RIPQDVSWTS|PPSVDKTSSP 5040|
|SSFLSSPAMT|TPSLISSTLP|EDKLSSPMTS|LLTSGLVKIT|DILRTRLEPV|TSSLPNFSST 5100|
|SDKILATSKD|SKDTKEIFPS|INTEETNVKA|NNSGHESHSP|ALADSETPKA|TTQMVITTTV 5160|
|GDPAPSTSMP|VHGSSETTNI|KREPTYFLTP|RLRETSTSQE|SSFPTDTSFL|LSKVPTGTIT 5220|
|EVSSTGVNSS|SKISTPDHDK|STVPPDTFTG|EIPRVFTSSI|KTKSAEMTIT|TQASPPESAS 5280|
|HSTLPLDTST|TLSQGGTHST|VTQGFPYSEV|TTLMGMGPGN|VSWMTTPPVE|ETSSVSSLMS 5340|
|SPAMTSPSPV|SSTSPQSIPS|SPLPVTALPT|SVLVTTTDVL|GTTSPESVTS|SPPNLSSITH 5400|
|ERPATYKDTA|HTEAAMHHST|NTAVTNVGTS|GSGHKSQSSV|LADSETSKAT|PLMSTTSTLG 5460|
|DTSVSTSTPN|ISQTNQIQTE|PTASLSPRLR|ESSTSEKTSS|TTETNTAFSY|VPTGAITQAS 5520|
|RTEISSSRTS|ISDLDRPTIA|PDISTGMITR|LFTSPIMTKS|AEMVTTQTT|TPGATSQGIL 5580|
|PWDTSTTLFQ|GGTHSTVSQG|FPHSEITTLR|SRTPGDVSWM|TTPPVEETSS|GFSLMSPSMT 5640|
|SPSPVSSTSP|ESIPSSPLPV|TALLTSVLVT|TTNVLGTTSP|EPVTSSPPNL|SSPTQERLTT 5700|
|YKDTAHTEAM|HASMMHTNTAV|ANVGTSISGH|ESQSSVPADS|HTSKATSPMG|ITFAMGDTSV 5760|
|STSTPAFFET|RIQTESTSSL|IPGLRDTRTS|EEINTVTETS|TVLSEVPTTT|TTEVSRTEVI 5820|
|TSSRTTISGP|DHSKMSPYIS|TETITRLSTF|PFVTGSTEMA|ITNQTGPIGT|ISQATLTLDT 5880|
|SSTASWEGTH|SPVTQRFPHS|EETTTMSRST|KGVSWQSPPS|VEETSSPSSP|VPLPAITSHS 5940|
|SLYSAVSGSS|PTSALPVTSL|LTSGRRKTID|MLDTHSELVT|SSLPSASSFS|GEILTSEAST 6000|
|NTETIHFSEN|TAETNMGTTN|SMHKLHSSVS|IHSQPSGHTP|PKVTGSMMED|AIVSTSTPGS 6060|
|PETKNVDRDS|TSPLTPELKE|DSTALVMNST|TESNTVFSSV|SLDAATEVSR|AEVTYYDPTF 6120|
|MPSASAQSTKS|PDISPEASSS|HSNSPPLTIS|THKTIATQTG|PSGVTSLGQL|TLDTSTIATS 6180|
|AGTPSARTQD|FVDSETTSVM|NNDLNDVLKT|SPFSAEEANS|LSSQAPLLVT|TSPSPVTSTL 6240|
|QEHSTSSLVS|VTSVPTPTLA|KITDMDTNLE|PVTRSPQNLR|NTLATSEATT|DTHTMHPSIN 6300|
|TAVANVGTTS|SPNEFYFTVS|PDSDPYKATS|AVVITSTSGD|SIVSTSMPRS|SAMKKIESET 6360|
|TFSLIFRLRE|TSTSQKIGSS|SDTSTVFDKA|FTAATTEVSR|TELTSSSRTS|IQGTEKPTMS 6420|
|PDTSTRSVTM|LSTFAGLTKS|EERTIATQTG|PHRATSQGTL|TWDTSITTSQ|AGTHSAMTHG 6480|
|FSQLDLSTLT|SRVPEYISGT|SPPSVEKTSS|SSSLLLSLPAI|TSPSPVPTTL|PESRPSSPVH 6540|
|LTSLPTSGLV|KTTDMLASVA|SLPPNLGSTS|HKIPTTSEDI|KDTEKMYPST|NIAVTNVGTT 6600|
|TSEKESYSSV|PAYSEPPKVT|SPMVTSFNIR|DTIVSTSMPG|SSEITRIEME|STFSLAHGLK 6660|
|GTSTSQDPIV|STEKSAVLHK|LTTGATETSR|TEVASSRRTS|IPGPDHSTES|PDISTEVIPS 6720|
|LPISLGITES|SNMTIITRTG|PPLGSTSQGT|FTLDTPTTSS|RAGTHSMATQ|EFPHSEMTTV 6780|
|MNKDPEILSW|TIPPSIEKTS|FSSSLMPSPA|MTSPPVSSTL|PKTIHTTPSP|MTSLLTPSLV 6840|
|MTTDTLGTSP|EPTTSSPPNL|SSTSHEILTT|DEDTTAIEAM|HPSTSTAATN|VETTSSGHGS 6900|
|QSSVLADSEK|TKATAPMDTT|STMGHTTVST|SMVSSSETTK|IKRESTYSLT|PGLRETSISQ 6960|
|NASFSTDTSI|VLSEVPTGTT|AEVSRTEVTS|SGRTSIPGPS|QSTVLPEIST|RTMTRLFASP 7020|
|TMTESAEMTI|PTQTGPSGST|SQDTLTLDTS|TTKSQAKTHS|TLTQRFPHSE|MTTLMSRGPG 7080|
|DMSWQSSPSL|ENPSSLPSLL|SLPATTSPPP|ISSTLPVTIS|SSPLPVTSLL|TSSPVTTTDM 7140|
|LHTSPELVTS|SPPKLSHTSD|ERLTTGKDTT|NTEAVHPSTN|TAASNVEIPS|SGHESPSSAL 7200|
|ADSETSKATS|PMFITSTQED|TTVAISTPHF|LETSRIQKES|ISSLSPKLRE|TGSSVETSSA 7260|
|IETSAVLSEV|SIGATTEISR|TEVTSSSRTS|ISGSAESTML|PEISTTRKII|KPPTSPILAE 7320|
|SSEMTIKTQT|SPPGSTSEST|FTLDTSTTPS|LVITHSTMTQ|RLPHSEITTL|VSRGAGDVPR 7380|
|PSSLPVEETS|PPSSQLSLSA|MISPSPVSST|LPASSHSSSA|SVTSLLTPGQ|VKTTEVLDAS 7440|
|AEPETSSPPS|LSSTSVEILA|TSEVTTDTEK|IHPFSNTAVT|KVGTSSSGHE|SPSSVLPDSE 7500|
|TTKATSAMGT|ISIMGDTSVS|TLTPALSNTR|KIQSEPASSL|TTRLRETSTS|EETSLATEAN 7560|
|TVLSKVSTGA|TTEVSRTEAI|SFSRTSMSGP|EQSTMSQDIS|IGTIPRISAS|SVLTESAKMT 7620|
|ITTQTGPSES|TLESTLNLNT|ATTPSWVETH|SIVIQGFPHP|EMTTSMGRGP|GGVSWPSPPF 7680|
|VKETSPPSSP|LSLPAVTSPH|PVSTTFLAHI|PPSPLPVTSL|LTSGPATTTD|ILGTSTEPGT 7740|
|SSSSSLSTTS|HERLTTYKDT|AHTEAVHPST|NTGGTNVATT|SSGYKSQSSV|LADSSPMCTT 7800|
|STMGDTSVLT|STPAFLETRR|IQTELASSLT|PGLRESSGSE|QTSSGTKMST|VLSKVPTGAT 7860|
|TEISKEDVTS|IPGPAQSTIS|PDISTRTVSW|FSTSPVMTES|AEITMNTHTS|PLGATTQGTS 7920|
|TLDTSSTTSL|TMTHSTISQG|FSHSQMSTLM|RRGPEDVSWM|SPPLLEKTRP|SFSLMSSPAT 7980|
|TSPSPVSSTL|PESISSSPLP|VTSLLTSGLA|KTTDMLHKSS|EPVTNSPANL|SSTSVEILAT 8040|
|SEVTTDTEKT|HPSSNRTVTD|VGTSSSGHES|TSFVLADSQT|SKVTSPMVIT|STMEDTSVST 8100|
|STPGFFETSR|IQTEPTSSLT|LGLRKTSSSE|GTSLATEMST|VLSGVPTGAT|AEVSRTEVTS 8160|
|SSRTSISGFA|QLTVSPETST|ETITRLPTSS|IMTESAEMMI|KTQTDPPPEST|PESTHTVDIS 8220|
|TTPNWVETHS|TVTQRFSHSE|MTTLVSRSPG|DMLWPSQSSV|EETSSASSLL|SLPATTSPSP 8280|
|VSSTLVEDFP|SASLPVTSLL|NPGLVITTDR|MGISREPGTS|STSNLSSTSH|ERLTTLEDTV 8340|
|DTEDMQPSTH|TAVTNVRTSI|SGHESQSSVL|SDSETPKATS|PMGTTYTMGE|TSVSISTSDF 8400|
|FETSRIQIEP|TSSLTSGLRE|TSSSERISSA|TEGSTVLSEV|PSGATTEVSR|TEVISSRGTS 8460|
|MSGPDQFTIS|PDISTEAITR|LSTSPIMTES|AESAITIETG|SPGATSEGTL|TLDTSTTTFW 8520|

```
SGTHSTASPG FSHSEMTTLM SRTPGDVPWP SLPSVEEASS VSSSLSSPAM TSTSFFSTLP   8580
ESISSSPHPV TALLTLGPVK TTDMLRTSSE PETSSPPNLS STSAEILATS EVTKDREKIH   8640
PSSNTPVVNV GTVIYKHLSP SSVLADLVTT KPTSPMATTS TLGNTSVSTS TPAFPETMMT   8700
QPTSSLTSGL REISTSQETS SATERSASLS GMPTGATTKV SRTEALSLGR TSTPGPAQST   8760
ISPEISTETI TRISTPLTTT GSAEMTITPK TGHSGASSQG TFTLDTSSRA SWPGTHSAAT   8820
HRSPHSGMTT PMSRGPEDVS WPSRPSVEKT SPPSSLVSLS AVTSPSPLYS TPSESSHSSP   8880
LRVTSLFTPV MMKTTDMLDT SLEPVTTSPP SMNITSDESL ATSKATMETE AIQLSENTAV   8940
TQMGTISARQ EFYSSYPGLP EPSKVTSPVV TSSTIKDIVS TTIPASSEIT RIEMESTSTL   9000
TPTPRETSTS QEIHSATKPS TVPYKALTSA TIEDSMTQVM SSSRGPSPDQ STMSQDISTE   9060
VITRLSTSPI KTESTEMTIT TQTGSPGATS RGTLTLDTST TFMSGTHSTA SQGFSHSQMT   9120
ALMSRTPGDV PWLSHPSVEE ASSASFSLSS PVMTSSSPVS STLPDSIHSS SLPVTSLLTS   9180
GLVKTTELLG TSSEPETSSP PNLSSTSAEI LAITEVTTDT EKLEMTNVVT SGYTHESPSS   9240
VLADSVTTKA TSSMGITYPT GDTNVLTSTP AFSDTSRIQT KSKLSLTPGL METSISEETS   9300
SATEKSTVLS SVPTGATTEV SRTEAISSSR TSIPGPAQST MSSDTSMETI TRISTPLTRK   9360
ESTDMAITPK TGPSGATSQG TFTLDSSSTA SWPGTHSATT QRFPQSVVTT PMSRGPEDVS   9420
WPSPLSVEKN SPPSSLVSSS SVTSPSPLYS TPSGSSHSSP VPVTSLFTSI MMKATDMLDA   9480
SLEPETTSAP NMNITSDESL AASKATTETE AIHVFENTAA SHVETTSATE ELYSSSPGFS   9540
EPTKVISPVV TSSSIRDNMV STTMPGSSGI TRIEIESMSS LTPGLRETRT SQDITSSTET   9600
STVLYKMPSG ATPEVSRTEV MPSSRTSIPG PAQSTMSLDI SDEVVTRLST SPIMTESAEI   9660
TITTTQTGYSL ATSQVTLPLG TSMTFLSGTH STMSQGLSHS EMTNLMSRGP ESLSWTSPRF   9720
VETTRSSSSL TSLPLTTSLS PVSSTLLDSS PSSPLPVTSL ILPGLVKTTE VLDTSSEPKT   9780
SSSPNLSSTS VEIPATSEIM TDTEKIHPSS NTAVAKVRTS SSVHESHSSV LADSETTITI   9840
PSMGITSAVD DTTVFTSNPA FSETRRIPTE PTFSLTPGFR ETSTSEETTS ITETSAVLYG   9900
VPTSATTEVS MTEIMSSNRI HIPDSDQSTM SPDIITEVIT RLSSSSMMSE STQMTITTQK   9960
SSPGATAQST LTLATTTAPL ARTHSTVPPR FLHSEMTTLM SRSPENPSWK SSLFVEKTSS  10020
SSSLLSLPVT TSPSVSSTLP QSIPSSSFSV TSLLTPGMVK TTDTSTEPGT SLSPNLSGTS  10080
VEILAASEVT TDTEKIHPSS SMAVTNVGTT SSGHELYSSV SIHSEPSKAT YPVGTPSSMA  10140
ETSISTSMPA NFETTGFEAE PFSHLTSGFR KTNMSLDTSS VTPTNTPSSP GSTHLLQSSK  10200
TDFTSSAKTS SPDWPPASQY TEIPVDIITP FNASPSITES TGITSFPESR FTMSVTESTH  10260
HLSTDLLPSA ETISTGTVMP SLSEAMTSFA TTGVPRAISG SGSPFSRTES GPGDATLSTI  10320
AESLPSSTPV PFSSSTFTTT DSSTIPALHE ITSSSATPYR VDTSLGTESS TTEGRLVMVS  10380
TLDTSSQPGR TSSSPILDTR MTESVELGTV TSAYQVPSLS TRLTRTDGIM EHITKIPNEA  10440
AHRGTIRPVK GPQTSTSPAS PKGLHTGGTK RMETTTTALK TTTTALKTTS RATLTTSVYT  10500
PTLGTLTPLN ASMQMASTIP TEMMITTPYV FPDVPETTSS LATSLGAETS TALPRTTPSV  10560
FNRESETTAS LVSRSGAERS PVIQTLDVSS SEPDTTASWV IHPAETIPTV SKTTPNFFHS  10620
ELDTVSSTAT SHGADVSSAI PTNISPSELD ALTPLVTISG TDTSTTFPTL TKSPHETETR  10680
TTWLTHPAET SSTIPRTIPN FSHHESDATP SIATSPGAET SSAIPIMTVS PGAEDLVTSQ  10740
VTSSGTDRNM TIPTLTLSPG EPKTIASLVT HPEAQTSSAI PTSTISPAVS RLVTSMVTSL  10800
AAKTSTTNRA LTNSPGEPAT TVSLVTHPAQ TSPTVPWTTS IFFHSKSDTT PSMTTSHGAE  10860
SSSAVPTPTV STEVPGVVTP LVTSSRAVIS TTIPILTLSP GEPETTPSMA TSHGEEASSA  10920
IPTPTVSPGV PGVVTSLVTS SRAVTSTTIP ILTFSLGEPE TTPSMATSHG TEAGSAVPTV  10980
LPEVPGMVTS LVASSRAVTS TTLPTLTLSP GEPETTPSMA TSHGAEASST VPTVSPEVPG  11040
VVTSLVTSSS GVNSTSIPTL ILSPGELETT PSMATSHGAE ASSAVPTPTV SPGVSGVVTP  11100
LVTSSRAVTS TTIPILTLSS SEPETTPSMA TSHGVEASSA VLTVSPEVPG MVTSLVTSSR  11160
AVTSTTIPTL TISSDEPETT TSLVTHSEAK MISAIPTLAV SPTVQGLVTS LVTSSGSETS  11220
AFSNLTVASS QPETIDSWVA HPGTEASSVV PTLTVSTGEP FTNISLVTHP AESSSTLPRT  11280
TSRFSHSELD TMPSTVTSPE AESSSAISTT ISPGIPGPVT LVTSSGRDI SATFPTVPES  11340
PHESEATASW VTHPAVTSTT VPRTTPNYSH SEPDTTPSIA TSPGAEATSD FPTITVSPDV  11400
PDMVTSQVTS SGTDTSITIP TLTLSSGEPE TTTSFITYSE THTSSAIPTL PVSPGASKML  11460
TSLVISSGTD STTTFPTLTE TPYEPETTAI QLIHPAETNT MVPRTTPKFS HSKSDTTLPV  11520
AITSPGPEAS SAVSTTTISP DMSDLVTSLV PSSGTDTSLV FPTLSETPYE PETTATWLTH  11580
PAETSTTVSG TIPNFSHRGS DTAPSMVTSP GVDTRSGVPT TIIPPSIPGV VTSQVTSSAT  11640
DTSTAIPTLT PSPGEPETTA SSATHPGTQT GFTVPIRTVP SSEPDTMASW VTHPPQTSTP  11700
VSRTTSSFSH SSPDATPVMA TSPRTEASSA VLTTISPGAP EMVTSQITSS GAATSTTVPT  11760
LTHSPGMPET TALLSTHPRT ETSKTFPAST VFPQVSETTA SLTIRPGAET STALPTQTTS  11820
SLFTLLVTGT SRVDLSPTAS PGVSAKTAPL STHPGTETST MIPTSTLSLG LLETTGLLAT  11880
SSSAETSTST LTLTVSPAVS GLSSASITTD KPQTVTSWNT ETSPSVTSVG PPEFSRTVTG  11940
TTMTLIPSEM PTPPKTSHGE GVSPTTILRT TMVEATNLAT TGSSPTVAKT TTTFNTLAGS  12000
LFTPLTTPGM STLASESVTS RTSYNHRSWI STTSSYNRRY WTPATSTPVT STFSPGISTS  12060
SIPSSTAATV PFMVPFTLNF TITNLQYEED MRHPGSRKFN ATERELQGLL KPLFRNSSLE  12120
YLYSGCRLAS LRPEKDSSAT AVDAICTHRP DPEDLGLDRE RLYWELSNLT NGIQELGPYT  12180
LDRNSLYVNG FTHRSSMPTT STPGTSTVDV GTSGTPSSSP SPTTAGPLLM PFTLNFTITN  12240
LQYEEDMRRT GSRKFNTMES VLQGLLKPLF KNTSVGPLYS GCRLTLLRPE KDGAATGVDA  12300
ICTHRLDPKS PGLNREQLYW ELSKLTNDIE ELGPYTLDRN SLYVNGFTHQ SSVSTTSTPG  12360
TSTVDLRTSG TPSSLSSPTI MAAGPLLVPF TLNFTITNLQ YGEDMGHPGS RKFNTTERVL  12420
QGLLGPIFKN TSVGPLYSGC RLTSLRSEKD GAATGVDAIC IHHLDPKSPG LNRERLYWEL  12480
SQLTNGIKEL GPYTLDRNSL YVNGFTHRTS VPTSSTPGTS TVDLGTSGTP FSLPSPATAG  12540
PLLVPFTLNF TITNLKYEED MHRPGSRKFN TTERVLQTLL GPMFKNTSVG LLYSGCRLTL  12600
LRSEKDGAAT GVDAICTHRL DPKSPGVDRE QLYWELSQLT NGIKELGPYT LDRNSLYVNG  12660
FTHWIPVPTS STPGTSTVDL GSGTPSSLPS PTTAGPLLVP FTLNFTITNL KYEEDMHCPG  12720
SRKFNTTERV LQSLLGPMFK NTSVGPLYSG CRLTLLRSEK DGAATGVDAI CTHRLDPKSP  12780
GVDREQLYWE LSQLTNGIKE LGPYTLDRNS LYVNGFTHQT SAPNTSTPGT STVDLGTSGT  12840
PSSLPSPTSA GPLLVPFTLN FTITNLQYEE DMHHPGSRKF NTTERVLQGL LGPMFKNTSV  12900
GLLYSGCRLT LLRPEKNGAA TGMDAICSHR LDPKSPGLNR EQLYWELSQL THGIKELGPY  12960
TLDRNSLYVN GFTHRSSVAP TSTPGTSTVD LGTSGTPSSL PSPTTAVPLL VPFTLNFTIT  13020
NLQYGEDMRH PGSRKFNTTE RVLQGLLGPL FKNSSVGPLY SGCRLISLRS EKDGAATGVD  13080
AICTHHLNPQ SPGLDREQLY WQLSQMTNGI KELGPYTLDR NSLYVNGFTH RSSGLTTSTP  13140
WTSTVDLGTS GTPSPVPSPT TTGPLLVPFT LNFTITNLQY EENMGHPGSR KFNITESVLQ  13200
GLLKPLFKST SVGPLYSGCR LTLLRPEKDG VATRVDAICT HRPDPKIPGL DRQQLYWELS  13260
```

```
QLTHSITELG PYTLDRDSLY VNGFTQRSSV PTTSTPGTFT VQPETSETPS SLPGPTATGP   13320
VLLPFTLNFT ITNLQYEEDM RRPGSRKFNT TERVLQGLLM PLFKNTSVSS LYSGCRLTLL   13380
RPEKDGAATR VDAVCTHRPD PKSPGLDRER LYWKLSQLTH GITELGPYTL DRHSLYVNGF   13440
THQSSMTTTR TPDTSTMHLA TSRTPASLSG PMTASPLLVL FTINFTITNL RYEENMHHPG   13500
SRKFNTTERV LQGLLRPVFK NTSVGPLYSG CRLTLLRPKK DGAATKVDAI CTYRPDPKSP   13560
GLDREQLYWE LSQLTHSITE LGPYTLDRDS LYVNGFTQRS SVPTTSIPGT PTVDLGTSGT   13620
PVSKPGPSAA SPLLVLFTLN FTITNLRYEE NMQHPGSRKF NTTERVLQGL LRSLFKSTSV   13680
GPLYSGCRLT LLRPEKDGTA TGVDAICTHH PDPKSPRLDR EQLYWELSQL THNITELGPY   13740
ALDNDSLFVN GFTHRSSVST TSTPGTPTVY LGASKTPASI FGPSAASHLL ILFTLNFTIT   13800
NLRYEENMWP GSRKFNTTER VLQGLLRPLF KNTSVGPLYS GCRLTLLRPE KDGEATGVDA   13860
ICTHRPDPTG PGLDREQLYL ELSQLTHSIT ELGPYTLDRD SLYVNGFTHR SSVPTTSTGV   13920
VSEEPFTLNF TINNLRYMAD MGQPGSLKFN ITDNVMQHLL SPLFQRSSLG ARYTGCRVIA   13980
LRSVKNGAET RVDLLCTYLQ PLSGPGLPIK QVFHELSQQT HGITRLGPYS LDKDSLYLNG   14040
YNEPGPDEPP TTPKPATTFL PPLSEATTAM GYHLKTLTLN FTISNLQYSP DMGKGSATFN   14100
STEGVLQHLL RPLFQKSSMG PFYLGCQLIS LRPEKDGAAT GVDTTCTYHP DPVGPGLDIQ   14160
QLYWELSQLT HGVTQLGFYV LDRDSLFING YAPQNLSIRG EYQINFHIVN WNLSNPDPTS   14220
SEYITLLRDI QDKVTTLYKG SQLHDTFRFC LVTNLTMDSV LVTVKALFSS NLDPSLVEQV   14280
FLDKTLNASF HWLGSTYQLV DIHVTEMESS VYQPTSSSST QHFYLNFTIT NLPYSQDKAQ   14340
PGTTNYQRNK RNIEDALNQL FRNSSIKSYF SDCQVSTFRS VPNRHHTGVD SLCNFSPLAR   14400
RVDRVAIYEE FLRMTRNGTQ LQNFTLDRSS VLVDGYSPNR NEPLTGNSDL PFWAVILIGL   14460
AGLLGVITCL ICGVLVTTRR RKKEGEYNVQ QQCPGYYQSH LDLEDLQ                14507

SEQ ID NO: 7           moltype = AA  length = 267
FEATURE                Location/Qualifiers
source                 1..267
                       mol_type = protein
                       organism = Homo sapiens
SEQUENCE: 7
MMSSKPTSHA EVNETIPNPY PPSSFMAPGF QQPLGSINLE NQAQGAQRAQ PYGITSPGIF    60
ASSQPGQGNI QMINPSVGTA VMNFKEEAKA LGVIQIMVGL MHIGFGIVLC LISFSFREVL   120
GFASTAVIGG YPFWGGLSFI ISGSLSVSAS KELSRCLVKG SLGMNIVSSI LAFIGVILLL   180
VDMCINGVAG QDYWAVLSGK GISATLMIFS LLEFFVACAT AHFANQANTT TNMSVLVIPN   240
MYESNPVTPA SSSAPPRCNN YSANAPK                                      267

SEQ ID NO: 8           moltype = AA  length = 535
FEATURE                Location/Qualifiers
source                 1..535
                       mol_type = protein
                       organism = Homo sapiens
SEQUENCE: 8
MLGPCMLLLL LLLGLRLQLS LGIIPVEEEN PDFWNREAAE ALGAAKKLQP AQTAAKNLII    60
FLGDGMGVST VTAARILKGQ KKDKLGPEIP LAMDRFPYVA LSKTYNVDKH VPDSGATATA   120
YLCGVKGNFQ TIGLSAAARF NQCNTTRGNE VISVMNRAKK AGKSVGVVTT TRVQHASPAG   180
TYAHTVNRNW YSDADVPASA RQEGCQDIAT QLISNMDIDV ILGGGRKYMF RMGTPDPEYP   240
DDYSQGGTRL DGKNLVQEWL AKRQGARYVW NRTELMQASL DPSVTHLMGL FEPGDMKYEI   300
HRDSTLDPSL MEMTEAALRL LSRNPRGFFL FVEGGRIDHG HHESRAYRAL TETIMFDDAI   360
ERAGQLTSEE DTLSLVTADH SHVFSFGGYP LRGSSIFGLA PGKARDRKAY TVLLYGNGPG   420
YVLKDGARPD VTESESGSPE YRQQSAVPLD EETHAGEDVA VFARGPQAHL VHGVQEQTFI   480
AHVMAFAACL EPYTACDLAP PAGTTDAAHP GRSVVPALLP LLAGTLLLLE TATAP        535

SEQ ID NO: 9           moltype = AA  length = 520
FEATURE                Location/Qualifiers
source                 1..520
                       mol_type = protein
                       organism = Homo sapiens
SEQUENCE: 9
MEFHNGGHVS GIGGFLVSLT SRMKPHTLAV TPALIFAITV ATIGSFQFGY NTGVINAPET    60
IIKEFINKTL TDKANAPPSE VLLTNLWSLS VAIFSVGGMI GSFSVGLFVN RFGRRNSMLI   120
VNLLAATGGC LMGLCKIAES VEMLILGRLV IGLFCGLCTG FVPMYIGEIS PTALRGAFGT   180
LNQLGIVIGI LVAQIFGLEL ILGSEELWPL LLGFTILPAI LQSAALPCCP ESPRFLLINR   240
KKEENATRIL QRLWGTQDVS QDIQEMKDES ARMSQEKQVT VLELFRVSSY RQPIIISIVL   300
QLSQQLSGIN AVFYYSTGIF KDAGVQQPIY ATISAGVVNT IFTLLSLFLV ERAGRRTLHM   360
IGLGGMAFCS TLMTVSLLLK NHYNGMSFVC IGAILVFVAC FEIGPGPIPW FIVAELFSQG   420
PRPAAMAVAG CSNWTSNFLV GLLFPSAAYY LGAYVFIIFT GFLITFLAFT FFKVPETRGR   480
TFEDITRAFE GQAHGADRSG KDGVMGMNSI EPAKETTTNV                        520

SEQ ID NO: 10          moltype = AA  length = 221
FEATURE                Location/Qualifiers
source                 1..221
                       mol_type = protein
                       organism = Homo sapiens
SEQUENCE: 10
MLTLEDKDMK GFSWAIVPAL TSLGYLIILV VSIFPPFWVRL TNEESHEVFF SGLFENCFNA    60
KCWKPRPLSI YIILGRVFLL SAVFLAFVTT FIMMPFASEF FPRTWKQNFV LACISFFTGA   120
CAFLALVLHA LEIKALRMKL GPLQFSVLWP YYVLGFGIFL FIVAGTICLI QEMVCPCWHL   180
LSTSQSMEED HGSLYLDNLE SLGGEPSSVQ KETQVTAETV I                      221

SEQ ID NO: 11          moltype = AA  length = 538
FEATURE                Location/Qualifiers
```

```
source                  1..538
                        mol_type = protein
                        organism = Homo sapiens
SEQUENCE: 11
MGLLLLVLIL TPSLAAYRHP DFPLLEKAQQ LLQSTGSPYS TNCWLCTSSS TETPGTAYPA    60
SPREWTSIEA ELHISYRWDP NLKGLMRPAN SLLSTVKQDF PDIRQKPPIF GPIFTNINLM   120
GIAPICVMAK RKNGTNVGTL PSTVCNVTFT VDSNQQTYQT YTHNQFRHQP RFPKPPNITF   180
PQGTLLDKSS RFCQGRPSSC STRNFWFRPA DYNQCLQISN LSSTAEWVLL DQTRNSLFWE   240
NKTKGANQSQ TPCVQVLAGM TIATSYLGIS AVSEFFGTSL TPLFHFHIST CLKTQGAFYI   300
CGQSIHQCLP SNWTGTCTIG YVTPDIFIAP GNLSLPIPIY GNSPLPRVRR AIHFIPLLAG   360
LGILAGTGTG IAGITKASLT YSQLSKEIAN NIDTMAKALT TMQEQIDSLA AVVLQNRRGL   420
DMLTAAQGGI CLALDEKCCF WVNQSGKVQD NIRQLLNQAS SLRERATQGW LNWEGTWKWF   480
SWVLPLTGPL VSLLLLLLFG PCLLNLITQF VSSRLQAIKL QTNLSAGRHP RNIQESPF    538

SEQ ID NO: 12           moltype = AA  length = 1017
FEATURE                 Location/Qualifiers
source                  1..1017
                        mol_type = protein
                        organism = Homo sapiens
SEQUENCE: 12
MVFSVRQCGH VGRTEEVLLT FKIFLVIICL HVVLVTSLEE DTDNSSLSPP PAKLSVVSFA    60
PSSNGTPEVE TTSLNDVTLS LLPSNETEKT KITIVKTFNA SGVKPQRNIC NLSSICNDSA   120
FFRGEIMFQY DKESTVPQNQ HITNGTLTGV LSLSELKRSE LNKTLQTLSE TYFIMCATAE   180
AQSTLNCTFT IKLNNTMNAC AVIAALERVK IRPMEHCCCS VRIPCPSSPE ELEKLQCDLQ   240
DPIVCLADHP RGPPFSSSQS IPVVPRATVL SQVPKATSFA EPPDYSPVTH NVPSPIGEIQ   300
PLSPQPSAPI ASSPAIDMPP QSETISSPMP QTHVSGTPPP VKASFSSPTV SAPANVNTTS   360
APPVQTDIVN TSSISDLENQ VLQMEKALSL GSLEPNLAGE MINQVSRLLH SPPDMLAPLA   420
QRLLKVVDDI GLQLNFSNTT ISLTSPSLAL AVIRVNASSF NTTTFVAQDP ANLQVSLETQ   480
APENSIGTIT LPSSSLMNNLP AHDMELASRV QFNFFETPAL FQDPSLENLS LISYVISSSV   540
ANLTVRNLTR NVTVTLKHIN PSQDELTVRC VFWDLGRNGG RGGWSDNGCS VKDRRLNETI   600
CTCSHLTSFG VLLDLSRTSV LPAQMMALTF ITYIGCGLSS IFLSVTLVTY IAFEKIRRDY   660
PSKILIQLCA ALLLLNLVFL LDSWIALYKM QGLCISVAVF LHYFLLVSFT WMGLEAFHMY   720
LALVKVFNTY IRKYILKFCI VGWGVPAVVV TIILTISPDN YGLGSYGKFP NGSPDDFCWI   780
NNNAVFYITV VGYFCVIFLL NVSMFIVVLV QLCRIKKKKQ LGAQRKTSIQ DLRSIAGLTF   840
LLGITWGFAF FAWGPVNVTF MYLFAIFNTL QGFFIFIFYC VAKENVRKQW RRYLCCGKLR   900
LAENSDWSKT ATNGLKKQTV NQGVSSSSNS LQSSSNSTNS TTLLVNNDCS VHASGNGNAS   960
TERNGVSFSV QNGDVCLHDF TGKQHMFNEK EDSCNGKGRM ALRRTSKRGS LHFIEQM    1017

SEQ ID NO: 13           moltype = AA  length = 775
FEATURE                 Location/Qualifiers
source                  1..775
                        mol_type = protein
                        organism = Homo sapiens
SEQUENCE: 13
MEPPYSLTAH YDEFQEVKYV SRCGAGGARG ASLPPGFPLG AARSATGARS GLPRWNRREV    60
CLLSGLVFAA GLCAILAAML ALKYLGPVAA GGGACPEGCP ERKAFARAAR FLAANLDASI   120
DPCQDFYSFA CGGWLRRHAI PDDKLTYGTI AAIGEQNEER LRRLLARPGG GPGGAAQRKV   180
RAFFRSCLDM REIERLGPRP MLEVIEDCGG WDLGGAEERP GVAARWDLNR LLYKAQGVYS   240
AAALFSLTVS LDDRNSSRYV IRIDQDGLTL PERTLYLAQD EDSEKILAAY RVFMERVLSL   300
LGADAVEQKA QEILQVEQQL ANITVSEHDD LRRDVSSMYN KVTLGQLQKI TPHLRWKWLL   360
DQIFQEDFSE EEEVVLLATD YMQQVSQLIR STPHRVLHNY LVWRVVVVLS EHLSPPFREA   420
LHELAQEMEG SDKPQELARV CLGQANRHFG MALGALFVHE HFSAASKAKV QQLVEDIKYI   480
LGQRLEELDW MDAETRAAAR AKLQYMMVMV GYPDFLLKPD AVDKEYEFEV HEKTYFKNIL   540
NSIRFSIQLS VKKIRQEVDK STWLLPPQAL NAYYLPNKNQ MVFPAGILQP TLYDPDFPQS   600
LNYGGIGTII GHELTHGYDD WGGQYDRSGN LLHWWTEASY SRFLRKAECI VRLYDNFTYY   660
NQRVNGKHTL GENIADMGGL KLAYHAYQKW VREHGPEHPL PRLKYTHDQL FFIAFAQNWC   720
IKRRSQSIYL QVLTDKHAPE HYRVLGSVSQ FEEFGRAFHC PKDSPMNPAH KCSVW       775

SEQ ID NO: 14           moltype = AA  length = 529
FEATURE                 Location/Qualifiers
source                  1..529
                        mol_type = protein
                        organism = Homo sapiens
SEQUENCE: 14
MGPSCPVFLS FTKLSLWWLL LTPAGGEEAK RPPPRAPGDP LSSPSPTALP QGGSHTETED    60
RLFKHLFRGY NRWARPVPNT SDVVIVRFGL SIAQLIDVDE KNQMMTTNVW LKQEWSDYKL   120
RWNPTDFGNI TSLRVPSEMI WIPDIVLYNN ADGEFAVTHM TKAHLFSTGT VHWVPPAIYK   180
SSCSIDVTFF PFDQQNCKMK FGSWTYDKAK IDLEQMEQTV DLKDYWESGE WAIVNATGTY   240
NSKKYDCCAE IYPDVTYAFV IRRLPLFYTI NLIIPCLLIS CLTVLVFYLP SDCGEKITLC   300
ISVLLSLTVF LLLITEIIPS TSLVIPLIGE YLLFTMIFVT LSIVITVFVL NVHHRSPSTH   360
TMPHWVRGAL LGCVPRWLLM NRPPPPVELC HPLRLKLSPS YHWLESNVDA EEREVVVEEE   420
DRWACAGHVA PSVGTLCSHG HLHSGASGPK AEALLQEGEL LLSPHMQKAL EGVHYIADHL   480
RSEDADSSVK EDWKYVAMVI DRIFLWLFII VCFLGTIGLF LPPFLAGMI             529

SEQ ID NO: 15           moltype = AA  length = 537
FEATURE                 Location/Qualifiers
source                  1..537
                        mol_type = protein
                        organism = Homo sapiens
```

```
SEQUENCE: 15
MPHLMERMVG SGLLWLALVS CILTQASAVQ RGYGNPIEAS SYGLDLDCGA PGTPEAHVCF    60
DPCQNYTLLD EPFRSTENSA GSQGCDKNMS GWYRFVGEGG VRMSETCVQV HRCQTDAPMW   120
LNGTHPALGD GITNHTACAH WSGNCCFWKT EVLVKACPGG YHVYRLEGTP WCNLRYCTVP   180
RDPSTVEDKC EKACRPEEEC LALNSTWGCF CRQDLNSSDV HSLQPQLDCG PREIKVKVDK   240
CLLGGLGLGE EVIAYLRDPN CSSILQTEER NWVSVTSPVQ ASACRNILER NQTHAIYKNT   300
LSLVNDFIIR DTILNINFQC AYPLDMKVSL QAALQPIVSS LNVSVDGNGE FIVRMALFQD   360
QNYTNPYEGD AVELSVESVL YVGAILEQGD TSRFNLVLRN CYATPTEDKA DLVKYFIIRN   420
SCSNQRDSTI HVEENGQSSE SRFSVQMFMF AGHYDLVFLH CEIHLCDSLN EQCQPSCSRS   480
QVRSEVPAID LARVLDLGPI TRRGAQSPGV MNGTPSTAGF LVAWPMVLLT VLLAWLF     537

SEQ ID NO: 16              moltype = AA  length = 426
FEATURE                    Location/Qualifiers
source                     1..426
                           mol_type = protein
                           organism = Homo sapiens
SEQUENCE: 16
MGPLPAPSCT QRITWKGLLL TASLLNFWNP PTTAEVTIEA QPPKVSEGKD VLLLVHNLPQ    60
NLPGYFWYKG EMTDLYHYII SYIVDGKIII YGPAYSGRET VYSNASLLIQ NVTRKDAGTY   120
TLHIIKRGDE TREEIRHFTF TLYLETPKPY ISSSNLNPRE AMEAVRLICD PETLDASYLW   180
WMNGQSLPVT HRLQLSKTNR TLYLFGVTKY IAGPYECEIR NPVSASRSDP VTLNLLPKLP   240
IPYITINNLN PRENKDVLAF TCEPKSENYT YIWWLNGQSL PVSPGVKRPI ENRILILPSV   300
TRNETGPYQC EIRDRYGGLR SNPVILNVLY GPDLPRIYPS FTYYRSGENL DLSCFTESNP   360
PAEYFWTING KFQQSGQKLF IPQITRNHSG LYACSVHNSA TGKEISKSMT VKVSGPCHGD   420
LTESQS                                                              426

SEQ ID NO: 17              moltype = AA  length = 328
FEATURE                    Location/Qualifiers
source                     1..328
                           mol_type = protein
                           organism = Homo sapiens
SEQUENCE: 17
MEKSIWLLAC LAWVLPTGSF VRTKIDTTEN LLNTEVHSSP AQRWSMQVPP EVSAEAGDAA    60
VLPCTFTHPH RHYDGPLTAI WRAGEPYAGP QVFRCAAARG SELCQTALSL HGRFRLLGNP   120
RRNDLSLRVE RLALADDRRY FCRVEFAGDV HDRYESRHGV RLHVTAAPRI VNISVLPSPA   180
HAFRALCTAE GEPPPALAWS GPALGNSLAA VRSPREGHGH LVTAELPALT HDGRYTCTAA   240
NSLGRSEASV YLFRFHGASG ASTVALLLGA LGFKALLLLG VLAARAARRR PEHLDTPDTP   300
PRSQAQESNY ENLSQMNPRS PPATMCSP                                      328

SEQ ID NO: 18              moltype = AA  length = 620
FEATURE                    Location/Qualifiers
source                     1..620
                           mol_type = protein
                           organism = Homo sapiens
SEQUENCE: 18
MSKSKCSVGL MSSVVAPAKE PNAVGPKEVE LILVKEQNGV QLTSSTLTNP RQSPVEAQDR    60
ETWGKKIDFL LSVIGFAVDL ANVWRFPYLC YKNGGGAFLV PYLLFMVIAG MPLFYMELAL   120
GQFNREGAAG VWKICPILKG VGFTVILISL YVGFFYNVII AWALHYLFSS FTTELPWIHC   180
NNSWNSPNCS DAHPGDSSGD SSGLNDTFGT TPAAEYFERG VLHLHQSHGI DDLGPPRWQL   240
TACLVLVIVL LYFSLWKGVK TSGKVVWITA TMPYVVLTAL LLRGVTLPGA IDGIRAYLSV   300
DFYRLCAGDL LYLFLCMAV WIDAATQVCF SLGVGFGVLI AFSSYNKFTN NCYRDAIVTT SINSLTSFSS   360
GFVVFSFLGY MAQKHSVPIG DVAKDGPGLI FIIYPEAIAT LPLSSAWAVV FFIMLLTLGI   420
DSAMGGMESV ITGLIDEFQL LHRHRELFTL FIVLATFLLS LFCVTNGGIY VFTLLDHFAA   480
GTSILFGVLI EAIGVAWFYG VGQFSDDIQQ MTGQRPSLYW RLCWKLVSPC FLLFVVVSI   540
VTFRPPHYGA YIFPDWANAL GWVIATSSMA MVPIYAAYKF CSLPGSFREK LAYAIAPEKD   600
RELVDRGEVR QFTLRHWLKV                                               620

SEQ ID NO: 19              moltype = AA  length = 398
FEATURE                    Location/Qualifiers
source                     1..398
                           mol_type = protein
                           organism = Homo sapiens
SEQUENCE: 19
MHTVATSGPN ASWGAPANAS GCPGCGANAS DGPVPSPRAV DAWLVPLFFA ALMLLGLVGN    60
SLVIYVICRH KPMRTVTNFY IANLAATDVT FLLCCVPFTA LLYPLPGWVL GDFMCKFVNY   120
IQQVSVQATC ATLTAMSVDR WYVTVFPLRA LHRRTPRLAL AVSLSIWVGS AAVSAPVLAL   180
HRLSPGPRAY CSEAFPSRAL ERAFALYNLL ALYLLPLLAT CACYAAMLRH LGRVAVRPAP   240
ADSALQGQVL AERAGAVRAK VSRLVAAVVL LFAACWGPIQ LFLVLQALGP AGSWHPRSYA   300
AYALKTWAHC MSYSNSALNP LLYAFLGSHF RQAFRRVCPC APRRPRRPRR PGPSDPAAPH   360
AELLRLGSHP APARAQKPGS SGLAARGLCV LGEDNAPL                           398

SEQ ID NO: 20              moltype = AA  length = 431
FEATURE                    Location/Qualifiers
source                     1..431
                           mol_type = protein
                           organism = Homo sapiens
SEQUENCE: 20
MQALNITPEQ FSRLLRDHNL TREQFIALYR LRPLVYTPEL PGRAKLALVL TGVLIFALAL    60
FGNALVFYVV TRSKAMRTVT NIFICSLALS DLLITFFCIP VTMLQNISDN WLGGAFICKM   120
```

```
VPFVQSTAVV TEILTMTCIA VERHQGLVHP FKMKWQYTNR RAFTMLGVVW LVAVIVGSPM    180
WHVQQLEIKY DFLYEKEHIC CLEEWTSPVH QKIYTTFILV ILFLLPLMVM LILYSKIGYE    240
LWIKKRVGDG SVLRTIHGKE MSKIARKKKR AVIMMVTVVA LFAVCWAPFH VVHMMIEYSN    300
FEKEYDDVTI KMIFAIVQII GFSNSICNPI VYAFMNENFK KNVLSAVCYC IVNKTFSPAQ    360
RHGNSGITMM RKKAKFSLRE NPVEETKGEA FSDGNIEVKL CEQTEEKKKL KRHLALFRSE    420
LAENSPLDSG H                                                        431

SEQ ID NO: 21               moltype = AA   length = 335
FEATURE                     Location/Qualifiers
source                      1..335
                            mol_type = protein
                            organism = Homo sapiens
SEQUENCE: 21
MESSFSFGVI LAVLASLIIA TNTLVAVAVL LLIHKNDGVS LCFTLNLAVA DTLIGVAISG     60
LLTDQLSSPS RPTQKTLCSL RMAFVTSSAA ASVLTVMLIT FDRYLAIKQP FRYLKIMSGF    120
VAGACIAGLW LVSYLIGFLP LGIPMFQQTA YKGQCSFFAV FHPHFVLTLS CVGFFPAMLL    180
FVFFYCDMLK IASMHSQQIR KMEHAGAMAG GYRSPRTPSD FKALRTVSVL IGSFALSWTP    240
FLITGIVQVA CQECHLYLVL ERYLWLLGVG NSLLNPLIYA YWQKEVRLQL YHMALGVKKV    300
LTSFLLFLSA RNCGPERPRE SSCHIVTISS SEFDG                               335

SEQ ID NO: 22               moltype = AA   length = 220
FEATURE                     Location/Qualifiers
source                      1..220
                            mol_type = protein
                            organism = Homo sapiens
SEQUENCE: 22
MASAGMQILG VVLTLLGWVN GLVSCALPMW KVTAFIGNSI VVAQVVWEGL WMSCVVQSTG     60
QMQCKVYDSL LALPQDLQAA RALCVIALLV ALFGLLVYLA GAKCTTCVEE KDSKARLVLT    120
SGIVFVISGV LTLIPVCWTA HAIIRDFYNP LVAEAQKREL GASLYLGWAA SGLLLLGGGL    180
LCCTCPSGGS QGPSHYMARY STSAPAISRG PSEYPTKNYV                          220

SEQ ID NO: 23               moltype = AA   length = 21
FEATURE                     Location/Qualifiers
source                      1..21
                            mol_type = protein
                            organism = synthetic construct
SEQUENCE: 23
MALPVTALLL PLALLLHAAR P                                               21

SEQ ID NO: 24               moltype = AA   length = 15
FEATURE                     Location/Qualifiers
source                      1..15
                            mol_type = protein
                            organism = synthetic construct
SEQUENCE: 24
GGGGSGGGGS GGGGS                                                      15

SEQ ID NO: 25               moltype = AA   length = 45
FEATURE                     Location/Qualifiers
source                      1..45
                            mol_type = protein
                            organism = synthetic construct
SEQUENCE: 25
TTTPAPRPPT PAPTIASQPL SLRPEACRPA AGGAVHTRGL DFACD                     45

SEQ ID NO: 26               moltype = AA   length = 23
FEATURE                     Location/Qualifiers
source                      1..23
                            mol_type = protein
                            organism = synthetic construct
SEQUENCE: 26
YIWAPLAGTC GVLLLSLVIT LYC                                             23

SEQ ID NO: 27               moltype = AA   length = 42
FEATURE                     Location/Qualifiers
source                      1..42
                            mol_type = protein
                            organism = synthetic construct
SEQUENCE: 27
KRGRKKLLYI FKQPFMRPVQ TTQEEDGCSC RFPEEEEGGC EL                        42

SEQ ID NO: 28               moltype = AA   length = 112
FEATURE                     Location/Qualifiers
source                      1..112
                            mol_type = protein
                            organism = synthetic construct
SEQUENCE: 28
RVKFSRSADA PAYKQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112
```

```
SEQ ID NO: 29            moltype = AA  length = 485
FEATURE                  Location/Qualifiers
source                   1..485
                         mol_type = protein
                         organism = synthetic construct
SEQUENCE: 29
MALPVTALLL PLALLLHAAR PQIVLTQSPA IMSASLGERV TMTCTASSVV ISTYLHWYQQ  60
KPGSSPKLWI YSTSNLASGV PVRFSGSGSG TSYSLTISSM EAEDAATYYC HQYHRSPWTF 120
GGGTKLEIKG GGGSGGGGSG GGGSEVQLQQ SGPELVKPGG SMKISCKASG YSFTGYTMNW 180
VKQSHGKNLE WIGLINPYNG GISYNQKFKD KATLTMDKSS STAYMELLSL TSEDSAIYFC 240
ARDYRYEGFD YWGQGTLVTV SATTTPAPRP PTPAPTIASQ PLSLRPEACR PAAGGAVHTR 300
GLDFACDIYI WAPLAGTCGV LLLSLVITLY CKRGRKKLLY IFKQPFMRPV QTTQEEDGCS 360
CRFPEEEEGG CELRVKFSRS ADAPAYKQGQ NQLYNELNLG RREEYDVLDK RRGRDPEMGG 420
KPRRKNPQEG LYNELQKDKM AEAYSEIGMK GERRRGKGHD GLYQGLSTAT KDTYDALHMQ 480
ALPPR                                                            485

SEQ ID NO: 30            moltype = AA  length = 241
FEATURE                  Location/Qualifiers
source                   1..241
                         mol_type = protein
                         organism = synthetic construct
SEQUENCE: 30
QIVLTQSPAI MSASLGERVT MTCTASSVVI STYLHWYQQK PGSSPKLWIY STSNLASGVP  60
VRFSGSGSGT SYSLTISSME AEDAATYYCH QYHRSPWTFG GGTKLEIKGG GGSGGGGSGG 120
GGSEVQLQQS GPELVKPGGS MKISCKASGY SFTGYTMNWV KQSHGKNLEW IGLINPYNGG 180
ISYNQKFKDK ATLTMDKSSS TAYMELLSLT SEDSAIYFCA RDYRYEGFDY WGQGTLVTVS 240
A                                                                241

SEQ ID NO: 31            moltype = AA  length = 108
FEATURE                  Location/Qualifiers
source                   1..108
                         mol_type = protein
                         organism = synthetic construct
SEQUENCE: 31
QIVLTQSPAI MSASLGERVT MTCTASSVVI STYLHWYQQK PGSSPKLWIY STSNLASGVP  60
VRFSGSGSGT SYSLTISSME AEDAATYYCH QYHRSPWTFG GGTKLEIK             108

SEQ ID NO: 32            moltype = AA  length = 118
FEATURE                  Location/Qualifiers
source                   1..118
                         mol_type = protein
                         organism = synthetic construct
SEQUENCE: 32
EVQLQQSGPE LVKPGGSMKI SCKASGYSFT GYTMNWVKQS HGKNLEWIGL INPYNGGISY  60
NQKFKDKATL TMDKSSSTAY MELLSLTSED SAIYFCARDY RYEGFDYWGQ GTLVTVSA   118

SEQ ID NO: 33            moltype = AA  length = 488
FEATURE                  Location/Qualifiers
source                   1..488
                         mol_type = protein
                         organism = synthetic construct
SEQUENCE: 33
MALPVTALLL PLALLLHAAR PENVLTQSPA IMSATLGEKV TMSCRATSNV KYMYWYQQKS  60
GASPKLWIYY TSNLASGVPA RFSGSGSGTS YSLTISSVEA ADAATYYCQQ FTSSPSTFGA 120
GTKLELKGGG GSGGGGSGGG GSEVQLQQSG PELVKPGASV KISCKASGYS FTGYFMNWVK 180
QSHGKSLEWI GRINPYNGDT FYNQKFKGKA TLTVDKSSNT AHMELRSLTS EDSAVYYCAR 240
VLFLDFDDPY LMDYWGQGTS VTVSSTTTPA PRPPTPAPTI ASQPLSLRPE ACRPAAGGAV 300
HTRGLDFACD IYIWAPLAGT CGVLLLSLVI TLYCKRGRKK LLYIFKQPFM RPVQTTQEED 360
GCSCRFPEEE EGGCELRVKF SRSADAPAYK QGQNQLYNEL NLGRREEYDV LDKRRGRDPE 420
MGGKPRRKNP QEGLYNELQK DKMAEAYSEI GMKGERRRGK GHDGLYQGLS TATKDTYDAL 480
HMQALPPR                                                         488

SEQ ID NO: 34            moltype = AA  length = 244
FEATURE                  Location/Qualifiers
source                   1..244
                         mol_type = protein
                         organism = synthetic construct
SEQUENCE: 34
ENVLTQSPAI MSATLGEKVT MSCRATSNVK YMYWYQQKSG ASPKLWIYYT SNLASGVPAR  60
FSGSGSGTSY SLTISSVEAA DAATYYCQQF TSSPSTFGAG TKLELKGGGG SGGGGSGGGG 120
SEVQLQQSGP ELVKPGASVK ISCKASGYSF TGYFMNWVKQ SHGKSLEWIG RINPYNGDTF 180
YNQKFKGKAT LTVDKSSNTA HMELRSLTSE DSAVYYCARV LFLDFDDPYL MDWGQGTSV 240
TVSS                                                             244

SEQ ID NO: 35            moltype = AA  length = 106
FEATURE                  Location/Qualifiers
source                   1..106
                         mol_type = protein
```

```
                            organism = synthetic construct
SEQUENCE: 35
NVLTQSPAIM SATLGEKVTM SCRATSNVKY MYWYQQKSGA SPKLWIYYTS NLASGVPARF     60
SGSGSGTSYS LTISSVEAAD AATYYCQQFT SSPSTFGAGT KLELKE                   106

SEQ ID NO: 36           moltype = AA   length = 123
FEATURE                 Location/Qualifiers
source                  1..123
                        mol_type = protein
                        organism = synthetic construct
SEQUENCE: 36
EVQLQQSGPE LVKPGASVKI SCKASGYSFT GYFMNWVKQS HGKSLEWIGR INPYNGDTFY     60
NQKFKGKATL TVDKSSNTAH MELRSLTSED SAVYYCARVL FLDFDDPYLM DYWGQGTSVT    120
VSS                                                                  123

SEQ ID NO: 37           moltype = AA   length = 485
FEATURE                 Location/Qualifiers
source                  1..485
                        mol_type = protein
                        organism = synthetic construct
SEQUENCE: 37
MALPVTALLL PLALLLHAAR PDIQMTQSPA SLSASVGETV TITCRASENI DSYLAWYQQK     60
QGKSPQLLVY ASTLLVDGVP SRFSGSRSGT QFSLKINSLQ SEDVARYYCQ HYYSIPYTFG    120
SGTKLEIKGG GGSGGGGSGG GGSEVKLVES GGGLVKPGGS LKLSCAASGF TFNSYTMSWV    180
RQTPAKRLEW VVTISSGGGR TYYPDSVKGR FTISRDNARN TLYLQMSSLR SEDTAMYYCI    240
RGDYRYDGFA YWGQGTLVTV STTTTPAPRP PTPAPTIASQ PLSLRPEACR PAAGGAVHTR    300
GLDFACDIYI WAPLAGTCGV LLLSLVITLY CKRGRKKLLY IFKQPFMRPV QTTQEEDGCS    360
CRFPEEEEGG CELRVKFSRS ADAPAYKQGQ NQLYNELNLG RREEYDVLDK RRGRDPEMGG    420
KPRRKNPQEG LYNELQKDKM AEAYSEIGMK GERRRGKGHD GLYQGLSTAT KDTYDALHMQ    480
ALPPR                                                                485

SEQ ID NO: 38           moltype = AA   length = 241
FEATURE                 Location/Qualifiers
source                  1..241
                        mol_type = protein
                        organism = synthetic construct
SEQUENCE: 38
DIQMTQSPAS LSASVGETVT ITCRASENID SYLAWYQQKQ GKSPQLLVYA STLLVDGVPS     60
RFSGSRSGTQ FSLKINSLQS EDVARYYCQH YYSIPYTFGS GTKLEIKGGG SGGGGSGGGG    120
GSEVKLVESG GGLVKPGGSL KLSCAASGFT FNSYTMSWVR QTPAKRLEWV VTISSGGGRT    180
YYPDSVKGRF TISRDNARNT LYLQMSSLRS EDTAMYYCIR GDYRYDGFAY WGQGTLVTVS    240
T                                                                    241

SEQ ID NO: 39           moltype = AA   length = 107
FEATURE                 Location/Qualifiers
source                  1..107
                        mol_type = protein
                        organism = synthetic construct
SEQUENCE: 39
DIQMTQSPAS LSASVGETVT ITCRASENID SYLAWYQQKQ GKSPQLLVYA STLLVDGVPS     60
RFSGSRSGTQ FSLKINSLQS EDVARYYCQH YYSIPYTFGS GTKLEIK                  107

SEQ ID NO: 40           moltype = AA   length = 119
FEATURE                 Location/Qualifiers
source                  1..119
                        mol_type = protein
                        organism = synthetic construct
SEQUENCE: 40
EVKLVESGGG LVKPGGSLKL SCAASGFTFN SYTMSWVRQT PAKRLEWVVT ISSGGGRTYY     60
PDSVKGRFTI SRDNARNTLY LQMSSLRSED TAMYYCIRGD YRYDGFAYWG QGTLVTVST    119

SEQ ID NO: 41           moltype = AA   length = 488
FEATURE                 Location/Qualifiers
source                  1..488
                        mol_type = protein
                        organism = synthetic construct
SEQUENCE: 41
MALPVTALLL PLALLLHAAR PENVLTQSPA IMSATLGEKV TMSCRATSNV KYMYWYQQKS     60
GASPKLWIYY TSNLASGVPA RFSGSGSGTS YSLTISSVEA ADAATYYCQQ FTSSPSTFGA    120
GTKLELKGGG SGGGGSGGGG GSEVQLQQSG PELVKPGASV KISCKASGYS FTGYFMNWVK    180
QSHGKSLEWI GRINPYNGDT FYNQKFKGKA TLTVDKSSST AHMELRSLTS EDSAVYYCAR    240
VLFLDFDDPY LMDYWGQGTS VTVSSTTTPA PRPPTPAPTI ASQPLSLRPE ACRPAAGGAV    300
HTRGLDFACD IYIWAPLAGT CGVLLLSLVI TLYCKRGRKK LLYIFKQPFM RPVQTTQEED    360
GCSCRFPEEE EGGCELRVKF SRSADAPAYK QGQNQLYNEL NLGRREEYDV LDKRRGRDPE    420
MGGKPRRKNP QEGLYNELQK DKMAEAYSEI GMKGERRRGK GHDGLYQGLS TATKDTYDAL    480
HMQALPPR                                                             488

SEQ ID NO: 42           moltype = AA   length = 244
FEATURE                 Location/Qualifiers
```

| | | |
|---|---|---|
| source | 1..244 | |
| | mol_type = protein | |
| | organism = synthetic construct | |

SEQUENCE: 42

```
ENVLTQSPAI MSATLGEKVT MSCRATSNVK YMYWYQQKSG ASPKLWIYYT SNLASGVPAR  60
FSGSGSGTSY SLTISSVEAA DAATYYCQQF TSSPSTFGAG TKLELKGGGG SGGGGSGGGG  120
SEVQLQQSGP ELVKPGASVK ISCKASGYSF TGYFMNWVKQ SHGKSLEWIG RINPYNGDTF  180
YNQKFKGKAT LTVDKSSSTA HMELRSLTSE DSAVYYCARV LFLDFDDPYL MDYWGQGTSV  240
TVSS                                                              244
```

| | | |
|---|---|---|
| SEQ ID NO: 43 | moltype = AA length = 106 | |
| FEATURE | Location/Qualifiers | |
| source | 1..106 | |
| | mol_type = protein | |
| | organism = synthetic construct | |

SEQUENCE: 43

```
ENVLTQSPAI MSATLGEKVT MSCRATSNVK YMYWYQQKSG ASPKLWIYYT SNLASGVPAR  60
FSGSGSGTSY SLTISSVEAA DAATYYCQQF TSSPSTFGAG TKLELK                106
```

| | | |
|---|---|---|
| SEQ ID NO: 44 | moltype = AA length = 123 | |
| FEATURE | Location/Qualifiers | |
| source | 1..123 | |
| | mol_type = protein | |
| | organism = synthetic construct | |

SEQUENCE: 44

```
EVQLQQSGPE LVKPGASVKI SCKASGYSFT GYFMNWVKQS HGKSLEWIGR INPYNGDTFY  60
NQKFKGKATL TVDKSSSTAH MELRSLTSED SAVYYCARVL FLDFDDPYLM DYWGQGTSVT  120
VSS                                                               123
```

| | | |
|---|---|---|
| SEQ ID NO: 45 | moltype = AA length = 482 | |
| FEATURE | Location/Qualifiers | |
| source | 1..482 | |
| | mol_type = protein | |
| | organism = synthetic construct | |

SEQUENCE: 45

```
MALPVTALLL PLALLLHAAR PSSELTQDPA VSVALGQTVR ITCRGDSLRK YYASWYQQKP  60
RQAPQLVIYH KNNRASGIPD RFSGSISGNT ASLTITGAQA EDEAAYFCNS RDTSGNYLVF  120
GGGTKVTVLG GGGGSGGGGS GGGGSQLQLQ ESGPGLVKPS ETLSLTCAVS GASISNWWSW  180
VRQPPGKGLE WIGEVHHSGV TTYKPSLKSR VTISVDNSKN QLSLKLTSVT AADTAVYYCA  240
REFADDAFDI WGRGTMVTVT TTPAPRPPTP APTIASQPLS LRPEACRPAA GGAVHTRGLD  300
FACDIYIWAP LAGTCGVLLL SLVITLYCKR GRKKLLYIFK QPFMRPVQTT QEEDGCSCRF  360
PEEEEGGCEL RVKFSRSADA PAYKQGQNQL YNELNLGRRE EYDVLDKRRG RDPEMGGKPR  420
RKNPQEGLYN ELQKDKMAEA YSEIGMKGER RRGKGHDGLY QGLSTATKDT YDALHMQALP  480
PR                                                                482
```

| | | |
|---|---|---|
| SEQ ID NO: 46 | moltype = AA length = 238 | |
| FEATURE | Location/Qualifiers | |
| source | 1..238 | |
| | mol_type = protein | |
| | organism = synthetic construct | |

SEQUENCE: 46

```
SSELTQDPAV SVALGQTVRI TCRGDSLRKY YASWYQQKPR QAPQLVIYHK NNRASGIPDR  60
FSGSISGNTA SLTITGAQAE DEAAYFCNSR DTSGNYLVFG GGTKVTVLGG GGGSGGGGSG  120
GGGSQLQLQE SGPGLVKPSE TLSLTCAVSG ASISNWWSWV RQPPGKGLEW IGEVHHSGVT  180
TYKPSLKSRV TISVDNSKNQ LSLKLTSVTA ADTAVYYCAR EFADDAFDIW GRGTMVTV    238
```

| | | |
|---|---|---|
| SEQ ID NO: 47 | moltype = AA length = 109 | |
| FEATURE | Location/Qualifiers | |
| source | 1..109 | |
| | mol_type = protein | |
| | organism = synthetic construct | |

SEQUENCE: 47

```
SSELTQDPAV SVALGQTVRI TCRGDSLRKY YASWYQQKPR QAPQLVIYHK NNRASGIPDR  60
FSGSISGNTA SLTITGAQAE DEAAYFCNSR DTSGNYLVFG GGTKVTVLG              109
```

| | | |
|---|---|---|
| SEQ ID NO: 48 | moltype = AA length = 114 | |
| FEATURE | Location/Qualifiers | |
| source | 1..114 | |
| | mol_type = protein | |
| | organism = synthetic construct | |

SEQUENCE: 48

```
QLQLQESGPG LVKPSETLSL TCAVSGASIS NWWSWVRQPP GKGLEWIGEV HHSGVTTYKP  60
SLKSRVTISV DNSKNQLSLK LTSVTAADTA VYYCAREFAD DAFDIWGRGT MVTV        114
```

| | | |
|---|---|---|
| SEQ ID NO: 49 | moltype = AA length = 250 | |
| FEATURE | Location/Qualifiers | |
| source | 1..250 | |
| | mol_type = protein | |
| | organism = synthetic construct | |

```
SEQUENCE: 49
DIVMTQSPLS LPVTPGEPAS ISCRSTKSLL HSNGNTYLYW YLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVRQAPGQ GLEWMGTIDP   180
ETGGTAYNQK FKGRVTITAD KSTSTAYMEL SSLRSEDTAV YYCTSFYYTY SNYDVGFAYW   240
GQGTLVTVSS                                                          250

SEQ ID NO: 50           moltype = AA  length = 250
FEATURE                 Location/Qualifiers
source                  1..250
                        mol_type = protein
                        organism = synthetic construct
SEQUENCE: 50
DIVMTQSPLS LPVTPGEPAS ISCRSTKSLL HSNGNTYLYW YLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVRQAPGQ GLEWIGTIDP   180
ETGGTAYNQK FKGRATLTAD RSTSTAYMEL SSLRSEDTAV YYCTSFYYTY SNYDVGFAYW   240
GQGTLVTVSS                                                          250

SEQ ID NO: 51           moltype = AA  length = 250
FEATURE                 Location/Qualifiers
source                  1..250
                        mol_type = protein
                        organism = synthetic construct
SEQUENCE: 51
DIVMTQSPLS LPVTPGEPAS ISCRSTKSLL HSNGNTYLYW YLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVKQAPGQ GLEWIGTIDP   180
ETGGTAYNQK FKGKATLTAD RSTSTAYMEL SSLRSEDTAV YYCTSFYYTY SNYDVGFAYW   240
GQGTLVTVSS                                                          250

SEQ ID NO: 52           moltype = AA  length = 250
FEATURE                 Location/Qualifiers
source                  1..250
                        mol_type = protein
                        organism = synthetic construct
SEQUENCE: 52
DIVMTQSPLS LPVTPGEPAS ISCRSTKSLL HSNGNTYLYW YLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVKQAPGH GLEWIGTIDP   180
ETGGTAYNQK FKGKATLTAD RSTSTAYMEL SSLTSEDTAV YYCTSFYYTY SNYDVGFAYW   240
GQGTLVTVSS                                                          250

SEQ ID NO: 53           moltype = AA  length = 250
FEATURE                 Location/Qualifiers
source                  1..250
                        mol_type = protein
                        organism = synthetic construct
SEQUENCE: 53
DIVMTQSPLS LPVTPGEPAS ISCRSTKSLL HSNGNTYLYW FLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVRQAPGQ GLEWMGTIDP   180
ETGGTAYNQK FKGRVTITAD KSTSTAYMEL SSLRSEDTAV YYCTSFYYTY SNYDVGFAYW   240
GQGTLVTVSS                                                          250

SEQ ID NO: 54           moltype = AA  length = 250
FEATURE                 Location/Qualifiers
source                  1..250
                        mol_type = protein
                        organism = synthetic construct
SEQUENCE: 54
DIVMTQSPLS LPVTPGEPAS ISCRSTKSLL HSNGNTYLYW FLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVRQAPGQ GLEWIGTIDP   180
ETGGTAYNQK FKGRATLTAD RSTSTAYMEL SSLRSEDTAV YYCTSFYYTY SNYDVGFAYW   240
GQGTLVTVSS                                                          250

SEQ ID NO: 55           moltype = AA  length = 250
FEATURE                 Location/Qualifiers
source                  1..250
                        mol_type = protein
                        organism = synthetic construct
SEQUENCE: 55
DIVMTQSPLS LPVTPGEPAS ISCRSTKSLL HSNGNTYLYW FLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVKQAPGQ GLEWIGTIDP   180
ETGGTAYNQK FKGKATLTAD RSTSTAYMEL SSLRSEDTAV YYCTSFYYTY SNYDVGFAYW   240
GQGTLVTVSS                                                          250
```

```
SEQ ID NO: 56           moltype = AA  length = 250
FEATURE                 Location/Qualifiers
source                  1..250
                        mol_type = protein
                        organism = synthetic construct
SEQUENCE: 56
DIVMTQSPLS LPVTPGEPAS ISCRSTKSLL HSNGNTYLYW FLQKPGQSPQ LLIYRMSNLA    60
SGVPDRFSGS GSGTDFTLKI SRVEAEDVGV YYCMQHLEYP FTFGGGTKVE IKGGGGSGGG   120
GSGGGGSEIQ LQQSGAEVKK PGSSVKVSCK ASGYTFTDYD MHWVKQAPGH GLEWIGTIDP   180
ETGGTAYNQK FKGKATLTAD RSTSTAYMEL SSLTSEDTAV YYCTSFYYTY SNYDVGFAYW   240
GQGTLVTVSS                                                         250

SEQ ID NO: 57           moltype = AA  length = 112
FEATURE                 Location/Qualifiers
source                  1..112
                        mol_type = protein
                        organism = synthetic construct
SEQUENCE: 57
DIVMTQSPLS LPVTPGEPAS ISCRSTKSLL HSNGNTYLYW YLQKPGQSPQ LLIYRMSNLA    60
SGVPDRFSGS GSGTDFTLKI SRVEAEDVGV YYCMQHLEYP FTFGGGTKVE IK           112

SEQ ID NO: 58           moltype = AA  length = 112
FEATURE                 Location/Qualifiers
source                  1..112
                        mol_type = protein
                        organism = synthetic construct
SEQUENCE: 58
DIVMTQSPLS LPVTPGEPAS ISCRSTKSLL HSNGNTYLYW FLQKPGQSPQ LLIYRMSNLA    60
SGVPDRFSGS GSGTDFTLKI SRVEAEDVGV YYCMQHLEYP FTFGGGTKVE IK           112

SEQ ID NO: 59           moltype = AA  length = 123
FEATURE                 Location/Qualifiers
source                  1..123
                        mol_type = protein
                        organism = synthetic construct
SEQUENCE: 59
EIQLQQSGAE VKKPGSSVKV SCKASGYTFT DYDMHWVRQA PGQGLEWMGT IDPETGGTAY    60
NQKFKGRVTI TADKSTSTAY MELSSLRSED TAVYYCTSFY YTSNYDVGF AYWGQGTLVT    120
VSS                                                                123

SEQ ID NO: 60           moltype = AA  length = 123
FEATURE                 Location/Qualifiers
source                  1..123
                        mol_type = protein
                        organism = synthetic construct
SEQUENCE: 60
EIQLQQSGAE VKKPGSSVKV SCKASGYTFT DYDMHWVRQA PGQGLEWIGT IDPETGGTAY    60
NQKFKGRATL TADRSTSTAY MELSSLRSED TAVYYCTSFY YTSNYDVGF AYWGQGTLVT    120
VSS                                                                123

SEQ ID NO: 61           moltype = AA  length = 123
FEATURE                 Location/Qualifiers
source                  1..123
                        mol_type = protein
                        organism = synthetic construct
SEQUENCE: 61
EIQLQQSGAE VKKPGSSVKV SCKASGYTFT DYDMHWVKQA PGQGLEWIGT IDPETGGTAY    60
NQKFKGKATL TADRSTSTAY MELSSLRSED TAVYYCTSFY YTSNYDVGF AYWGQGTLVT    120
VSS                                                                123

SEQ ID NO: 62           moltype = AA  length = 123
FEATURE                 Location/Qualifiers
source                  1..123
                        mol_type = protein
                        organism = synthetic construct
SEQUENCE: 62
EIQLQQSGAE VKKPGSSVKV SCKASGYTFT DYDMHWVKQA PGHGLEWIGT IDPETGGTAY    60
NQKFKGKATL TADRSTSTAY MELSSLTSED TAVYYCTSFY YTSNYDVGF AYWGQGTLVT    120
VSS                                                                123

SEQ ID NO: 63           moltype = AA  length = 482
FEATURE                 Location/Qualifiers
source                  1..482
                        mol_type = protein
                        organism = synthetic construct
SEQUENCE: 63
MALPVTALLL PLALLLHAAR PDIQMTQSPS SLSASVGDRV TITCKASDLI HNWLAWYQQK    60
PGKAPKLLIY GATSLETGVP SRFSGSGSGT DFTLTISSLQ PEDFATYYCQ QYWTTPFTFG   120
QGTKVEIKGG GGSGGGGSGG GGSEVQLVES GGGLVQPGGS LRLSCAASGY SITNDYAWNW   180
```

```
VRQAPGKGLE WVGYISYSGY TTYNPSLKSR FTISRDTSKN TLYLQMNSLR AEDTAVYYCA    240
RWTSGLDYWG QGTLVTVSST TTPAPRPPTP APTIASQPLS LRPEACRPAA GGAVHTRGLD    300
FACDIYIWAP LAGTCGVLLL SLVITLYCKR GRKKLLYIFK QPFMRPVQTT QEEDGCSCRF    360
PEEEEGGCEL RVKFSRSADA PAYKQGQNQL YNELNLGRRE EYDVLDKRRG RDPEMGGKPR    420
RKNPQEGLYN ELQKDKMAEA YSEIGMKGER RRGKGHDGLY QGLSTATKDT YDALHMQALP    480
PR                                                                   482

SEQ ID NO: 64           moltype = AA  length = 238
FEATURE                 Location/Qualifiers
source                  1..238
                        mol_type = protein
                        organism = synthetic construct
SEQUENCE: 64
DIQMTQSPSS LSASVGDRVT ITCKASDLIH NWLAWYQQKP GKAPKLLIYG ATSLETGVPS    60
RFSGSGSGTD FTLTISSLQP EDFATYYCQQ YWTTPFTFGQ GTKVEIKGGG GSGGGGSGGG    120
GSEVQLVESG GGLVQPGGSL RLSCAASGYS ITNDYAWNWV RQAPGKGLEW VGYISYSGYT    180
TYNPSLKSRF TISRDTSKNT LYLQMNSLRA EDTAVYYCAR WTSGLDYWGQ GTLVTVSS     238

SEQ ID NO: 65           moltype = AA  length = 107
FEATURE                 Location/Qualifiers
source                  1..107
                        mol_type = protein
                        organism = synthetic construct
SEQUENCE: 65
DIQMTQSPSS LSASVGDRVT ITCKASDLIH NWLAWYQQKP GKAPKLLIYG ATSLETGVPS    60
RFSGSGSGTD FTLTISSLQP EDFATYYCQQ YWTTPFTFGQ GTKVEIK                 107

SEQ ID NO: 66           moltype = AA  length = 116
FEATURE                 Location/Qualifiers
source                  1..116
                        mol_type = protein
                        organism = synthetic construct
SEQUENCE: 66
EVQLVESGGG LVQPGGSLRL SCAASGYSIT NDYAWNWVRQ APGKGLEWVG YISYSGYTTY    60
NPSLKSRFTI SRDTSKNTLY LQMNSLRAED TAVYYCARWT SGLDYWGQGT LVTVSS       116

SEQ ID NO: 67           moltype = AA  length = 482
FEATURE                 Location/Qualifiers
source                  1..482
                        mol_type = protein
                        organism = synthetic construct
SEQUENCE: 67
MALPVTALLL PLALLLHAAR PDIQMTQSSS FLSVSLGGRV TITCKASDLI HNWLAWYQQK    60
PGNAPRLLIS GATSLETGVP SRFSGSGSGN DYTLSIASLQ TEDAATYYCQ QYWTTPFTFG    120
SGTKVEIKGG GGSGGGGSGG GGSDVQLQES GPGLVNPSQS LSLTCTVTGY SITNDYAWNW    180
IRQFPGNKLE WMGYINYSGY TTYNPSLKSR ISITRDTSKN QFFLHLNSVT TEDTATYYCA    240
RWDGGLTYWG QGTLVTVSAT TTPAPRPPTP APTIASQPLS LRPEACRPAA GGAVHTRGLD    300
FACDIYIWAP LAGTCGVLLL SLVITLYCKR GRKKLLYIFK QPFMRPVQTT QEEDGCSCRF    360
PEEEEGGCEL RVKFSRSADA PAYKQGQNQL YNELNLGRRE EYDVLDKRRG RDPEMGGKPR    420
RKNPQEGLYN ELQKDKMAEA YSEIGMKGER RRGKGHDGLY QGLSTATKDT YDALHMQALP    480
PR                                                                   482

SEQ ID NO: 68           moltype = AA  length = 238
FEATURE                 Location/Qualifiers
source                  1..238
                        mol_type = protein
                        organism = synthetic construct
SEQUENCE: 68
DIQMTQSSSF LSVSLGGRVT ITCKASDLIH NWLAWYQQKP GNAPRLLISG ATSLETGVPS    60
RFSGSGSGND YTLSIASLQT EDAATYYCQQ YWTTPFTFGS GTKVEIKGGG GSGGGGSGGG    120
GSDVQLQESG PGLVNPSQSL SLTCTVTGYS ITNDYAWNWI RQFPGNKLEW MGYINYSGYT    180
TYNPSLKSRI SITRDTSKNQ FFLHLNSVTT EDTATYYCAR WDGGLTYWGQ GTLVTVSA     238

SEQ ID NO: 69           moltype = AA  length = 107
FEATURE                 Location/Qualifiers
source                  1..107
                        mol_type = protein
                        organism = synthetic construct
SEQUENCE: 69
DIQMTQSSSF LSVSLGGRVT ITCKASDLIH NWLAWYQQKP GNAPRLLISG ATSLETGVPS    60
RFSGSGSGND YTLSIASLQT EDAATYYCQQ YWTTPFTFGS GTKVEIK                 107

SEQ ID NO: 70           moltype = AA  length = 116
FEATURE                 Location/Qualifiers
source                  1..116
                        mol_type = protein
                        organism = synthetic construct
SEQUENCE: 70
DVQLQESGPG LVNPSQSLSL TCTVTGYSIT NDYAWNWIRQ FPGNKLEWMG YINYSGYTTY    60
```

```
NPSLKSRISI TRDTSKNQFF LHLNSVTTED TATYYCARWD GGLTYWGQGT LVTVSA         116

SEQ ID NO: 71                moltype = AA   length = 298
FEATURE                      Location/Qualifiers
source                       1..298
                             mol_type = protein
                             organism = synthetic construct
SEQUENCE: 71
MALPVTALLL PLALLLHAAR PGTSLSPPPE SSGSPQQPGL SAPHSRQIPA PQGAVLVQRE      60
KDLPNYNWNS FGLRFTTTPA PRPPTPAPTI ASQPLSLRPE ACRPAAGGAV HTRGLDFACD     120
IYIWAPLAGT CGVLLLSLVI TLYCKRGRKK LLYIFKQPFM RPVQTTQEED GCSCRFPEEE     180
EGGCELRVKF SRSADAPAYK QGQNQLYNEL NLGRREEYDV LDKRRGRDPE MGGKPRRKNP     240
QEGLYNELQK DKMAEAYSEI GMKGERRRGK GHDGLYQGLS TATKDTYDAL HMQALPPR       298

SEQ ID NO: 72                moltype = AA   length = 54
FEATURE                      Location/Qualifiers
source                       1..54
                             mol_type = protein
                             organism = synthetic construct
SEQUENCE: 72
GTSLSPPPES SGSPQQPGLS APHSRQIPAP QGAVLVQREK DLPNYNWNSF GLRF            54

SEQ ID NO: 73                moltype = DNA   length = 330
FEATURE                      Location/Qualifiers
source                       1..330
                             mol_type = other DNA
                             organism = synthetic construct
SEQUENCE: 73
cagagcgtgc tgacacaacc cgccagcgtg agcggcagcc ccggccaatc cgtgacaatc      60
agctgcaccg gaaccagctc cgatgtgggc ggctacaact atgtcagctg gtaccagcag    120
caccccggca agccccctaa gctcatgatc tacgaggtca gcaagagacc ctccggagtg    180
cccgacagat tctccggctc caaatccggc aacaccgctt ccctcaccat cagcggactc    240
caagccgaag atgaggccga ctactactgc tccagccaca ccagcagcaa cacactgatc    300
tttggcggcg gcaccaaagt gacagtgctg                                      330

SEQ ID NO: 74                moltype = DNA   length = 354
FEATURE                      Location/Qualifiers
source                       1..354
                             mol_type = other DNA
                             organism = synthetic construct
SEQUENCE: 74
gaagtgcagc tggtgcaatc cggcgctgag gtgaagaagc ccggcgaatc tctgaagatt      60
agctgcaaag gctccggcta caccttcaca aactactgga tcggctgggt gagacagatg    120
cccggcaagg gactggagtg gatgggaaga atctacccca gcgactccta caccaactac    180
tccccctcct ccaaggccaa agtgaccatt agcgccgaca gagcatctc accgcctat     240
ctgcagtggt ccagcctcaa ggccagcgat acagccatgt actactgcgc cagagacctc    300
gagcctaccc atcattacag ctggggccaa ggcacactcg tgacagtgag ctcc           354

SEQ ID NO: 75                moltype = DNA   length = 330
FEATURE                      Location/Qualifiers
source                       1..330
                             mol_type = other DNA
                             organism = synthetic construct
SEQUENCE: 75
ctcccgtgc tgacacagcc tccttccgcc tccggaacac ccggccagag agtgaccatc      60
agctgcagcg gctccagctc caacatcggc agcaacgccg tggactggta tcagcaactg    120
cccggcacag ctcccaagct gctgatctac accaacaaca gaaggccag cggcgtgccc    180
gatagattca gcggcagcaa atccggcaca agcggctctc tggccatttc cggactgcag    240
tcgaggacg aggctgacta ctactgcgct gcttgggatg actctctgtc cggcgtgatc    300
tttggcggag gcaccaaggt cacagtgctg                                      330

SEQ ID NO: 76                moltype = DNA   length = 363
FEATURE                      Location/Qualifiers
source                       1..363
                             mol_type = other DNA
                             organism = synthetic construct
SEQUENCE: 76
caagtgcaac tggtgcagag cggcgctgag gtgaagaagc ccggcagcag cgtgaaggtc      60
agctgcaagg ccagcggcgg cacattcagc tcctacgtga tcagctgggt gagacaagct    120
cccggccaag gactggagtg gatgggagct tcatccctc tgctgggcag agtgcactat    180
gcccaagagt tccaaggcag actgacaatc accgccgacg agtccaccgg caccgcttac    240
atggagctga aaggactgag gagcgacgac accgccatgt actactgcgc cagagatcaa    300
ggcttcgccg gcgatgacgc cttcgatatc tggggccaag gcacaatggt gacagtgagc    360
agc                                                                   363

SEQ ID NO: 77                moltype = DNA   length = 324
FEATURE                      Location/Qualifiers
source                       1..324
                             mol_type = other DNA
```

|  |  |  |
|---|---|---|
| | organism = synthetic construct | |
| SEQUENCE: 77 | | |
| cagcccgtgc tgacccaaga ccccgtggtg tccgtggctc tgggacagac cgtgaggatc | | 60 |
| acatgccaag gcgattctct gaggagctac tatgccacat ggtaccagca gaaacccgga | | 120 |
| ctggccccccg tgagagtcat cttcggaaag aactctcaca ccagcggcat ccccgataga | | 180 |
| ttcagcggca gcagcagcgg caataccgcc tccctcacca tcaccggcgc ccaagccgag | | 240 |
| gacgaagccg actactactg caacagctgg gacaacagcg ccaaccatcc cgtgttcggc | | 300 |
| ggcggcacaa agctgacagt gctc | | 324 |
| | | |
| SEQ ID NO: 78 | moltype = DNA  length = 366 | |
| FEATURE | Location/Qualifiers | |
| source | 1..366 | |
| | mol_type = other DNA | |
| | organism = synthetic construct | |
| SEQUENCE: 78 | | |
| gaggtgcagc tcgtgcagtc cggcgccgaa gtgaggaagc ccggcagctc cgtgaaggtg | | 60 |
| agctgtaagg ccagcggcga caacttcaac aactacggca tcacatgggt gagacaagcc | | 120 |
| cccggccaag gactggagtg gatgggaaga ctgatcaccg tgctgggcat ggacaactac | | 180 |
| gcccagaagt tccaaggaag actgacaatc accgctgacg agtccaccgg caccgcctat | | 240 |
| atggaactga ccggactgga gcccgaggat accgccgtgt actattgcgc tagagacatc | | 300 |
| atgtccccccg aggccatcga tgccttcgac gtgtggggac aaggcacact ggtgaccgtg | | 360 |
| agctcc | | 366 |
| | | |
| SEQ ID NO: 79 | moltype = DNA  length = 321 | |
| FEATURE | Location/Qualifiers | |
| source | 1..321 | |
| | mol_type = other DNA | |
| | organism = synthetic construct | |
| SEQUENCE: 79 | | |
| gacatccaga tgacacagag ccccttcctct ctgagcgcct ccgtcggaga tagagtgacc | | 60 |
| atcacatgca gagcctccca agacgtcagc aactatctga actggtacca gcagaaagccc | | 120 |
| ggcaaggccc ctaaactgct gatctatggc gccagcaata gacagaccgg cgtgccttcc | | 180 |
| agattctccg gcagcggaag cggcaccgat ttcacactga caatttcctc tctgcagccc | | 240 |
| gaggactttg ccacctacta ctgccagcaa gaggacagat ccctacaac cttcggccaa | | 300 |
| ggcacaaagg tggagatcaa a | | 321 |
| | | |
| SEQ ID NO: 80 | moltype = DNA  length = 366 | |
| FEATURE | Location/Qualifiers | |
| source | 1..366 | |
| | mol_type = other DNA | |
| | organism = synthetic construct | |
| SEQUENCE: 80 | | |
| gaagtgcagc tggtgcagag cggagctgag gtgagaaagc ccggcagcag cgtcaaggtg | | 60 |
| agctgtaagg ccagcggcga caacttcaac aactacggca tcacatgggt gaggcaagcc | | 120 |
| cccggccaag gcctcgagtg gatgggaaga ctgatcaccg tgctcggact ggacaactac | | 180 |
| gcccagaagt tccaaggcag actgacaatc accgccgatg agtccaccgg aacagcctac | | 240 |
| atggaactga ccggactgga gcccgaagac acagctgtgt actactgcgc tagagacatc | | 300 |
| atgtccccccg aggccatcga tgcctttgac gtgtggggcc aaggcacact ggtgacagtc | | 360 |
| agcagc | | 366 |
| | | |
| SEQ ID NO: 81 | moltype = DNA  length = 45 | |
| FEATURE | Location/Qualifiers | |
| source | 1..45 | |
| | mol_type = other DNA | |
| | organism = synthetic construct | |
| SEQUENCE: 81 | | |
| ggaggaggag gcagcggagg cggaggcagc ggaggaggcg gcagc | | 45 |
| | | |
| SEQ ID NO: 82 | moltype = AA  length = 110 | |
| FEATURE | Location/Qualifiers | |
| source | 1..110 | |
| | mol_type = protein | |
| | organism = synthetic construct | |
| SEQUENCE: 82 | | |
| QSVLTQPASV SGSPGQSVTI SCTGTSSDVG GYNYVSWYQQ HPGKPPKLMI YEVSKRPSGV | | 60 |
| PDRFSGSKSG NTASLTISGL QAEDEADYYC SSHTSSNTLI FGGGTKVTVL | | 110 |
| | | |
| SEQ ID NO: 83 | moltype = AA  length = 118 | |
| FEATURE | Location/Qualifiers | |
| source | 1..118 | |
| | mol_type = protein | |
| | organism = synthetic construct | |
| SEQUENCE: 83 | | |
| EVQLVQSGAE VKKPGESLKI SCKGSGYTFT NYWIGWVRQM PGKGLEWMGR IYPSDSYTNY | | 60 |
| SPSFQGQVTI SADKSISTAY LQWSSLKASD TAMYYCARDL EPTHHYSWGQ GTLVTVSS | | 118 |
| | | |
| SEQ ID NO: 84 | moltype = AA  length = 110 | |
| FEATURE | Location/Qualifiers | |
| source | 1..110 | |

```
                        mol_type = protein
                        organism = synthetic construct
SEQUENCE: 84
LPVLTQPPSA SGTPGQRVTI SCSGSSSNIG SNAVDWYQQL PGTAPKLLIY TNNRRPSGVP    60
DRFSGSKSGT SGSLAISGLQ FEDEADYYCA AWDDSLSGVI FGGGTKVTVL              110

SEQ ID NO: 85           moltype = AA   length = 121
FEATURE                 Location/Qualifiers
source                  1..121
                        mol_type = protein
                        organism = synthetic construct
SEQUENCE: 85
QVQLVQSGAE VKKPGSSVKV SCKASEDTFS SYVISWVRQA PGQGLEWMGA FIPLLGRVHY    60
AQEFQGRLTI TADESTGTAY MELKGLRSDD TAMYYCARDQ GFAGDDAFDI WGQGTMVTVS   120
S                                                                  121

SEQ ID NO: 86           moltype = AA   length = 108
FEATURE                 Location/Qualifiers
source                  1..108
                        mol_type = protein
                        organism = synthetic construct
SEQUENCE: 86
QPVLTQDPVV SVALGQTVRI TCQGDSLRSY YATWYQQKPG LAPVRVIFGK NSRPSGIPDR    60
FSGSSSGNTA SLTITGAQAE DEADYYCNSW DNSANHPVFG GGTKLTVL                108

SEQ ID NO: 87           moltype = AA   length = 122
FEATURE                 Location/Qualifiers
source                  1..122
                        mol_type = protein
                        organism = synthetic construct
SEQUENCE: 87
EVQLVQSGAE VRKPGSSVKV SCKASGDNFN NYGITWVRQA PGQGLEWMGR LITVLGLDNY    60
AQKFQGRLTI TADESTGTAY MELTGLEPED TAVYYCARDI MSPEAIDAFD VWGQGTLVTV   120
SS                                                                 122

SEQ ID NO: 88           moltype = AA   length = 107
FEATURE                 Location/Qualifiers
source                  1..107
                        mol_type = protein
                        organism = synthetic construct
SEQUENCE: 88
DIQMTQSPSS LSASVGDRVT ITCRASQDVS NYLNWYQQKP GKAPKLLIYG ASNRQTGVPS    60
RFSGSGSGTD FTLTISSLQP EDFATYYCQQ EDRFPTTFGQ GTKVEIK                 107

SEQ ID NO: 89           moltype = AA   length = 122
FEATURE                 Location/Qualifiers
source                  1..122
                        mol_type = protein
                        organism = synthetic construct
SEQUENCE: 89
EVQLVQSGAE VRKPGSSVKV SCKASGDNFN NYGITWVRQA PGQGLEWMGR LITVLGLDNY    60
AQKFQGRLTI TADESTGTAY MELTGLEPED TAVYYCARDI MSPEAIDAFD VWGQGTLVTV   120
SS                                                                 122

SEQ ID NO: 90           moltype = AA   length = 15
FEATURE                 Location/Qualifiers
source                  1..15
                        mol_type = protein
                        organism = synthetic construct
SEQUENCE: 90
GGGGSGGGGS GGGGS                                                    15

SEQ ID NO: 91           moltype = DNA   length = 717
FEATURE                 Location/Qualifiers
source                  1..717
                        mol_type = other DNA
                        organism = synthetic construct
SEQUENCE: 91
gaggtccaac tgcagcagtc tggagctgag ctgatgaagc ctgggacttc agtgaagatg    60
tcctgcaagg ctgctggata caccttcact aagtactgga taggttgggt aaagcagagg   120
cctggacatg gccttgagtg gattggagat atttaccctg gaggtggtta tactctcttc   180
aatgagaagt tcaagggcaa ggccacactg actgcagaca catcctccag cacagcctac   240
atgcagctca gcagcctgac atctgaggac tctgccatct attactgtgc aagagggaac   300
tactgggcc aaggcaccac tctcaccgtc tcctcaggtg gtggtggtag cggcggcagc   360
ggctctggtg tggtggatc cgatgttgtg atgacccaaa ctccactcac tttgtcggtt   420
accattggac aaccagcctc catctcttgc aagtcaagtc agagcctctt agatagtgat   480
ggaaagacat atttgaattg gttgttacag aggccaggcc agtctccaaa agcgcctaatc  540
tatctggtgt ctaaactgga ctctggagtc cctgacaggt tcactggcag tggatcaggg   600
acagatttca cactgaaaat cagcagagtg gaggctgagg atttgggagt ttattattgc   660
```

-continued

```
tggcaaggta cacattttcc tcacacgttc ggagggggca ccaagctgga aatgaaa      717

SEQ ID NO: 92           moltype = AA  length = 239
FEATURE                 Location/Qualifiers
source                  1..239
                        mol_type = protein
                        organism = synthetic construct
SEQUENCE: 92
EVQLQQSGAE LMKPGTSVKM SCKAAGYTFT KYWIGWVKQR PGHGLEWIGD IYPGGGYTLF      60
NEKFKGKATL TADTSSSTAY MQLSSLTSED SAIYYCARGN YWGQGTTLTV SSGGGGSGGG     120
GSGGGGSDVV MTQTPLTLSV TIGQPASISC KSSQSLLDSD GKTYLNWLLQ RPGQSPKRLI     180
YLVSKLDSGV PDRFTGSGSG TDFTLKISRV EAEDLGVYYC WQGTHFPHTF GGGTKLEMK      239

SEQ ID NO: 93           moltype = AA  length = 112
FEATURE                 Location/Qualifiers
source                  1..112
                        mol_type = protein
                        organism = synthetic construct
SEQUENCE: 93
EVQLQQSGAE LMKPGTSVKM SCKAAGYTFT KYWIGWVKQR PGHGLEWIGD IYPGGGYTLF      60
NEKFKGKATL TADTSSSTAY MQLSSLTSED SAIYYCARGN YWGQGTTLTV SS             112

SEQ ID NO: 94           moltype = AA  length = 112
FEATURE                 Location/Qualifiers
source                  1..112
                        mol_type = protein
                        organism = synthetic construct
SEQUENCE: 94
DVVMTQTPLT LSVTIGQPAS ISCKSSQSLL DSDGKTYLNW LLQRPGQSPK RLIYLVSKLD      60
SGVPDRFTGS GSGTDFTLKI SRVEAEDLGV YYCWQGTHFP HTFGGGTKLE MK             112

SEQ ID NO: 95           moltype = DNA  length = 708
FEATURE                 Location/Qualifiers
source                  1..708
                        mol_type = other DNA
                        organism = synthetic construct
SEQUENCE: 95
caggtcaagc tgcaacagtc tgggcccgag ctggtgaggc ctggggcttc agtgaagatg      60
tcctgcaagg cttcaggcta taccttcacc acctactgga tgcactgggt gaaacagagg     120
ccaggacaag gccttgagtg gattggcatg attgatccct ccaatagtga cactaggtta     180
aatcagaagt tcaaggacaa ggccacattg aatgttgaca catcctccaa cacagcctac     240
atgcacctca gcagcctgac atctgaggac tctgcagtct attactgtac attaggtggg     300
actgagtatt ggggccaagg cgccactctc acagtctcct caggtggtgg tggtagcggc     360
ggcggcggct ctggtggtgg tggatccagt attgtgatga cccagtctcc agccaccctg     420
tctgtgactc caggagatag agtctctctt tcctgcaggg ccagcagag tattggcgac     480
tacctacact ggtttcaaca aaaatcacat gagtctccaa ggcttctcat caaatatgct     540
tcccaatcca tctctgggat ccctccagg ttcagtggca gtggatcagg gtcagatttc     600
actctcatta tcaacactat ggaacctgaa gatgttggag tgtattactg tcaaaatgct     660
cacacctatc cgtacacgtt cggagggggc accaagctgg aaatcaaa                 708

SEQ ID NO: 96           moltype = AA  length = 236
FEATURE                 Location/Qualifiers
source                  1..236
                        mol_type = protein
                        organism = synthetic construct
SEQUENCE: 96
QVKLQQSGPE LVRPGASVKM SCKASGYTFT TYWMHWVKQR PGQGLEWIGM IDPSNSDTRL      60
NQKFKDKATL NVDTSSNTAY MHLSSLTSED SAVYYCTLGG TEYWGQGATL TVSSGGGGSG     120
GGGSGGGGSS IVMTQSPATL SVTPGDRVSL SCRASQSIGD YLHWFQQKSH ESPRLLIKYA     180
SQSISGIPSR FSGSGSGSDF TLIINTMEPE DVGVYYCQNA HTYPYTFGGG TKLEIK         236

SEQ ID NO: 97           moltype = AA  length = 114
FEATURE                 Location/Qualifiers
source                  1..114
                        mol_type = protein
                        organism = synthetic construct
SEQUENCE: 97
QVKLQQSGPE LVRPGASVKM SCKASGYTFT TYWMHWVKQR PGQGLEWIGM IDPSNSDTRL      60
NQKFKDKATL NVDTSSNTAY MHLSSLTSED SAVYYCTLGG TEYWGQGATL TVSS           114

SEQ ID NO: 98           moltype = AA  length = 107
FEATURE                 Location/Qualifiers
source                  1..107
                        mol_type = protein
                        organism = synthetic construct
SEQUENCE: 98
SIVMTQSPAT LSVTPGDRVS LSCRASQSIG DYLHWFQQKS HESPRLLIKY ASQSISGIPS      60
RFSGSGSGSD FTLIINTMEP EDVGVYYCQN AHTYPYTFGG GTKLEIK                   107
```

| | | |
|---|---|---|
| SEQ ID NO: 99 | moltype = DNA length = 738 | |
| FEATURE | Location/Qualifiers | |
| source | 1..738 | |
| | mol_type = other DNA | |
| | organism = synthetic construct | |

SEQUENCE: 99
```
gaagtgaagc tgaagcagtc tggggctgaa ctggtgaagc ctggggcttc agtgaagttg   60
tcctgcaagg cttctggcta caccctcacc agttactata tttactgggt gaagcagagg  120
cctggacaag gccttgagtg gattgggggg attagtccta gcaatggtaa tacttacttc  180
actgagaagt tcaagaacat ggccacactg actgtagaca aatcctccaa cacagcctac  240
atgcaactca gcagcctgac atctgaggac tctgcggtct attactgtgc aagaaactat  300
gattacgacg tggggtttgc ttactgggc caagggactc tggtcacagt ctcctcaggt   360
ggtggtggta gcggcggcgg cggctctggt ggtggtggat ccgatgttgt gatgacccaa  420
actccactct ccctgcctgt cagtcttgga gatcaagcct ccatctcttg cagatctagt  480
cagagcattg tacatagtaa tggaaacacc tatttagaat ggtacctgca gaaaccaggc  540
cagtctccaa agctcctgat ctacaaagtt tccaaccgat tttctgggt ccagacagg    600
ttcagtggca gtggatcagg gacagatttc acactcaaga tcagcagagt ggaggctgag  660
gatctgggag tttattactg cttcaaggt tcacatgttc cattcacgtt cggctcgggg   720
accaagctgg aaatcaaa                                                738
```

| | | |
|---|---|---|
| SEQ ID NO: 100 | moltype = AA length = 246 | |
| FEATURE | Location/Qualifiers | |
| source | 1..246 | |
| | mol_type = protein | |
| | organism = synthetic construct | |

SEQUENCE: 100
```
EVKLKQSGAE LVKPGASVKL SCKASGYTLT SYYIYWVKQR PGQGLEWIGG ISPSNGNTYF   60
TEKFKNMATL TVDKSSNTAY MQLSSLTSED SAVYYCARNY DYDVGFAYWG QGTLVTVSSG  120
GGGSGGGGSG GGGSDVVMTQ TPLSLPVSLG DQASISCRSS QSIVHSNGNT YLEWYLQKPG  180
QSPKLLIYKV SNRFSGVPDR FSGSGSGTDF TLKISRVEAE DLGVYYCFQG SHVPFTFGSG  240
TKLEIK                                                             246
```

| | | |
|---|---|---|
| SEQ ID NO: 101 | moltype = AA length = 119 | |
| FEATURE | Location/Qualifiers | |
| source | 1..119 | |
| | mol_type = protein | |
| | organism = synthetic construct | |

SEQUENCE: 101
```
EVKLKQSGAE LVKPGASVKL SCKASGYTLT SYYIYWVKQR PGQGLEWIGG ISPSNGNTYF   60
TEKFKNMATL TVDKSSNTAY MQLSSLTSED SAVYYCARNY DYDVGFAYWG QGTLVTVSS   119
```

| | | |
|---|---|---|
| SEQ ID NO: 102 | moltype = AA length = 112 | |
| FEATURE | Location/Qualifiers | |
| source | 1..112 | |
| | mol_type = protein | |
| | organism = synthetic construct | |

SEQUENCE: 102
```
DVVMTQTPLS LPVSLGDQAS ISCRSSQSIV HSNGNTYLEW YLQKPGQSPK LLIYKVSNRF   60
SGVPDRFSGS GSGTDFTLKI SRVEAEDLGV YYCFQGSHVP FTFGSGTKLE IK          112
```

| | | |
|---|---|---|
| SEQ ID NO: 103 | moltype = DNA length = 726 | |
| FEATURE | Location/Qualifiers | |
| source | 1..726 | |
| | mol_type = other DNA | |
| | organism = synthetic construct | |

SEQUENCE: 103
```
caggtgcagc tgaaggagtc tgggggaggc ttagtgcagc ctggggagtc cctgaaactc   60
tcctgtgaat ccagtgaatt cccattccct tccatgaca tgtcttgggt ccgcaagact   120
ccggagaaga ggctggagtt ggtcgcagcc attaatagtg atggtggtag cacctactat  180
ccagacacca tggagagacg attcatcatc tccagagaca ataccaagaa gaccctgtac  240
ctgcaaatga gcagtctgag gtctgaggac acagccttgt attactgtgc aagcctaccc  300
acgtttgctt actggggcca agggactctg gtcactgtct ctgcaggtgg tggtggtagc  360
ggcggcggcg gctctggtgg tggtggatcc agtattgtga tgacccaaac tccactcact  420
ttgtcggtta ccattggaca accagcctct atctcttgca agtcaagtca gagcctctta  480
tatagtgatg gacaacccta tttgaattgg ttattacaga ggccaggcca gtctccaaag  540
cgcctaatct atctggtgtc taaactggac tctggagtcc ctgacaggtt cactggcagt  600
ggatcaggta cagattttac actgaaaatc agcagagtgg aggctgagga tttgggagtt  660
tattactgcg tgcaaactac acattttccg tacacgttcg gagggggac caagctggaa   720
atgaaa                                                             726
```

| | | |
|---|---|---|
| SEQ ID NO: 104 | moltype = AA length = 242 | |
| FEATURE | Location/Qualifiers | |
| source | 1..242 | |
| | mol_type = protein | |
| | organism = synthetic construct | |

SEQUENCE: 104
```
QVQLKESGGG LVQPGESLKL SCESSEFPFP SHDMSWVRKT PEKRLELVAA INSDGGSTYY   60
PDTMERRFII SRDNTKKTLY LQMSSLRSED TALYYCASLP TFAYWGQGTL VTVSAGGGGS  120
GGGGSGGGGS SIVMTQTPLT LSVTIGQPAS ISCKSSQSLL YSDGQTYLNW LLQRPGQSPK  180
```

```
RLIYLVSKLD SGVPDRFTGS GSGTDFTLKI SRVEAEDLGV YYCVQTTHFP YTFGGGTKLE   240
MK                                                                 242

SEQ ID NO: 105          moltype = AA  length = 115
FEATURE                 Location/Qualifiers
source                  1..115
                        mol_type = protein
                        organism = synthetic construct
SEQUENCE: 105
QVQLKESGGG LVQPGESLKL SCESSEFPFP SHDMSWVRKT PEKRLELVAA INSDGGSTYY   60
PDTMERRFII SRDNTKKTLY LQMSSLRSED TALYYCASLP TFAYWGQGTL VTVSA        115

SEQ ID NO: 106          moltype = AA  length = 112
FEATURE                 Location/Qualifiers
source                  1..112
                        mol_type = protein
                        organism = synthetic construct
SEQUENCE: 106
SIVMTQTPLT LSVTIGQPAS ISCKSSQSLL YSDGQTYLNW LLQRPGQSPK RLIYLVSKLD   60
SGVPDRFTGS GSGTDFTLKI SRVEAEDLGV YYCVQTTHFP YTFGGGTKLE MK           112

SEQ ID NO: 107          moltype = DNA  length = 720
FEATURE                 Location/Qualifiers
source                  1..720
                        mol_type = other DNA
                        organism = synthetic construct
SEQUENCE: 107
caggttcagc tgcagcagtc tggggcagag cttgtgaggt caggggcctc agtcaagttg   60
tcctgcacag attctggctt caacattaaa gactactata tgaactgggt gaaacagcgg   120
cctgaacagg gcctggagtg gattggatgg attgatcctg aaaatggtgt tactcaatat   180
gacccgaagt tccagggcaa ggccactgtg actgcagaca cattctccaa cacagcctac   240
ctgcagctca gcagcctgac atctgaggac actgccgtct attactgtaa tgcaaactat   300
aagtacgact ggtttggtta ctggggccaa gggactctgg tcactgtctc tgcaggtggt   360
ggtggtagcg gcggcggcgg ctcggtggt ggtggatcca acattgtaat gacccagtct   420
ccatcctcct tatctgcctc tctgggagaa agagtcagtc tcacttgtcg ggcaagtcag   480
gaaattagtg gttacttaag ctggcttcag cagaaaccag atggaactat aaacgcctg    540
atctacgccg catccacttt agattctggt gtcccagaaa ggttcagtgg cagtaggtct   600
gggtcagatt attctctcac catcagcagc cttgagtctg aagattttgc agactattac   660
tgtctacaat atgctagtta tccgtggacg ttcggtggag ggaccaagct ggaaatgaaa   720

SEQ ID NO: 108          moltype = AA  length = 240
FEATURE                 Location/Qualifiers
source                  1..240
                        mol_type = protein
                        organism = synthetic construct
SEQUENCE: 108
QVQLQQSGAE LVRSGASVKL SCTDSGFNIK DYYMNWVKQR PEQGLEWIGW IDPENGVTQY   60
DPKFQGKATV TADTFSNTAY LQLSSLTSED TAVYYCNANY KYDWFGYWGQ GTLVTVSAGG   120
GGSGGGGSGG GGSNIVMTQS PSSLSASLGE RVSLTCRASQ EISGYLSWLQ QKPDGTIKRL   180
IYAASTLDSG VPERFSGSRS GSDYSLTISS LESEDFADYY CLQYASYPWT FGGGTKLEMK   240

SEQ ID NO: 109          moltype = AA  length = 118
FEATURE                 Location/Qualifiers
source                  1..118
                        mol_type = protein
                        organism = synthetic construct
SEQUENCE: 109
QVQLQQSGAE LVRSGASVKL SCTDSGFNIK DYYMNWVKQR PEQGLEWIGW IDPENGVTQY   60
DPKFQGKATV TADTFSNTAY LQLSSLTSED TAVYYCNANY KYDWFGYWGQ GTLVTVSA     118

SEQ ID NO: 110          moltype = AA  length = 107
FEATURE                 Location/Qualifiers
source                  1..107
                        mol_type = protein
                        organism = synthetic construct
SEQUENCE: 110
NIVMTQSPSS LSASLGERVS LTCRASQEIS GYLSWLQQKP DGTIKRLIYA ASTLDSGVPE   60
RFSGSRSGSD YSLTISSLES EDFADYYCLQ YASYPWTFGG GTKLEMK                 107

SEQ ID NO: 111          moltype = DNA  length = 723
FEATURE                 Location/Qualifiers
source                  1..723
                        mol_type = other DNA
                        organism = synthetic construct
SEQUENCE: 111
caggtgcagc tgaagcagtc tgggcctggg ctggtgaggc tggggcttc agtgacgatg    60
tcctgcaagg cttcaggcta taccttcacc agcaactgga tgcactgggt aaacagagg    120
cctggacaag gccttgattg gattggcatg attgatcctt ccaatagtga cactaggtta   180
aatcagaagt tcaaggacaa ggccacattg aatgtagaca atcctccaa cacagcctac    240
```

```
atgcagctca gcagcctgac gtctgatgac tctgcagtct attactgtat gagaggggc      300
ggcgactact ggggccaagg caccactctc acagtctcct caggtggtgg tggtagcggc      360
ggcggctctg gtggtggtgg atccgacatt gtgatgtcac agtctccatc ctccctagct      420
gtgtcagttg gagagaaggt tactatgagc tgcaagtcca gtcagagcct tttatatagt      480
agcaatcaaa agaactactt ggcctggtac cagcagaaac caggccagtc tcctaaactg      540
ctgatttact gggcatccac tagggaatcc ggggtccctg atcgcttcac aggcagtgga      600
tctgggacag atttcactct caccatcagc agtgtgaagg ctgaagacct ggcagtttat      660
tactgtcagc aatattatag ctatccgtac acgttcggag gggggaccaa gctggaaatg      720
aaa                                                                    723

SEQ ID NO: 112             moltype = AA  length = 242
FEATURE                    Location/Qualifiers
source                     1..242
                           mol_type = protein
                           organism = synthetic construct
SEQUENCE: 112
QVQLKQSGPG LVRPGASVTM SCKASGYTFT SNWMHWVKQR PGQGLDWIGM IDPSNSDTRL      60
NQKFKDKATL NVDKSSNTAY MQLSSLTSDD SAVYYCMRGG GDYWGQGTTL TVSSGGGGSG      120
GGGSGGGGSD IVMSQSPSSL AVSVGEKVTM SCKSSQSLLY SSNQKNYLAW YQQKPGQSPK      180
LLIYWASTRE SGVPDRFTGS GSGTDFTLTI SSVKAEDLAV YYCQQYYSYP YTFGGGTKLE      240
MK                                                                     242

SEQ ID NO: 113             moltype = AA  length = 114
FEATURE                    Location/Qualifiers
source                     1..114
                           mol_type = protein
                           organism = synthetic construct
SEQUENCE: 113
QVQLKQSGPG LVRPGASVTM SCKASGYTFT SNWMHWVKQR PGQGLDWIGM IDPSNSDTRL      60
NQKFKDKATL NVDKSSNTAY MQLSSLTSDD SAVYYCMRGG GDYWGQGTTL TVSS            114

SEQ ID NO: 114             moltype = AA  length = 113
FEATURE                    Location/Qualifiers
source                     1..113
                           mol_type = protein
                           organism = synthetic construct
SEQUENCE: 114
DIVMSQSPSS LAVSVGEKVT MSCKSSQSLL YSSNQKNYLA WYQQKPGQSP KLLIYWASTR      60
ESGVPDRFTG SGSGTDFTLT ISSVKAEDLA VYYCQQYYSY PYTFGGGTKL EMK             113

SEQ ID NO: 115             moltype = DNA  length = 720
FEATURE                    Location/Qualifiers
source                     1..720
                           mol_type = other DNA
                           organism = synthetic construct
SEQUENCE: 115
gaggtgcagc tgaaggagtc tggggcagag cttgtgaggt caggggcctc agtcaagttg      60
tcctgcacag cttctgcctt caacattaaa gactactata tgaactggat gaagcagagg      120
cctgaacagg gcctggagtg gattggatgg attgatcctg agaatggtga ctactaaatat     180
gccccgaagt tccagggcaa ggccactatc actgcagaca catcctccag cacagcctac      240
ctgcagctca ccagcctgac atctgaggac tctgccgtct tctattgtaa tgtaaactat      300
aagtacgact ggtttgctta ctggggccaa gggactctgg tcactgtctc tgcaggtggt      360
ggtggtagcg gcggcggcgg ctctggtggt ggtggatccg atgttgtgat gacccagtcc      420
caaaaattca tgtccacatc agtaggagac agggtcagcg tcacctgcaa ggccagtcag      480
aatgtgggta ctaatgtagc ctggtatcaa cagaaaccag gcaatctcc tagagcactg       540
atttactcgg catcctaccg gtacagtgga gtccctgatc gcttcacagg cagtggatct      600
gggacagatt tcactctcac catcagcaat gtgcagtctg aagacttggc agagtatttc      660
tgtcagcaat ataacaccta tccgtggacg ttcggtgggg gacaaagct ggaaataaaa       720

SEQ ID NO: 116             moltype = AA  length = 240
FEATURE                    Location/Qualifiers
source                     1..240
                           mol_type = protein
                           organism = synthetic construct
SEQUENCE: 116
EVQLKESGAE LVRSGASVKL SCTASAFNIK DYYMNWMKQR PEQGLEWIGW IDPENGDTKY      60
APKFQGKATI TADTSSSTAY LQLTSLTSED SAVFYCNVNY KYDWFAYWGQ GTLVTVSAGG      120
GGSGGGGSGG GGSDVVMTQS QKFMSTSVGD RVSVTCKASQ NVGTNVAWYQ QKPGQSPRAL      180
IYSASYRYSG VPDRFTGSGS GTDFTLTISN VQSEDLAEYF CQQYNTYPWT FGGGTKLEIK      240

SEQ ID NO: 117             moltype = AA  length = 118
FEATURE                    Location/Qualifiers
source                     1..118
                           mol_type = protein
                           organism = synthetic construct
SEQUENCE: 117
EVQLKESGAE LVRSGASVKL SCTASAFNIK DYYMNWMKQR PEQGLEWIGW IDPENGDTKY      60
APKFQGKATI TADTSSSTAY LQLTSLTSED SAVFYCNVNY KYDWFAYWGQ GTLVTVSA       118
```

```
SEQ ID NO: 118            moltype = AA  length = 107
FEATURE                   Location/Qualifiers
source                    1..107
                          mol_type = protein
                          organism = synthetic construct
SEQUENCE: 118
DVVMTQSQKF MSTSVGDRVS VTCKASQNVG TNVAWYQQKP GQSPRALIYS ASYRYSGVPD   60
RFTGSGSGTD FTLTISNVQS EDLAEYFCQQ YNTYPWTFGG GTKLEIK                107

SEQ ID NO: 119            moltype = DNA  length = 720
FEATURE                   Location/Qualifiers
source                    1..720
                          mol_type = other DNA
                          organism = synthetic construct
SEQUENCE: 119
caggtccaac tgcagcagtc tgggcctgag ctggtgaggc ctggggcttc agtgacgatg   60
tcctgcaagg cttcaggcta taccttcacc agcaactgga tgcactgggt taaacagagg  120
cctggacaag gccttgattg gattggcatg attgatcct  ccaatagtga cactaggtta  180
aatcagaagt tcaaggacaa ggccacattg aatgtagaca atcctccaa  cacagcctac  240
atgcagctca gcagcctgac gtctgaggac tctgcagtct attactgtat gagagggggc  300
ggcgactact ggggccaagg caccactctc acagtctcct caggtggtgg tggtagcggc  360
ggcggcggct ctggtggtgg tggatccgac atttgtgatga cccagtctcc agcttctttg  420
gctgtgtctc tagggcagag ggccaccatc tcctgcaagg ccagccaaag tgttgattat  480
gatggtgata gttatatgaa ctggtaccaa cagaaaccag gacagccacc caaactcctc  540
atctatgctg catccaatct agaatctggg atcccagcca ggtttagtgg cagtgggtct  600
gggacagact tcaccctcaa catccatcct gtggaggagg aggatgctgc aacctattac  660
tgtcagcaca gttgggagat tccgtacacg ttcggagggg gcaccaagct ggaaatgaaa  720

SEQ ID NO: 120            moltype = AA  length = 240
FEATURE                   Location/Qualifiers
source                    1..240
                          mol_type = protein
                          organism = synthetic construct
SEQUENCE: 120
QVQLQQSGPE LVRPGASVTM SCKASGYTFT SNWMHWVKQR PGQGLDWIGM IDPSNSDTRL   60
NQKFKDKATL NVDKSSNTAY MQLSSLTSED SAVYYCMRGG GDYWGQGTTL TVSSGGGGSG  120
GGGSGGGGSD IVMTQSPASL AVSLGQRATI SCKASQSVDY DGDSYMNWYQ QKPGQPPKLL  180
IYAASNLESG IPARFSGSGS GTDFTLNIHP VEEEDAATYY CQHSWEIPYT FGGGTKLEMK  240

SEQ ID NO: 121            moltype = AA  length = 114
FEATURE                   Location/Qualifiers
source                    1..114
                          mol_type = protein
                          organism = synthetic construct
SEQUENCE: 121
QVQLQQSGPE LVRPGASVTM SCKASGYTFT SNWMHWVKQR PGQGLDWIGM IDPSNSDTRL   60
NQKFKDKATL NVDKSSNTAY MQLSSLTSED SAVYYCMRGG GDYWGQGTTL TVSS        114

SEQ ID NO: 122            moltype = AA  length = 111
FEATURE                   Location/Qualifiers
source                    1..111
                          mol_type = protein
                          organism = synthetic construct
SEQUENCE: 122
DIVMTQSPAS LAVSLGQRAT ISCKASQSVD YDGDSYMNWY QQKPGQPPKL LIYAASNLES   60
GIPARFSGSG SGTDFTLNIH PVEEEDAATY YCQHSWEIPY TFGGGTKLEM K           111

SEQ ID NO: 123            moltype = AA  length = 499
FEATURE                   Location/Qualifiers
source                    1..499
                          mol_type = protein
                          organism = synthetic construct
SEQUENCE: 123
QVQLQQSDAE LVKPGSSVKI SCKASGYTFT DHAIHWVKQK PEQGLEWIGH FSPGNTDIKY   60
NDKFKGKATL TVDRSSTAY  MQLNSLTSED SAVYFCKTST FFFDYWGQGT TLTVSSGGGG  120
SGGGGSGGGG SDIVMTQSPS SLTVTAGEKV TMICKSSQSL LNSGDQKNYL TWYQQKPGQP  180
PKLLIFWAST RESGVPDRFT GSGSGTDFTL TISSVQAEDL AVYYCQNDYS YPLTFGAGTK  240
LELKSGGGGS EVQLVESGGG LVQPGGSLKL SCAASGFTFN KYAMNWVRQA PGKGLEWVAR  300
IRSKYNNYAT YYADSVKDRF TISRDDSKNT AYLQMNNLKT EDTAVYYCVR HGNFGNSYIS  360
YWAYWGQGTL VTVSSGGGGS GGGGSGGGGS QTVVTQEPSL TVSPGGTVTL TCGSSTGAVT  420
SGNYPNWVQQ KPGQAPRGLI GGTKFLAPGT PARFSGSLLG GKAALTLSGV QPEDEAEYYC  480
VLWYSNRWVF GGGTKLTVL                                               499

SEQ ID NO: 124            moltype = AA  length = 501
FEATURE                   Location/Qualifiers
source                    1..501
                          mol_type = protein
                          organism = synthetic construct
SEQUENCE: 124
```

```
EVKLVESGGG LVQPGGSMKL SCVASGFTFS NYWMNWVRQS PEKGLEWVAE IRLKSNNYTT   60
HYAESVKGRF TISRDDSKSS VSLQMNNLRV EDTGIYYCTR HYYFDYWGQG TTLTVSSGGG  120
GSGGGGSGGG GSDIVMTQAA FSNPVTLGTS ASISCRSSKS LLHSNGITYF FWYLQKPGLS  180
PQLLIYQMSN LASGVPDRFS SSGSGTDFTL RISRVEAEDV GVYYCAQNLE LPPTFGGGTK  240
LEIKRASGGG GSEVQLVESG GGLVQPGGSL KLSCAASGFT FNKYAMNWVR QAPGKGLEWV  300
ARIRSKYNNY ATYYADSVKD RFTISRDDSK NTAYLQMNNL KTEDTAVYYC VRHGNFGNSY  360
ISYWAYWGQG TLVTVSSGGG GSGGGGSGGG GSQTVVTQEP SLTVSPGGTV TLTCGSSTGA  420
VTSGNYPNWV QQKPGQAPRG LIGGTKFLAP GTPARFSGSL LGGKAALTLS GVQPEDEAEY  480
YCVLWYSNRW VFGGGTKLTV L                                           501

SEQ ID NO: 125         moltype = AA  length = 492
FEATURE                Location/Qualifiers
source                 1..492
                       mol_type = protein
                       organism = synthetic construct
SEQUENCE: 125
EVQLQQSGAE LVKPGASVKL SCTASGFNIN DTYMHWVKQR PEQGLEWIGR IDPANGNTKY   60
DPKFQGKATI TADTSSNTAY LQLSSLTSED TAVYYCARGA RGSRFAYWGQ GTLVTVSAGG  120
GGSGGGGSGG GGSDIQMTQS PASLSVSVGE TVTITCRASE NIYSNLAWYQ QKQGKSPQLL  180
VYVATNLADG VPSRFSGSGS GTQYSLKINS LQSEDFGSYY CQHFWGTPYT FGGGTKLSGG  240
GGSEVQLVES GGGLVQPGGS LKLSCAASGF TFNKYAMNWV RQAPGKGLEW VARIRSKYNN  300
YATYYADSVK DRFTISRDDS KNTAYLQMNN LKTEDTAVYY CVRHGNFGNS YISYWAYWGQ  360
GTLVTVSSGG GGSGGGGSGG GGSQTVVTQE PSLTVSPGGT VTLTCGSSTG AVTSGNYPNW  420
VQQKPGQAPR GLIGGTKFLA PGTPARFSGS LLGGKAALTL SGVQPEDEAE YYCVLWYSNR  480
WVFGGGTKLT VL                                                     492

SEQ ID NO: 126         moltype = AA  length = 499
FEATURE                Location/Qualifiers
source                 1..499
                       mol_type = protein
                       organism = synthetic construct
SEQUENCE: 126
EVQLVQSGAE VKKPGQSLKI SCKASGYSLT DNWIGWVRQK PGKGLEWMGI IYPGDSDTRY   60
SPSFQGQVTI SADKSINTAY LQWSSLKASD TAIYYCVGLD WNYNPLRYWG PGTLVTVSSG  120
GGGSGGGGSG GGGSQSVLTQ PPSVSAAPGQ KVTISCSGSS SDIGSNYVSW YQQFPGTAPK  180
LLIYDNNKRP SAIPDRFSGS KSGTSATLGI TGLQTGDEAD YYCGTWDSRL GIAVFGGGTQ  240
LTVLSGGGGS EVQLVESGGG LVQPGGSLKL SCAASGFTFN KYAMNWVRQA PGKGLEWVAR  300
IRSKYNNYAT YYADSVKDRF TISRDDSKNT AYLQMNNLKT EDTAVYYCVR HGNFGNSYIS  360
YWAYWGQGTL VTVSSGGGGS GGGGSGGGGS QTVVTQEPSL TVSPGGTVTL TCGSSTGAVT  420
SGNYPNWVQQ KPGQAPRGLI GGTKFLAPGT PARFSGSLLG GKAALTLSGV QPEDEAEYYC  480
VLWYSNRWVF GGGTKLTVL                                              499

SEQ ID NO: 127         moltype = AA  length = 507
FEATURE                Location/Qualifiers
source                 1..507
                       mol_type = protein
                       organism = synthetic construct
SEQUENCE: 127
EVQLVESGGD LVKPGGSLKL SCAVSGFTFS SYGMSWVRQT PDKRLEWVAT VSSGGTYTYY   60
PDSVKGRFTI SRDNAKNTLY LQMSSLKSED SAMYYCARHR GNYYATYYYA MDYWGQGTSV  120
TVSSGGGSSG GGGSGGGGSD IVLTQSPASL AVSLGQGATI SCRASKSVST SGYTYMHWYQ  180
QKPGQPPKLL IYLASNLESG VPARFSGSGS GTDFTLNIHP VEEEDAATYY CQHSGELPPS  240
FGGGTKLEIK RASGGGGSEV QLVESGGGLV QPGGSLKLSC AASGFTFNKY AMNWVRQAPG  300
KGLEWVARIR SKYNNYATYY ADSVKDRFTI SRDDSKNTAY LQMNNLKTED TAVYYCVRHG  360
NFGNSYISYW AYWGQGTLVT VSSGGGGSGG GGSGGGGSQT VVTQEPSLTV SPGGTVTLTC  420
GSSTGAVTSG NYPNWVQQKP GQAPRGLIGG TKFLAPGTPA RFSGSLLGGK AALTLSGVQP  480
EDEAEYYCVL WYSNRWVFGG GTKLTVL                                     507

SEQ ID NO: 128         moltype = AA  length = 498
FEATURE                Location/Qualifiers
source                 1..498
                       mol_type = protein
                       organism = synthetic construct
SEQUENCE: 128
QVQLQQPGAE LVRPGASVKL SCKASGYTFT TYWMNWVKQR PEQGLEWIGR IDPYDSETHY   60
NQKFKDKAIL TVDKSSTAY MQLSSLTSED SAVYYCARGP YYGTNPWFPY WGQGTLVTVS  120
SGGGGSGGGG SGGGGSDVQI TQSPSYLAAS PGETITINCR ASKSISKYLA WYQEKPGKTN  180
KLLIYSGSTL QSGIPSRFSG SGSGTDFTLT ISSLEPEDFA MYYCQQHHEY PYTFGGGTKL  240
EIKSGGGGSE VQLVESGGGL VQPGGSLKLS CAASGFTFNK YAMNWVRQAP GKGLEWVARI  300
RSKYNNYATY YADSVKDRFT ISRDDSKNTA YLQMNNLKTE DTAVYYCVRH GNFGNSYISY  360
WAYWGQGTLV TVSSGGGGSG GGGSGGGGSQ TVVTQEPSLT VSPGGTVTLT CGSSTGAVTS  420
GNYPNWVQQK PGQAPRGLIG GTKFLAPGTP ARFSGSLLGG KAALTLSGVQ PEDEAEYYCV  480
LWYSNRWVFG GGTKLTVL                                               498

SEQ ID NO: 129         moltype = AA  length = 496
FEATURE                Location/Qualifiers
source                 1..496
                       mol_type = protein
                       organism = synthetic construct
```

```
SEQUENCE: 129
QVQLQQWGAG LLKPSETLSL TCAVFGGSFS GYYWSWIRQP PGKGLEWIGE INHRGNTNDN    60
PSLKSRVTIS VDTSKNQFAL KLSSVTAADT AVYYCARERG YTYGNFDHWG QGTLVTVSSG   120
GGGSGGGGSG GGGSEIVMTQ SPATLSVSPG ERATLSCRAS QSVSRNLAWY QQKPGQAPRL   180
LIYGASTRAT GIPARFSGSG SGTEFTLTIG SLQSEDFAVY YCQQYKTWPR TFGQGTNVEI   240
KSGGGGSEVQ LVESGGGLVQ PGGSLKLSCA ASGFTFNKYA MNWVRQAPGK GLEWVARIRS   300
KYNNYATYYA DSVKDRFTIS RDDSKNTAYL QMNNLKTEDT AVYYCVRHGN FGNSYISYWA   360
YWGQGTLVTV SSGGGGSGGG GSGGGGSQTV VTQEPSLTVS PGGTVTLTCG SSTGAVTSGN   420
YPNWVQQKPG QAPRGLIGGT KFLAPGTPAR FSGSLLGGKA ALTLSGVQPE DEAEYYCVLW   480
YSNRWVFGGG TKLTVL                                                  496

SEQ ID NO: 130          moltype = AA  length = 501
FEATURE                 Location/Qualifiers
source                  1..501
                        mol_type = protein
                        organism = synthetic construct
SEQUENCE: 130
QVQLRQSGPE LVKPGASVKM SCKASGYTFT DYVISWVKQR TGQGLEWIGD IYPGSGYSFY    60
NENFKGKATL TADKSSTTAY MQLSSLTSED SAVYFCATYY NYPFAYWGQG TLVTVSAGGG   120
GSGGGGSGGG GSDVVMTQTP LSLPVRLGDQ ASISCRSSQS LVHSNGNTYL HWYLQKPGQS   180
PKLLIYKVSN RFSGVPDRFS GSGSGTNFTL KISRVEAEDL GLYFCSQSTH VPYTFGGGTK   240
LEIKRASGGG GSEVQLVESG GGLVQPGGSL KLSCAASGFT FNKYAMNWVR QAPGKGLEWV   300
ARIRSKYNNY ATYYADSVKD RFTISRDDSK NTAYLQMNNL KTEDTAVYYC VRHGNFGNSY   360
ISYWAYWGQG TLVTVSSGGG GSGGGGSGGG GSQVVTQEP SLTVSPGGTV TLTCGSSTGA   420
VTSGNYPNWV QQKPGQAPRG LIGGTKFLAP GTPARFSGSL LGGKAALTLS GVQPEDEAEY   480
YCVLWYSNRW VFGGGTKLTV L                                            501

SEQ ID NO: 131          moltype = AA  length = 501
FEATURE                 Location/Qualifiers
source                  1..501
                        mol_type = protein
                        organism = synthetic construct
SEQUENCE: 131
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSGG   120
GGSGGGGSGG GGSDIVMTQS PSSLTVTAGE KVTMSCKSSQ SLLNSGNQKN YLTWYQQKPG   180
QPPKLLIYWA STRESGVPDR FTGSGSGTDF TLTISSVQAE DLAVYYCQND YSYPFTFGSG   240
TKLEIKSGGG GSEVQLVESG GGLVQPGGSL KLSCAASGFT FNKYAMNWVR QAPGKGLEWV   300
ARIRSKYNNY ATYYADSVKD RFTISRDDSK NTAYLQMNNL KTEDTAVYYC VRHGNFGNSY   360
ISYWAYWGQG TLVTVSSGGG GSGGGGSGGG GSQVVTQEP SLTVSPGGTV TLTCGSSTGA   420
VTSGNYPNWV QQKPGQAPRG LIGGTKFLAP GTPARFSGSL LGGKAALTLS GVQPEDEAEY   480
YCVLWYSNRW VFGGGTKLTV L                                            501

SEQ ID NO: 132          moltype = AA  length = 496
FEATURE                 Location/Qualifiers
source                  1..496
                        mol_type = protein
                        organism = synthetic construct
SEQUENCE: 132
EVQLQQSGPE LVKPGGSMKI SCKASGYSFT GYTMNWVKQS HGKNLEWIGL INPYNGGISY    60
NQKFKDKATL TMDKSSSTAY MELLSLTSED SAIYFCARDY RYEGFDYWGQ GTLVTVSAGG   120
GGSGGGGSGG GGSQIVLTQS PAIMSASLGE RVTMTCTASS VVISTYLHWY QQKPGSSPKL   180
WIYSTSNLAS GVPVRFSGSG SGTSYSLTIS SMEAEDAATY YCHQYHRSPW TFGGGTKLEI   240
KSGGGGSEVQ LVESGGGLVQ PGGSLKLSCA ASGFTFNKYA MNWVRQAPGK GLEWVARIRS   300
KYNNYATYYA DSVKDRFTIS RDDSKNTAYL QMNNLKTEDT AVYYCVRHGN FGNSYISYWA   360
YWGQGTLVTV SSGGGGSGGG GSGGGGSQTV VTQEPSLTVS PGGTVTLTCG SSTGAVTSGN   420
YPNWVQQKPG QAPRGLIGGT KFLAPGTPAR FSGSLLGGKA ALTLSGVQPE DEAEYYCVLW   480
YSNRWVFGGG TKLTVL                                                  496

SEQ ID NO: 133          moltype = AA  length = 505
FEATURE                 Location/Qualifiers
source                  1..505
                        mol_type = protein
                        organism = synthetic construct
SEQUENCE: 133
EIQLQQSGAE VKKPGSSVKV SCKASGYTFT DYDMHWVRQA PGQGLEWMGT IDPETGGTAY    60
NQKFKGRVTI TADKSTSTAY MELSSLRSED TAVYYCTSFY YTYSNYDVGF AYWGQGTLVT   120
VSSGGGGSGG GSGGGGSDI VMTQSPLSLP VTPGEPASIS CRSTKSLLHS NGNTYLYWYL   180
QKPGQSPQLL IYRMSNLASG VPDRFSGSGS GTDFTLKISR VEAEDVGVYY CMQHLEYPFT   240
FGGGTKVEIK SGGGGSEVQL VESGGGLVQP GGSLKLSCAA SGFTFNKYAM NWVRQAPGKG   300
LEWVARIRSK YNNYATYYAD SVKDRFTISR DDSKNTAYLQ MNNLKTEDTA VYYCVRHGNF   360
GNSYISYWAY WGQGTLVTVS SGGGGSGGGG SGGGGSQTVV TQEPSLTVSP GGTVTLTCGS   420
STGAVTSGNY PNWVQQKPGQ APRGLIGGTK FLAPGTPARF SGSLLGGKAA LTLSGVQPED   480
EAEYYCVLWY SNRWVFGGGT KLTVL                                        505

SEQ ID NO: 134          moltype = AA  length = 493
FEATURE                 Location/Qualifiers
source                  1..493
                        mol_type = protein
```

```
                        organism = synthetic construct
SEQUENCE: 134
EVQLVESGGG LVQPGGSLRL SCAASGYSIT NDYAWNWVRQ APGKGLEWVG YISYSGYTTY    60
NPSLKSRFTI SRDTSKNTLY LQMNSLRAED TAVYYCARWT SGLDYWGQGT LVTVSSGGGG   120
SGGGGSGGGG SDIQMTQSPS SLSASVGDRV TITCKASDLI HNWLAWYQQK PGKAPKLLIY   180
GATSLETGVP SRFSGSGSGT DFTLTISSLQ PEDFATYYCQ QYWTTPFTFG QGTKVEIKSG   240
GGGSEVQLVE SGGGLVQPGG SLKLSCAASG FTFNKYAMNW VRQAPGKGLE WVARIRSKYN   300
NYATYYADSV KDRFTISRDD SKNTAYLQMN NLKTEDTAVY YCVRHGNFGN SYISYWAYWG   360
QGTLVTVSSG GGGSGGGGSG GGGSQTVVTQ EPSLTVSPGG TVTLTCGSST GAVTSGNYPN   420
WVQQKPGQAP RGLIGGTKFL APGTPARFSG SLLGGKAALT LSGVQPEDEA EYYCVLWYSN   480
RWVFGGGTKL TVL                                                     493

SEQ ID NO: 135          moltype = AA  length = 109
FEATURE                 Location/Qualifiers
source                  1..109
                        mol_type = protein
                        organism = synthetic construct
SEQUENCE: 135
QTVVTQEPSL TVSPGGTVTL TCGSSTGAVT SGNYPNWVQQ KPGQAPRGLI GGTKFLAPGT    60
PARFSGSLLG GKAALTLSGV QPEDEAEYYC VLWYSNRWVF GGGTKLTVL               109

SEQ ID NO: 136          moltype = AA  length = 244
FEATURE                 Location/Qualifiers
source                  1..244
                        mol_type = protein
                        organism = synthetic construct
SEQUENCE: 136
QSVLTQPPSV SAAPGQKVTI SCSGSSSDIG SNYVSWYQQF PGTAPKLLIY DNNKRPSAIP    60
DRFSGSKSGT SATLGITGLQ TGDEADYYCG TWDSRLGIAV FGGGTQLTVL GGGGSGGGGS   120
GGGGSEVQLV QSGAEVKKPG QSLKISCKAS GYSLTDNWIG WVRQKPGKGL EWMGIIYPGD   180
SDTRYSPSFQ GQVTISADKS INTAYLQWSS LKASDTAIYY CVGLDWNYNP LRYWGPGTLV   240
TVSS                                                                244

SEQ ID NO: 137          moltype = AA  length = 252
FEATURE                 Location/Qualifiers
source                  1..252
                        mol_type = protein
                        organism = synthetic construct
SEQUENCE: 137
DIVLTQSPAS LAVSLGQGAT ISCRASKSVS TSGYTYMHWY QQKPGQPPKL LIYLASNLES    60
GVPARFSGSG SGTDFTLNIH PVEEEDAATY YCQHSGELPP SFGGGTKLEI KRAGGGGSGG   120
GGSGGGGSEV QLVESGGDLV KPGGSLKLSC AVSGFTFSSY GMSWVRQTPD KRLEWVATVS   180
SGGTYTYYPD SVKGRFTISR DNAKNTLYLQ MSSLKSEDSA MYYCARHRGN YYATYYYAMD   240
YWGQGTSVTV SS                                                       252

SEQ ID NO: 138          moltype = AA  length = 243
FEATURE                 Location/Qualifiers
source                  1..243
                        mol_type = protein
                        organism = synthetic construct
SEQUENCE: 138
DVQITQSPSY LAASPGETIT INCRASKSIS KYLAWYQEKP GKTNKLLIYS GSTLQSGIPS    60
RFSGSGSGTD FTLTISSLEP EDFAMYYCQQ HHEYPYTFGG GTKLEIKGGG GSGGGGSGGG   120
GSQVQLQQPG AELVRPGASV KLSCKASGYT FTTYWMNWVK QRPEQGLEWI GRIDPYDSET   180
HYNQKFKDKA ILTVDKSSST AYMQLSSLTS EDSAVYYCAR GPYYGTNPWF PYWGQGTLVT   240
VSS                                                                 243

SEQ ID NO: 139          moltype = AA  length = 241
FEATURE                 Location/Qualifiers
source                  1..241
                        mol_type = protein
                        organism = synthetic construct
SEQUENCE: 139
EIVMTQSPAT LSVSPGERAT LSCRASQSVS RNLAWYQQKP GQAPRLLIYG ASTRATGIPA    60
RFSGSGSGTE FTLTIGSLQS EDFAVYYCQQ YKTWPRTFGQ GTNVEIKGGG GSGGGGSGGG   120
GSQVQLQQWG AGLLKPSETL SLTCAVFGGS FSGYYWSWIR QPPGKGLEWI GEINHRGNTN   180
DNPSLKSRVT ISVDTSKNQF ALKLSSVTAA DTAVYYCARE RGYTYGNFDH WGQGTLVTVS   240
S                                                                   241

SEQ ID NO: 140          moltype = AA  length = 246
FEATURE                 Location/Qualifiers
source                  1..246
                        mol_type = protein
                        organism = synthetic construct
SEQUENCE: 140
DVVMTQTPLS LPVRLGDQAS ISCRSSQSLV HSNGNTYLHW YLQKPGQSPK LLIYKVSNRF    60
SGVPDRFSGS GSGTNFTLKI SRVEAEDLGL YFCSQSTHVP YTFGGGTKLE IKRAGGGGSG   120
GGGSGGGGSQ VQLRQSGPEL VKPGASVKMS CKASGYTFTD YVISWVKQRT GQGLEWIGDI   180
YPGSGYSFYN ENFKGKATLT ADKSSTTAYM QLSSLTEEDS AVYFCATYYN YPFAYWGQGT   240
```

```
LVTVSA                                                                           246

SEQ ID NO: 141         moltype = AA  length = 199
FEATURE                Location/Qualifiers
source                 1..199
                       mol_type = protein
                       organism = synthetic construct
SEQUENCE: 141
LPICPGGAAR CQVTLRDLFD RAVVLSHYIH NLSSEMFSEF DKRYTHGRGF ITKAINSCHT     60
SSLATPEDKE QAQQMNQKDF LSLIVSILRS WNEPLYHLVT EVRGMQEAPE AILSKAVEIE    120
EQTKRLLEGM ELIVSQVHPE TKENEIYPVW SGLPSLQMAD EESRLSAYYN LLHCLRRDSH    180
KIDNYLKLLK CRIIHNNNC                                                 199

SEQ ID NO: 142         moltype = AA  length = 240
FEATURE                Location/Qualifiers
source                 1..240
                       mol_type = protein
                       organism = synthetic construct
SEQUENCE: 142
DIVMTQSPDS LAVSLGERAT INCKSSQSLL NSRTRKNYLA WYQQKPGQPP KLLIYWASTR     60
ESGVPDRFSG SGSGTDFTLT ISSLQAEDVA VYYCTQSFIL RTFGQGTKVE IKGGGGGSGG    120
GGSGGGGSDI VMTQSPDSLA VSLGERATIN CKSSQSLLNS RTRKNYLAWY QQKPGQPPKL    180
LIYWASTRES GVPDRFSGSG SGTDFTLTIS SLQAEDVAVY YCTQSFILRT FGQGTKVEIK    240

SEQ ID NO: 143         moltype = AA  length = 281
FEATURE                Location/Qualifiers
source                 1..281
                       mol_type = protein
                       organism = synthetic construct
SEQUENCE: 143
MNVPTQLLGL LLLWLTGGKC DIQMTQSPAS LSASLEEIVT ITCKASQAID AYLSWYQQKP     60
GKSPQLLIYD ATSLADGVPS RFSGSRSGTQ YSLKISRPQV DDSGIYYCLQ SYSTPFTFGS    120
GTKLEIKGGG GGSGGGGSGG GGSMAVLVLL CLLLIFPSCV LSQVQLKESG PGLVQPSQTL    180
SLTCTVSGSS LTSNSVSWIR QPPGKGLEWM GVIWSNGDAD YNSAIKSRLS ISRDTSKSQV    240
FLKMNSLQTE DTAMYFCASP YYGYYFPFDY WGQGVMVTVS S                        281

SEQ ID NO: 144         moltype = AA  length = 285
FEATURE                Location/Qualifiers
source                 1..285
                       mol_type = protein
                       organism = synthetic construct
SEQUENCE: 144
METDTLLLWV LLLWVPGSTG DIVLTQSPAL AVSLGQRATI SCRASQSVSI SSHDLMQWYQ     60
QKPGQQPKLL IYDAFNLASG IPVRFSGSGS GTDFTLTIDP VQADDIATYY CQQSKDDPYT    120
FGAGTKLELK GGGGGSGGGG SGGGGSMDIR LSLAFLVLFI KGVQCEVQLV ESGGGLVQPG    180
RSMKLSCAAS GFTFSNYGMA WVRQAPTKGL EWVATISYDG SITYYRDSVK GRFTISRDHA    240
KSTLYLQMNS LRSEDTATYY CTREEQYSSW YFDFWGPGIM VTVSS                    285

SEQ ID NO: 145         moltype = AA  length = 242
FEATURE                Location/Qualifiers
source                 1..242
                       mol_type = protein
                       organism = synthetic construct
SEQUENCE: 145
NIVMTQSPSS LSASVGDRVT ITCQASQDVG TAVAWYQQKP DQSPKLLIYW TSTRHTGVPD     60
RFTGSGSGTD FTLTISSLQP EDIATYFCHQ YNSYNTFGSG TKLEIKGGGG GSGGGGSGGG    120
GSQVTLKESG PVLVKPTETL TLTCTFSGFS LSTSGMGVGW IRQAPGKGLE WVAHIWWDDD    180
VYYNPSLKSR LTITKDASKD QVSLKLSSVT AADTAVYYCV RRRATGTGFD YWGQGTLVTV    240
SS                                                                   242

SEQ ID NO: 146         moltype = AA  length = 246
FEATURE                Location/Qualifiers
source                 1..246
                       mol_type = protein
                       organism = synthetic construct
SEQUENCE: 146
EIVLTQSPGS LAVSPGERVT MSCKSSQSVF FSSSQKNYLA WYQQIPGQSP RLLIYWASTR     60
ESGVPDRFTG SGSGTDFTLT ISSVQPEDLA IYYCHQYLSS RTFGQGTKLE IKRGGGGSGG    120
GGSGGGGSQV QLQQPGAEVV KPGASVKMSC KASGYTFTSY YIHWIKQTPG QGLEWVGVIY    180
PGNDDISYNQ KFQGKATLTA DKSSTTAYMQ LSSLTSEDSA VYYCAREVRL RYFDVWGQGT    240
TVTVSS                                                               246

SEQ ID NO: 147         moltype = AA  length = 255
FEATURE                Location/Qualifiers
source                 1..255
                       mol_type = protein
                       organism = synthetic construct
SEQUENCE: 147
MADYKDIVMT QSPSSVSASV GDRVTITCRA SQNVDSAVAW YQQKPGKAPK ALIYSASYRY     60
```

```
SGVPSRFSGR GSGTDFTLTI SSLQPEDFAT YYCQQYYSTP WTFGQGTKVE IKRGGGGSGG   120
GGSGGGGSEV KLVESGGGLV QPGRSLRLSC TASGFTFTDY YMSWVRQAPG KGLEWVGLIR   180
SKADGYTTEY SASVKGRFTI SRDDSKSILY LQMNSLKTED TAVYYCARDA AYYSYYSPEG   240
AMDYWGQGTL VTVSS                                                  255

SEQ ID NO: 148          moltype = AA  length = 244
FEATURE                 Location/Qualifiers
source                  1..244
                        mol_type = protein
                        organism = synthetic construct
SEQUENCE: 148
QSVLTQPPSA SGTPGQRVTI SCSGSSSNIG INTVNWYQQL PGTAPKLLIY DNNKRPSGVP    60
DRFSGSKSGT SASLAISGLR SEDEADYYCA TWDDSLSGWV FGGGTKLTVL GGGGSGGGGS   120
GGGGSEVQLL ESGGGLVQPG GSLRLSCAAS GFTFSDYYMS WIRQAPGKGL EWVSAISGSG   180
GSTYYADSVK GRFTISRDNS KNTLYLQMNS LRAEDTAVYY CAKEDWEGAS FDYWGQGTLV   240
TVSS                                                              244

SEQ ID NO: 149          moltype = AA  length = 245
FEATURE                 Location/Qualifiers
source                  1..245
                        mol_type = protein
                        organism = synthetic construct
SEQUENCE: 149
DIVMTQSPDS LAVSLGERAT INCRASKSVS TSGYSFMHWY QQKPGQPPKL LIYLASNLES    60
GVPDRFSGSG SGTDFTLTIS SLQAEDVAVY YCQHSREVPW TFGQGTKVEI KRGGGGSGGG   120
GSGGGGSQVQ LVQSGAEVKK PGASVKVSCK ASGYTFTNYG MNWVRQAPGQ GLEWMGWINT   180
YTGEPTYADA FKGRVTMTTD TSTSTAYMEL RSLRSDDTAV YYCARDYGDY GMDYWGQGTT   240
VTVSS                                                             245

SEQ ID NO: 150          moltype = AA  length = 263
FEATURE                 Location/Qualifiers
source                  1..263
                        mol_type = protein
                        organism = synthetic construct
SEQUENCE: 150
AQAAELDIVL SQSPAIMSAS PGEKVTISCS ASSSVSYMYW YQQKPGSSPK PWIYRTSNLA    60
SGVPARFSGS GSGTSYSLTI SSMEAEDAAT YYCQQYHSYP PTFGAGTKLE LKSSGGGGSG   120
GGGGGSSRSS LEVLKVESGP ELKKPGETVK ISCKASGYTF TDYSMHWVNQ APGKGLKWMG   180
WINTETGEPS YADDFKGRFA FSLETSASTA YLQINNLKNE DTATYFCATD YGDYFDYWGQ   240
GTTLTVSSAK TTPPSVTSGQ AGQ                                         263

SEQ ID NO: 151          moltype = AA  length = 239
FEATURE                 Location/Qualifiers
source                  1..239
                        mol_type = protein
                        organism = synthetic construct
SEQUENCE: 151
EVQLLESGGG LVQPGGSLRL SCAASGFTFS SYAMSWVRQA PGKGLEWVST IQKQGLPTEY    60
ADSVKGRFTI SRDNSKNTLY LQMNSLRAED TAVYYCAKNR AKFDYWGQGT LVTVSSGGGG   120
SGGGGSGGGG STDIQMTQSP SSLSASVGDR VTITCRASQS ISSYLNWYQQ KPGKAPKLLI   180
YNASMLQSGV PSRFSGSGSG TDFTLTISSL QPEDFATYYC QQNRGFPLTF GQGTKVEIK    239

SEQ ID NO: 152          moltype = AA  length = 239
FEATURE                 Location/Qualifiers
source                  1..239
                        mol_type = protein
                        organism = synthetic construct
SEQUENCE: 152
EIVMTQSPAT LSVSPGERAT LSCRASQSVS SNLAWYQQKP GQAPRLIIYG ASTTASGIPA    60
RFSASGSGTD FTLTISSLQS EDFAVYYCQQ YNNWPPAYTF GQGTKLEIKG GGSGGGGSG   120
GGGSQVQLVQ SGAEVKKPGS SVKVSCKASG GTFSSYAISW VRQAPGQGLE WMGGIIPIFG   180
TANYAQKFQG RVTITADEST STAYMELSSL RSEDTAVYYC ARGLLWNYWG QGTLVTVSS    239

SEQ ID NO: 153          moltype = AA  length = 246
FEATURE                 Location/Qualifiers
source                  1..246
                        mol_type = protein
                        organism = synthetic construct
SEQUENCE: 153
STVMTQSPSF LSASVGDRVT ITCKASQSVS NDVAWYQQKP CQSPKVLIYF ASNRYTGVPD    60
RFSGSGYGTD FTLTISSLQA EDVAVYFCQQ DYSSPLTFGA GTKLEIKGGG SGGGGSGGGG   120
GSQIQLVQS SELKKPGASV KVSCKASGYT FTNFFVNWVK QAPGKGLKWM GWINTYTGEP   180
SYADDFKGRF AFSLDASAST AYLQISSLKA EDMATYFCTR RTNYYGTSYY YAMDYWGQGT   240
TVTVSS                                                            246

SEQ ID NO: 154          moltype = AA  length = 458
FEATURE                 Location/Qualifiers
source                  1..458
                        mol_type = protein
```

```
                          organism = synthetic construct
SEQUENCE: 154
RIVMTQSPGT LSVSPGETAT LSCRASQSFS NMLAWYQQKS GQPPRLLIYG VSTRAAGVPA      60
RFSGSGSGTE FTLTISNLQS EDFAVYYCQQ YGDWPRYTFG QGTKVERKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGECGGGGS GGGGSGGGGS EVQLVQSGGG     240
VVRPGGSLRL PCAASGFTFD DYGMSWVRQA PGKGLEWVSG INWNGGSTGY ADSVKGRFTI     300
SRDNAKNSLY LQMNSLRAED TALYHCARGG DDAFDIWGQG TMVTVSSAST KGPSVFPLAP     360
SSKSTSGGTA ALGCLVKDYF PEPVTVSWNS GALTSGVHTF PAVLQSSGLY SLSSVVTVPS     420
SSLGTQTYIC NVNHKPSNTK VDKKVEPKSC DKTSGQAG                             458

SEQ ID NO: 155          moltype = AA  length = 239
FEATURE                 Location/Qualifiers
source                  1..239
                        mol_type = protein
                        organism = synthetic construct
SEQUENCE: 155
EIVLTQSPGT LSLSPGERAT LSCRASQSVS SSYLAWYQQK PGQAPRLLIY GASSRATGIP      60
DRFSGSGSGT DFTLTISSLE PEDFAVYYCQ QYGSSPWTFG QGTKVEIKGG GGSGGGGSGG     120
GGSEVQLVES GGGLVQPGGS LRLSCVASGF TFSNSWMSWV RQAPGKGLEW VANINEDGSE     180
KFYVDSVKGR FTFSRDNAEN SLYLQMNSLR AEDTAVYYCA RVHWYFHLWG RGTLVTVSS      239

SEQ ID NO: 156          moltype = AA  length = 242
FEATURE                 Location/Qualifiers
source                  1..242
                        mol_type = protein
                        organism = synthetic construct
SEQUENCE: 156
NIVMTQSPSS LSASVGDRVT ITCQASQDVG TAVAWYQQKP DQSPKLLIYW TSTRHTGVPD      60
RFTGSGSGTD FTLTISSLQP EDIATYFCHQ YNSYNTFGGG TKLEIKGGGG SGGGGGSGGG     120
GSQVTLKESG PVLVKPTETL TLTCTFSGFS LSTSGMGVGW IRQAPGKGLE WVAHIWWDDD     180
VYYNPSLKSR LTITKDASKD QVSLKLSSVT AADTAVYYCV RRRATGTGFD YWGQGTLVTV     240
SS                                                                    242

SEQ ID NO: 157          moltype = AA  length = 679
FEATURE                 Location/Qualifiers
source                  1..679
                        mol_type = protein
                        organism = synthetic construct
SEQUENCE: 157
DIQMTQSPSS LSASVGDRVT ITCRASQDVN TAVAWYQQKP GKAPKLLIYS ASFLYSGVPS      60
RFSGSRSGTD FTLTISSLQP EDFATYYCQQ HYTTPPTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGGGGSG GGGSGGGGSE VQLVESGGGL     240
VQPGGSLRLS CAASGFNIKD TYIHWVRQAP GKGLEWVARI YPTNGYTRYA DSVKGRFTIS     300
ADTSKNTAYL QMNSLRAEDT AVYYCSRWGG DGFYAMDYWG QGTLVTVSSA STKGPSVFPL     360
APSSKSTSGG TAALGCLVKD YFPEPVTVSW NSGALTSGVH TFPAVLQSSG LYSLSSVVTV     420
PSSSLGTQTY ICNVNHKPSN TKVDKKVEPK SCDKTHTCPP CPAPELLGGP SVFLFPPKPK     480
DTLMISRTPE VTCVVVDVSH EDPEVKFNWY VDGVEVHNAK TKPREEQYNS TYRVVSVLTV     540
LHQDWLNGKE YKCKVSNKAL PAPIEKTISK AKGQPREPQV YTLPPSRDEL TKNQVSLTCL     600
VKGFYPSDIA VEWESNGQPE NNYKTTPPVL DSDGSFFLYS KLTVDKSRWQ QGNVFSCSVM     660
HEALHNHYTQ KSLSLSPGK                                                  679

SEQ ID NO: 158          moltype = AA  length = 246
FEATURE                 Location/Qualifiers
source                  1..246
                        mol_type = protein
                        organism = synthetic construct
SEQUENCE: 158
DIQMTQSPSS LSASVGDRVT ITCKASAAVG TYVAWYQQKP GKAPKLLIYS ASYRKRGVPS      60
RFSGSGSGTD FTLTISSLQP EDFATYYCHQ YYTYPLFTFG QGTKLEIKRT GGGGSGGGGS     120
GGGGSQVQLV QSGSELKKPG ASVKVSCKAS GYTFTEFGMN WVRQAPGQGL EWMGWINTKT     180
GEATYVEEFK GRFVFSLDTS VSTAYLQISS LKAEDTAVYY CARWDFYDYV EAMDYWGQGT     240
TVTVSS                                                                246

SEQ ID NO: 159          moltype = AA  length = 392
FEATURE                 Location/Qualifiers
source                  1..392
                        mol_type = protein
                        organism = synthetic construct
SEQUENCE: 159
SRAATMETDT LLLWVLLLWV PGSTGDIQLT QSPSSLSASV GDRVTITCSA SSSVRFIHWY      60
QQKPGKAPKR LIYDTSKLAS GVPSRPSGSG SGTDFTLTIS SLQPEDFATY YCQQWSSSPF     120
TFGQGTKVEI KGSTSGGGSG GGSGGGGSSE VQLVESGGGL VQPGGSLRLS CAASGFNIKD     180
YYIHWVRQAP GKGLEWVAWI DPENGDTEFV PKFQGRATIS ADTSKNTAYL QMNSLRAEDT     240
AVYYCKTGGF WGQGTLVTVS SEPKSCDKTH TCPPCGGGSS GGGSGGQPRE PQVYTLPPSR     300
DELTKNQVSL TCLVKGFYPS DIAVEWESNG QPENNYKTTP PVLDSDGSFF LYSKLTVDKS     360
RWQQGNVFSC SVMHEALHNH YTQKSLSLSP GK                                   392
```

| SEQ ID NO: 160 | moltype = AA length = 243 |
| FEATURE | Location/Qualifiers |
| source | 1..243 |
| | mol_type = protein |
| | organism = synthetic construct |

SEQUENCE: 160
```
DIVMTQSPDS LAVSLGERAT INCKSSQSVL YSSNNKNYLA WYQQKPGQPP KLLIYWASTR   60
ESGVPDRFSG SGSGTDFTLT ISSLQAEDVA VYYCQQYYSY PLTFGGGTKV EIKGGGGSGG  120
GGSGGGGSQV QLVQSGAEVK KPGASVKVSC KASGYTFTDH AIHWVRQAPG QRLEWMGYFS  180
PGNDDFKYSQ KFQGRVTITA DKSASTAYME LSSLRSEDTA VYYCARSLNM AYWGQGTLVT  240
VSS                                                               243
```

| SEQ ID NO: 161 | moltype = AA length = 243 |
| FEATURE | Location/Qualifiers |
| source | 1..243 |
| | mol_type = protein |
| | organism = synthetic construct |

SEQUENCE: 161
```
DIQMTQSPSS LSASVGDRVT ITCRASQGIR SWLAWYQQKP EKAPKSLIYA ASSLQSGVPS   60
RFSGSGSGTD FTLTISSLQP EDFATYYCQQ YNSYPLTFGG GTKVEIKGGG GSGGGGSGGG  120
GSQVQLVQSG AEVKKPGSSV KVSCKAFGGT FSSYAISWVR QAPGQGLEWM GRIIRFLGKT  180
NHAQKFQGRV TLTADKSTNT AYMELSSLRS EDTAVYYCAG EPGDRDPDAV DIWGQGTMVT  240
VSS                                                               243
```

| SEQ ID NO: 162 | moltype = AA length = 249 |
| FEATURE | Location/Qualifiers |
| source | 1..249 |
| | mol_type = protein |
| | organism = synthetic construct |

SEQUENCE: 162
```
DIVMTQTPLS SPVTLGQPAS ISCRSSQSLV HSDGNTYLSW LHQRPGQPPR LLIYKISNRF   60
SGVPDRFSGS GAGTAFTLKI SRVEAEDVGV YYCMQATQLP RTFGQGTKVE IKRGGGGSGG  120
GGSGGGGSQV QLVESGGGVV QPGRSLRLSC AASGFTFSSY GMHWVRQAPG KGLEWVAVIW  180
YDGSNKYYVD SVKGRFTISR DNSKNTLYLQ MNSLRAEDTA VYYCARDGWQ QLAPFDYWGQ  240
GTLVTVSSA                                                         249
```

| SEQ ID NO: 163 | moltype = AA length = 237 |
| FEATURE | Location/Qualifiers |
| source | 1..237 |
| | mol_type = protein |
| | organism = synthetic construct |

SEQUENCE: 163
```
DIKMTQSPSS MYASLGERVT ITCKASQDIN NYLSWFQQKP GKSPKTLIYR ANRLVDGVPS   60
RFSGSGSGQD YSLTISSLEY EDMGIYYCLK YDEFPYTFGG GTKLEIKGGG GSGGGGSGGG  120
GSDVKLVESG GGLVKPGGSL KLSCAASGFT FSSYTMSWVR QTPEKRLEWV ATISSGGTYT  180
YYPDSVKGRF TISRDNAKNT LYLQMSSLKS EDTAMYYCTR EAIFTYWGQG TLVTVSA    237
```

| SEQ ID NO: 164 | moltype = AA length = 239 |
| FEATURE | Location/Qualifiers |
| source | 1..239 |
| | mol_type = protein |
| | organism = synthetic construct |

SEQUENCE: 164
```
EIVLTQSPGT LSLSPGERAT LSCRASQSVS RSYLAWYQQK PGQAPRLLII GASTRATGIP   60
DRFSGSGSGT DFTLTISRLE PEDFAVYYCQ QGQVIPPFTG QGTKVEIGGG GSGGGGSGGG  120
GSEVQLLESG GGLVQPGGSL RLSCAASGFT FSSYAMSWVR QAPGKGLEWV SAISGSGGST  180
YYADSVKGRF TISRDNSKNT LYLQMNSLRA EDTAVYYCAK GWLGNFDYWG QGTLVTVSS  239
```

| SEQ ID NO: 165 | moltype = AA length = 441 |
| FEATURE | Location/Qualifiers |
| source | 1..441 |
| | mol_type = protein |
| | organism = synthetic construct |

SEQUENCE: 165
```
EIVMTQTPAT LSVSAGERVT ITCKASQSVS NHVTWYQQKP GQAPRLLIYS ASNRYSGVPA   60
RFSGSGYGTE FTFTISSVQS EDFAVYFCQQ DYSSFGQGTK LEIKRTVAAP SVIFPPSDE   120
QLKSGTASVV CYELLAENNF YPREAKVQWK VDNALQSGNS QESVTEQDSK DSTYSLSSTL  180
TLSKADYEKH KVYACEVTHQ GLSSPVTKSF NRGECGGGGS GGGGSGGGGS KIVMTQTPAT  240
LSVSAGERVT ITCKASQSVS NHVTWYQQKP GQAPRLLIYS ASNRYSGVPA RFSGSGYGTE  300
FTFTISSVQS EDFAVYFCQQ DYSSFGQGTK LEIKRTVAAP SVIFPPSDE QLKSGTASVV   360
CLLNNFYPRE AKVQWKVDNA LQSGNSQESV TEQDSKDSTY SLSSTLTLSK ADYEKHKVYA  420
CEVTHQGLSS PVTKSFNRGE C                                           441
```

| SEQ ID NO: 166 | moltype = AA length = 685 |
| FEATURE | Location/Qualifiers |
| source | 1..685 |
| | mol_type = protein |
| | organism = synthetic construct |

SEQUENCE: 166

```
DIQMTQSPSS LSASVGDRVT ITCRASQDIG NFLNWYQQKP GKAPKLLIYY TSRLQSGVPS    60
RFSGSGSGTD YTLTISSLQP EDFATYYCQQ GKTLPYTFGG GTKVEIKDIR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGECGGGG SGGGGSGGGG SQVQLVESGG   240
GVVQPGRSLR LSCAASGFTF SNFGMHWVRQ APGKGLEWVA YISSGGSSIN YADTVKGRFT   300
ISRDNSKNTL YLQMNSLRAE DTAVYYCTRG GTGTRSLYYF DYWGQGTTVT VSSDIPSTKG   360
PSVFPLAPSS KSTSGGTAAL GCLVKDYFPE PVTVSWNSGA LTSGVHTFPA VLQSSGLYSL   420
SSVVTVPSSS LGTQTYICNV NHKPSNTKVD KKVEPKSCDK THTCPPCPAP ELLGGPSVFL   480
FPPKPKDTLM ISRTPEVTCV VVDVSHEDPE VKFNWYVDGV EVHNAKTKPR EEQYNSTYRV   540
VSVLTVLHQD WLNGKEYKCK VSNKALPAPI EKTISKAKGQ PREPQVYTLP PSRDELTKNQ   600
VSLTCLVKGF YPSDIAVEWE SNGQPENNYK TTPPVLDSDG SFFLYSKLTV DKSRWQQGNV   660
FSCSVMHEAL HNHYTQKSLS LSPGK                                        685

SEQ ID NO: 167          moltype = AA   length = 239
FEATURE                 Location/Qualifiers
source                  1..239
                        mol_type = protein
                        organism = synthetic construct
SEQUENCE: 167
EIVMTQTPLI LSVTIGQPAS ISCKSSQSVL YSNGKTYLNW LLQRPGQSPK RLIYLVSKLD    60
SGVPDRFTGS GSGTDFTLKI SRVEAEDLGV YYCVQGSHFP YTFGGGTKLE IKRADAGGGG   120
SGGGGSGGGG SGPELKKPGE TVKIYCKASG YSFRDYSVHW VKQAPGKGLK WMGWINTETG   180
EPTYVDEFKG RFAFFLEASA NTVYLQISNL KNEDTATYFC DYRFTYWGQG TLVTVSAAK    239

SEQ ID NO: 168          moltype = AA   length = 243
FEATURE                 Location/Qualifiers
source                  1..243
                        mol_type = protein
                        organism = synthetic construct
SEQUENCE: 168
DIQMTQSPSS LSASVGDRVT ITCRASQGIS SWLAWYQQKP EKAPKSLIYA ASSLQSGVPS    60
RESGSGSGTD FTLTISSLQP EDEATYYCQQ YNGYPYTEGQ GTKLEIKGGG GSGGGGSGGG   120
GSEVQLVESG GGLVKPGGSL RLSCAASGFT FSSYSMNWVR QAPGKGLEWV SSITSSSSYI   180
YYADSVKGRF TISRDNAKNS LYLQMNSLRA EDTAVYYCAR DRRYFDWFPI DYRGQGTLVT   240
VSS                                                                243

SEQ ID NO: 169          moltype = AA   length = 285
FEATURE                 Location/Qualifiers
source                  1..285
                        mol_type = protein
                        organism = synthetic construct
SEQUENCE: 169
MRVPAQLLGL LLLCFPGARC DIQMTQSPSS LSASVGDRVT ITCRASQGIT NYLAWFQQKP    60
GKAPKSLIYA ASSLQSGVPS KFSGSGSGTD FSLTISSLQP EDFATYYCQQ YNSYPITFGQ   120
GTRLEIKGGG GSGGGGSGGG GSMELGLRWV LLVALLRGVQ CQVQLVESGG GVVQPGRSLR   180
LSCAASGFTF SNYVMHWRQ APGKGLEWVA IIWYDGSNKY YADSVKGRFT ISRDNSKNTL    240
YLQMNSLRAE DTAVYYCAGG YNWNYEYHYY GMDVWGQGTT VTVSS                  285

SEQ ID NO: 170          moltype = AA   length = 279
FEATURE                 Location/Qualifiers
source                  1..279
                        mol_type = protein
                        organism = synthetic construct
SEQUENCE: 170
MDFQVQIFSF LLISASVILS SGQIGLTQSP AIMSASPGEK VTMTCSASSS ISYMHWYQQK    60
PGTSPKTWIY DTSKLASGVP ARFSGSGSGT SYSLTISSME AEDAATYYCH QRSSHHTFGG   120
GTKLEIKGGG GSGGGGSGGG GSMGWLWNLL FLMAAAQSAQ AQIQLVQSGP ELKKPGETVK   180
ISCKASGYTF TTYGMSWVKQ APGRGLKWMG WINPYSGVPT YAVDFKGRFA FSLETSASTA   240
YLQINNLKNE DTATYFCARG GRRGDFGYWG QGTTLTVSS                          279

SEQ ID NO: 171          moltype = AA   length = 244
FEATURE                 Location/Qualifiers
source                  1..244
                        mol_type = protein
                        organism = synthetic construct
SEQUENCE: 171
DIVMTQSPSS LTVTAGEKVT MICKSSQSLL NSGDQKNYLT WYQQKPGQPP KLLIFWASTR    60
ESGVPDRFTG SGSGTDFTLT ISSVQAEDLA VYYCQNDYSY PLTFGAGTKL ELKGGGGSGG   120
GGSGGGGSQV QLQQSDAELV KPGSSVKISC KASGYTFTDH AIHWVKQKPE QGLEWIGHFS   180
PGNTDIKYND KFKGKATLTV DRSSSTAYMQ LNSLTSEDSA VYFCKTSTFF FDYWGQGTTL   240
TVSS                                                               244

SEQ ID NO: 172          moltype = AA   length = 254
FEATURE                 Location/Qualifiers
source                  1..254
                        mol_type = protein
                        organism = synthetic construct
SEQUENCE: 172
QVQLEQSGLG LVKPSQTLSL TCAISGDTVS SDSAAWNWIR QSPSRGLEWL GRTYYRSKWF    60
```

```
NDYAVSVKGR ITINSDTSKN QFSLQLNSVT PEDTAVYYCA RSNSYYYYAM DVWGQGTLVT    120
VSSGGGGSGG GGSGGGGSQA VLTQPSSLSA SPGASASLTC TLRSGINVGI YRIYWYQQRP    180
GSPPQILLTY KSDSDKYQGS GVPSRFSGSK DASANAGILL ISGLQSEDEA DYYCMIWHSG    240
GWVFGGGTKV TVLG                                                     254

SEQ ID NO: 173           moltype = AA  length = 264
FEATURE                  Location/Qualifiers
source                   1..264
                         mol_type = protein
                         organism = synthetic construct
SEQUENCE: 173
MALPVTALLL PLALLLHAAR PQSVLTQPAS VSGSPGQSVT ISCTGTSSDV GGYNYVSWYQ     60
QHPGKPPKLM IYEVSKRPSG VPDRFSGSKS GNTASLTISG LQAEDEADYY CSSHTSSNTL    120
IFGGGTKVTV LGGGGSGGGG SGGGGSEVQL VQSGAEVKKP GESLKISCKG SGYTFTNYWI    180
GWVRQMPGKG LEWMGRIYPS DSYTNYSPSF QGQVTISADK SISTAYLQWS SLKASDTAMY    240
YCARDLEPTH HYSWGQGTLV TVSS                                          264

SEQ ID NO: 174           moltype = AA  length = 267
FEATURE                  Location/Qualifiers
source                   1..267
                         mol_type = protein
                         organism = synthetic construct
SEQUENCE: 174
MALPVTALLL PLALLLHAAR PLPVLTQPPS ASGTPGQRVT ISCSGSSSNI GSNAVDWYQQ     60
LPGTAPKLLI YTNNRRPSGV PDRFSGSKSG TSGSLAISGL QFEDEADYYC AAWDDSLSGV    120
IFGGGTKVTV LGGGGSGGGG SGGGGSQVQL VQSGAEVKKP GSSVKVSCKA SEDTFSSYVI    180
SWVRQAPGQG LEWMGAFIPL LGRVHYAQEF QGRLTITADE STGTAYMELK GLRSDDTAMY    240
YCARDQGFAG DDAFDIWGQG TMVTVSS                                       267

SEQ ID NO: 175           moltype = AA  length = 266
FEATURE                  Location/Qualifiers
source                   1..266
                         mol_type = protein
                         organism = synthetic construct
SEQUENCE: 175
MALPVTALLL PLALLLHAAR PQPVLTQDPV VSVALGQTVR ITCQGDSLRS YYATWYQQKP     60
GLAPVRVIFG KNSRPSGIPD RFSGSSSGNT ASLTITGAQA EDEADYYCNS WDNSANHPVF    120
GGGTKLTVLG GGGSGGGGSG GGSEVQLVQ SGAEVRKPGS SVKVSCKASG DNFNNYGITW    180
VRQAPGQGLE WMGRLITVLG LDNYAQKFQG RLTITADEST GTAYMELTGL EPEDTAVYYC    240
ARDIMSPEAI DAFDVWGQGT LVTVSS                                        266

SEQ ID NO: 176           moltype = AA  length = 265
FEATURE                  Location/Qualifiers
source                   1..265
                         mol_type = protein
                         organism = synthetic construct
SEQUENCE: 176
MALPVTALLL PLALLLHAAR PDIQMTQSPS SLSASVGDRV TITCRASQDV SNYLNWYQQK     60
PGKAPKLLIY GASNRQTGVP SRFSGSGSGT DFTLTISSLQ PEDFATYYCQ QDRFPTTFG    120
QGTKVEIKGG GGSGGGGSGG GGSEVQLVQS GAEVRKPGSS VKVSCKASGD NFNNYGITWV    180
RQAPGQGLEW MGRLITVLGL DNYAQKFQGR LTITADESTG TAYMELTGLE PEDTAVYYCA    240
RDIMSPEAID AFDVWGQGTL VTVSS                                         265

SEQ ID NO: 177           moltype = AA  length = 270
FEATURE                  Location/Qualifiers
source                   1..270
                         mol_type = protein
                         organism = synthetic construct
SEQUENCE: 177
MALPVTALLL PLALLLHAAR PEIVLTQSAS SLSASVGDRV TITCRTSQNI YRYLNWYQQK     60
PGKAPKLLIF GASTLQTGVP SRFSGSGSGT DFTLTITGLQ PEDLATYYCQ HSFKLPFTFG    120
QGTRLEIKGG GGSGGGGSGG GGSQMLVQSG AEVKRPGSSV TVSCETSGDT FSRYAISWLR    180
QAPGQGLEWL GWISGNSRA DYAQNFQGRV TMTTDRSTST AYLNLRSLRS DDTAVYYCAR    240
DAPMLFGVRG GGYYFGMDVW GQGTTVTVSS                                    270

SEQ ID NO: 178           moltype = AA  length = 258
FEATURE                  Location/Qualifiers
source                   1..258
                         mol_type = protein
                         organism = synthetic construct
SEQUENCE: 178
MALPVTALLL PLALLLHAAR PQPVLTQDPA VSVALGQTVR ITCQGDSLRK YYASWYQQKP     60
GQAPRLVMYD ENDRPSGIPD RFSGSSSGNT ASLTITGAQA DDEADYYCNS RDSSGHHVVF    120
GGGTKVTVLG GGGSGGGGSG GGSQMLVQSG AEVRRPGSSV KVSCKTSG GTLNNYDINW    180
VRQAPGQGLE WMGWMNPTSG QADFAQKFQG RVSMTRDTSI NTAFMELNTL RSEDTAVYYC    240
VRRGGKYWGQ GTLVTVSS                                                 258

SEQ ID NO: 179           moltype = AA  length = 267
FEATURE                  Location/Qualifiers
```

```
source                  1..267
                        mol_type = protein
                        organism = synthetic construct
SEQUENCE: 179
MALPVTALLL PLALLLHAAR PSYELTQPPS VSVAPGQTAR ITCGGDALPN NSVRWYQQKP    60
GQAPVLVIYG NSERPSGIPE RFSGSNSGNT ATLTISGTQA EDEADYYCQV SDKSTKYSVF   120
GGGTKLTVLG GGGSGGGGSG GGGSEVQLVE SGGGLVQPGG SLRLSCAASG FTFSNYWMSW   180
VRQAPGKGLE WVAGISASGG NKYYADSVKG RFTISRDNSK NTLYLQMNSL RAEDTAVYYC   240
AKGPIQLKRH KYVLDYWGQG TLVTVSS                                      267

SEQ ID NO: 180          moltype = AA  length = 108
FEATURE                 Location/Qualifiers
source                  1..108
                        mol_type = protein
                        organism = synthetic construct
SEQUENCE: 180
QPVLTQDPVV SVALGQTVRI TCQGDSLRSY YATWYQQKPG LAPVRVIFGK NSRPSGIPDR    60
FSGSSSGNTA SLTITGAQAE DEADYYCNSW DNSANHPVFG GGTKLTVL               108

SEQ ID NO: 181          moltype = AA  length = 122
FEATURE                 Location/Qualifiers
source                  1..122
                        mol_type = protein
                        organism = synthetic construct
SEQUENCE: 181
EVQLVQSGAE VRKPGSSVKV SCKASGDNFN NYGITWVRQA PGQGLEWMGR LITVLGLDNY    60
AQKFQGRLTI TADESTGTAY MELTGLEPED TAVYYCARDI MSPEAIDAFD VWGQGTLVTV   120
SS                                                                 122

SEQ ID NO: 182          moltype = AA  length = 127
FEATURE                 Location/Qualifiers
source                  1..127
                        mol_type = protein
                        organism = synthetic construct
SEQUENCE: 182
QMLVQSGAEV KRPGSSVTVS CETSGDTFSR YAISWLRQAP GQGLEWLGWI SGNSGRADYA    60
QNFQGRVTMT TDRSTSTAYL NLRSLRSDDT AVYYCARDAP MLFGVRGGGY YFGMDVWGQG   120
TTVTVSS                                                            127

SEQ ID NO: 183          moltype = AA  length = 107
FEATURE                 Location/Qualifiers
source                  1..107
                        mol_type = protein
                        organism = synthetic construct
SEQUENCE: 183
EIVLTQSASS LSASVGDRVT ITCRTSQNIY RYLNWYQQKP GKAPKLLIFG ASTLQTGVPS    60
RFSGSGSGTD FTLTITGLQP EDLATYYCQH SFKLPFTFGQ GTRLEIK                107

SEQ ID NO: 184          moltype = AA  length = 114
FEATURE                 Location/Qualifiers
source                  1..114
                        mol_type = protein
                        organism = synthetic construct
SEQUENCE: 184
QMQLVQSGAE VRRPGSSVKV SCKTSGGTLN NYDINWVRQA PGQGLEWMGW MNPTSGQADF    60
AQKFQGRVSM TRDTSINTAF MELNTLRSED TAVYYCVRRG GKYWGQGTLV TVSS         114

SEQ ID NO: 185          moltype = AA  length = 108
FEATURE                 Location/Qualifiers
source                  1..108
                        mol_type = protein
                        organism = synthetic construct
SEQUENCE: 185
QPVLTQDPAV SVALGQTVRI TCQGDSLRKY YASWYQQKPG QAPRLVMYDE NDRPSGIPDR    60
FSGSSSGNTA SLTITGAQAD DEADYYCNSR DSSGHHVVFG GGTKVTVL               108

SEQ ID NO: 186          moltype = AA  length = 123
FEATURE                 Location/Qualifiers
source                  1..123
                        mol_type = protein
                        organism = synthetic construct
SEQUENCE: 186
EVQLVESGGG LVQPGGSLRL SCAASGFTFS NYWMSWVRQA PGKGLEWVAG ISASGGNKYY    60
ADSVKGRFTI SRDNSKNTLY LQMNSLRAED TAVYYCAKGP IQLKRHKYVL DYWGQGTLVT   120
VSS                                                                123

SEQ ID NO: 187          moltype = AA  length = 108
FEATURE                 Location/Qualifiers
source                  1..108
```

```
                              mol_type = protein
                              organism = synthetic construct
SEQUENCE: 187
SYELTQPPSV SVAPGQTARI TCGGDALPNN SVRWYQQKPG QAPVLVIYGN SERPSGIPER    60
FSGSNSGNTA TLTISGTQAE DEADYYCQVS DKSTKYSVFG GGTKLTVL                108

SEQ ID NO: 188                moltype = AA   length = 20
FEATURE                       Location/Qualifiers
source                        1..20
                              mol_type = protein
                              organism = synthetic construct
SEQUENCE: 188
GGGGSGGGGS GGGGSGGGGS                                                20

SEQ ID NO: 189                moltype = DNA   length = 19
FEATURE                       Location/Qualifiers
source                        1..19
                              mol_type = other DNA
                              organism = synthetic construct
SEQUENCE: 189
tgcatttgaa ctccttgcc                                                 19

SEQ ID NO: 190                moltype = DNA   length = 20
FEATURE                       Location/Qualifiers
source                        1..20
                              mol_type = other DNA
                              organism = synthetic construct
SEQUENCE: 190
ccatcaatct tccacttgac                                                20

SEQ ID NO: 191                moltype = AA   length = 10
FEATURE                       Location/Qualifiers
source                        1..10
                              mol_type = protein
                              organism = synthetic construct
SEQUENCE: 191
APFTKPSPFT                                                           10

SEQ ID NO: 192                moltype = AA   length = 9
FEATURE                       Location/Qualifiers
source                        1..9
                              mol_type = protein
                              organism = synthetic construct
SEQUENCE: 192
DIRLSGRTD                                                            9

SEQ ID NO: 193                moltype = AA   length = 10
FEATURE                       Location/Qualifiers
source                        1..10
                              mol_type = protein
                              organism = synthetic construct
SEQUENCE: 193
GSVFRFYGMG                                                           10

SEQ ID NO: 194                moltype = AA   length = 16
FEATURE                       Location/Qualifiers
source                        1..16
                              mol_type = protein
                              organism = synthetic construct
SEQUENCE: 194
QRNIPRIGLG SRNYDY                                                    16

SEQ ID NO: 195                moltype = AA   length = 10
FEATURE                       Location/Qualifiers
source                        1..10
                              mol_type = protein
                              organism = synthetic construct
SEQUENCE: 195
AISGGGIYTD                                                           10

SEQ ID NO: 196                moltype = AA   length = 10
FEATURE                       Location/Qualifiers
source                        1..10
                              mol_type = protein
                              organism = synthetic construct
SEQUENCE: 196
GRTASSNAMG                                                           10

SEQ ID NO: 197                moltype = AA   length = 15
```

```
FEATURE              Location/Qualifiers
source               1..15
                     mol_type = protein
                     organism = synthetic construct
SEQUENCE: 197
LSTNYPFLRP RDANY                                                         15

SEQ ID NO: 198       moltype = AA  length = 10
FEATURE              Location/Qualifiers
source               1..10
                     mol_type = protein
                     organism = synthetic construct
SEQUENCE: 198
TISRDGTRTY                                                               10

SEQ ID NO: 199       moltype = AA  length = 10
FEATURE              Location/Qualifiers
source               1..10
                     mol_type = protein
                     organism = synthetic construct
SEQUENCE: 199
GRTFTTYRMG                                                               10

SEQ ID NO: 200       moltype = AA  length = 123
FEATURE              Location/Qualifiers
source               1..123
                     mol_type = protein
                     organism = synthetic construct
SEQUENCE: 200
DVQLQESGGG LVQAGGSLRL SCAASGRTFS TYRITWFRQA PGKQREFVAT ISRSSSNPYY         60
ADSVKGRFTI SRDNAKNTVY LQMNSLRPED TAVYSCAGST AYPFLSPRDA NYWGQGTQVT        120
VSS                                                                     123

SEQ ID NO: 201       moltype = AA  length = 114
FEATURE              Location/Qualifiers
source               1..114
                     mol_type = protein
                     organism = synthetic construct
SEQUENCE: 201
DVQLQESGGG SVQPGGSLRL SCVASGSISS DNAMGWYRQT APWKQRESVA SLTRDGSAIY         60
ADSVKGRFTI SRDNAANTVY LQMNSLKPED TAVYYCFRTP PTYWGQGTQV TVSS              114

SEQ ID NO: 202       moltype = AA  length = 113
FEATURE              Location/Qualifiers
source               1..113
                     mol_type = protein
                     organism = synthetic construct
SEQUENCE: 202
DVQLQESGGG SVQPGGSLRL SCVVSGSGSS INSMGWYRQA PGKQRESVAS ITRAGSAIYA         60
DSVKGRFTIS RDNAANTAYL QMNSLKPEDT AVYYCFHTPP TYWGQGTQVT VSS               113

SEQ ID NO: 203       moltype = AA  length = 117
FEATURE              Location/Qualifiers
source               1..117
                     mol_type = protein
                     organism = synthetic construct
SEQUENCE: 203
DVQLQESGGG LVQPGGSLRL SCSASGSGFR FYGMGWYRQA PGKQRELVAD IRLSGRAEYA         60
DSVKGRFTIS RDNAKNTVYL QMNSLKPEDT AVYYCNAPFT SPSPFAWGQG TQVTVSS           117

SEQ ID NO: 204       moltype = AA  length = 119
FEATURE              Location/Qualifiers
source               1..119
                     mol_type = protein
                     organism = synthetic construct
SEQUENCE: 204
DVQLQESGGG LVQAGGSLRL SCAASGRTFS NLAMGWFRQA PGKAREFVAA ISGSGGSIFY         60
ADSVKGRFTI SRDNAKNTMY LQMNSLKPED TAVYYCAAGP YGSPDFDSWG QGTQVTVSS         119

SEQ ID NO: 205       moltype = AA  length = 123
FEATURE              Location/Qualifiers
source               1..123
                     mol_type = protein
                     organism = synthetic construct
SEQUENCE: 205
DVQLQESGGG SVQAGGSLRL SCAASGRTFT TYRIAWFRQA PGKEREFVAT ISRDGTRTYY         60
ADSVKGRFTI SRDNAKNTVY LQMNSLRPED TAVYYCAGST DYPFLRPRDA NYWGQGTQVT        120
VSS                                                                     123
```

```
SEQ ID NO: 206          moltype = AA  length = 123
FEATURE                 Location/Qualifiers
source                  1..123
                        mol_type = protein
                        organism = synthetic construct
SEQUENCE: 206
DVQLQESGGG SVQAGGSLRL SCAASGRTFT TYRMGWFRQA PGKQREFVAT ISRDGTRTYY   60
ADSVKGRFTI SRDNAENTVY LQMNSLRPED TAAYYCAVST DYPFLRPRDA AYWGQGTQVT  120
VSS                                                                123

SEQ ID NO: 207          moltype = AA  length = 126
FEATURE                 Location/Qualifiers
source                  1..126
                        mol_type = protein
                        organism = synthetic construct
SEQUENCE: 207
DVQLQESGGG LVQAGESLRL SCAASGRTSS TYTMAWFRQA PGKDREFVGR IRWNSGSADY   60
AGSVKGRFTI SRDNAKNTVY LQMNSLKPED TAVYYCAAAS WGYSSSYYSS RGYDVWGQGT  120
QVTVSS                                                             126

SEQ ID NO: 208          moltype = AA  length = 124
FEATURE                 Location/Qualifiers
source                  1..124
                        mol_type = protein
                        organism = synthetic construct
SEQUENCE: 208
DVQLQESGGG LVQAGGSLRL ACAASGRTAS SNAMGWFRQA PGKEREFVAA ISGGGIYTDY   60
ADSVKGRFTI SRDNSKNTMY LQMNSLKPED TAVYYCAQRN IPRIGLGSGN YDYWGQGTQV  120
TVSS                                                               124

SEQ ID NO: 209          moltype = AA  length = 116
FEATURE                 Location/Qualifiers
source                  1..116
                        mol_type = protein
                        organism = synthetic construct
SEQUENCE: 209
DVQLQESGGG LVQVGGSLTL SCAASGRTFS KYTMSWFRQA PGQEREFVAT ITSSGRSTSY   60
GDSVKGRFTI SRDNAKNTMY LQMNSLKFED TAVYYCRAAD SVSAYWGQGT QVTVSS      116

SEQ ID NO: 210          moltype = AA  length = 113
FEATURE                 Location/Qualifiers
source                  1..113
                        mol_type = protein
                        organism = synthetic construct
SEQUENCE: 210
DVQLQESGGG SVQPGGSLRL SCVASGSGSS IAAMGWYRQV PGKQRESVAS LTREGRVIYA   60
DSVKGRFTIS RDNAANTVYL QMNSLKPEDT AVYYCFRTPP TLWGQGTQVT VSS         113

SEQ ID NO: 211          moltype = AA  length = 113
FEATURE                 Location/Qualifiers
source                  1..113
                        mol_type = protein
                        organism = synthetic construct
SEQUENCE: 211
DVQLQESGGG SVQPGGSLRL SCVASGNISS NNAMGWYRQA PGKQRESVAS MPRGGTAIYA   60
DSVKGRFTIS RDNAANTVYL QMNSLKPEDT AVYYCFRTPP TYWGQGTQVT VSS         113

SEQ ID NO: 212          moltype = AA  length = 123
FEATURE                 Location/Qualifiers
source                  1..123
                        mol_type = protein
                        organism = synthetic construct
SEQUENCE: 212
DVQLQESGGG LVQAGGSLRL SCAASGRTFS THRITWFRQA PGKQREFVAT ISRSSSNPYY   60
ADSVKGRFTI SRDNAKNTVY LQMNSLRPED TAVYSCAGST AYPFLSPRDA NYWGQGTQVT  120
VSS                                                                123

SEQ ID NO: 213          moltype = AA  length = 123
FEATURE                 Location/Qualifiers
source                  1..123
                        mol_type = protein
                        organism = synthetic construct
SEQUENCE: 213
DVQLQESGGG LVQTGGSLRL SCAASGRFFS TYAMGWFRQA PGKEREFVAA ITRGGAGTLY   60
ADSAKGRFTI SRDNAKNTVY LQMNSLKAED TGVYYCAPNN GSRSWYGYEY DYWGQGTQVT  120
VSS                                                                123

SEQ ID NO: 214          moltype = AA  length = 117
FEATURE                 Location/Qualifiers
```

```
source                  1..117
                        mol_type = protein
                        organism = synthetic construct
SEQUENCE: 214
DVQLQESGGG LVQPGGSLRL ECSAPGNIFR FYAMGWYRQA PGKQRELVAD IRLSGSTNIA    60
NSVKDRFTIS RDNAKNTVYL QMNSLKPEDT AVYYCNAPFT KPSPFAWGQG TQVTVSS      117

SEQ ID NO: 215          moltype = AA  length = 124
FEATURE                 Location/Qualifiers
source                  1..124
                        mol_type = protein
                        organism = synthetic construct
SEQUENCE: 215
DVQLQESGGG LVQAGGSLRL SCTASGLTFR SYAMGWFRQA PGKEREFLAH ISVSGSITPY    60
ADSVKGRFTL SRDNAKNTVY LQMNSLKPED TAVYYCAARR VGSWYSTKEE YDYWGQGTQV   120
TVSS                                                                124

SEQ ID NO: 216          moltype = AA  length = 117
FEATURE                 Location/Qualifiers
source                  1..117
                        mol_type = protein
                        organism = synthetic construct
SEQUENCE: 216
DVQLQESGGG LVQPGGSLRL SCSASGNVFR FYGMGWYRQA PGKQRELVAD IRLSGRTDYA    60
DSVKGRFTIS RDNAGNTVYL QMNGLKPEDT AVYYCNAPFT KPSPFTWGQG TQVTVSS      117

SEQ ID NO: 217          moltype = AA  length = 118
FEATURE                 Location/Qualifiers
source                  1..118
                        mol_type = protein
                        organism = synthetic construct
SEQUENCE: 217
DVQLQESGGG LVQPGGSLRL SCAASGFTFG SYAMGWYRQA PGNERELVAL ISVAGGITHY    60
ADSVKGRFRI SRDNAENMVY LQMNSLKPED TAVYYCSARR ERFTTAYWGQ GTQVTVSS     118

SEQ ID NO: 218          moltype = AA  length = 117
FEATURE                 Location/Qualifiers
source                  1..117
                        mol_type = protein
                        organism = synthetic construct
SEQUENCE: 218
DVQLQESGGG LVQPGGSLRL SCSASGSVFR FYGMGWYRQA PGKQRELVAD IRLSGRTDYA    60
DPVKGRFTIS RDNAGNTVYL QMNGLKPEDA AVYYCNAPFT KPSPFTWGQG TQVTVSS      117

SEQ ID NO: 219          moltype = AA  length = 123
FEATURE                 Location/Qualifiers
source                  1..123
                        mol_type = protein
                        organism = synthetic construct
SEQUENCE: 219
DVQLQESGGG SVQAGGSLRL SCAASGRTFT TYRMGWFRQA PGKQREFVAT ISRDGTRTYY    60
ADSVKGRFTI SRDNAESTVY LQMNSLRPED TAVYYCAVST DYPFLRPRDA AYWGQGTQVT   120
VSS                                                                 123

SEQ ID NO: 220          moltype = AA  length = 119
FEATURE                 Location/Qualifiers
source                  1..119
                        mol_type = protein
                        organism = synthetic construct
SEQUENCE: 220
DVQLQESGGG LVQPGGSLRL SCAASGFTFS NYAMTWVRQA PGKGAEWVSA INIYGDITHY    60
ADSVKGRFTI SRDNAKNTLY LQMNSLQLDD TAVYYCGTKL DGNSNKVYRG QGTQVTVSS    119

SEQ ID NO: 221          moltype = AA  length = 125
FEATURE                 Location/Qualifiers
source                  1..125
                        mol_type = protein
                        organism = synthetic construct
SEQUENCE: 221
DVQLQESGGG LVQAGGSLSL SCAASGQTFS RNVMGWFRQA PGKEREFVAA ITVGGAGTYY    60
ADSVKGRFTI SRDNPKNTVY LQMNSLKPED TAVYYCAANR RFARPVVAIA SYDVWGQGTQ   120
VTVSS                                                               125

SEQ ID NO: 222          moltype = AA  length = 123
FEATURE                 Location/Qualifiers
source                  1..123
                        mol_type = protein
                        organism = synthetic construct
SEQUENCE: 222
```

```
DVQLQESGGG SVQAGDSLRL SCAASGRTFT TYRMAWFRQA PGKQREFVAT VSRDGTRTYY    60
ADSVKGRFTI SRDNAKNTVY LQMSSLRPED TAAYYCAVST DYPFLRPRDA AYWGQGTQVT   120
VSS                                                                123

SEQ ID NO: 223          moltype = AA  length = 123
FEATURE                 Location/Qualifiers
source                  1..123
                        mol_type = protein
                        organism = synthetic construct
SEQUENCE: 223
DVQLQESGGG SVQAGGSLRL SCAASGRTFT TYRMSWFRQA PGNEREFVAT ISPDGTRTYY    60
ADSVKGRFTI SRDNAKNTAY LQMNSLRPED TAVYYCAGST VYPFLRPRDA NYWGQGTQVT   120
VSS                                                                123

SEQ ID NO: 224          moltype = AA  length = 123
FEATURE                 Location/Qualifiers
source                  1..123
                        mol_type = protein
                        organism = synthetic construct
SEQUENCE: 224
DVQLQESGGG SVQAGDTLRL SCAASGRTFA TYRMAWFRQA PGKQREFVAT VSRDGTSTYY    60
ADSVKGRFTI SRDNAKNTVY LQMNSLRPED TAVYYCAVST DYPFLRPRDA AYWGQGTQVT   120
VSS                                                                123

SEQ ID NO: 225          moltype = AA  length = 140
FEATURE                 Location/Qualifiers
source                  1..140
                        mol_type = protein
                        organism = synthetic construct
SEQUENCE: 225
DVQLQESGGG LVQAGGSLRL ACAASGRTAS SNAMGWFRQA PGKEREFVAA ISGGGIYTDY    60
ADSVKGRFTI SRDNSKNTMY LQMNSLKPED TAVYYCAQRN IPRIGSGSRN YDYWGQGTQV   120
TVSSQRNIPR IGSGSRNYDY                                              140

SEQ ID NO: 226          moltype = AA  length = 123
FEATURE                 Location/Qualifiers
source                  1..123
                        mol_type = protein
                        organism = synthetic construct
SEQUENCE: 226
DVQLQESGGG SVQAGGSLRL SCAASGRTFG TYRMTWFRQA PGKQREFVAT ISRNGGSTYY    60
ADSVKGRFTI SRDNAKNTVF LQMNSLRPED TAVYYCAGST AYPFLSPRDA NYWGQGTQVT   120
VSS                                                                123

SEQ ID NO: 227          moltype = AA  length = 123
FEATURE                 Location/Qualifiers
source                  1..123
                        mol_type = protein
                        organism = synthetic construct
SEQUENCE: 227
DVQLQESGGG SVQAGGSLRL SCAASGRTFT TYRMSWFRQA PGNEREFVAT ISPDGTRTYY    60
ADSVKGRFTI SRDNAKNTVY LQMNSLRPED TAVYYCAGST VYPFLRPRDA NYWGQGTQVT   120
VSS                                                                123

SEQ ID NO: 228          moltype = AA  length = 123
FEATURE                 Location/Qualifiers
source                  1..123
                        mol_type = protein
                        organism = synthetic construct
SEQUENCE: 228
DVQLQESGGG SVQAGGSLRL SCAASGRTFT TYRMAWFRQA PGKQREFVAT ISRNGGSTYY    60
ADSVKGRFTI SRDNAKNTVF LQMNSLRPED TAVYYCAGST DYPFLRPRDA NYWGQGTQVT   120
VSS                                                                123

SEQ ID NO: 229          moltype = AA  length = 117
FEATURE                 Location/Qualifiers
source                  1..117
                        mol_type = protein
                        organism = synthetic construct
SEQUENCE: 229
DVQLQESGGG LVQPGGSLRL ECSAPGSIFR FYAMGWYRQA PGKQRELVAD IRLSGRAVYA    60
DSVKGRFTIS RDNAKNTVYL QMDSLKPEDT AVYYCNAPFT KPSPFAWGQG TQVTVSS      117

SEQ ID NO: 230          moltype = AA  length = 123
FEATURE                 Location/Qualifiers
source                  1..123
                        mol_type = protein
                        organism = synthetic construct
SEQUENCE: 230
```

```
DVQLQESGGG SVQAGGSLRL SCAASERTFT TYRMAWFRQA PGKQREFVAT ISRDGTRTYY    60
ADSVKGRFTI SSDNAKNTVY LQMNSLRPED TAVYYCAGST DYPFLRPRDA NYWGQGTQVT   120
VSS                                                                123

SEQ ID NO: 231         moltype = AA  length = 123
FEATURE                Location/Qualifiers
source                 1..123
                       mol_type = protein
                       organism = synthetic construct
SEQUENCE: 231
DVQLQESGGG SVQAGGSPRL SCAASGRTFT TYRIAWFRQA PGKEREFVAT ISRDGTRTYY    60
ADSVKGRFTI SRDNARNTVY LQMNSLRPED TAVYYCAGST DYPFLRPRDA NYWGQGTQVT   120
VSS                                                                123

SEQ ID NO: 232         moltype = AA  length = 113
FEATURE                Location/Qualifiers
source                 1..113
                       mol_type = protein
                       organism = synthetic construct
SEQUENCE: 232
DVQLQESGGG SVQPGGSLRL SCVASGSGSS IVSMGWYRQT PGKQRESVAS ITSDGSRLYA    60
DSVKGRFTIS RVNAANTVYL QMNSLKPEDT ATYYCFLTPP TYWGQGTQVT VSS          113

SEQ ID NO: 233         moltype = AA  length = 123
FEATURE                Location/Qualifiers
source                 1..123
                       mol_type = protein
                       organism = synthetic construct
SEQUENCE: 233
DVQLQESGGG SVQAGGSLRL SCAASGRTFT TYRIAWFRQA PGKEREFVAT ISRDGTRTYY    60
ADSVKGRFTT SRDNAKNTVY LQMNSLRPED TAVYYCAGST DYPFLRPRDA NYWGQGTQVT   120
VSS                                                                123

SEQ ID NO: 234         moltype = AA  length = 123
FEATURE                Location/Qualifiers
source                 1..123
                       mol_type = protein
                       organism = synthetic construct
SEQUENCE: 234
DVQLQESGGG SVQAGGSLRL SCAASGRTFT TYRMGWFRQA PGKEREFVAT ISRDGTRPYY    60
ADSVKGRFTI SRDNTKNTVY LQMNSLRPED TAVYYCARST DYPFLRPRDA NYWGQGTQVT   120
VSS                                                                123

SEQ ID NO: 235         moltype = AA  length = 123
FEATURE                Location/Qualifiers
source                 1..123
                       mol_type = protein
                       organism = synthetic construct
SEQUENCE: 235
DVQLQESGGG SVQAGGSLRL SCAASGRTFT TYRMSWFRQA PGNEREFVAT ISPDGTRTYY    60
ADSVKGRFTI SRDNAKNTVY LHMNSLRPED TAVYYCAGST VYPFLRPRDA NYWGQGTQVT   120
VSS                                                                123

SEQ ID NO: 236         moltype = AA  length = 123
FEATURE                Location/Qualifiers
source                 1..123
                       mol_type = protein
                       organism = synthetic construct
SEQUENCE: 236
DVQLQESGGG SVQAGGSLRL SCAASGRTFM TYRMGWFRQA PGNEREFVGN ISPDGTRTYY    60
ADSVKGRFTI SRDNAKNTVY LQMNSLRPED TAVYYCAGST VYPFLRPRDA NYWGQGTQVT   120
VSS                                                                123

SEQ ID NO: 237         moltype = AA  length = 121
FEATURE                Location/Qualifiers
source                 1..121
                       mol_type = protein
                       organism = synthetic construct
SEQUENCE: 237
DVQLQESGGG LVQAGGSLRL TCTTTFSSYA MGWFRQAPGK EREFVATISG GGVYTYYADS    60
VKGRFTISRD NSKNTMYLQM NSLKFEDTAV YYCAQRNIPR YGLESRNYDY WGQGTQVTVS   120
S                                                                  121

SEQ ID NO: 238         moltype = AA  length = 117
FEATURE                Location/Qualifiers
source                 1..117
                       mol_type = protein
                       organism = synthetic construct
SEQUENCE: 238
```

```
DVQLQESGGG LVQPGGSLRL SCSASGSVFR FYGMGWYRQA PGKQRELVAD IRLSGRTNYA    60
DSVKGRFTIS RDNAGNTVYL QMNSLKPEDT AVYYCNAPFT IPSPFAWGQG TQVTVSS      117

SEQ ID NO: 239            moltype = AA  length = 114
FEATURE                   Location/Qualifiers
source                    1..114
                          mol_type = protein
                          organism = synthetic construct
SEQUENCE: 239
DVQLQESGGG SVQPGGSLRL SCVASGSISS DNAMGWYRQA APWKQRESVA SLTRDGSAIY    60
ADSVKGRFTI SRDNAANTVY LQMNSLKPED TAVYYCFRTP PTYWGQGTQV TVSS         114

SEQ ID NO: 240            moltype = AA  length = 123
FEATURE                   Location/Qualifiers
source                    1..123
                          mol_type = protein
                          organism = synthetic construct
SEQUENCE: 240
DVQLQESGGG SVQAGGSLRL SCAASGRTFS TYRMTWFRQA PGKQREFVAT ISRNGGSTYY    60
ADSVKGRFTI SRDNAKNTVF LQMNSLRPED TAVYYCAGST AYPFLSPRDA NYWGQGTQVT   120
VSS                                                                 123

SEQ ID NO: 241            moltype = AA  length = 123
FEATURE                   Location/Qualifiers
source                    1..123
                          mol_type = protein
                          organism = synthetic construct
SEQUENCE: 241
DVQLQESGGG LVQAGGSLRL SCAASGRTFS TYRITWFRQA PGKQREFVAT ISRSSSNPYY    60
ADSVKGRFTI SRDNAKNTVY LQMNSLRPED TAVYSCAGST AYPFLSPRDA NYWGQGTQVT   120
VSS                                                                 123

SEQ ID NO: 242            moltype = AA  length = 117
FEATURE                   Location/Qualifiers
source                    1..117
                          mol_type = protein
                          organism = synthetic construct
SEQUENCE: 242
DVQLQESGGG LVQPGGSLRL SCSANGSVFR FYGMGWYRQA PGKQRELVAD IRLSGRADYA    60
DSVKGRFTIS RDNAGNTVYL QMNSLKPEDT AVYYCNAPFT IPSPFAWGQG TQVTVSS      117

SEQ ID NO: 243            moltype = AA  length = 114
FEATURE                   Location/Qualifiers
source                    1..114
                          mol_type = protein
                          organism = synthetic construct
SEQUENCE: 243
DVQLQESGGG SVQPGGSLRL SCVASGSGSS INTSMGWYRQ RPGKQRESVA SMPRGGGTIY    60
ADSVKGRFTI SRDNAANTVY LQMNNLKPED TAVYYCFRTP PTYWGQGTQV TVSS         114

SEQ ID NO: 244            moltype = AA  length = 113
FEATURE                   Location/Qualifiers
source                    1..113
                          mol_type = protein
                          organism = synthetic construct
SEQUENCE: 244
DVQLQESGGG SVQPGGSLRL SCVASGSISS INAMGWYRQA PGKQHESVAS MPRSGTAIYA    60
DSVKGRFTIS RDNAANTVYL QMNSLKPEDT AKYYCFHTPP TYWGQGTQVT VSS          113

SEQ ID NO: 245            moltype = AA  length = 114
FEATURE                   Location/Qualifiers
source                    1..114
                          mol_type = protein
                          organism = synthetic construct
SEQUENCE: 245
DVQLQESGGG SVQPGGSLRL SCVASGSGSS INTSMGWYRQ TPGKQRESVA SMPRGGGAIY    60
ADSVKGRFTI SRDYAANTVY LQMNSLKPED TAVYYCFQTP PTYWGQGTQV TVSS         114

SEQ ID NO: 246            moltype = AA  length = 117
FEATURE                   Location/Qualifiers
source                    1..117
                          mol_type = protein
                          organism = synthetic construct
SEQUENCE: 246
DVQLQESGGG LVQPGGSLRL SCSASGSIFR FYGMGWYRQT PGKQRELVAY IRLSGRTDYA    60
DSVKGRFTIS RDNAGNTVYL QMNSLKPEDT AVYYCNPPFT KPSPFAWGQG TPVTVSS      117

SEQ ID NO: 247            moltype = AA  length = 123
FEATURE                   Location/Qualifiers
```

```
source                  1..123
                        mol_type = protein
                        organism = synthetic construct
SEQUENCE: 247
DVQLQESGGG SVQAGGSLRL SCAASGRTFS TYRMAWFRQA PGKEREFVAT ISPNGASTYY      60
ADSVKGRFTI SRDNAKNTLY LQMNSLRPEA TAVYYCAGST DYPFLRPRDA NFWGQGTQVT     120
VSS                                                                   123

SEQ ID NO: 248          moltype = AA  length = 117
FEATURE                 Location/Qualifiers
source                  1..117
                        mol_type = protein
                        organism = synthetic construct
SEQUENCE: 248
DVQLQESGGG LVQPGGSLRL SCSASGSIFR FYGMGWYRQA PGKQRELVAD IRLSGRTDYA      60
DSVKGRFTIS RDNAGNTVYL QMNSLKPEDT AVYYCNAPFT KPSPFAWGQG TQVTVSS        117

SEQ ID NO: 249          moltype = AA  length = 123
FEATURE                 Location/Qualifiers
source                  1..123
                        mol_type = protein
                        organism = synthetic construct
SEQUENCE: 249
DVQLQESGGG SVQAGGSLRL SCAASGRTFT TYRMSWFRQA PGNERGFVAT ISPDGTRTYY      60
ADSVKGRFTI SRDNAKNTVY LQMNSLRPED TAVYYCAGST VYPFLRPRDA NYWGQGTQVT     120
VSS                                                                   123

SEQ ID NO: 250          moltype = AA  length = 123
FEATURE                 Location/Qualifiers
source                  1..123
                        mol_type = protein
                        organism = synthetic construct
SEQUENCE: 250
DVQLQESGGG SVQAGGSLRL SCAASGRTFS TYRMGWFRQA PGKQREFVAE ISRNGGYTYY      60
ADSVKGRFTI SRDNAKNTVY LQMNSLRPED TAVYYCAGST TYPFLSPRDA NYWGQGTQVT     120
VSS                                                                   123

SEQ ID NO: 251          moltype = AA  length = 123
FEATURE                 Location/Qualifiers
source                  1..123
                        mol_type = protein
                        organism = synthetic construct
SEQUENCE: 251
DVQLQESGGG SVQAGGSLRL SCAASGRTFT TYRMGWFRQA PGKQREFVAT ISRDGTRTYY      60
ADSVKGRFTI SRDNAENTVY LQMNSLRPED TAVYYCAVST DYPFLRPRDA AYWGQGTQVT     120
VSS                                                                   123

SEQ ID NO: 252          moltype = AA  length = 114
FEATURE                 Location/Qualifiers
source                  1..114
                        mol_type = protein
                        organism = synthetic construct
SEQUENCE: 252
DVQLQESGGG SVQPGGSLRL SCVASGSGSS INTSMGWYRQ APGKQRESVA SMPRGGGALY      60
ADSVKGRFTI SRDNAANTVY LQMNSLKPED TAVYYCFQTP PTFWGQGTQV TVSS           114

SEQ ID NO: 253          moltype = AA  length = 123
FEATURE                 Location/Qualifiers
source                  1..123
                        mol_type = protein
                        organism = synthetic construct
SEQUENCE: 253
DVQLQESGGG SVQAGGSLRL SCAASGRTFT TDRMAWFRQA PGKEREFVAT ISRDGTRPYY      60
ADSVKGRFTI SRDNAKNTVY LQMNSLRPED TAVYYCAGST VYPFLRPRDA NYWGQGTQVT     120
VSS                                                                   123

SEQ ID NO: 254          moltype = AA  length = 123
FEATURE                 Location/Qualifiers
source                  1..123
                        mol_type = protein
                        organism = synthetic construct
SEQUENCE: 254
DVQLQESGGG SVQAGGSLRL SCAASEGTFS TYRMTWFRQA PGKQREFVAT ISRNGGSTYY      60
VDSVKGRFTI SRDNAKNTVF LQMNSLRPED TAVYYCAGST AYPFLSPRDA NYWGQGTQVT     120
VSS                                                                   123

SEQ ID NO: 255          moltype = AA  length = 123
FEATURE                 Location/Qualifiers
source                  1..123
```

```
                        mol_type = protein
                        organism = synthetic construct
SEQUENCE: 255
DVQLQESGGG SVQAGGSLRL SCAASGRTFT TYRVAWFRQA PGKEREFVAT VSRDGTRAYY    60
ADSVKGRFTI SRDNAKNTVY LQMNSLRPED TAVYYCAGST DYPFLRPRDA NYWGQGTQVT   120
VSS                                                                 123

SEQ ID NO: 256          moltype = AA  length = 123
FEATURE                 Location/Qualifiers
source                  1..123
                        mol_type = protein
                        organism = synthetic construct
SEQUENCE: 256
DVQLQESGGG SVQAGGSLRL SCAASGRTFT TYRMSWFRQA PGNEREFVAT ISPDGTRTYY    60
ADSVKGRFTI SRDNAKNTVY LQMNSLRPED TAVYYCAGST VYPFLRPRDA NYWGPGTQVT   120
VSS                                                                 123

SEQ ID NO: 257          moltype = AA  length = 123
FEATURE                 Location/Qualifiers
source                  1..123
                        mol_type = protein
                        organism = synthetic construct
SEQUENCE: 257
DVQLQESGGG SVQAGGSLRL SCVASGGTVT TYRMAWFRQA PGKQREFVAT ISRDGTSTYY    60
ADSVKGRFTI SRDNAKNTAY LQMNSLRPED TAVYYCAGST TYPFLRPRDA NYWGQGTQVT   120
VSS                                                                 123

SEQ ID NO: 258          moltype = AA  length = 119
FEATURE                 Location/Qualifiers
source                  1..119
                        mol_type = protein
                        organism = synthetic construct
SEQUENCE: 258
DVQLQESGGG LVQPGDSLRL SCAAGGSSLN IYAIGWFRQA PGKEREGVQC ISRSDGITFY    60
DDDSVKGRFTV SRDRAKGTVY LQMNGLQPED AAVCYCAAGY RCALYMDYWG KGTQVTVSS   119

SEQ ID NO: 259          moltype = AA  length = 123
FEATURE                 Location/Qualifiers
source                  1..123
                        mol_type = protein
                        organism = synthetic construct
SEQUENCE: 259
DVQLQESGGG SVQAGDSLRL SCAASGRTFT TYRVAWFRQA PGKQREFVAT VSRDGTRTYY    60
ADSVKGRFTI SRDNAKNTVY LQMNSLRPED TAVYYCAVST DYPFLRPRDA AYWGQGTQVT   120
VSS                                                                 123

SEQ ID NO: 260          moltype = AA  length = 113
FEATURE                 Location/Qualifiers
source                  1..113
                        mol_type = protein
                        organism = synthetic construct
SEQUENCE: 260
DVQLQESGGG SVQPGGSLRL SCVASGSISS NVSMGWYRQA PGKQRESVAS MPRGGSAIYA    60
DSVKGRFVIS RDNAANTVYL QMNSLKPEDT AVYYCFRTPP TYWGQGTQVT VSS          113

SEQ ID NO: 261          moltype = AA  length = 117
FEATURE                 Location/Qualifiers
source                  1..117
                        mol_type = protein
                        organism = synthetic construct
SEQUENCE: 261
DVQLQESGGG LVQPGGSLRL ECSAPGNIFR FYAMGWYRQA PGKQRELVAD IRLSGSTNIA    60
NSVKGRFTIS RDNAKNTVYL QMNSLKPEDT AVYYCNAPFT KPSPFAWGQG TQVTVSS      117

SEQ ID NO: 262          moltype = AA  length = 123
FEATURE                 Location/Qualifiers
source                  1..123
                        mol_type = protein
                        organism = synthetic construct
SEQUENCE: 262
DVQLQESGGG SVQAGGSLRL SCAASGRTFT TYRMGWLRQA PGKQREFVAT ISRDGTRTYY    60
ADSVEGRFTI SRDNAKNTAY LQMNSLRPED TAVYYCALST NYPFLRPRDA NYWGQGTQVT   120
VSS                                                                 123

SEQ ID NO: 263          moltype = AA  length = 114
FEATURE                 Location/Qualifiers
source                  1..114
                        mol_type = protein
                        organism = synthetic construct
```

```
SEQUENCE: 263
DVQLQESGGG SVQPGGSLRL SCVASGSGSS INTSMGWYRQ APGKQRESVA SMPRGGGAIY    60
ADSVKGRFTI SRDNAANTVY LQMNSLKPED TAVYYCFQTP PTYWGQGTQV TVSS         114

SEQ ID NO: 264          moltype = AA  length = 123
FEATURE                 Location/Qualifiers
source                  1..123
                        mol_type = protein
                        organism = synthetic construct
SEQUENCE: 264
DVQLQESGGG SVQAGGSLRL SCAASGRTFT TYRMGWFRQA PGKEREFVAT ISGDGTRPYY    60
ADSVKGRFTI SRDNTKNTVY LQMNSLRPED TAVYYCAGST DYPFLRPRDA NYWGQGTQVT    120
VSS                                                                  123

SEQ ID NO: 265          moltype = AA  length = 123
FEATURE                 Location/Qualifiers
source                  1..123
                        mol_type = protein
                        organism = synthetic construct
SEQUENCE: 265
DVQLQESGGG SVQAGGSLRL SCAASGRTFT TYRMSWFRQA PGNEREFVAT ISPDGTRTYY    60
ADSVKGRFTI SRDNAKNTVY LQMNSLRPED TAVYYCAGST VYPFLRPRDA NYWGQGTQVT    120
VSS                                                                  123

SEQ ID NO: 266          moltype = AA  length = 123
FEATURE                 Location/Qualifiers
source                  1..123
                        mol_type = protein
                        organism = synthetic construct
SEQUENCE: 266
DVQLQESGGG SVQAGGSLRL SCAASEGTFS TYRMTWFRQA PGKQREFVAT ISRNGGSTYY    60
ADSVKGRFTI SRDNAKNTVF LQMNSLRPED TAVYYCAGST AYPFLSPRDA NYWGQGTQVT    120
VSS                                                                  123

SEQ ID NO: 267          moltype = AA  length = 123
FEATURE                 Location/Qualifiers
source                  1..123
                        mol_type = protein
                        organism = synthetic construct
SEQUENCE: 267
DVQLQESGGG SVQAGGSLRL SCAASGRTFT TYRMGWFRQA PGKQREFVAT ISRDGTRTYY    60
ADSVEGRFTI SRDNAKNTVY LQMNSLRPED TAVYYCALST NYPFLRPRDA NYWGQGTQVT    120
VSS                                                                  123

SEQ ID NO: 268          moltype = AA  length = 124
FEATURE                 Location/Qualifiers
source                  1..124
                        mol_type = protein
                        organism = synthetic construct
SEQUENCE: 268
DVQLQESGGG LVQAGGSLRL ACAASGRTAS SNAMGWFRQA PGKEREFVAA ISGGGIYTDY    60
ADSVKGRFTI SRDNSKNTMY LQMNSLKPED TAVYYCAQRN IPRIGLGSRN YDYWGQGTQV    120
TVSS                                                                 124

SEQ ID NO: 269          moltype = AA  length = 117
FEATURE                 Location/Qualifiers
source                  1..117
                        mol_type = protein
                        organism = synthetic construct
SEQUENCE: 269
DVQLQESGGG LVQPGGSLRL SCSASGSVFR FYGMGWYRQA PGKQRELVAD IRLSGRTDYA    60
DSVKGRFTIS RDNAGNTVYL QMNGLKPEDT AVYYCNAPFT KPSPFTWGQG TQVTVSS       117

SEQ ID NO: 270          moltype = AA  length = 10
FEATURE                 Location/Qualifiers
source                  1..10
                        mol_type = protein
                        organism = synthetic construct
SEQUENCE: 270
GRTFSTYRIT                                                           10

SEQ ID NO: 271          moltype = AA  length = 10
FEATURE                 Location/Qualifiers
source                  1..10
                        mol_type = protein
                        organism = synthetic construct
SEQUENCE: 271
TISRSSSNPY                                                           10
```

```
SEQ ID NO: 272              moltype = AA   length = 15
FEATURE                     Location/Qualifiers
source                      1..15
                            mol_type = protein
                            organism = synthetic construct
SEQUENCE: 272
GSTAYPFLSP RDANY                                                           15

SEQ ID NO: 273              moltype = AA   length = 10
FEATURE                     Location/Qualifiers
source                      1..10
                            mol_type = protein
                            organism = synthetic construct
SEQUENCE: 273
GSISSDNAMG                                                                 10

SEQ ID NO: 274              moltype = AA   length = 9
FEATURE                     Location/Qualifiers
source                      1..9
                            mol_type = protein
                            organism = synthetic construct
SEQUENCE: 274
SLTRDGSAI                                                                   9

SEQ ID NO: 275              moltype = AA   length = 6
FEATURE                     Location/Qualifiers
source                      1..6
                            mol_type = protein
                            organism = synthetic construct
SEQUENCE: 275
RTPPTY                                                                      6

SEQ ID NO: 276              moltype = AA   length = 10
FEATURE                     Location/Qualifiers
source                      1..10
                            mol_type = protein
                            organism = synthetic construct
SEQUENCE: 276
GSGSSINSMG                                                                 10

SEQ ID NO: 277              moltype = AA   length = 9
FEATURE                     Location/Qualifiers
source                      1..9
                            mol_type = protein
                            organism = synthetic construct
SEQUENCE: 277
SITRAGSAI                                                                   9

SEQ ID NO: 278              moltype = AA   length = 6
FEATURE                     Location/Qualifiers
source                      1..6
                            mol_type = protein
                            organism = synthetic construct
SEQUENCE: 278
HTPPTY                                                                      6

SEQ ID NO: 279              moltype = AA   length = 10
FEATURE                     Location/Qualifiers
source                      1..10
                            mol_type = protein
                            organism = synthetic construct
SEQUENCE: 279
GSGFRFYGMG                                                                 10

SEQ ID NO: 280              moltype = AA   length = 9
FEATURE                     Location/Qualifiers
source                      1..9
                            mol_type = protein
                            organism = synthetic construct
SEQUENCE: 280
DIRLSGRAE                                                                   9

SEQ ID NO: 281              moltype = AA   length = 10
FEATURE                     Location/Qualifiers
source                      1..10
                            mol_type = protein
                            organism = synthetic construct
SEQUENCE: 281
APFTSPSPFA                                                                 10
```

```
SEQ ID NO: 282            moltype = AA   length = 10
FEATURE                   Location/Qualifiers
source                    1..10
                          mol_type = protein
                          organism = synthetic construct
SEQUENCE: 282
GRTFSNLAMG                                                                10

SEQ ID NO: 283            moltype = AA   length = 10
FEATURE                   Location/Qualifiers
source                    1..10
                          mol_type = protein
                          organism = synthetic construct
SEQUENCE: 283
AISGSGGSIF                                                                10

SEQ ID NO: 284            moltype = AA   length = 11
FEATURE                   Location/Qualifiers
source                    1..11
                          mol_type = protein
                          organism = synthetic construct
SEQUENCE: 284
AGPYGSPDFD S                                                              11

SEQ ID NO: 285            moltype = AA   length = 10
FEATURE                   Location/Qualifiers
source                    1..10
                          mol_type = protein
                          organism = synthetic construct
SEQUENCE: 285
GRTFTTYRIA                                                                10

SEQ ID NO: 286            moltype = AA   length = 10
FEATURE                   Location/Qualifiers
source                    1..10
                          mol_type = protein
                          organism = synthetic construct
SEQUENCE: 286
TISRDGTRTY                                                                10

SEQ ID NO: 287            moltype = AA   length = 15
FEATURE                   Location/Qualifiers
source                    1..15
                          mol_type = protein
                          organism = synthetic construct
SEQUENCE: 287
GSTDYPFLRP RDANY                                                          15

SEQ ID NO: 288            moltype = AA   length = 10
FEATURE                   Location/Qualifiers
source                    1..10
                          mol_type = protein
                          organism = synthetic construct
SEQUENCE: 288
GRTFTTYRMG                                                                10

SEQ ID NO: 289            moltype = AA   length = 10
FEATURE                   Location/Qualifiers
source                    1..10
                          mol_type = protein
                          organism = synthetic construct
SEQUENCE: 289
TISRDGTRTY                                                                10

SEQ ID NO: 290            moltype = AA   length = 15
FEATURE                   Location/Qualifiers
source                    1..15
                          mol_type = protein
                          organism = synthetic construct
SEQUENCE: 290
VSTDYPFLRP RDAAY                                                          15

SEQ ID NO: 291            moltype = AA   length = 10
FEATURE                   Location/Qualifiers
source                    1..10
                          mol_type = protein
                          organism = synthetic construct
SEQUENCE: 291
```

GRTSSTYTMA 10

SEQ ID NO: 292         moltype = AA  length = 10
FEATURE                Location/Qualifiers
source                 1..10
                       mol_type = protein
                       organism = synthetic construct

SEQUENCE: 292
RIRWNSGSAD 10

SEQ ID NO: 293         moltype = AA  length = 18
FEATURE                Location/Qualifiers
source                 1..18
                       mol_type = protein
                       organism = synthetic construct

SEQUENCE: 293
AASWGYSSSY YSSRGYDV 18

SEQ ID NO: 294         moltype = AA  length = 10
FEATURE                Location/Qualifiers
source                 1..10
                       mol_type = protein
                       organism = synthetic construct

SEQUENCE: 294
GRTASSNAMG 10

SEQ ID NO: 295         moltype = AA  length = 10
FEATURE                Location/Qualifiers
source                 1..10
                       mol_type = protein
                       organism = synthetic construct

SEQUENCE: 295
AISGGGIYTD 10

SEQ ID NO: 296         moltype = AA  length = 16
FEATURE                Location/Qualifiers
source                 1..16
                       mol_type = protein
                       organism = synthetic construct

SEQUENCE: 296
QRNIPRIGLG SGNYDY 16

SEQ ID NO: 297         moltype = AA  length = 10
FEATURE                Location/Qualifiers
source                 1..10
                       mol_type = protein
                       organism = synthetic construct

SEQUENCE: 297
GRTFSKYTMS 10

SEQ ID NO: 298         moltype = AA  length = 10
FEATURE                Location/Qualifiers
source                 1..10
                       mol_type = protein
                       organism = synthetic construct

SEQUENCE: 298
TITSSGRSTS 10

SEQ ID NO: 299         moltype = AA  length = 8
FEATURE                Location/Qualifiers
source                 1..8
                       mol_type = protein
                       organism = synthetic construct

SEQUENCE: 299
AADSVSAY 8

SEQ ID NO: 300         moltype = AA  length = 10
FEATURE                Location/Qualifiers
source                 1..10
                       mol_type = protein
                       organism = synthetic construct

SEQUENCE: 300
GSGSSIAAMG 10

SEQ ID NO: 301         moltype = AA  length = 9
FEATURE                Location/Qualifiers
source                 1..9
                       mol_type = protein
                       organism = synthetic construct -continued

```
SEQUENCE: 301
SLTREGRVI                                                                        9

SEQ ID NO: 302          moltype = AA  length = 6
FEATURE                 Location/Qualifiers
source                  1..6
                        mol_type = protein
                        organism = synthetic construct
SEQUENCE: 302
RTPPTL                                                                           6

SEQ ID NO: 303          moltype = AA  length = 10
FEATURE                 Location/Qualifiers
source                  1..10
                        mol_type = protein
                        organism = synthetic construct
SEQUENCE: 303
GNISSNNAMG                                                                      10

SEQ ID NO: 304          moltype = AA  length = 9
FEATURE                 Location/Qualifiers
source                  1..9
                        mol_type = protein
                        organism = synthetic construct
SEQUENCE: 304
SMPRGGTAI                                                                        9

SEQ ID NO: 305          moltype = AA  length = 6
FEATURE                 Location/Qualifiers
source                  1..6
                        mol_type = protein
                        organism = synthetic construct
SEQUENCE: 305
RTPPTY                                                                           6

SEQ ID NO: 306          moltype = AA  length = 10
FEATURE                 Location/Qualifiers
source                  1..10
                        mol_type = protein
                        organism = synthetic construct
SEQUENCE: 306
GRTFSTHRIT                                                                      10

SEQ ID NO: 307          moltype = AA  length = 10
FEATURE                 Location/Qualifiers
source                  1..10
                        mol_type = protein
                        organism = synthetic construct
SEQUENCE: 307
TISRSSSNPY                                                                      10

SEQ ID NO: 308          moltype = AA  length = 15
FEATURE                 Location/Qualifiers
source                  1..15
                        mol_type = protein
                        organism = synthetic construct
SEQUENCE: 308
GSTAYPFLSP RDANY                                                                15

SEQ ID NO: 309          moltype = AA  length = 10
FEATURE                 Location/Qualifiers
source                  1..10
                        mol_type = protein
                        organism = synthetic construct
SEQUENCE: 309
GRFFSTYAMG                                                                      10

SEQ ID NO: 310          moltype = AA  length = 10
FEATURE                 Location/Qualifiers
source                  1..10
                        mol_type = protein
                        organism = synthetic construct
SEQUENCE: 310
AITRGGAGTL                                                                      10

SEQ ID NO: 311          moltype = AA  length = 15
FEATURE                 Location/Qualifiers
source                  1..15
                        mol_type = protein
```

-continued

```
SEQUENCE: 311
PNNGSRSWYG YEYDY                                                    15

SEQ ID NO: 312          moltype = AA  length = 10
FEATURE                 Location/Qualifiers
source                  1..10
                        mol_type = protein
                        organism = synthetic construct
SEQUENCE: 312
GNIFRFYAMG                                                          10

SEQ ID NO: 313          moltype = AA  length = 9
FEATURE                 Location/Qualifiers
source                  1..9
                        mol_type = protein
                        organism = synthetic construct
SEQUENCE: 313
DIRLSGSTN                                                            9

SEQ ID NO: 314          moltype = AA  length = 10
FEATURE                 Location/Qualifiers
source                  1..10
                        mol_type = protein
                        organism = synthetic construct
SEQUENCE: 314
APFTKPSPFA                                                          10

SEQ ID NO: 315          moltype = AA  length = 10
FEATURE                 Location/Qualifiers
source                  1..10
                        mol_type = protein
                        organism = synthetic construct
SEQUENCE: 315
GLTFRSYAMG                                                          10

SEQ ID NO: 316          moltype = AA  length = 10
FEATURE                 Location/Qualifiers
source                  1..10
                        mol_type = protein
                        organism = synthetic construct
SEQUENCE: 316
HISVSGSITP                                                          10

SEQ ID NO: 317          moltype = AA  length = 16
FEATURE                 Location/Qualifiers
source                  1..16
                        mol_type = protein
                        organism = synthetic construct
SEQUENCE: 317
ARRVGSWYST KEEYDY                                                   16

SEQ ID NO: 318          moltype = AA  length = 10
FEATURE                 Location/Qualifiers
source                  1..10
                        mol_type = protein
                        organism = synthetic construct
SEQUENCE: 318
GNVFRFYGMG                                                          10

SEQ ID NO: 319          moltype = AA  length = 9
FEATURE                 Location/Qualifiers
source                  1..9
                        mol_type = protein
                        organism = synthetic construct
SEQUENCE: 319
DIRLSGRTD                                                            9

SEQ ID NO: 320          moltype = AA  length = 10
FEATURE                 Location/Qualifiers
source                  1..10
                        mol_type = protein
                        organism = synthetic construct
SEQUENCE: 320
APFTKPSPFT                                                          10

SEQ ID NO: 321          moltype = AA  length = 10
FEATURE                 Location/Qualifiers
source                  1..10
```

```
                        mol_type = protein
                        organism = synthetic construct
SEQUENCE: 321
GFTFGSYAMG                                                         10

SEQ ID NO: 322          moltype = AA  length = 10
FEATURE                 Location/Qualifiers
source                  1..10
                        mol_type = protein
                        organism = synthetic construct
SEQUENCE: 322
LISVAGGITH                                                         10

SEQ ID NO: 323          moltype = AA  length = 10
FEATURE                 Location/Qualifiers
source                  1..10
                        mol_type = protein
                        organism = synthetic construct
SEQUENCE: 323
ARRERFTTAY                                                         10

SEQ ID NO: 324          moltype = AA  length = 10
FEATURE                 Location/Qualifiers
source                  1..10
                        mol_type = protein
                        organism = synthetic construct
SEQUENCE: 324
GSVFRFYGMG                                                         10

SEQ ID NO: 325          moltype = AA  length = 9
FEATURE                 Location/Qualifiers
source                  1..9
                        mol_type = protein
                        organism = synthetic construct
SEQUENCE: 325
DIRLSGRTD                                                           9

SEQ ID NO: 326          moltype = AA  length = 10
FEATURE                 Location/Qualifiers
source                  1..10
                        mol_type = protein
                        organism = synthetic construct
SEQUENCE: 326
APFTKPSPFT                                                         10

SEQ ID NO: 327          moltype = AA  length = 10
FEATURE                 Location/Qualifiers
source                  1..10
                        mol_type = protein
                        organism = synthetic construct
SEQUENCE: 327
GRTFTTYRMG                                                         10

SEQ ID NO: 328          moltype = AA  length = 10
FEATURE                 Location/Qualifiers
source                  1..10
                        mol_type = protein
                        organism = synthetic construct
SEQUENCE: 328
TISRDGTRTY                                                         10

SEQ ID NO: 329          moltype = AA  length = 15
FEATURE                 Location/Qualifiers
source                  1..15
                        mol_type = protein
                        organism = synthetic construct
SEQUENCE: 329
VSTDYPFLRP RDAAY                                                   15

SEQ ID NO: 330          moltype = AA  length = 10
FEATURE                 Location/Qualifiers
source                  1..10
                        mol_type = protein
                        organism = synthetic construct
SEQUENCE: 330
GFTFSNYAMT                                                         10

SEQ ID NO: 331          moltype = AA  length = 10
FEATURE                 Location/Qualifiers
```

| | | |
|---|---|---|
| source | 1..10<br>mol_type = protein<br>organism = synthetic construct | |
| SEQUENCE: 331<br>AINIYGDITH | | 10 |
| SEQ ID NO: 332<br>FEATURE<br>source | moltype = AA  length = 11<br>Location/Qualifiers<br>1..11<br>mol_type = protein<br>organism = synthetic construct | |
| SEQUENCE: 332<br>TKLDGNSNKV Y | | 11 |
| SEQ ID NO: 333<br>FEATURE<br>source | moltype = AA  length = 10<br>Location/Qualifiers<br>1..10<br>mol_type = protein<br>organism = synthetic construct | |
| SEQUENCE: 333<br>GQTFSRNVMG | | 10 |
| SEQ ID NO: 334<br>FEATURE<br>source | moltype = AA  length = 10<br>Location/Qualifiers<br>1..10<br>mol_type = protein<br>organism = synthetic construct | |
| SEQUENCE: 334<br>AITVGGAGTY | | 10 |
| SEQ ID NO: 335<br>FEATURE<br>source | moltype = AA  length = 17<br>Location/Qualifiers<br>1..17<br>mol_type = protein<br>organism = synthetic construct | |
| SEQUENCE: 335<br>ANRRFARPVV AIASYDV | | 17 |
| SEQ ID NO: 336<br>FEATURE<br>source | moltype = AA  length = 10<br>Location/Qualifiers<br>1..10<br>mol_type = protein<br>organism = synthetic construct | |
| SEQUENCE: 336<br>GRTFTTYRMA | | 10 |
| SEQ ID NO: 337<br>FEATURE<br>source | moltype = AA  length = 10<br>Location/Qualifiers<br>1..10<br>mol_type = protein<br>organism = synthetic construct | |
| SEQUENCE: 337<br>TVSRDGTRTY | | 10 |
| SEQ ID NO: 338<br>FEATURE<br>source | moltype = AA  length = 15<br>Location/Qualifiers<br>1..15<br>mol_type = protein<br>organism = synthetic construct | |
| SEQUENCE: 338<br>VSTDYPFLRP RDAAY | | 15 |
| SEQ ID NO: 339<br>FEATURE<br>source | moltype = AA  length = 10<br>Location/Qualifiers<br>1..10<br>mol_type = protein<br>organism = synthetic construct | |
| SEQUENCE: 339<br>GRTFTTYRMS | | 10 |
| SEQ ID NO: 340<br>FEATURE<br>source | moltype = AA  length = 10<br>Location/Qualifiers<br>1..10<br>mol_type = protein<br>organism = synthetic construct | |
| SEQUENCE: 340<br>TISPDGTRTY | | 10 |
| SEQ ID NO: 341 | moltype = AA  length = 15 | |

```
FEATURE                 Location/Qualifiers
source                  1..15
                        mol_type = protein
                        organism = synthetic construct
SEQUENCE: 341
GSTVYPFLRP RDANY                                                        15

SEQ ID NO: 342          moltype = AA  length = 10
FEATURE                 Location/Qualifiers
source                  1..10
                        mol_type = protein
                        organism = synthetic construct
SEQUENCE: 342
GRTFATYRMA                                                              10

SEQ ID NO: 343          moltype = AA  length = 9
FEATURE                 Location/Qualifiers
source                  1..9
                        mol_type = protein
                        organism = synthetic construct
SEQUENCE: 343
TVSRDGTST                                                               9

SEQ ID NO: 344          moltype = AA  length = 15
FEATURE                 Location/Qualifiers
source                  1..15
                        mol_type = protein
                        organism = synthetic construct
SEQUENCE: 344
VSTDYPFLRP RDAAY                                                        15

SEQ ID NO: 345          moltype = AA  length = 10
FEATURE                 Location/Qualifiers
source                  1..10
                        mol_type = protein
                        organism = synthetic construct
SEQUENCE: 345
GRTASSNAMG                                                              10

SEQ ID NO: 346          moltype = AA  length = 10
FEATURE                 Location/Qualifiers
source                  1..10
                        mol_type = protein
                        organism = synthetic construct
SEQUENCE: 346
AISGGGIYTD                                                              10

SEQ ID NO: 347          moltype = AA  length = 16
FEATURE                 Location/Qualifiers
source                  1..16
                        mol_type = protein
                        organism = synthetic construct
SEQUENCE: 347
QRNIPRIGSG SRNYDY                                                       16

SEQ ID NO: 348          moltype = AA  length = 10
FEATURE                 Location/Qualifiers
source                  1..10
                        mol_type = protein
                        organism = synthetic construct
SEQUENCE: 348
GRTFGTYRMT                                                              10

SEQ ID NO: 349          moltype = AA  length = 10
FEATURE                 Location/Qualifiers
source                  1..10
                        mol_type = protein
                        organism = synthetic construct
SEQUENCE: 349
TISRNGGSTY                                                              10

SEQ ID NO: 350          moltype = AA  length = 15
FEATURE                 Location/Qualifiers
source                  1..15
                        mol_type = protein
                        organism = synthetic construct
SEQUENCE: 350
GSTAYPFLSP RDANY                                                        15
```

```
SEQ ID NO: 351        moltype = AA   length = 10
FEATURE               Location/Qualifiers
source                1..10
                      mol_type = protein
                      organism = synthetic construct
SEQUENCE: 351
GRTFTTYRMS                                                                10

SEQ ID NO: 352        moltype = AA   length = 10
FEATURE               Location/Qualifiers
source                1..10
                      mol_type = protein
                      organism = synthetic construct
SEQUENCE: 352
TISPDGTRTY                                                                10

SEQ ID NO: 353        moltype = AA   length = 15
FEATURE               Location/Qualifiers
source                1..15
                      mol_type = protein
                      organism = synthetic construct
SEQUENCE: 353
GSTVYPFLRP RDANY                                                          15

SEQ ID NO: 354        moltype = AA   length = 10
FEATURE               Location/Qualifiers
source                1..10
                      mol_type = protein
                      organism = synthetic construct
SEQUENCE: 354
GRTFTTYRMA                                                                10

SEQ ID NO: 355        moltype = AA   length = 10
FEATURE               Location/Qualifiers
source                1..10
                      mol_type = protein
                      organism = synthetic construct
SEQUENCE: 355
TISRNGGSTY                                                                10

SEQ ID NO: 356        moltype = AA   length = 15
FEATURE               Location/Qualifiers
source                1..15
                      mol_type = protein
                      organism = synthetic construct
SEQUENCE: 356
GSTDYPFLRP RDANY                                                          15

SEQ ID NO: 357        moltype = AA   length = 10
FEATURE               Location/Qualifiers
source                1..10
                      mol_type = protein
                      organism = synthetic construct
SEQUENCE: 357
GSIFRFYAMG                                                                10

SEQ ID NO: 358        moltype = AA   length = 9
FEATURE               Location/Qualifiers
source                1..9
                      mol_type = protein
                      organism = synthetic construct
SEQUENCE: 358
DIRLSGRAV                                                                 9

SEQ ID NO: 359        moltype = AA   length = 10
FEATURE               Location/Qualifiers
source                1..10
                      mol_type = protein
                      organism = synthetic construct
SEQUENCE: 359
APFTKPSPFA                                                                10

SEQ ID NO: 360        moltype = AA   length = 10
FEATURE               Location/Qualifiers
source                1..10
                      mol_type = protein
                      organism = synthetic construct
SEQUENCE: 360
ERTFTTYRMA                                                                10
```

| | | |
|---|---|---|
| SEQ ID NO: 361<br>FEATURE<br>source | moltype = AA   length = 10<br>Location/Qualifiers<br>1..10<br>mol_type = protein<br>organism = synthetic construct | |
| SEQUENCE: 361<br>TISRDGTRTY | | 10 |
| SEQ ID NO: 362<br>FEATURE<br>source | moltype = AA   length = 15<br>Location/Qualifiers<br>1..15<br>mol_type = protein<br>organism = synthetic construct | |
| SEQUENCE: 362<br>GSTDYPFLRP RDANY | | 15 |
| SEQ ID NO: 363<br>FEATURE<br>source | moltype = AA   length = 10<br>Location/Qualifiers<br>1..10<br>mol_type = protein<br>organism = synthetic construct | |
| SEQUENCE: 363<br>GRTFTTYRIA | | 10 |
| SEQ ID NO: 364<br>FEATURE<br>source | moltype = AA   length = 10<br>Location/Qualifiers<br>1..10<br>mol_type = protein<br>organism = synthetic construct | |
| SEQUENCE: 364<br>TISRDGTRTY | | 10 |
| SEQ ID NO: 365<br>FEATURE<br>source | moltype = AA   length = 15<br>Location/Qualifiers<br>1..15<br>mol_type = protein<br>organism = synthetic construct | |
| SEQUENCE: 365<br>GSTDYPFLRP RDANY | | 15 |
| SEQ ID NO: 366<br>FEATURE<br>source | moltype = AA   length = 10<br>Location/Qualifiers<br>1..10<br>mol_type = protein<br>organism = synthetic construct | |
| SEQUENCE: 366<br>GSGSSIVSMG | | 10 |
| SEQ ID NO: 367<br>FEATURE<br>source | moltype = AA   length = 9<br>Location/Qualifiers<br>1..9<br>mol_type = protein<br>organism = synthetic construct | |
| SEQUENCE: 367<br>SITSDGSRL | | 9 |
| SEQ ID NO: 368<br>FEATURE<br>source | moltype = AA   length = 6<br>Location/Qualifiers<br>1..6<br>mol_type = protein<br>organism = synthetic construct | |
| SEQUENCE: 368<br>LTPPTY | | 6 |
| SEQ ID NO: 369<br>FEATURE<br>source | moltype = AA   length = 10<br>Location/Qualifiers<br>1..10<br>mol_type = protein<br>organism = synthetic construct | |
| SEQUENCE: 369<br>GRTFTTYRIA | | 10 |
| SEQ ID NO: 370<br>FEATURE<br>source | moltype = AA   length = 10<br>Location/Qualifiers<br>1..10<br>mol_type = protein<br>organism = synthetic construct | |
| SEQUENCE: 370 | | |

TISRDGTRTY                                                                          10

SEQ ID NO: 371           moltype = AA  length = 15
FEATURE                  Location/Qualifiers
source                   1..15
                         mol_type = protein
                         organism = synthetic construct
SEQUENCE: 371
GSTDYPFLRP RDANY                                                                    15

SEQ ID NO: 372           moltype = AA  length = 10
FEATURE                  Location/Qualifiers
source                   1..10
                         mol_type = protein
                         organism = synthetic construct
SEQUENCE: 372
GRTFTTYRMG                                                                          10

SEQ ID NO: 373           moltype = AA  length = 10
FEATURE                  Location/Qualifiers
source                   1..10
                         mol_type = protein
                         organism = synthetic construct
SEQUENCE: 373
TISRDGTRPY                                                                          10

SEQ ID NO: 374           moltype = AA  length = 15
FEATURE                  Location/Qualifiers
source                   1..15
                         mol_type = protein
                         organism = synthetic construct
SEQUENCE: 374
RSTDYPFLRP RDANY                                                                    15

SEQ ID NO: 375           moltype = AA  length = 10
FEATURE                  Location/Qualifiers
source                   1..10
                         mol_type = protein
                         organism = synthetic construct
SEQUENCE: 375
GRTFTTYRMS                                                                          10

SEQ ID NO: 376           moltype = AA  length = 10
FEATURE                  Location/Qualifiers
source                   1..10
                         mol_type = protein
                         organism = synthetic construct
SEQUENCE: 376
TISPDGTRTY                                                                          10

SEQ ID NO: 377           moltype = AA  length = 15
FEATURE                  Location/Qualifiers
source                   1..15
                         mol_type = protein
                         organism = synthetic construct
SEQUENCE: 377
GSTVYPFLRP RDANY                                                                    15

SEQ ID NO: 378           moltype = AA  length = 10
FEATURE                  Location/Qualifiers
source                   1..10
                         mol_type = protein
                         organism = synthetic construct
SEQUENCE: 378
GRTFMTYRMG                                                                          10

SEQ ID NO: 379           moltype = AA  length = 10
FEATURE                  Location/Qualifiers
source                   1..10
                         mol_type = protein
                         organism = synthetic construct
SEQUENCE: 379
NISPDGTRTY                                                                          10

SEQ ID NO: 380           moltype = AA  length = 15
FEATURE                  Location/Qualifiers
source                   1..15
                         mol_type = protein
                         organism = synthetic construct

```
SEQUENCE: 380
GSTVYPFLRP RDANY                                                         15

SEQ ID NO: 381         moltype = AA  length = 10
FEATURE                Location/Qualifiers
source                 1..10
                       mol_type = protein
                       organism = synthetic construct
SEQUENCE: 381
TTTFSSYAMG                                                               10

SEQ ID NO: 382         moltype = AA  length = 10
FEATURE                Location/Qualifiers
source                 1..10
                       mol_type = protein
                       organism = synthetic construct
SEQUENCE: 382
TISGGGVYTY                                                               10

SEQ ID NO: 383         moltype = AA  length = 16
FEATURE                Location/Qualifiers
source                 1..16
                       mol_type = protein
                       organism = synthetic construct
SEQUENCE: 383
QRNIPRYGLE SRNYDY                                                        16

SEQ ID NO: 384         moltype = AA  length = 10
FEATURE                Location/Qualifiers
source                 1..10
                       mol_type = protein
                       organism = synthetic construct
SEQUENCE: 384
GSVFRFYGMG                                                               10

SEQ ID NO: 385         moltype = AA  length = 9
FEATURE                Location/Qualifiers
source                 1..9
                       mol_type = protein
                       organism = synthetic construct
SEQUENCE: 385
DIRLSGRTN                                                                9

SEQ ID NO: 386         moltype = AA  length = 10
FEATURE                Location/Qualifiers
source                 1..10
                       mol_type = protein
                       organism = synthetic construct
SEQUENCE: 386
APFTIPSPFA                                                               10

SEQ ID NO: 387         moltype = AA  length = 11
FEATURE                Location/Qualifiers
source                 1..11
                       mol_type = protein
                       organism = synthetic construct
SEQUENCE: 387
SGSISSDNAM G                                                             11

SEQ ID NO: 388         moltype = AA  length = 9
FEATURE                Location/Qualifiers
source                 1..9
                       mol_type = protein
                       organism = synthetic construct
SEQUENCE: 388
SLTRDGSAI                                                                9

SEQ ID NO: 389         moltype = AA  length = 6
FEATURE                Location/Qualifiers
source                 1..6
                       mol_type = protein
                       organism = synthetic construct
SEQUENCE: 389
RTPPTY                                                                   6

SEQ ID NO: 390         moltype = AA  length = 11
FEATURE                Location/Qualifiers
source                 1..11
                       mol_type = protein
```

```
                           organism = synthetic construct
SEQUENCE: 390
SGRTFSTYRM T                                                            11

SEQ ID NO: 391         moltype = AA   length = 10
FEATURE                Location/Qualifiers
source                 1..10
                       mol_type = protein
                       organism = synthetic construct
SEQUENCE: 391
TISRNGGSTY                                                              10

SEQ ID NO: 392         moltype = AA   length = 15
FEATURE                Location/Qualifiers
source                 1..15
                       mol_type = protein
                       organism = synthetic construct
SEQUENCE: 392
GSTAYPFLSP RDANY                                                        15

SEQ ID NO: 393         moltype = AA   length = 10
FEATURE                Location/Qualifiers
source                 1..10
                       mol_type = protein
                       organism = synthetic construct
SEQUENCE: 393
GRTFSTYRIT                                                              10

SEQ ID NO: 394         moltype = AA   length = 10
FEATURE                Location/Qualifiers
source                 1..10
                       mol_type = protein
                       organism = synthetic construct
SEQUENCE: 394
TISRSSSNPY                                                              10

SEQ ID NO: 395         moltype = AA   length = 15
FEATURE                Location/Qualifiers
source                 1..15
                       mol_type = protein
                       organism = synthetic construct
SEQUENCE: 395
GSTAYPFLSP RDANY                                                        15

SEQ ID NO: 396         moltype = AA   length = 10
FEATURE                Location/Qualifiers
source                 1..10
                       mol_type = protein
                       organism = synthetic construct
SEQUENCE: 396
GSVFRFYGMG                                                              10

SEQ ID NO: 397         moltype = AA   length = 9
FEATURE                Location/Qualifiers
source                 1..9
                       mol_type = protein
                       organism = synthetic construct
SEQUENCE: 397
DIRLSGRAD                                                               9

SEQ ID NO: 398         moltype = AA   length = 10
FEATURE                Location/Qualifiers
source                 1..10
                       mol_type = protein
                       organism = synthetic construct
SEQUENCE: 398
APFTIPSPFA                                                              10

SEQ ID NO: 399         moltype = AA   length = 11
FEATURE                Location/Qualifiers
source                 1..11
                       mol_type = protein
                       organism = synthetic construct
SEQUENCE: 399
GSGSSINTSM G                                                            11

SEQ ID NO: 400         moltype = AA   length = 9
FEATURE                Location/Qualifiers
source                 1..9
```

```
                       mol_type = protein
                       organism = synthetic construct
SEQUENCE: 400
SMPRGGGTI                                                               9

SEQ ID NO: 401         moltype = AA   length = 6
FEATURE                Location/Qualifiers
source                 1..6
                       mol_type = protein
                       organism = synthetic construct
SEQUENCE: 401
RTPPTY                                                                  6

SEQ ID NO: 402         moltype = AA   length = 10
FEATURE                Location/Qualifiers
source                 1..10
                       mol_type = protein
                       organism = synthetic construct
SEQUENCE: 402
GSISSINAMG                                                             10

SEQ ID NO: 403         moltype = AA   length = 9
FEATURE                Location/Qualifiers
source                 1..9
                       mol_type = protein
                       organism = synthetic construct
SEQUENCE: 403
SMPRSGTAI                                                               9

SEQ ID NO: 404         moltype = AA   length = 6
FEATURE                Location/Qualifiers
source                 1..6
                       mol_type = protein
                       organism = synthetic construct
SEQUENCE: 404
HTPPTY                                                                  6

SEQ ID NO: 405         moltype = AA   length = 11
FEATURE                Location/Qualifiers
source                 1..11
                       mol_type = protein
                       organism = synthetic construct
SEQUENCE: 405
GSGSSINTSM G                                                           11

SEQ ID NO: 406         moltype = AA   length = 9
FEATURE                Location/Qualifiers
source                 1..9
                       mol_type = protein
                       organism = synthetic construct
SEQUENCE: 406
SMPRGGGAI                                                               9

SEQ ID NO: 407         moltype = AA   length = 6
FEATURE                Location/Qualifiers
source                 1..6
                       mol_type = protein
                       organism = synthetic construct
SEQUENCE: 407
QTPPTY                                                                  6

SEQ ID NO: 408         moltype = AA   length = 10
FEATURE                Location/Qualifiers
source                 1..10
                       mol_type = protein
                       organism = synthetic construct
SEQUENCE: 408
GSIFRFYGMG                                                             10

SEQ ID NO: 409         moltype = AA   length = 9
FEATURE                Location/Qualifiers
source                 1..9
                       mol_type = protein
                       organism = synthetic construct
SEQUENCE: 409
YIRLSGRTD                                                               9

SEQ ID NO: 410         moltype = AA   length = 10
FEATURE                Location/Qualifiers
```

| | | |
|---|---|---|
| source | 1..10<br>mol_type = protein<br>organism = synthetic construct | |
| SEQUENCE: 410<br>PPFTKPSPFA | | 10 |
| SEQ ID NO: 411<br>FEATURE<br>source | moltype = AA length = 10<br>Location/Qualifiers<br>1..10<br>mol_type = protein<br>organism = synthetic construct | |
| SEQUENCE: 411<br>GRTFSTYRMA | | 10 |
| SEQ ID NO: 412<br>FEATURE<br>source | moltype = AA length = 10<br>Location/Qualifiers<br>1..10<br>mol_type = protein<br>organism = synthetic construct | |
| SEQUENCE: 412<br>TISPNGASTY | | 10 |
| SEQ ID NO: 413<br>FEATURE<br>source | moltype = AA length = 15<br>Location/Qualifiers<br>1..15<br>mol_type = protein<br>organism = synthetic construct | |
| SEQUENCE: 413<br>GSTDYPFLRP RDANF | | 15 |
| SEQ ID NO: 414<br>FEATURE<br>source | moltype = AA length = 10<br>Location/Qualifiers<br>1..10<br>mol_type = protein<br>organism = synthetic construct | |
| SEQUENCE: 414<br>GSIFRFYGMG | | 10 |
| SEQ ID NO: 415<br>FEATURE<br>source | moltype = AA length = 9<br>Location/Qualifiers<br>1..9<br>mol_type = protein<br>organism = synthetic construct | |
| SEQUENCE: 415<br>DIRLSGRTD | | 9 |
| SEQ ID NO: 416<br>FEATURE<br>source | moltype = AA length = 10<br>Location/Qualifiers<br>1..10<br>mol_type = protein<br>organism = synthetic construct | |
| SEQUENCE: 416<br>APFTKPSPFA | | 10 |
| SEQ ID NO: 417<br>FEATURE<br>source | moltype = AA length = 10<br>Location/Qualifiers<br>1..10<br>mol_type = protein<br>organism = synthetic construct | |
| SEQUENCE: 417<br>GRTFTTYRMS | | 10 |
| SEQ ID NO: 418<br>FEATURE<br>source | moltype = AA length = 10<br>Location/Qualifiers<br>1..10<br>mol_type = protein<br>organism = synthetic construct | |
| SEQUENCE: 418<br>TISPDGTRTY | | 10 |
| SEQ ID NO: 419<br>FEATURE<br>source | moltype = AA length = 15<br>Location/Qualifiers<br>1..15<br>mol_type = protein<br>organism = synthetic construct | |
| SEQUENCE: 419<br>GSTVYPFLRP RDANY | | 15 |
| SEQ ID NO: 420 | moltype = AA length = 10 | |

```
FEATURE              Location/Qualifiers
source               1..10
                     mol_type = protein
                     organism = synthetic construct
SEQUENCE: 420
GRTFSTYRMG                                                                       10

SEQ ID NO: 421       moltype = AA  length = 10
FEATURE              Location/Qualifiers
source               1..10
                     mol_type = protein
                     organism = synthetic construct
SEQUENCE: 421
EISRNGGYTY                                                                       10

SEQ ID NO: 422       moltype = AA  length = 15
FEATURE              Location/Qualifiers
source               1..15
                     mol_type = protein
                     organism = synthetic construct
SEQUENCE: 422
GSTTYPFLSP RDANY                                                                 15

SEQ ID NO: 423       moltype = AA  length = 10
FEATURE              Location/Qualifiers
source               1..10
                     mol_type = protein
                     organism = synthetic construct
SEQUENCE: 423
GRTFTTYRMG                                                                       10

SEQ ID NO: 424       moltype = AA  length = 10
FEATURE              Location/Qualifiers
source               1..10
                     mol_type = protein
                     organism = synthetic construct
SEQUENCE: 424
TISRDGTRTY                                                                       10

SEQ ID NO: 425       moltype = AA  length = 15
FEATURE              Location/Qualifiers
source               1..15
                     mol_type = protein
                     organism = synthetic construct
SEQUENCE: 425
VSTDYPFLRP RDAAY                                                                 15

SEQ ID NO: 426       moltype = AA  length = 9
FEATURE              Location/Qualifiers
source               1..9
                     mol_type = protein
                     organism = synthetic construct
SEQUENCE: 426
GSSINTSMG                                                                        9

SEQ ID NO: 427       moltype = AA  length = 9
FEATURE              Location/Qualifiers
source               1..9
                     mol_type = protein
                     organism = synthetic construct
SEQUENCE: 427
SMPRGGGAL                                                                        9

SEQ ID NO: 428       moltype = AA  length = 6
FEATURE              Location/Qualifiers
source               1..6
                     mol_type = protein
                     organism = synthetic construct
SEQUENCE: 428
QTPPTF                                                                           6

SEQ ID NO: 429       moltype = AA  length = 10
FEATURE              Location/Qualifiers
source               1..10
                     mol_type = protein
                     organism = synthetic construct
SEQUENCE: 429
GRTFTTDRMA                                                                       10
```

-continued

```
SEQ ID NO: 430          moltype = AA   length = 10
FEATURE                 Location/Qualifiers
source                  1..10
                        mol_type = protein
                        organism = synthetic construct
SEQUENCE: 430
TISRDGTRPY                                                              10

SEQ ID NO: 431          moltype = AA   length = 15
FEATURE                 Location/Qualifiers
source                  1..15
                        mol_type = protein
                        organism = synthetic construct
SEQUENCE: 431
GSTVYPFLRP RDANY                                                        15

SEQ ID NO: 432          moltype = AA   length = 10
FEATURE                 Location/Qualifiers
source                  1..10
                        mol_type = protein
                        organism = synthetic construct
SEQUENCE: 432
EGTFSTYRMT                                                              10

SEQ ID NO: 433          moltype = AA   length = 10
FEATURE                 Location/Qualifiers
source                  1..10
                        mol_type = protein
                        organism = synthetic construct
SEQUENCE: 433
TISRNGGSTY                                                              10

SEQ ID NO: 434          moltype = AA   length = 15
FEATURE                 Location/Qualifiers
source                  1..15
                        mol_type = protein
                        organism = synthetic construct
SEQUENCE: 434
GSTAYPFLSP RDANY                                                        15

SEQ ID NO: 435          moltype = AA   length = 8
FEATURE                 Location/Qualifiers
source                  1..8
                        mol_type = protein
                        organism = synthetic construct
SEQUENCE: 435
GRTFTTYR                                                                 8

SEQ ID NO: 436          moltype = AA   length = 10
FEATURE                 Location/Qualifiers
source                  1..10
                        mol_type = protein
                        organism = synthetic construct
SEQUENCE: 436
TVSRDGTRAY                                                              10

SEQ ID NO: 437          moltype = AA   length = 15
FEATURE                 Location/Qualifiers
source                  1..15
                        mol_type = protein
                        organism = synthetic construct
SEQUENCE: 437
GSTDYPFLRP RDANY                                                        15

SEQ ID NO: 438          moltype = AA   length = 10
FEATURE                 Location/Qualifiers
source                  1..10
                        mol_type = protein
                        organism = synthetic construct
SEQUENCE: 438
GRTFTTYRMS                                                              10

SEQ ID NO: 439          moltype = AA   length = 10
FEATURE                 Location/Qualifiers
source                  1..10
                        mol_type = protein
                        organism = synthetic construct
SEQUENCE: 439
TISPDGTRTY                                                              10
```

```
SEQ ID NO: 440           moltype = AA  length = 15
FEATURE                  Location/Qualifiers
source                   1..15
                         mol_type = protein
                         organism = synthetic construct
SEQUENCE: 440
GSTVYPFLRP RDANY                                                             15

SEQ ID NO: 441           moltype = AA  length = 10
FEATURE                  Location/Qualifiers
source                   1..10
                         mol_type = protein
                         organism = synthetic construct
SEQUENCE: 441
GGTVTTYRMA                                                                   10

SEQ ID NO: 442           moltype = AA  length = 10
FEATURE                  Location/Qualifiers
source                   1..10
                         mol_type = protein
                         organism = synthetic construct
SEQUENCE: 442
TISRDGTSTY                                                                   10

SEQ ID NO: 443           moltype = AA  length = 15
FEATURE                  Location/Qualifiers
source                   1..15
                         mol_type = protein
                         organism = synthetic construct
SEQUENCE: 443
GSTTYPFLRP RDANY                                                             15

SEQ ID NO: 444           moltype = AA  length = 10
FEATURE                  Location/Qualifiers
source                   1..10
                         mol_type = protein
                         organism = synthetic construct
SEQUENCE: 444
GSSLNIYAIG                                                                   10

SEQ ID NO: 445           moltype = AA  length = 10
FEATURE                  Location/Qualifiers
source                   1..10
                         mol_type = protein
                         organism = synthetic construct
SEQUENCE: 445
CISRSDGITF                                                                   10

SEQ ID NO: 446           moltype = AA  length = 11
FEATURE                  Location/Qualifiers
source                   1..11
                         mol_type = protein
                         organism = synthetic construct
SEQUENCE: 446
AGYRCALYMD Y                                                                 11

SEQ ID NO: 447           moltype = AA  length = 8
FEATURE                  Location/Qualifiers
source                   1..8
                         mol_type = protein
                         organism = synthetic construct
SEQUENCE: 447
GRTFTTYR                                                                      8

SEQ ID NO: 448           moltype = AA  length = 10
FEATURE                  Location/Qualifiers
source                   1..10
                         mol_type = protein
                         organism = synthetic construct
SEQUENCE: 448
TVSRDGTRTY                                                                   10

SEQ ID NO: 449           moltype = AA  length = 15
FEATURE                  Location/Qualifiers
source                   1..15
                         mol_type = protein
                         organism = synthetic construct
SEQUENCE: 449
```

```
VSTDYPFLRP RDAAY                                                        15

SEQ ID NO: 450          moltype = AA  length = 10
FEATURE                 Location/Qualifiers
source                  1..10
                        mol_type = protein
                        organism = synthetic construct SEQUENCE: 450
GSISSNVSMG                                                              10

SEQ ID NO: 451          moltype = AA  length = 9
FEATURE                 Location/Qualifiers
source                  1..9
                        mol_type = protein
                        organism = synthetic construct SEQUENCE: 451
SMPRGGSAI                                                                9

SEQ ID NO: 452          moltype = AA  length = 6
FEATURE                 Location/Qualifiers
source                  1..6
                        mol_type = protein
                        organism = synthetic construct SEQUENCE: 452
RTPPTY                                                                   6

SEQ ID NO: 453          moltype = AA  length = 10
FEATURE                 Location/Qualifiers
source                  1..10
                        mol_type = protein
                        organism = synthetic construct SEQUENCE: 453
GNIFRFYAMG                                                              10

SEQ ID NO: 454          moltype = AA  length = 10
FEATURE                 Location/Qualifiers
source                  1..10
                        mol_type = protein
                        organism = synthetic construct SEQUENCE: 454
DIRLSGSTNI                                                              10

SEQ ID NO: 455          moltype = AA  length = 10
FEATURE                 Location/Qualifiers
source                  1..10
                        mol_type = protein
                        organism = synthetic construct SEQUENCE: 455
APFTKPSPFA                                                              10

SEQ ID NO: 456          moltype = AA  length = 10
FEATURE                 Location/Qualifiers
source                  1..10
                        mol_type = protein
                        organism = synthetic construct SEQUENCE: 456
GRTFTTYRMG                                                              10

SEQ ID NO: 457          moltype = AA  length = 10
FEATURE                 Location/Qualifiers
source                  1..10
                        mol_type = protein
                        organism = synthetic construct SEQUENCE: 457
TISRDGTRTY                                                              10

SEQ ID NO: 458          moltype = AA  length = 15
FEATURE                 Location/Qualifiers
source                  1..15
                        mol_type = protein
                        organism = synthetic construct SEQUENCE: 458
LSTNYPFLRP RDANY                                                        15

SEQ ID NO: 459          moltype = AA  length = 11
FEATURE                 Location/Qualifiers
source                  1..11
                        mol_type = protein
                        organism = synthetic construct
```

```
SEQUENCE: 459
GSGSSINTSM G                                                              11

SEQ ID NO: 460          moltype = AA  length = 9
FEATURE                 Location/Qualifiers
source                  1..9
                        mol_type = protein
                        organism = synthetic construct
SEQUENCE: 460
SMPRGGGAI                                                                  9

SEQ ID NO: 461          moltype = AA  length = 6
FEATURE                 Location/Qualifiers
source                  1..6
                        mol_type = protein
                        organism = synthetic construct
SEQUENCE: 461
QTPPTY                                                                     6

SEQ ID NO: 462          moltype = AA  length = 10
FEATURE                 Location/Qualifiers
source                  1..10
                        mol_type = protein
                        organism = synthetic construct
SEQUENCE: 462
GRTFTTYRMG                                                                10

SEQ ID NO: 463          moltype = AA  length = 10
FEATURE                 Location/Qualifiers
source                  1..10
                        mol_type = protein
                        organism = synthetic construct
SEQUENCE: 463
TISGDGTRPY                                                                10

SEQ ID NO: 464          moltype = AA  length = 15
FEATURE                 Location/Qualifiers
source                  1..15
                        mol_type = protein
                        organism = synthetic construct
SEQUENCE: 464
GSTDYPFLRP RDANY                                                          15

SEQ ID NO: 465          moltype = AA  length = 10
FEATURE                 Location/Qualifiers
source                  1..10
                        mol_type = protein
                        organism = synthetic construct
SEQUENCE: 465
GRTFTTYRMS                                                                10

SEQ ID NO: 466          moltype = AA  length = 10
FEATURE                 Location/Qualifiers
source                  1..10
                        mol_type = protein
                        organism = synthetic construct
SEQUENCE: 466
TISPDGTRTY                                                                10

SEQ ID NO: 467          moltype = AA  length = 15
FEATURE                 Location/Qualifiers
source                  1..15
                        mol_type = protein
                        organism = synthetic construct
SEQUENCE: 467
GSTVYPFLRP RDANY                                                          15

SEQ ID NO: 468          moltype = AA  length = 10
FEATURE                 Location/Qualifiers
source                  1..10
                        mol_type = protein
                        organism = synthetic construct
SEQUENCE: 468
EGTFSTYRMT                                                                10

SEQ ID NO: 469          moltype = AA  length = 10
FEATURE                 Location/Qualifiers
source                  1..10
                        mol_type = protein
```

-continued

```
                    organism = synthetic construct
SEQUENCE: 469
TISRNGGSTY                                                            10

SEQ ID NO: 470      moltype = AA  length = 15
FEATURE             Location/Qualifiers
source              1..15
                    mol_type = protein
                    organism = synthetic construct
SEQUENCE: 470
GSTAYPFLSP RDANY                                                      15
```